(12) United States Patent
Comeau et al.

(10) Patent No.: US 8,163,284 B2
(45) Date of Patent: Apr. 24, 2012

(54) METHODS OF TREATING TSLP-RELATED INFLAMMATORY DISORDERS

(75) Inventors: Michael R Comeau, Bainbridge Island, WA (US); James F Smothers, Quincy, MA (US); Bo-Rin P Yoon, Sammamish, WA (US); Christopher Mehlin, Seattle, WA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/185,021

(22) Filed: Jul. 18, 2011

(65) Prior Publication Data

US 2011/0274687 A1 Nov. 10, 2011

Related U.S. Application Data

(62) Division of application No. 12/231,944, filed on Sep. 8, 2008, now Pat. No. 7,982,016.

(60) Provisional application No. 61/091,676, filed on Aug. 25, 2008, provisional application No. 60/971,178, filed on Sep. 10, 2007.

(51) Int. Cl.
*A61K 39/00* (2006.01)

(52) U.S. Cl. ............... 424/133.1; 424/142.1; 424/158.1; 530/350; 530/387.1; 530/387.3; 530/388.15; 530/388.23

(58) Field of Classification Search .................. 530/350, 530/387.1, 387.3, 388.15, 388.23; 424/133.1, 424/142.1, 158.1
See application file for complete search history.

(56) References Cited

U.S. PATENT DOCUMENTS

| | | | |
|---|---|---|---|
| 5,011,912 | A | 4/1991 | Hopp et al. |
| 6,555,520 | B2 | 4/2003 | Sims et al. |
| 6,844,170 | B1 | 1/2005 | Moore et al. |
| 2002/0146819 | A1 | 10/2002 | Sims et al. |
| 2003/0099947 | A1 | 5/2003 | Bazan et al. |
| 2003/0186875 | A1 | 10/2003 | De Waal Malefyt et al. |
| 2005/0249712 | A1 | 11/2005 | Leonard et al. |
| 2009/0186022 | A1 | 7/2009 | Bardroff et al. |

FOREIGN PATENT DOCUMENTS

| | | |
|---|---|---|
| WO | 93/21946 | 11/1993 |
| WO | 95/00103 | 1/1995 |
| WO | 98/36061 | 8/1998 |
| WO | 99/47538 | 9/1999 |
| WO | 00/017362 | 3/2000 |
| WO | 00/29581 | 5/2000 |
| WO | 00/039149 | 7/2000 |
| WO | 01/12672 | 2/2001 |
| WO | 01/62272 | 8/2001 |
| WO | 01/87328 | 11/2001 |
| WO | 02/00723 | 1/2002 |
| WO | 02/00724 | 1/2002 |
| WO | 03/065985 | 8/2003 |
| WO | 03/099823 | 12/2003 |
| WO | 2004/022718 | 3/2004 |
| WO | 2005/007186 | 1/2005 |
| WO | 2006/023791 | 3/2006 |
| WO | 2007/112146 | 10/2007 |
| WO | 2008/076321 | 6/2008 |
| WO | 2008/155365 | 12/2008 |

OTHER PUBLICATIONS

Huang, "Structural chemistry and therapeutic intervention of protein-protein interactions in immune response, human immunodeficiency virus entry, and apoptosis," Pharmacol Ther 86(3):201-215, 2000.
Ichinose and Barnes., "Cytokine-directed therapy in asthma," Curr Drug Targets Inflamm Allergy 3(3):263-269, 2004.
Isaksen et al., "Requirement for stat5 in thymic stromal lymphopoietin-mediated signal transduction," J Immunol 163 (11):5971-5977, 1999.
Jakubzick et al., "Therapeutic targeting of IL-4- and IL-13-responsive cells in pulmonary fibrosis," Immunol Res 30 (3):339-349, 2004.
Jessup et al., "Intradermal administration of thymic stromal lymphopoietin induces a T cell- and eosinophil-dependent systemic Th2 inflammatory response," J Immunol 181:4311-4319, 2008.
Kimura et al., "Sharing of the IL-2 receptor γ chain with the functional IL-9 receptor complex," Int Immunol 7:115-120, 1995.
Kobayashi et al., "Cloning and sequencing of the cDNA encoding a mouse IL-2 receptor γ," Gene 130:303-304, 1993.
Kondo et al., "Functional participation of the IL-2 receptor γ chain in IL-7 receptor complexes," Science 263:1453-1454, 1994.
Kondo et al., "Sharing of the interleukin-2 (IL-2) receptor γ chain between receptors for IL-2 and IL-4," Science 262:1874-1877, 1993.
Kowalewska et al., "Thymic stromal lymphopoietin transgenic mice develop cryoglobulinemia and hepatitis with similarities to human hepatitis C liver disease," Am J Pathol 170:981-989, 2007.
Lambrecht and Hammad, "Taking our breath away: dendritic cells in the pathogenesis of asthma," Nat Rev Immunol 3:994-1003, 2003.
Leckie et al., "Effects of an interleukin-5 blocking monoclonal antibody on eosinophils, airway hyper-responsiveness, and the late asthmatic response," Lancet 356:2144-2148, 2000.
Lee et al., "Normal B cell precursors responsive to recombinant murine IL-7 and inhibition of IL-7 activity by transforming growth factor-β," J Immunol 142:3875-3883, 1989.
Leonard and O'Shea, "JAKS and STATS: Biological implications," Annu Rev Immunol 16:293-322, 1998.
Leonard et al., "Role of the common cytokine receptor γ chain in cytokine signaling and lymphoid development," Immunol Rev 148:97-114, 1995.
Leonard, "Chapter 21. Type I cytokines and interferons and their receptors," Fundam Immunol (Paul, ed., Lippincott Raven Publishers 4 Ed.), pp. 741-774, 1999.

(Continued)

*Primary Examiner* — Stephen Rawlings
(74) *Attorney, Agent, or Firm* — Thomas J. Wrona

(57) ABSTRACT

The present disclosure provides compositions and methods relating to antigen binding proteins which bind to human thymic stromal lymphopoietin (TSLP), including antibodies. In particular embodiments, the disclosure provides fully human, humanized and chimeric anti-TSLP antibodies and derivatives of such antibodies. The disclosure further provides nucleic acids encoding such antibodies and antibody fragments and derivatives, and methods of making and using such antibodies including methods of treating and preventing TSLP-related inflammatory and fibrotic disorders.

14 Claims, 12 Drawing Sheets

OTHER PUBLICATIONS

Levin et al., "Thymic Stromal Lymphopoietin: A cytokine that promotes the development of IgM+ B cells in vitro and signals via a noval mechanism," J Immunol 162:677-683, 1999.

Li et al., "Identification of the CD8 DE loop as a surface functional epitope," J Biol Chem 273(26):16442-16445, 1998.

Menneki, "The role of TSLP for B cell lymphopoesis," Immunol Frontier, 10(2):40-43, 2000 (with partial English translation).

Mikayama et al., "Molecular cloning and functional expression of a cDNA encoding glycosylation-inhibiting factor," Proc Natl Acad Sci USA 90:10056-10060, 1993.

Miyajima et al., "Signal transduction by the GM-CSF, IL-3 and IL-5 receptors," Leukemia 11(Suppl3):418-422, 1997.

Nelson et al., "Cytoplasmic domains of the interleukin-2 receptor β and γ chains mediate the signal for T-cell proliferation," Nature 369:333-336, 1994.

Noguchi et al., "Interleukin-2 receptor γ chain mutation results in X-linked severe combined immunodeficiency in humans," Cell 73:147-157, 1993.

Noguchi et al., "Interleukin-2 receptor γ chain: a functional component of the interleukin-7 receptor," Science 262:1877-1880, 1993.

"Omalizumab for allergy related asthma," Medical Policy [Online], Retrieved from the Internet: URL:http://www.wellmark.com/e_business/provider/medical_policies/policies/Xolair.htm [retrieved Jan. 25, 2006].

Ong et al., "Anti-IL-4 treatment prevents dermal collagen deposition in the tight-skin mouse model of scleroderma," Eur J Immunol 28(9):2619-2629, 1998.

Pandey et al., "Cloning of a receptor subunit required for signaling by thymic stromal lymphopoietin," Nat Immunol, 1 (1):59-64, 2000.

Pape et al., "Inflammatory cytokines enhance the in vivo clonal expansion and differentiation of antigen-activated CD4+T cells," J Immunol 159(2):591-598, 1997.

Pape et al., "Use of adoptive transfer of T-cell-antigen-receptor-transgenic T cells for the study of T-cell activation in vivo," Immunol Rev 156:67-78, 1997.

Park et al., "Cloning of the murine thymic stromal lymphopoietin (TSLP) receptor: formation of a functional heteromeric complex requires interleukin 7 receptor," J Exp Med 192(5):659-669, 2000.

Peschon et al., "Early lymphocyte expansion is severely impaired in interleukin 7 receptor-deficient mice," J Exp Med 180:1955-1960, 1994.

R&D Systems online catalog, printed Apr. 27, 2007 (TSLP antibodies, IL-1.alpha.antibodies, TNF.alpha.antibodies).

Reche et al., "Human thymic stromal lymphopoietin preferentially stimulates myeloid cells," J Immunol 167:336-343, 2001.

Russell et al., "Interaction of IL-2Rβ and γc chains with Jak1 and Jak3: implications for XSCID and XCID," Science 266:1042-1045, 1994.

Russell et al., "Interleukin-2 receptor γ chain: a functional component of the interleukin-4 receptor," Science 262:1880-1883, 1993.

Sims et al., "Molecular cloning and biological characterizations of a novel murine lymphoid growth factor," J. Exp Med 192(5):671-680, 2000.

Sin et al., "Pharmacological management to reduce exacerbations in adults with asthma: a systematic review and meta-analysis," JAMA 292(3):367-376, 2004.

Singh and Suruchi, "Anti-TNF-alpha strategy: present status of this therapeutic paradigm," Indian J Pharmacol 36 (1):10-14, 2004.

Soumelis et al., "Human epithelial cells trigger dendritic cell mediated allergic inflammation by producing TSLP," Nat Immunol 3(7):673-680, 2002.

Soumelis and Liu, "Human thymic stromal lymphopoietin: a novel epithelial cell-derived cytokine and a potential key player in the induction of allergic inflammation," Springer Semin Immunopathol 25:325-333, 2004.

Suda et al., "A stimulatory effect of recombinant murine interleukin-7 (IL-7) on B-cell colony formation and an inhibitory effect of IL-1α," Blood 74:1936-1941, 1989.

Sudo et al., "Interleukin 7 production and function in stromal cell-dependent B cell development," J Exp Med 170:333-338, 1989.

Taga and Kishimoto, "GP130 and the interleukin-6 family of cytokines," Annu Rev Immunol 15:797-819, 1997.

Takeshita et al., "Cloning of the γ chain of the human IL-2 receptor," Science 257:379-382, 1992.

von Freeden-Jeffrey et al., "Lymphopenia in interleukin (IL)-7 gene-deleted mice identifies IL-7 as a nonredundant cytokine," J Exp Med 181:1519-1526, 1995.

Wells, "Additivity of mutational effects in proteins," Biochemistry 29(37):8509-8517, 1990.

Wynn, "Fibrotic disease and the TH1/TH2 paradigm," Nat Rev Immunol 4(8):583-594, 2004.

Zhou et al., "Thymic stromal lymphopoietin as a key initiator of allergic airway inflammation in mice," Nat Immunol 6:1047-1053, 2005.

Ziegler et al., "Reconstitution of a functional interleukin (IL)-7 receptor demonstrates that the IL-2 receptor γ chain is required for IL-7 signal transduction," Eur J Immunol 25:399-404, 1995.

Allakhverdi et al., "Thymic stromal lymphopoietin is released by human epithelial cells in response to microbes, trauma, or inflammation and potently activates mast cells," J Exp Med, 204(2):253-258, 2007.

Barnes et al., "New therapeutic approaches," Br Med Bull 48(1):231-247, 1992.

Barnes, "Cytokine-directed therapies for asthma," J Allergy Clin Immunol 108(Suppl.2):S72-S76, 2001.

Barnes, "Corticosteroid effects on cell signalling," Eur Respir J 27(2):413-426, 2006.

Bazan, "Haemopoietic receptors and helical cytokines," Immunol Today 11:350-354, 1990.

Blyth et al., "Airway subepithelial fibrosis in a murine model of atopic asthma: suppression by dexamethasone or anti-interleukin-5 antibody," Am J Respir Cell Mol Biol 23(2):241-246, 2000.

Borish et al., "Efficacy of soluble IL-4 receptor for the treatment of adults with asthma," J Allergy Clin Immunol 107 (6):963-970, 2001.

Bork et al., "Go hunting in sequence databases but watch out for the traps," Trends Genet 12:425-427, 1996.

Bork, "Powers and pitfalls in sequence analysis: the 70% hurdle," Genome Res 10:398-400, 2000.

Brenner, "Errors in genome annotation," Trends Genet 15:132-133, 1999.

Burdach et al., "The physiologic role of interleukin-3, interleukin-5, granulocyte-macrophage colony-stimulating factor, and the βc receptor system," Curr Opin Hematol 5:177-180, 1998.

Candéias et al., "IL-7 receptor and VDJ recombination: trophic versus mechanistic actions," Immunity 6:501-508, 1997.

Cao et al., "Characterization of cDNAs encoding the murine interleukin 2 receptor (IL-2R) γ chain: chromosomal mapping and tissue specificity of IL-2R γ chain expression," Proc Natl Acad Sci USA 90:8464-8468, 1993.

Cohn et al., "T helper 1 cells and interferon gamma regulate allergic airway inflammation and mucus production," J Exp Med 190(9):1309-1317, 1999.

Cunningham and Wells, "High-resolution epitope mapping of hGH-receptor interactions by alanine-scanning mutagenesis," Science 244:1081-1085, 1989.

Database EMBL Online Accession No. AB031333, Kitamura and Fujio, *Mus musculus* mRNA for cytokine receptor deltal, complete cds, Feb. 24, 2000.

Database EMBL Online Accession No. AB039945, Hiroyama et al., *Mus musculus* CRLM2 mRNA for cytokine receptor like molecule 2, complete cds, Mar. 14, 2000.

Database EST, Accession No. AA021949, Marra et al., Marra M/Mouse EST Project, Jan. 21, 1997.

Doerks et al., "Protein annotation: detective work for function prediction," Trends Genet 14:248-250, 1998.

DosReis et al., "The central role of Fas-ligand cell signaling in inflammatory lung diseases," J Cell Mol Med 8 (3):285-293, 2004.

Fujio et al., "Molecular cloning of a novel type I cytokine receptor similar to the common gamma chain," Blood 95 (7):2204-2211, 2000.

Garcia et al., "Evaluation of inflammatory cytokine secretion by human alveolar macrophages," Mediators Inflamm 8 (1):43-51, 1999.

Giri et al., "Utilization of the β and γ chains of the IL-2 receptor by the novel cytokine IL-15," EMBO J 13:2822-2830, 1994.

Grunewald et al., "An antagonistic IL-4 mutant prevents Type I allergy in the mouse: inhibition of the IL-4/IL-13 receptor system completely abrogates humoral immune response to allergen and development of allergic symptoms in vivo," J Immunol 160(8):4004-4009, 1998.

Guthridge et al., "Mechanism of activation of the GM-CSF, IL-3, and IL-5 family of receptors," Stem Cells 16:301-313, 1998.

He et al., "The common γ-chain of cytokine receptors regulates intrathymic T cell development at multiple states," J Immunol 158:2592-2599, 1997.

He et al., "Small-molecule inhibition of TNF-α," Science 310(5750):1022-1025, 2005.

Hirano et al., "Signaling mechanisms through gp130: a model of the cytokine system,"Cytokine Growth Factor Rev 8:241-252, 1997.

Hiroyama et al., "Molecular cloning and characterization of CRLM-2, a novel type I cytokine receptor preferentially expressed in hematopoietic cells," Biochem Biophys Res Commun 272(1):224-229, 2000.

Hosaka, et al., "Arg-X-Lys/Arg-Arg Motif as a signal for precursor cleavage catalyzed by furin within the constitutive secretory pathway," J Biol Chem 266(19):12127-12130, 1991.

Edwards et al., "Therapy directed against thymic stromal lymphopoietin," Drug News Perspect 21(6):312-316, 2008.

He et al., "A thymic stromal lymphopoietin gene variant is associated with asthma and airway hyperresponsiveness," J Allergy Clin Immunol, doi:10.1016/j.jaci.2009.04.018, in press 2009.

Corrigan et al., "Early production of thymic stromal lymphopoietin precedes infiltration of dendritic cells expressing its receptor in allergen-induced late phase cutaneous responses in atopic subjects," Allergy 64:1014-1022, 2009.

Candéias, et al., "Defective T-cell receptor γ gene rearrangement in interleukin-7 receptor knockout mice," Immunol Lett, 57:9-14, 1997.

Carpino, "Absence of an essential role for thymic stromal lymphopoietin receptor in murine B cell development," Mol Cell Biol, 24(6):2584-2592, 2004.

Database EST, Accession No. AA889581, "EST; *h. sapiens* cDNA clone IMAGE: 1407260," Apr. 6, 1998.

Friend et al., "A thymic stromal cell line supports in vitro development of surface IgM+ B cells and produces a novel growth factor affecting B and T lineage cells," Exp Hematol 22(3):321-328, 1994.

Friend and Far, "Initial characterization of Thymic Stromal Derived Lymphopoietin (TSLP), " FASEB J. 8:A506, 1994 (Abstract).

Lai, L. et al., Identification of an IL-7 associated pre-pro-B cell growth-stimulating factor (PPBSF) II. PPBSF is a covalently linked heterodimer of IL-7 and a Mr 30,000 Co-factor1, J Immunol 160:2280-2286, 1998.

Liu, "Thymic stromal lymphopoietin: master switch for allergic inflammation," J Exp Med 203(2):269-273, 2006.

Quentmeier et al., "Cloning of human thymic stromal lymphopoietin (TSLP) and signaling mechanisms leading to proliferation," Leukemia 15:1286-1292, 2001.

Ray et al., "Characterization of thymic stromal-derived lymphopoietin (TSLP) in murine B cell development in vitro," Eur J Immunol 26:10-16, 1996.

Ziegler and Liu, "Thymic stronal lymphopoietin in normal and pathogenic T cell development and function," Nat Immunol, 7(7):709-714, 2006.

Leonard, "TSLP: finally in the limelight," Nat Immunol, 3(7):605-607, 2002.

Gao et al., "Establishment of allergic dermatitis in NC/Nga mice as a model for severe atopic dermatitis," Biol Pharm Bull 27(9):1376-1381, 2004.

Shimizu et al., "The appearance of S-100 protein-positive dendritic cells and the distribution of lymphocyte subsets in idiopathic non-specific interstitial pneumonia," Respir Med 96:770-776, 2002.

Williams et al., "Identification of spontaneous feline idiopathic pulmonary fibrosis," Chest 125:2278-2288, 2004.

Ramalingam et al., Regulation of helminth-induced Th2 responses by thymic stromal lymphopoietin, J Immunol 182:6452-6459, 2009.

Marchal-Sommé et al., "Dendritic cells accumulate in human fibrotic interstitial lung disease," Am J Respir Crit Care Med 176:1007-1014, 2007.

Semlali et al., "Thymic stromal lymphopoietin-induced human asthmatic airway epithelial cell proliferation through an IL-13-dependent pathway," J Allergy Clin Immunol 125:844-850, 2010.

Wilson and Wynn, "Pulmonary fibrosis: pathogenesis, etiology and regulation," Mucosal Immunol 2(2):103-121, 2009.

Davies, "The role of the epithelium in airway remodeling in asthma," Proc Am Thorac Soc 6:678-682, 2009.

MacCallum et al., "Antibody-antigen interactions: contact analysis and binding site topography," J Mol Biol 262:732-745, 1996.

Holm et al., "Functional mapping and single chain construction of the anti-cytokeratin 8 monoclonal antibody TS1," Mol Immunol 44(6):1075-1084, 2007.

Rudikoff et al., "Single amino acid substitution altering antigen-binding specificity," Proc Natl Acad Sci USA 79 (6):1979-1983, 1982.

| Ab | VARIABLE LIGHT CDRs | | |
|---|---|---|---|
| | CDR 1 | CDR 2 | CDR 3 |
| A1 NA | CAAGGAGACAGCCTCAGAAGCTATTA TGCAAGC (SEQ ID NO: 5) | GGTAAAAACTACCGGCCCTCA (SEQ ID NO: 52) | AACTCCCGGGACAGAAGTGGTAACCATCTGGTG TT (SEQ ID NO: 97) |
| AA | QGDSLRSYYAS (SEQ ID NO: 6) | GKNYRPS (SEQ ID NO: 53) | NSRDRSGNHLV (SEQ ID NO: 98) |
| A2 NA | CAAGGAGACAGCCTCAGAACCTATTA TGCAAGC (SEQ ID NO: 7) | GATAAAAACAACCGGCCCCTCA (SEQ ID NO: 54) | AACTCCCGGGACAGCAGTGATAACCATCTAGTG GTAT (SEQ ID NO: 99) |
| AA | QGDSLRTYYAS (SEQ ID NO: 8) | DKNNRPS (SEQ ID NO: 55) | NSRDSSDNHLVV (SEQ ID NO: 100) |
| A3 NA | ACTGGGAGCAGCTCCAACATCGGGGC AGGTTTTGATGTGCAC (SEQ ID NO: 9) | GATAACAACAATCGGCCCTCA (SEQ ID NO: 56) | CAGTCCTATGACAGCAACCTGAGTGGTTCGATT GTGGTTT (SEQ ID NO: 101) |
| AA | TGSSSNIGAGFDVH (SEQ ID NO: 10) | DNNNRPS (SEQ ID NO: 57) | QSYDSNLSGSIVV (SEQ ID NO: 102) |
| A4 NA | ACTGGGAGCAGCTCCAACATCGGGGC AGGTTTTGATGTGCAC (SEQ ID NO: 11) | GATAACAACAATCGCCCCTCA (SEQ ID NO: 58) | CAGTCCTATGACAGCAACCTGAGTGGTTCGATT GTGGTAT (SEQ ID NO: 103) |
| AA | TGSSSNIGAGFDVH (SEQ ID NO: 10) | DNNNRPS (SEQ ID NO: 57) | QSYDSNLSGSIVV (SEQ ID NO: 102) |
| A5 NA | GGGGGAAACAACCTTGGAAGTAAAA GTGTGCAC (SEQ ID NO: 12) | GATGATAGCGACCGGCCCTCA (SEQ ID NO: 59) | CAGGTGTGGGATAGTAGTAGTGATCATGTGGTA T (SEQ ID NO: 104) |
| AA | GGNNLGSKSVH (SEQ ID NO: 13) | DDSDRPS (SEQ ID NO: 60) | QVWDSSSDHVV (SEQ ID NO: 105) |

FIGURE 1A

| Ab | CDR 1 | CDR 2 | CDR 3 |
|---|---|---|---|
| A6 NA | TCTGGAGATAAATTGGGGGATAAATA TGCTTGC (SEQ ID NO: 14) | CAAGATAAGAAGCGGCCCTC A (SEQ ID NO: 61) | CAGGCGTGGGACAGCAGCACTGTGGTAT (SEQ ID NO: 106) |
| AA | SGDKLGDKYAC (SEQ ID NO: 15) | QDKKRPS (SEQ ID NO: 62) | QAWDSSTVV (SEQ ID NO: 107) |
| A7 NA | TCTGGAGATAAATTGGGGGATAAATA TGCTTGC (SEQ ID NO: 14) | CAAGATAACAAGCGGCCCCTCA (SEQ ID NO: 63) | CAGGCGTGGGACAGCACCACTGCGATAT (SEQ ID NO: 108) |
| AA | SGDKLGDKYAC (SEQ ID NO: 15) | QKNKPRPS (SEQ ID NO: 64) | QAWDSTTAI (SEQ ID NO: 109) |
| A8 NA | TCTGGAGATAAATTGGGGGATAAATA TGCTTGC (SEQ ID NO: 14) | CAAGATAACAAGCGGCCCTCA (SEQ ID NO: 63) | CAGGCGTGGGACAGGCAGCACTGTGGTAT (SEQ ID NO: 109) |
| AA | SGDKLGDKYAC (SEQ ID NO: 15) | QDNKRPS (SEQ ID NO: 65) | QAWDSSTVV (SEQ ID NO: 107) |
| A9 NA | CAAGGAGACAGCCTCAGAATCTTTTA TGCAAAC (SEQ ID NO: 16) | GGTAAAAACAACCGGCCCCTCA (SEQ ID NO: 66) | AACTCCCGGACAGCAGTGGTAACCATGTGGTA T (SEQ ID NO: 110) |
| AA | QGDSLRIFYAN (SEQ ID NO: 17) | GKNNRPS (SEQ ID NO: 67) | NSRDSSGNHVV (SEQ ID NO: 111) |
| A10 NA | CGGGCAAATCAGTACATTAGCACCTA TTTAAAT (SEQ ID NO: 18) | GCTGCATCCAGTTTGCAAAGT (SEQ ID NO: 68) | CAGCAGAGCTACACTACCCCGATCACCT (SEQ ID NO: 112) |
| AA | RANQYISTYLN (SEQ ID NO: 19) | AASSLQS (SEQ ID NO: 69) | QQSYTTPIT (SEQ ID NO: 113) |
| A11 NA | AAGTCCAGCCAGAGTGTTTTAAACAG CTCCAACAATAAGAACTACTTAGCT (SEQ ID NO: 20) | TGGACATCCACCCGGGAAGGC (SEQ ID NO: 70) | CAGCAGTATTTTACTACTCCGTGGACGT (SEQ ID NO: 114) |
| AA | KSSQSVLNSSNNKNYLA (SEQ ID NO: 21) | WTSTREG (SEQ ID NO: 71) | QQYFTTPWT (SEQ ID NO: 115) |

FIGURE 1B

| Ab | CDR 1 | CDR 2 | CDR 3 |
|---|---|---|---|
| A12 NA | CGGGGCGAGTCAGGGTATTAGTAGCTG GTTAGCC (SEQ ID NO: 22) | ACTGCATCCAGTTTGCAAAGT (SEQ ID NO: 72) | CAACAGGCTGACAGTTCCGCTCACTT (SEQ ID NO: 116) |
| AA | RASQGISSWLA (SEQ ID NO: 23) | TASSLQS (SEQ ID NO: 73) | QQADSFPLT (SEQ ID NO: 117) |
| A13.1 NA | AGGTCTAGTCAAAGCCTCGTCTACAG TGATGGAGACACCTACTTGAAT (SEQ ID NO: 24) | AAGGTTTCTAACTGGGACTCT (SEQ ID NO: 74) | ATGCAAGGTACACACTGGCCTCCGGCCT (SEQ ID NO: 118) |
| AA | RSSQSLVYSDGDTYLN (SEQ ID NO: 25) | KVSNWDS (SEQ ID NO: 75) | MQGTHWPPA (SEQ ID NO: 119) |
| A13.2 NA | CGGGCGAGTCAGGGTCTTAGCAGCTG GTTAGCC (SEQ ID NO: 26) | AACACATCCAGTTTGCAAAGT (SEQ ID NO: 76) | CAACAGGCTAACAGTTTCCCTCTCACTT (SEQ ID NO: 120) |
| AA | RASQGLSSWLA (SEQ ID NO: 27) | NTSSLQS (SEQ ID NO: 77) | QQANSFPLT (SEQ ID NO: 121) |
| A14.1 NA | AGGTCTAGTCAAAGCCTCGTCTACAG TGATGGAAACACCTACTTGAAT (SEQ ID NO: 28) | AAGGTTTCTAACTGGGACTCT (SEQ ID NO: 74) | ATGCAAGGTACACACTGGCCTCCGGCC (SEQ ID NO: 122) |
| AA | RSSQSLVYSDGNTYLN (SEQ ID NO: 29) | KVSNWDS (SEQ ID NO: 75) | MQGTHWPPA (SEQ ID NO: 119) |
| A14.2 NA | CGGGCGAGTCAGGGTCTTAGCAGCTG GTTAGCC (SEQ ID NO: 26) | AACACATCCAGTTTGCAAAGT (SEQ ID NO: 76) | CAACAGGCTAACAGTTTCCCTCTCACTT (SEQ ID NO: 120) |
| AA | RASQGLSSWLA (SEQ ID NO: 27) | NTSSLQS (SEQ ID NO: 77) | QQANSFPLT (SEQ ID NO: 121) |
| A15.1 NA | AGGTCTAGTCAAAGCCTCATATACAG TGATGGAAACACTTACTTGAAT (SEQ ID NO: 30) | AAGGTTTCTAACTGGGACTCT (SEQ ID NO: 74) | ATGCAAGGTACACACTGGCCTCCGGCC (SEQ ID NO: 122) |
| AA | RSSQSLIYSDGNTYLN (SEQ ID NO: 31) | KVSNWDS (SEQ ID NO: 75) | MQGTHWPPA (SEQ ID NO: 119) |

FIGURE 1C

| Ab | CDR 1 | CDR 2 | CDR 3 |
|---|---|---|---|
| A15.2 NA | CGGGGCGAGTCAGGGTCTTAGCAGCTG GTTAGCC (SEQ ID NO: 26) | ACTACATCCAGTTTGCAAAGT (SEQ ID NO: 78) | CAACAGGCTGACAGTTTCCCTCTCACTT (SEQ ID NO: 123) |
| AA | RASQGLSSWLA (SEQ ID NO: 27) | TTSSLQS (SEQ ID NO: 79) | QQADSFPLT (SEQ ID NO: 117) |
| A16.1 NA | AGGTCTAGTCAAAGCCTCGTATACAG TGATGGAAACACCTACTTGAAT (SEQ ID NO: 32) | AAGGTTTCTTACTGGGACTCT (SEQ ID NO: 80) | ATGCAAGGTACACACTGGCCTCCGGCCT (SEQ ID NO: 118) |
| AA | RSSQSLVYSDGNTYLN (SEQ ID NO: 33) | KVSYWDS (SEQ ID NO: 81) | MQGTHWPPA (SEQ ID NO: 119) |
| A16.2 NA | CGGGCGAGTCAGAGTCTTAGCAGCTG GTTAGCC (SEQ ID NO: 34) | AATGCATCCAGTTTGCAAAGT (SEQ ID NO: 82) | CAACAGGCTAACAGTTTCCCTCTCACTT (SEQ ID NO: 120) |
| AA | RASQSLSSWLA (SEQ ID NO: 35) | NASSLQS (SEQ ID NO: 83) | QQANSFPLT (SEQ ID NO: 121) |
| A-17 NA | GGCTTGAACTCTGGCTCAGTCTCTACT AGTTACTTCCCCAGC (SEQ ID NO: 36) | AGCACACAAACAGTCGCTCTTCT (SEQ ID NO: 84) | GTGCTGTATATGGGTAGAGGCATTTGGGTGT (SEQ ID NO: 124) |
| AA | GLNSGSVSTSYFPS (SEQ ID NO: 37) | STNSPSS (SEQ ID NO: 85) | VLYMGRGIWV (SEQ ID NO: 125) |
| A18.1 NA | AGGTCTAGTCAAAGCCTCGTATACAG TGATGGAAACACCTACTTGAAT (SEQ ID NO: 32) | AAGGTTTCTTACTGGGACTCT (SEQ ID NO: 80) | ATGCAAGGTACACACTGGCCTCCGGCCT (SEQ ID NO: 118) |
| AA | RSSQSLVYSDGNTYLN (SEQ ID NO: 33) | KVSYWDS (SEQ ID NO: 81) | MQGTHWPPA (SEQ ID NO: 119) |
| A18.2 NA | CGGGGCGAGTCAGAGTCTTAGCAGCTG GTTAGCC (SEQ ID NO: 34) | AATGCATCCAGTTTGCAAAGT (SEQ ID NO: 82) | CAACAGGCTAACAGTTTCCCTCTCACTT (SEQ ID NO: 120) |
| AA | RASQSLSSWLA (SEQ ID NO: 35) | NASSLQS (SEQ ID NO: 83) | QQANSFPLT (SEQ ID NO: 121) |

FIGURE 1D

| Ab | CDR 1 | CDR 2 | CDR 3 |
|---|---|---|---|
| A19.1 NA | AGGTCTAGTCAAAGCCTCGTCTACAG TGATGGAGACACCTACTTGAAT (SEQ ID NO: 38) | AAGGTTTCTAACTGGGACTCT (SEQ ID NO: 74) | ATGCAAGGTACAACTGGCCTCCGGCCT (SEQ ID NO: 118) |
| AA | RSSQSLVYSDGDTYLN (SEQ ID NO: 39) | KVSNWDS (SEQ ID NO: 75) | MQGTHWPPA (SEQ ID NO: 119) |
| A19.2 NA | CGGGCGAGTCAGGGTCTTAGCAGCTG GTTAGCC (SEQ ID NO: 26) | AACACATCCAGTTTGCAAAGT (SEQ ID NO: 76) | CAACAGGCTAACAGTTTCCCTCTCACTT (SEQ ID NO: 120) |
| AA | RASQGLSSWLA (SEQ ID NO: 27) | NTSSLQS (SEQ ID NO: 77) | QQANSFPLT (SEQ ID NO: 121) |
| A20.1 NA | AGGTCTAGTCAAAGCCTCGTCTACAG TGATGGAGACACCTACTTGAAT (SEQ ID NO: 38) | AAGGTTTCTAACTGGGACTCT (SEQ ID NO: 74) | ATGCAAGGTACAACTGGCCTCCGGCCT (SEQ ID NO: 118) |
| AA | RSSQSLVYSDGDTYLN (SEQ ID NO: 39) | KVSNWDS (SEQ ID NO: 75) | MQGTHWPPA (SEQ ID NO: 119) |
| A20.2 NA | CGGGCGAGTCAGGGTCTTAGCAGCTG GTTAGCC (SEQ ID NO: 26) | AACACATCCAGTTTGCAAAGT (SEQ ID NO: 76) | CAACAGGCTAACAGTTTCCCTCTCACTT (SEQ ID NO: 120) |
| AA | RASQGLSSWLA (SEQ ID NO: 27) | NTSSKQS (SEQ ID NO: 86) | QQANSFPLT (SEQ ID NO: 121) |
| A21 NA | ACTGGGAGCAGCTCCAACATTGGGGC GGGTTATGTTGTACAT (SEQ ID NO: 40) | GGTAACAGCAATCGGCCCTCA (SEQ ID NO: 87) | AAAGCATGGGATAACAGCCTGAATGCTCAAGG GGTAT (SEQ ID NO: 126) |
| AA | TGSSSNIGAGYVVH (SEQ ID NO: 41) | GNSNRPS (SEQ ID NO: 88) | KAWDNSLNAQGV (SEQ ID NO: 127) |
| A22 NA | AAGTCCAGCCAGAGTGTTTTATACAA CTCCAACAATAAGAACTACTTAGCT (SEQ ID NO: 42) | TGGGCTTCTACCCGGGAATCC (SEQ ID NO: 89) | CAGCAATTTTATGGTCCTCCTCTCACTT (SEQ ID NO: 128) |
| AA | KSSQSVLYNSNNKNYLA (SEQ ID NO: 43) | WASTRES (SEQ ID NO: 90) | QQFYGPPLT (SEQ ID NO: 129) |

FIGURE 1E

| Ab | CDR 1 | CDR 2 | CDR 3 |
|---|---|---|---|
| A23 NA | TCTGGTGTGATAAATTGGGGGATAAATT TGCTTTC (SEQ ID NO: 44) | CAAGATAGCAAGCGGCCCTCA (SEQ ID NO: 91) | CAGGCGTGGGACAGCAGCCGCGGGGGGTA (SEQ ID NO: 130) |
| AA | SGDKLGDKFAF (SEQ ID NO: 45) | QDSKRPS (SEQ ID NO: 92) | QAWDSSAGGV (SEQ ID NO: 131) |
| A24 NA | CAAGGAGACAGCCTCAGAAGCTATCA TGCAAGC (SEQ ID NO: 46) | GGTGAAAACAACCGGCCCTCA (SEQ ID NO: 93) | AATTATCGGGACAACAGTGGTAACCATCTGGTG T (SEQ ID NO: 132) |
| AA | QGDSLRSYHAS (SEQ ID NO: 47) | GENNRPS (SEQ ID NO: 94) | NYRDNSGNHLV (SEQ ID NO: 133) |
| A25 NA | AAGTCCAGCCAGAGTGTTTTATACAA CTCCAACAATAAGAACTACTTAGCT (SEQ ID NO: 42) | TGGGCTTCTACCCGGGAATCC (SEQ ID NO: 89) | CAGCAATTTTATGTCCTCTCTCACTT (SEQ ID NO: 128) |
| AA | KSSQSVLYNSNNKNYLA (SEQ ID NO: 43) | WASTRES (SEQ ID NO: 90) | QQFYGPPLT (SEQ ID NO: 129) |
| A26 NA | TCTGGAGATAAATTTGGGGGATAAATA TATTTGC (SEQ ID NO: 48) | CAAGATAACAAGCGGCCCTCA (SEQ ID NO: 63) | CAGGCGTGGGACAGCAGCACTGTGGTAT (SEQ ID NO: 106) |
| AA | SGDNLGDKYIC (SEQ ID NO: 49) | QDNKRPS (SEQ ID NO: 65) | QAWDSSTVV (SEQ ID NO: 107) |
| A27 NA | TCTGGAGATAAATTGGGGGAAAGCTA TGCTTGC (SEQ ID NO: 50) | CAAGATTACAAGGCGGCCCTCA (SEQ ID NO: 95) | CAGGCGTGGGACAGAAGTACTGTACTAT (SEQ ID NO: 134) |
| AA | SGDKLGESYAC (SEQ ID NO: 51) | QDYKRPS (SEQ ID NO: 96) | QAWDRSTVL (SEQ ID NO: 135) |

FIGURE 1F

| Ab | CDR 1 | VARIABLE HEAVY CDRs | |
|---|---|---|---|
| | | CDR 2 | CDR 3 |
| A1 NA | AACTATGGCATGCAC (SEQ ID NO: 136) | GTTATATGGTATGATGGAAGTAA TAAATACTATGCAGACTCCGTGA AGGGC (SEQ ID NO: 164) | CTAGTGGGAGCTACCAACTACTACGGTATGGACGTC (SEQ ID NO: 203) |
| AA | NYGMH (SEQ ID NO: 137) | VIWYDGSNKYYADSVKG (SEQ ID NO: 165) | LVGATNYYGMDV (SEQ ID NO: 204) |
| A2 NA | GATTTTACCATGCAC (SEQ ID NO: 138) | CTTATTAGTTGGGATGGTGGTAG CACATACTATGCAGACTCTGTGA AGGGC (SEQ ID NO: 166) | CCTTACTACTACTTCTACGGTATGGACGTC (SEQ ID NO: 205) |
| AA | DFTMH (SEQ ID NO: 139) | LISWDGGSTYYADSVKG (SEQ ID NO: 167) | PYYYFYGMDV (SEQ ID NO: 206) |
| A3 NA | GACTACTATATGTAC (SEQ ID NO: 140) | TGGATCAACCCTAACAGTGGTGG CACAAACTATGTACAGAAGTTTC AGGGC (SEQ ID NO: 168) | GATGGGGGTAGCAGTGGCTGGCCCCTCTTTGCCTAC (SEQ ID NO: 207) |
| AA | DYYMY (SEQ ID NO: 141) | WINPNSGGTNYVQKFQG (SEQ ID NO: 169) | DGGSSGWPLFAY (SEQ ID NO: 208) |
| A4 NA | GGCGACTATATGCAC (SEQ ID NO: 142) | TGGATCAACCCTAACAGTGGTGG CACAAACCATGCACGGAAGTTTC AGGGC (SEQ ID NO: 170) | GATAGGGGTACCAGTGGCTGGCCACTCTTTGACTAT (SEQ ID NO: 209) |
| AA | GDYMH (SEQ ID NO: 143) | WINPNSGGTNHARKFQG (SEQ ID NO: 171) | DRGTSGWPLFDY (SEQ ID NO: 210) |

FIGURE 2A

| Ab | CDR 1 | CDR 2 | CDR 3 |
|---|---|---|---|
| A5 NA | ACCTATGGCATGCAC (SEQ ID NO: 144) | GTTATATATGGTATGATGATGAAGTAA TAAACACTATGCAGACTCCGTGA AGGGC (SEQ ID NO: 172) | GCCCCTCAGTGGGAGCTAGTTCATGAAGCTTTGATATC (SEQ ID NO: 211) |
| AA | TYGMH (SEQ ID NO: 145) | VIWYDGSNKHYADSVKG (SEQ ID NO: 173) | APQWELVHEAFDI (SEQ ID NO: 212) |
| A6 NA | AGCTATGGCATTCAC (SEQ ID NO: 146) | GTTATATCATATGATGGAAGTTA TAAATACTATGCAGACTCCGTGA AGGGC (SEQ ID NO: 174) | GGGGACTCCTGGAACGACAGATTAAACTACTACTTCTACG ATATGGACGTC (SEQ ID NO: 213) |
| AA | SYGIH (SEQ ID NO: 147) | VISYDGSYKYYADSVKG (SEQ ID NO: 175) | GDSWNDRLNYYFYDMDV (SEQ ID NO: 214) |
| A7 NA | AGTGGTGGTTACTACTG GAGC (SEQ ID NO: 148) | TTCATCCATTACAGTGGGACCAC CTACTACAACCCGTCCCTCAAGA GT (SEQ ID NO: 176) | GAAGTTGGCAGCTCGTCGGGTAACTGGTTCGACCCC (SEQ ID NO: 215) |
| AA | SGGYYWS (SEQ ID NO: 149) | FIHYSGTTYYNPSLKS (SEQ ID NO: 177) | EVGSSSGNWFDP (SEQ ID NO: 216) |
| A8 NA | AGCTATGGCATTCAC (SEQ ID NO: 146) | GTTATATCATATGATGGAAGTAA TAAATACTATGCAGACTCCGTGA AGGGC (SEQ ID NO: 178) | GGGGACTCCTGGAACGACAGATTAAACTACTACTTCTACG ATATGGACGTC (SEQ ID NO: 213) |
| AA | SYGIH (SEQ ID NO: 147) | VISYDGSNKYYADSVKG (SEQ ID NO: 179) | GDSWNDRLNYYFYDMDV (SEQ ID NO: 214) |
| A9 NA | AGCTATGGCATGCAC (SEQ ID NO: 150) | GTTATATATGGTATGATGGAAGTAA TACATACTATGCAGACTCCGTGA AGGGC (SEQ ID NO: 180) | GAGGTCCGGGCGTATAGCAGTGGCTGTAGCGCCGCCTTTG ACTAC (SEQ ID NO: 217) |
| AA | SYGMH (SEQ ID NO: 151) | VIWYDGSNTYYADSVKG (SEQ ID NO: 181) | EVRAYSSGWYAAFDY (SEQ ID NO: 218) |

FIGURE 2B

| Ab | CDR 1 | CDR 2 | CDR 3 |
|---|---|---|---|
| A10 NA | AGTTATGGCATGCAC (SEQ ID NO: 152) | GTTATATGGTATGATGGAAGTAG TAAATACTATGCAGACTCCGTGA AGGGC (SEQ ID NO: 182) | GTAAGAAGTGGGAGCTACTACGAACAGTATTACTACGGTA TGGACGTC (SEQ ID NO: 219) |
| AA | SYGMH (SEQ ID NO: 151) | VIWYDGSSKYYADSVKG (SEQ ID NO: 183) | VRSGSYYEQYYYGMDV (SEQ ID NO: 220) |
| A11 NA | AGTTATAGCATGAAC (SEQ ID NO: 153) | TACATTAGTGGTCGTACTAGTAG CGTATACTACGCAGACTCTGTGA AGGGC (SEQ ID NO: 184) | AGTGGGATCTACTACGACTACTACGGTATGGACGTC (SEQ ID NO: 221) |
| AA | SYSMN (SEQ ID NO: 154) | YISGRTSSVYYADSVKG (SEQ ID NO: 185) | SGIYYDYYGMDV (SEQ ID NO: 222) |
| A12 NA | AGCTATGGCATGCAC (SEQ ID NO: 150) | GTTATATGGTATGATGGAAGTAA TAAATACTATGCAGACTCCGTGA AGGGC (SEQ ID NO: 164) | GGGGCAGCCACTGCTATAGATTACTACTACTCCTACGGTA TGGACGTC (SEQ ID NO: 223) |
| AA | SYGMH (SEQ ID NO: 151) | VIWYDGSNKYYADSVKG (SEQ ID NO: 165) | GAATAIDYYYSYGMDV (SEQ ID NO: 224) |
| A13 NA | AGCTATGGCATGCAC (SEQ ID NO: 150) | GTTATATGGTATGATGGAAGTAA TAAATACTATGCAGACTCCGTGA AGGGC (SEQ ID NO: 164) | GGGGGGGGTATACCAGTAGCTGACTACTACTACGGTA TGGACGTC (SEQ ID NO: 225) |
| AA | SYGMH (SEQ ID NO: 151) | VIWYDGSNKYYADSVKG (SEQ ID NO: 165) | GGGIPVADYYYGMDV (SEQ ID NO: 226) |
| A14 NA | AGCTATGGCATGCAC (SEQ ID NO: 150) | GTTATATGGTATGATGGAAGTAA TAAATACTATGCAGACTCCGTGA AGGGC (SEQ ID NO: 164) | GGGGGGGGTATACCAGTAGCTGACTACTACTACGGTA TGGACGTC (SEQ ID NO: 225) |
| AA | SYGMH (SEQ ID NO: 151) | VIWYDGSNKYYADSVKG (SEQ ID NO: 165) | GGGIPVADYYYGMDV (SEQ ID NO: 226) |

FIGURE 2C

| Ab | CDR 1 | CDR 2 | CDR 3 |
|---|---|---|---|
| A15 NA | AACTATGGCATGCAC (SEQ ID NO: 136) | GTTATATGGTTTGATGGAAGTAATAAATACTATGCGGACTCCGTGAAGGGC (SEQ ID NO: 186) | GGGGGGGGTATAGCAGTGGCTGACTACTACTTCTACGGTATGGACGTC (SEQ ID NO: 227) |
| AA | NYGMH (SEQ ID NO: 137) | VIWFDGSNKYYADSVKG (SEQ ID NO: 187) | GGGIAVADYYFYGMDV (SEQ ID NO: 228) |
| A16 NA | AACTATGGCATGCAC (SEQ ID NO: 136) | GTTATATGGTATGATGGAAGTAATAAATACTATGCAGAGACTCCGTGAAGGGC (SEQ ID NO: 164) | GGGGGGGGGTATAGCAGTGGCTGACTACTACTACTACGGTATGGACGTC (SEQ ID NO: 229) |
| AA | NYGMH (SEQ ID NO: 137) | VIWYDGSNKYYADSVKG (SEQ ID NO: 165) | GGGIAVADYYYYGMDV (SEQ ID NO: 230) |
| A17 NA | AGTTATATGGCATGCTC (SEQ ID NO: 155) | GTTTTATGGTTTGATGGAAGTTATAAAAACTATGCAGAGACTCCGTGAAGGGC (SEQ ID NO: 188) | GATAGTACAACTATGGCCCACTTTGACTAC (SEQ ID NO: 231) |
| AA | SYGML (SEQ ID NO: 156) | VLWFDGSYKNYADSVKG (SEQ ID NO: 189) | DSTTMAHFDY (SEQ ID NO: 232) |
| A18 NA | AACTATGGCATGCAC (SEQ ID NO: 136) | GTTATATGGTATGATGGAAGTAATAAATACTATGCAGAGACTCCGTGAAGGGC (SEQ ID NO: 164) | GGGGGGGGGTATAGCAGTGGCTGACTACTACTACTACGGTATGGACGTC (SEQ ID NO: 229) |
| AA | NYGMH (SEQ ID NO: 137) | VIWYDGSNKYYADSVKG (SEQ ID NO: 165) | GGGIAVADYYYYGMDV (SEQ ID NO: 230) |
| A19 NA | AGTTATGGCATGCAC (SEQ ID NO: 150) | GTTATATGGTATGATGGAAGTAATAAATACTATGCAGAGACTCCGTGAAGGGC (SEQ ID NO: 164) | GGGGGGGGGGTATACCAGTAGCTGACTACTACTACTACGGTATGGACGTC (SEQ ID NO: 225) |
| AA | SYGMH (SEQ ID NO: 151) | VIWYDGSNKYYADSVKG (SEQ ID NO: 165) | GGGIPVADYYYYGMDV (SEQ ID NO: 226) |

FIGURE 2D

| Ab | CDR 1 | CDR 2 | CDR 3 |
|---|---|---|---|
| A20 NA | AGCTATGGCATGCAC (SEQ ID NO: 150) | GTTATATGGTATGATGAAGTAATAAATACTATGCAGACTCCGTGAAGGGC (SEQ ID NO: 164) | GGGGGGGGTATACCAGTAGCTGACTACTACTACGGTATGGACGTC (SEQ ID NO: 225) |
| AA | SYGMH (SEQ ID NO: 151) | VIWYDGSNKYYADSVKG (SEQ ID NO: 165) | GGGIPVADYYYYGMDV (SEQ ID NO: 226) |
| A21 NA | AGCTATGCCATGAGC (SEQ ID NO: 157) | GCAATTAGTGGTAGTGGTGTGGAAGTACACACTACGCAGACTCCGTGAAGGGC (SEQ ID NO: 190) | GATCTCAACTGGGGAGCTTTTGATATC (SEQ ID NO: 233) |
| AA | SYAMS (SEQ ID NO: 158) | AISGSGGSTHYADSVKG (SEQ ID NO: 191) | DLNWGAFDI (SEQ ID NO: 234) |
| A22 NA | GGCTATGTCATGACT (SEQ ID NO: 159) | GGAATTAGTGGTAGTGGTGTGGTAGCACATACTACGCAGACTCCGTGAAGGGC (SEQ ID NO: 192) | GGAGACAGCTCGAACTACTACTCCGGTATGGACGTC (SEQ ID NO: 235) |
| AA | GYVMT (SEQ ID NO: 160) | GISGSGGSTYYADSVKG (SEQ ID NO: 193) | GDSSNYYSGMDV (SEQ ID NO: 236) |
| A23 NA | GGCTACTATATGCAC (SEQ ID NO: 161) | TGGATCAACCCTAACAATGGTGGCACAAACTATGGACAGAAGTTTC AGGGC (SEQ ID NO: 194) | GGGAACTGGAACGACGATGCTTTTGATATC (SEQ ID NO: 237) |
| AA | GYYMH (SEQ ID NO: 162) | WINPNNGGTNYGQKFQG (SEQ ID NO: 195) | GNWNDDAFDI (SEQ ID NO: 238) |
| A24 NA | AGCTATGGCATGCAC (SEQ ID NO: 150) | GTTATATGGTATGATGAAGTAATAAATACTATGTAGACTCCGTGAAGGGC (SEQ ID NO: 196) | ATGGGGTTTACTATGGTTCGGGGAGCCCTCTACTACGGTATGGACGTC (SEQ ID NO: 239) |
| AA | SYGMH (SEQ ID NO: 151) | VIWYDGSNKYYVDSVKG (SEQ ID NO: 197) | MGFTMVRGALYYGMDV (SEQ ID NO: 240) |

FIGURE 2E

| Ab | CDR 1 | CDR 2 | CDR 3 |
|---|---|---|---|
| A25 NA | AGCTATGCCATGAGC (SEQ ID NO: 157) | GCTATTAGTCGTAGTGGTAGTAC CACATACTACGCAGACTCCGTGA AGGGC (SEQ ID NO: 198) | CCGAGATATTTTGACTGGTTATTAGGCGAC (SEQ ID NO: 241) |
| AA | SYAMS (SEQ ID NO: 158) | AISRSGSTYYADSVKG (SEQ ID NO: 199) | RPYFDWLLGD (SEQ ID NO: 242) |
| A26 NA | AGCTATGGCATGCAC (SEQ ID NO: 150) | GTTAAATGGTATGAAGGAAGTA ATAAATACTATGGAGACTCCGTG AAGGGC (SEQ ID NO: 200) | GGCGCCCACGACTACGGTGACTTCTACTACGGTATGGACG TC (SEQ ID NO: 243) |
| AA | DFTMH (SEQ ID NO: 163) | LISWDGGSTYYADSVKG (SEQ ID NO: 167) | PYYYFYGMDV (SEQ ID NO: 206) |
| A27 NA | AGCTATGCCATGAGC (SEQ ID NO: 157) | GCTATTAGTTATAGTGGCGGTAG CACATACTACGCAGGCTCCGTGA AGGGC (SEQ ID NO: 201) | GATCGGGAGGGAGGCGACTTGGTACTACGGTATGGACGTC (SEQ ID NO: 244) |
| AA | SYAMS (SEQ ID NO: 158) | AISYSGGSTYYAGSVKG (SEQ ID NO: 202) | DREGATWYYGMDV (SEQ ID NO: 245) |

FIGURE 2F

METHODS OF TREATING TSLP-RELATED INFLAMMATORY DISORDERS

CROSS REFERENCE TO RELATED APPLICATIONS

This application is a divisional of U.S. patent application Ser. No. 12/231,944, filed Sep. 8, 2008, now U.S. Pat. No. 7,982,016, which is hereby incorporated by reference, which claims the benefit under 35 U.S.C. §119 of U.S. Provisional Application Ser. No. 61/091,676, filed Aug. 25, 2008 and U.S. Provisional Application Ser. No. 60/971,178 filed Sep. 10, 2007.

REFERENCE TO THE SEQUENCE LISTING

The present application is being filed along with a Sequence Listing in electronic format. The Sequence Listing is provided as a file entitled A-1276-US-DIV_Seq_List_ST25.txt, created Jul. 15, 2011, which is 155 KB in size. The information in the electronic format of the Sequence Listing is incorporated herein by reference in its entirety.

FIELD OF THE INVENTION

The field of this invention relates to compositions of antigen binding proteins including antibodies capable of binding human thymic stromal lymphopoietin, as well as related methods.

BACKGROUND OF THE INVENTION

The prevalence of allergic diseases such as asthma, allergic rhinitis, atopic dermatitis, and food allergies appears to be increasing in recent years, particularly in developed countries, affecting an increasing percentage of the population (Kay, N Engl. J. Med. 344:30-37 (2001)). Thymic stromal lymphopoietin (TSLP) is an epithelial cell derived cytokine produced in response to pro-inflammatory stimuli. TSLP has been discovered to promote allergic inflammatory responses primarily through its activity on dendritic and mast cells (Soumelis et al., Nat Immun 3(7): 673-680 (2002), Allakhverdi et al., J. Exp. Med. 204(2):253-258 (2007)). Human TSLP expression has been reported to be increased in asthmatic airways correlating to disease severity (Ying et al., J. Immunol. 174: 8183-8190 (2005)). In addition, TSLP protein levels are detectable in the concentrated bronchoalveoloar lavage (BAL) fluid of asthma patients, and other patients suffering from allergic disorders. Also, increased levels of TSLP protein and mRNA are found in the lesional skin of atopic dermatitis (AD) patients. Therefore, TSLP antagonists would be useful in treating inflammatory disorders.

In addition, TSLP has also been found to promote fibrosis, as reported in U.S. application Ser. No. 11/344,379. Fibrotic disease results during the tissue repair process if the fibrosis phase continues unchecked, leading to extensive tissue remodeling and the formation of permanent scar tissue (Wynn, Nature Rev. Immunol. 4, 583 (2004)). It has been estimated that up to 45% of deaths in the United States can be attributed to fibroproliferative diseases, which can affect many tissues and organ systems (Wynn, supra, at 595 (2004)).

Currently, anti-inflammatory treatments are used to treat fibrotic disorders, since fibrosis is common to many persistent inflammatory diseases such as idopathic pulmonary fibrosis, progressive kidney disease, and liver cirrhosis. However, the mechanisms involved in regulation of fibrosis appear to be distinctive from those of inflammation, and anti-inflammatory therapies are not always effective in reducing or preventing fibrosis (Wynn, supra). Therefore, a need remains for developing treatments to reduce and prevent fibrosis.

Therefore, antagonists to TSLP would be expected to be useful for treating these inflammatory and fibrotic disorders. The present disclosure provides such treatments and methods of treating.

SUMMARY OF THE INVENTION

In one aspect, the present disclosure provides an isolated antigen binding protein comprising a. a light chain CDR3 sequence selected from i. a light chain CDR3 sequence that differs by no more than a total of two amino acid additions, substitutions, and/or deletions from a CDR3 sequence selected from the group consisting of the light chain CDR3 sequences of A1 to A27; ii. QQAX$_8$SFPLT (SEQ ID NO: 251); and b. a heavy chain CDR3 sequence selected from i. a heavy chain CDR3 sequence that differs by no more than a total of three amino acid additions, substitutions, and/or deletions from a CDR3 sequence selected from the group consisting of the heavy chain CDR3 sequences of A1 to A27; ii. GGGIX$_{12}$VADYYX$_{13}$YGMDV (SEQ ID NO: 255); iii. DX$_{21}$GX$_{22}$SGWPLFX$_{23}$Y (SEQ ID NO: 259); wherein X$_8$ is an N residue or a D residue; X$_{12}$ is a P residue or an A residue; X$_{13}$ is a Y residue or an F residue; X$_{21}$ is a G residue or an R residue; X$_{22}$ is an S residue or a T residue; X$_{23}$ is an A residue or a D residue, and wherein said antigen binding protein specifically binds to TSLP.

In another aspect, the isolated antigen binding protein of the present disclosure further comprises at least one of the following: a. a light chain CDR1 sequence selected from i. a light chain CDR1 sequence that differs by no more than three amino acids additions, substitutions, and/or deletions from a light chain CDR1 sequence of A1-A27; ii. RSSQSLX$_1$YSDGX$_2$TYLN (SEQ ID NO: 246);
iii. RASQX$_4$X$_5$SSWLA (SEQ ID NO: 249); b. a light chain CDR2 sequence selected from i. a light chain CDR2 sequence that differs by no more than two amino acid additions, substitutions, and/or deletions from a CDR2 sequence of A1-A27; ii. KVSX$_3$ (residues 1-4 of SEQ ID NO: 247); iii. X$_6$X$_7$SSLQS (SEQ ID NO: 250); or iv. QDX$_9$KRPS (SEQ ID NO: 252); and c. a heavy chain CDR1 sequence selected from i. a heavy chain CDR1 sequence that differs by no more than two amino acid additions, substitutions, and/or deletions from a CDR1 sequence of A1-A27; ii. X$_{10}$YGMH (SEQ ID NO: 253); and iii. X$_{15}$X$_{16}$YMX$_{17}$ (SEQ ID NO: 257); and d. a heavy chain CDR2 sequence selected from i. a heavy chain CDR2 sequence that differs by no more than three amino acid additions, substitutions, and/or deletions from a CDR2 sequence of A1-A27; ii. VIWX$_{11}$DGSNKYYADSVKG (SEQ ID NO: 254); iii. VISYDGSX$_{14}$KYYADSVKG (SEQ ID NO: 256); and iv. WINPNSGGTNX$_{18}$X$_{19}$X$_{20}$KFQG (SEQ ID NO: 258); wherein X$_1$ is a V residue or an I residue; X$_2$ is an N residue or a D residue; X$_3$ is a Y residue or an N residue; X$_4$ is a G residue or a S residue; X$_5$ is a L residue or an I residue; X$_6$ is an N residue or a T residue; X$_7$ is a T residue or an A residue; X$_9$ is a K residue or an N residue; X$_{10}$ is an S residue or an N residue; X$_{11}$ is a Y residue or an F residue; X$_{14}$ is a Y residue or a N residue; X$_{15}$ is a D residue or G residue; X$_{16}$ is a Y residue or a D residue; X$_{17}$ is a Y residue or an H residue; X$_{18}$ is a Y residue or an H residue; X$_{19}$ is a V residue or an A residue; X$_{20}$ is a Q residue or an R residue, and wherein said antigen binding protein specifically binds to TSLP.

In another aspect of the present disclosure, the isolated antigen binding protein of claim 1 comprises either: a. a light chain variable domain comprising: i. a light chain CDR1 sequence selected from A1-A27; ii a light chain CDR2 sequence selected from A1-A27; iii. a light chain CDR3 sequence selected from A1-A27; or b. a heavy chain variable domain comprising i. a heavy chain CDR1 sequence selected from A1-A27; ii. a heavy chain CDR2 sequence selected from A1-A27, and iii. a heavy chain CDR3 sequence selected from A1-A27; or c. the light chain variable domain of (a) and the heavy chain variable domain of (b).

In a further aspect, the isolated antigen binding protein comprises either a. a light chain variable domain sequence selected from i amino acids having a sequence at least 80% identical to a light chain variable domain sequence selected from L1-L27; ii. a sequence of amino acids encoded by a polynucleotide sequence that is at least 80% identical to a polynucleotide sequence encoding the light chain variable domain sequence of L1-L27; iii. a sequence of amino acids encoded by a polynucleotide sequence that hybridizes under moderately stringent conditions to the complement of a polynucleotide consisting of a light chain variable domain sequence of L1-L27; b. a heavy chain variable domain sequence selected from i. a sequence of amino acids that is at least 80% identical to a heavy chain variable domain sequence of H1-H27; ii. a sequence of amino acids encoded by a polynucleotide sequence that is at least 80% identical to a polynucleotide sequence encoding the heavy chain variable domain sequence of H1-H27; iii. a sequence of amino acids encoded by a polynucleotide sequence that hybridizes under moderately stringent conditions to the complement of a polynucleotide consisting of a heavy chain variable domain sequence of H1-H27; or c. the light chain variable domain of (a) and the heavy chain variable domain of (b), wherein said antigen binding protein specifically binds to TSLP.

In a further aspect, an isolated antigen binding protein of the present disclosure comprises either: a. a light chain variable domain sequence selected from: L1-L27; b. a heavy chain variable domain sequence selected from H1-H27; or, c. the light chain variable domain of (a) and the heavy chain variable domain of (b), wherein the antigen binding protein specifically binds to TSLP.

In a further aspect, the isolated binding protein comprises a light chain variable domain sequence and a heavy chain variable domain sequence selected from L1H1, L2H2, L3H3, L4H4, L5H5, L6H6, L7H7, L8H8, L9H9, L10H10, L11H11, L12H12, L13.1H13, L13.2H13, L14.1H14, L14.2H14, L15.1H15, L15.2H15, L16.1H16, L16.2H16, L17H17, L18.1H18, L18.2H18, L19.1H19, L19.2H19, L20.1H20, L20.2H20, L21H21, L22H22, L23H23, L24H24, L25H25, L26H26, and L27H27.

In a further aspect, the isolated antigen binding protein comprises a binding protein that binds to TSLP with substantially the same Kd as a reference antibody selected from A2, A3, A4, and A5. In another aspect, the isolated antigen binding protein comprises a binding protein that inhibits TSLP activity according to the primary cell OPG assay with the same IC50 as a reference antibody selected from A2, A3, A4 or A5.

In a still further aspect, the isolated antigen binding protein cross-competes for binding of TSLP with a reference antibody. In another aspect, the isolated antigen binding protein binds the same epitope as a reference antibody, e.g., A2, A4, A5, A6, A7, A10, A21, A23, or A26.

In one aspect, the isolated antigen binding protein is selected from a human antibody, a humanized antibody, chimeric antibody, a monoclonal antibody, a polyclonal antibody, a recombinant antibody, an antigen-binding antibody fragment, a single chain antibody, a diabody, a triabody, a tetrabody, a Fab fragment, an F(fa')x fragment, a domain antibody, an IgD antibody, an IgE antibody, and IgM antibody, and IgG1 antibody, and IgG2 antibody, and IgG3 antibody, and IgG4 antibody, and IgG4 antibody having at least one mutation in the hinge region that alleviates a tendency to for intra H-chain disulfide bonds. In one aspect, the isolated antigen binding protein is a human antibody.

Also provided is an isolated nucleic acid molecule comprising a polynucleotide sequence encoding the light chain variable domain, the heavy chain variable domain, or both, of the antigen binding agent of the present disclosure. In one embodiment, the polynucleotide comprises a light chain variable sequence L1-L27, and/or a heavy chain variable sequence H1-H27, or both.

Also provided are vectors comprising the polynucleotides of the present disclosure. In one embodiment the vector is an expression vector. Also provided is a host cell comprising the vector. Also provided is a hybridoma capable of producing the antigen binding protein of the present invention. Also provided is a method of making the antigen binding protein comprising culturing the host cell under conditions that allow it to express the antigen binding protein.

Also provided is a pharmaceutical composition comprising the antigen binding proteins of the present invention. In one embodiment the pharmaceutical composition comprises a human antibody. Also provided is a method of treating a TSLP-related inflammatory condition in a subject in need of such treatment comprising administering a therapeutically effective amount of the composition to the subject. In one embodiment, the inflammatory condition is allergic asthma, allergic rhinosinusitis, allergic conjunctivitis, or atopic dermatitis. Also provided is a method of treating a TSLP-related fibrotic disorder in a subject in need of such treatment comprising administering a therapeutically effective amount of the composition to the subject. In one embodiment, the fibrotic disorder is scleroderma, interstitial lung disease, idiopathic pulmonary fibrosis, fibrosis arising from chronic hepatitis B or C, radiation-induced fibrosis, and fibrosis arising from wound healing.

BRIEF DESCRIPTION OF THE DRAWINGS

FIG. 1A-FIG. 1F. The figure provides the amino acid sequence of the light chain CDR1, CDR2, and CDR3 regions of A1-A27. Further provided is an exemplary nucleotide sequence encoding each CDR.

FIG. 2A-FIG. 2F. The figure provides the amino acid sequence of the heavy chain CDR1, CDR2, and CDR3 regions of A1-A27. Further provided is an exemplary nucleotide sequence encoding each CDR.

DETAILED DESCRIPTION OF THE INVENTION

The present invention relates to antigen binding agents, including antigen binding proteins, that specifically bind to the cytokine human thymic stromal lymphopoietin (TSLP), including antigen binding proteins that inhibit TSLP binding and signaling such as antagonistic TSLP antibodies, antibody fragments, and antibody derivatives. The antigen binding agents are useful for inhibiting or blocking binding of TSLP to its receptor, and for treating inflammatory diseases, fibrotic diseases, and other related conditions.

The present invention further provides compositions, kits, and methods relating to antigen binding proteins that bind to TSLP. Also provided are nucleic acid molecules, and derivatives and fragments thereof, comprising a sequence of polynucleotides that encode all or a portion of a polypeptide that binds to TSLP, such as a nucleic acid encoding all or part of an anti-TSLP antibody, antibody fragment, or antibody derivative. The present invention further provides vectors and plasmids comprising such nucleic acids, and cells or cell lines comprising such nucleic acids and/or vectors and plasmids. The provided methods include, for example, methods of making, identifying, or isolating antigen binding proteins that bind to human TSLP such as anti-TSLP antibodies, methods of determining whether an antigen binding protein binds to TSLP, methods of making compositions, such as pharmaceutical compositions, comprising an antigen binding protein that binds to TSLP, and methods for administering an antigen binding protein that binds to TSLP in a subject, for example, methods for treating a condition mediated by TSLP, and for modulating a biological activity associated with TSLP signalling in vivo or in vitro.

TSLP

Thymic stromal lymphopoietin (TSLP) refers to a four α-helical bundle type I cytokine which is a member of the IL-2 family but most closely related to IL-7. Cytokines are low molecular weight regulatory proteins secreted in response to certain stimuli, which act on receptors on the membrane of target cells. Cytokines regulate a variety of cellular responses. Cytokines are generally described in references such as *Cytokines*, A. Mire-Sluis and R. Thorne, ed., Academic Press, New York, (1998).

TSLP was originally cloned from a murine thymic stromal cell line (Sims et al J. Exp. Med. 192 (5), 671-680 (2000)), and found to support early B and T cell development. Human TSLP was later cloned and found to have a 43 percent identity in amino acid sequence to the murine homolog (Quentmeier et al. Leukemia 15, 1286-1292 (2001), and U.S. Pat. No. 6,555,520, which is herein incorporated by reference). The polynucleotide and amino acid sequence of human TSLP are presented in SEQ ID NO: 1 and 2 respectively. TSLP was found to bind with low affinity to a receptor chain from the hematopoietin receptor family called TSLP receptor (TSLPR), which is described in U.S. patent application Ser. No. 09/895,945 (publication No: 2002/0068323) (SEQ ID NO: 3 and 4). The polynucleotide sequence encoding human TSLPR is presented as SEQ ID NO: 3 of the present application, and the amino acid sequence is presented as SEQ ID NO: 4 of the present application respectively. The soluble domain of the TSLPR is approximately amino acids 25 through 231 of SEQ ID NO: 4. TSLP binds with high affinity to a heterodimeric complex of TSLPR and the interleukin 7 receptor alpha IL-7Rα (Park et al., J. Exp. Med. 192:5 (2000), U.S. patent application Ser. No. 09/895,945, publication number U.S. 2002/0068323). The sequence of IL-7 receptor α is shown in FIG. 2 of U.S. Pat. No. 5,264,416, which is herein incorporated by reference. The sequence of the soluble domain of the IL-7 receptor α is amino acid 1 to 219 of FIG. 2 in U.S. Pat. No. 5,264,416.

As used herein the term "TSLP polypeptides" refers to various forms of TSLP useful as immunogens. These include TSLP expressed in modified form, in which a furin cleavage site has been removed through modification of the amino acid sequence, as described in PCT patent application publication WO 03/032898. Modified TSLP retains activity but the full length sequence is more easily expressed in mammalian cells such as CHO cells. Examples of TSLP polypeptides include SEQ ID NO: 2, SEQ ID NO: 373, and SEQ ID NO: 375.

In addition, cynomolgus TSLP has been identified and is shown in Example 1 below and is set forth in SEQ ID NO: 380, for example.

TSLP is produced in human epithelial cells including skin, bronchial, tracheal, and airway epithelial cells, keratinocytes, stromal and mast cells, smooth muscle cells, and lung and dermal fibroblasts, as determined by quantitative mRNA analysis (Soumelis et al, Nature Immunol. 3 (7) 673-680 (2002)). Both murine and human TSLP are involved in promoting allergic inflammation.

TABLE 1

| Protein Name | Species | Synonyms | Database(s) (or Patent Application) | Accession No. |
|---|---|---|---|---|
| TSLP | Homo sapiens | Thymic stromal lymphopoietin protein | GenBank/ SEQ ID NO: 2 of U.S. Pat. No. 6,555,520 | AAK67490 |
| Modified TSLP | Homo sapiens | Thymic stromal lymphopoietin | SEQ ID NOS: 10, 12, 14, 16, 17, 18 of WO 03/032898 | |
| TSLP | Mus musculus | Thymic stroma derived lymphopoietin; Thymic stromal derived lymphopoietin | GenBank | AAF81677 |
| TSLPR | Homo sapiens | Cytokine receptor-like 2 (CRL2); IL-XR; Thymic stromal lymphopoietin protein receptor | SEQ ID NO: 5 of US 2002/0068323 | |
| TSLPR | Mus | Cytokine receptor-like factor 2; Type I cytokine receptor delta 1; Cytokine receptor-like molecule 2 (CRLM-2); Thymic stromal lymphopoietin protein receptor | GenBank, SWISSPROT | Q8CII9 |
| IL-7R | Homo sapiens | Interleukin-7 receptor | GenBank/ U.S. Pat. No. 5,264,416 | NM_002185 |

TSLP Activity

TSLP activities include the proliferation of BAF cells expressing human TSLPR (BAF/HTR), as described in PCT patent application publication WO 03/032898. The BAF/HTR bioassay utilizes a murine pro B lymphocyte cell line, which has been transfected with the human TSLP receptor. The BAF/HTR cells are dependent upon huTSLP for growth, and proliferate in response to active huTSLP added in test samples. Following an incubation period, cell proliferation is measured by the addition of Alamar Blue dye I or tritiated thymidine. Proliferation may also be measured using a commercially available kit such as the CYQUANT cell proliferation assay kit (Invitrogen).

Additional assays for huTSLP activity include, for example, an assay measuring induction of T cell growth from human bone marrow by TSLP as described in U.S. Pat. No. 6,555,520. Another TSLP activity is the ability to activate STATS as described in the reference to Levin et al., J. Immunol. 162:677-683 (1999) and PCT patent application WO 03/032898.

Additional assays include TSLP induced CCL17/TARC production from primary human monocytes and dendritic cells as described in U.S. application publication no. 2006/0039910 (Ser. No. 11/205,909).

Cell based assays useful for measuring TSLP activity are described in the examples below. These include the BAF cell proliferation assay described above, as well as the primary cell assay described below measuring TSLP induced osteoprotegerin (OPG) production from primary human dendritic cells, as well cynomolgus peripheral blood mononuclear cell assay, also described below.

TSLP activities further include in vivo activities. These can be measured in mouse models, for example, such as those described in Zhou et al., Nat Immunol 6(10), 1047-1053 (2005), and Yoo et al., J Exp Med. 202 (4), 541-549 (2005). For example, an anti-murine TSLP antibody was shown to decrease BALF cellularity and BALF levels of IL-5 and Il-13 in an Ova-asthma model (Zhou et al).

DEFINITIONS

Polynucleotide and polypeptide sequences are indicated using standard one- or three-letter abbreviations. Unless otherwise indicated, polypeptide sequences have their amino termini at the left and their carboxy termini at the right, and single-stranded nucleic acid sequences, and the top strand of double-stranded nucleic acid sequences, have their 5' termini at the left and their 3' termini at the right. A particular polypeptide or polynucleotide sequence also can be described by explaining how it differs from a reference sequence.

Polynucleotide and polypeptide sequences of particular light and heavy chain variable domains, L1 ("light chain variable domain 1"), H1 ("heavy chain variable domain 1"), etc. Antibodies comprising a light chain and heavy chain are indicated by combining the name of the light chain and the name of the heavy chain variable domains. For example, "L4H7," indicates an antibody comprising the light chain variable domain of L4 and the heavy chain variable domain of H7.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The following terms, unless otherwise indicated, shall be understood to have the following meanings: The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The terms "TSLP inhibitor" and "TSLP antagonist" are used interchangeably. Each is a molecule that detectably inhibits TSLP signalling. The inhibition caused by a TSLP inhibitor need not be complete so long as it is detectable using an assay. For example, the cell-based assay described in Example 4 below, demonstrates an assay useful for determining TSLP signaling inhibition.

The terms "peptide" "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or noncovalently, modified proteins. A peptide, polypeptide, or protein may be monomeric or polymeric.

The term "polypeptide fragment" as used herein refers to a polypeptide that has an amino-terminal and/or carboxy-terminal deletion as compared to a corresponding full-length protein. Fragments can be, for example, at least 5, 6, 7, 8, 9, 10, 11, 12, 13, 14, 15, 20, 50, 70, 80, 90, 100, 150 or 200 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

Polypeptides of the invention include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (4) confer or modify other physicochemical or functional properties. Analogs include muteins of a polypeptide. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

A "variant" of a polypeptide comprises an amino acid sequence wherein one or more amino acid residues are inserted into, deleted from and/or substituted into the amino acid sequence relative to another polypeptide sequence. Variants of the invention include fusion proteins. Variants of antibodies described herein also include those that result from processing. Such variants include those having one, two, three, four, five, six, seven, eight, nine ten or more additional amino acids at the N-terminus of a light or heavy chain, e.g., as a result of inefficient signal sequence cleavage. Such variants also include those missing one or more amino acids from the N- or C-termini of a light or heavy chain.

A "derivative" of a polypeptide is a polypeptide (e.g., an antibody) that has been chemically modified, e.g., via conjugation to another chemical moiety such as, for example, polyethylene glycol, albumin (e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" according to the present disclosure is a protein capable of binding to an antigen and, optionally, a scaffold or framework portion that allows the antigen binding portion to adopt a conformation that promotes binding of the antigen binding protein to the antigen. In one embodiment an antigen binding protein of the present invention comprises at least one CDR. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129; Roque et al., 2004, Biotechnol. Prog. 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., $2^{nd}$ ed. Raven Press, N.Y. (1989)) (incorporated by reference in its entirety for all purposes). The variable regions of each light/heavy chain pair form the antibody binding site such that an intact immunoglobulin has two binding sites.

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, $5^{th}$ Ed., US Dept. of Health and Human Services, PHS, NIH, NIH Publication no. 91-3242, 1991. Intact antibodies include polyclonal, monoclonal, chimeric, humanized or fully human having full length heavy and light chains.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include Fab, Fab', F(ab')$_2$, Fd, Fv, and domain antibodies (dAbs), and complementarity determining region (CDR) fragments, single-chain antibodies (scFv), diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_H1$ domains; a F(ab')$_2$ fragment is a bivalent fragment having two Fab fragments linked by a disulfide bridge at the hinge region; a Fd fragment has the $V_H$ and $C_H1$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634, 6,696,245, U.S. App.

Pub. No. 05/0202512, 04/0202995, 04/0038291, 04/0009507, 03/0039958, Ward et al., Nature 341:544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, Science 242:423-26 and Huston et al., 1988, Proc. Natl. Acad. Sci. USA 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. in Sequences of Proteins of Immunological Interest, 5$^{th}$ Ed., US Dept. of Health and Human Services, PHS, NIH, NIH Publication no. 91-3242, 1991. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886, 152 and 5,877,293.

The term "chimeric antibody" refers to an antibody that contains one or more regions from one antibody and one or more regions from one or more other antibodies. In one embodiment, one or more of the CDRs are derived from a human anti-TSLP antibody. In another embodiment, all of the CDRs are derived from a human anti-TSLP antibody. In another embodiment, the CDRs from more than one human anti-TSLP antibodies are mixed and matched in a chimeric antibody. For instance, a chimeric antibody may comprise a CDR1 from the light chain of a first human anti-TSLP antibody, a CDR2 and a CDR3 from the light chain of a second human anti-TSLP antibody, and the CDRs from the heavy chain from a third anti-TSLP antibody. Further, the framework regions may be derived from one of the same anti-TSLP antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody(-ies) from another species or belonging to another antibody class or subclass. Also included are fragments of such antibodies that exhibit the desired biological activity (i.e., the ability to specifically bind the human TSLP receptor).

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al., 1991, Science 253:164.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein including an antibody "specifically binds" to an antigen, such as TSLP if it binds to the antigen with a high binding affinity as determined by a Kd (or corresponding Kb, as defined below) value of $10^{-7}$ M or less.

An "antigen binding domain," "antigen binding region," or "antigen binding site" is a portion of an antigen binding protein that contains amino acid residues (or other moieties)

that interact with an antigen and contribute to the antigen binding protein's specificity and affinity for the antigen. For an antibody that specifically binds to its antigen, this will include at least part of at least one of its CDR domains.

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06.

A "host cell" is a cell that can be used to express a nucleic acid, e.g., a nucleic acid of the invention. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Exemplary host cells include Chinese hamster ovary (CHO) cell lines or their derivatives including CHO strain DXB-11, which is deficient in DHFR (see Urlaub et al., 1980, Proc. Natl. Acad. Sci. USA 77:4216-20), CHO cell lines which grow in serum-free media (see Rasmussen et al., 1998, Cytotechnology 28:31), CS-9 cells, a derivative of DXB-11 CHO cells, and AM-1/D cells (described in U.S. Pat. No. 6,210,924). Other CHO cells lines include CHO-K1 (ATCC# CCL-61), EM9 (ATCC# CRL-1861), and UV20 (ATCC# CRL-1862). Examples of other host cells include COS-7 line of monkey kidney cells (ATCC CRL 1651) (see Gluzman et al., 1981, Cell 23:175), L cells, C127 cells, 3T3 cells (ATCC CCL 163), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Antigen Binding Proteins

In one aspect, the present disclosure provides antigen binding proteins such as antibodies, antibody fragments, antibody derivatives, antibody muteins, and antibody variants that bind to human TSLP. Antigen binding proteins in accordance with the present disclosure includes antigen binding proteins that bind to human TSLP, and thereby reduce TSLP activity. For example, antigen binding proteins may interfere with the binding of TSLP to its receptor, and thus reduce TSLP activity.

In one embodiment, the present invention provides an antigen binding protein that comprises one or more CDR sequences that differ from a CDR sequence shown in FIG. 1A-1F or FIG. 2A-2F by no more than 5, 4, 3, 2, 1, or 0 amino acid residues.

In another embodiment, at least one of the antigen binding protein CDR3 sequence is a sequence from FIG. 1A-1F or FIG. 2A-2F. In another embodiment, the antigen binding protein's light chain CDR3 sequence is a light chain sequence from A1 through A27, and the antigen binding protein heavy chain CDR3 sequence is a heavy chain CDR3 sequence from A1 through A27.

In another embodiment, the antigen binding protein further comprises 1, 2, 3, 4, or 5 CDR sequences that each independently differs by 5, 4, 3, 2, 1, or 0 single amino acid additions, substitutions, and/or deletions from a CDR sequence of A1-A27. The light chain CDR's of exemplary antigen binding proteins A1-A27 and the heavy chain CDR's of exemplary binding proteins A1-A27 are shown in FIG. 1A-1F and FIG. 2A-2F, respectively. Also shown are polynucleotide sequences which encode the amino acid sequences of the CDRs. In addition, consensus sequences of the CDR sequences are provided below.

CDR CONSENSUS SEQUENCES

VARIABLE LIGHT CHAIN CDRs
Group 1a

LC CDR1 Consensus

```
              X1         X2
A16.1  R  S  SQ  S  L V Y  S D G  N  T  Y L N
A18.1                V              N
A13.1                V              D
A19.1                V              D
A20.1                V              D
A14.1                V              N
A15.1                I              N
```
(SEQ ID NO: 246)

$RSSQSLX_1YSDGX_2TYLN$
$X_1$ is a V (valine) residue or an
I (isoleucine) residue,
$X_2$ is a N (asparagine) residue
or a D (aspartic) acid residue;

LC CDR2 Consensus

```
              X3
A16.1  K  V  S Y  W D S
A18.1        Y
A13.1        N
A19.1        N
A20.1        N
A14.1        N
A15.1        N
```
(SEQ ID NO: 247)

$KVSX_3WDS$ $X_3$ is a Y (tyrosine) residue or
an N (asparagine) residue;

LC CDR3 consensus
```
A16.1  M  Q  G T  H  W P P  A
A18.1
A13.1
A19.1
A20.1
A14.1
A15.1
```
(SEQ ID NO: 248)

MQGTHQPPA

Group 1b

LC CDR1 consensus
```
              X4  X5
A13.2  R  A  SQ  G  L S S  W L A
A14.2             G  L
A19.2             G  L
A20.2             G  L
A16.2             S  L
A18.2             S  L
A15.2             G  I
```
(SEQ ID NO: 249)

$RASQX_4X_5SSWLA$
$X_4$ is a G (glycine) residue or
an S (serine) residue;
$X_5$ is a L (leucine) residue or
an I (isoleucine) residue;

LC CDR2 consensus
```
         X6  X7
A13.2    N   T    S S    L  Q S
A14.2    N   T
A19.2    N   T
A20.2    N   T
A16.2    N   A
A18.2    N   A
A15.2    T   T
```
(SEQ ID NO: 250)

$X_6X_7SSLQS$
$X_6$ is an N (asparagine) residue
or a T (threonine) residue;
$X_7$ ia a T (threonine) residue
or an A (alanine) residue;

LC CDR3 consensus
```
              X8
A13.2  Q  Q  A N  S  F P L  T
A14.2        N
A19.2        N
A20.2        N
A16.2        N
A18.2        N
A15.2        D
```
(SEQ ID NO: 251)

$QQAX_8SFPLT$
$X_8$ is a N (asparagine) residue
or a D (aspartic acid) residue;

Group 2

LC CDR1 consensus
```
A6    S  G  D K  L  G D K  Y A C
A8
```
(SEQ ID NO: 15)

SGDKLGDKYAC

LC CDR2 consensus
```
           X
A6    Q  D  K K  R  P S
A8           N
```
(SEQ ID NO: 252)

$QDX_9KRPS$
$X_9$ is a K (lysine) residue or
an N (asparagine) residue;

LC CDR3 consensus
```
A6    Q  A  W D  S  S T V  V
A8
```
(SEQ ID NO: 107)

QAWDSSTVV

Group 3

LC CDR1 consensus
```
A3    T  G  S S  S  N I G  A G F  D  V  H
A4
```
(SEQ ID NO: 10)

TGSSSNIGAGFDVH

LC CDR2 consensus
```
A3    D  N  N N  R  P S
A4
```

(SEQ ID NO: 57)

DNNNRPS

LC CDR3 consensus

```
A3    Q  S    YD    S  NLS  GSI  V  V
A4
```

(SEQ ID NO: 102)

QSYDSNLSGSIVV

VARIABLE HEAVY CHAIN CDRS

Group 1

HC CDR1 consensus

```
        X10
A13   S  Y   GM   H
A14   S
A19   S
A20   S
A16   N
A18   N
A15   N
```

(SEQ ID NO: 253)

$X_{10}$YGMH
$X_{10}$ is a S (serine) or an N (asparagine) residue;

HC CDR2 consensus

```
              X11
A13   V  I  WY   D  GSN  KYY  A  D  SVKG
A14            Y
A19            Y
A20            Y
A16            Y
A18            Y
A15            F
```

(SEQ ID NO: 254)

VIWX$_{11}$DGSNKYYADSVKG
$X_{11}$ is a Y (tyrosine) residue or a F (phenylalanine) residue.

HC CDR3 consensus

```
                 X12        X13
A13   G  G  GI   P  VAD  YYY  Y  G  MDV
A14              P          Y
A19              P          Y
A20              P          Y
A16              A          Y
A18              A          Y
A15              A          F
```

(SEQ ID NO: 255)

GGGIX$_{12}$VADYYX$_{13}$YGMDV
$X_{12}$ is a P (proline) residue or an A (alanine) residue.
$X_{13}$ is a Y (tyrosine) or a F (phenylalanine) residue.

Group 2

HC CDR1 consensus

```
A6   S  Y   GI   H
A8
```

(SEQ ID NO: 147)

SYGIH

HC CDR2 consensus

```
                         X14
A6   V  I  SY   D  GSY  KYY  A  D  SVKG
A8                        N
```

(SEQ ID NO: 256)

VISYDGSX$_{14}$KYYADSVKG
$X_{14}$ is a Y (tyrosine) or an N (asparagine) residue.

HC CDR3 consensus

```
A6   G  D   SW   N  DRL  NYY  F  Y  DMDV
A8
```

(SEQ ID NO: 214)

GDSWNDRLNYYFYDMDV

Group 3

HC CDR1 consensus

```
        X15 X16       X17
A3   D   Y   YM   Y
A4   G   D        H
```

(SEQ ID NO: 257)

$X_{15}X_{16}$YM$X_{17}$
$X_{15}$ is a D (aspartic acid) or G (glycine) residue;
$X_{16}$ is a Y (tyrosine) or D (aspartic acid) residue;
$X_{17}$ is a Y (tyrosine) or an H (histidine) residue.

HC CDR2 consensus

```
                              X18 X19 X20
A3   W  I   NP   N  SGG  TNY  V   Q   KFQG
A4                         H  A   R
```

(SEQ ID NO: 258)

WINPNSGGTNX$_{18}$X$_{19}$X$_{20}$KFQG $X_{18}$ is a Y (tyrosine) or H (histidine) residue;
$X_{19}$ ia a V (valine) or A (alanine) residue;
$X_{20}$ is a Q (glutamine) or R (arginine) residue.

HC CDR3 consensus

```
        X21    X22              X23
A3   D   G   GS    S  GWP  LFA   Y
A4       R   T                D
```

(SEQ ID NO: 259)

$X_{21}$ is a G (glycine) or R (arginine) residue;
$X_{22}$ is a S (serine) or T (threonine) residue;
$X_{23}$ is an A (alanine) or D (aspartic acid) residue.

Table 2 below provides nucleic acid (DNA) sequences encoding the variable heavy domains (H#) and variable light domains (L#), and the amino acid sequences of the variable heavy and variable light domains for exemplary TSLP antigen binding proteins A1-A27, respectively. CDRs 1, 2 & 3 for each variable domain are sequential from the beginning to the end of each sequence. Framework (Fr) regions are underlined. Frameworks 1, 2, 3 & 4 for each variable domain are sequential from the beginning to the end of each sequence (e.g., the first underlined portion of the sequence is Fr1, the second is Fr2, the third is Fr3 & the last is Fr4 in each sequence).

TABLE 2

H1 DNA
CAGGTGCAGCTGGTGGAGTCTGGGGGAGGCGTGGTCCAGCCTGGGAGGTCCCTGAGACT

CTCCTGTGCAGCGTCTGGATTCACCTTCAGTAACTATGGCATGCACTGGGTCCGCCAGGC

TCCAGGCAAGGGGCTGGAGTGGGTGGCAGTTATATGGTATGATGGAAGTAATAAATACT

ATGCAGACTCCGTGAAGGGCCGATTCACCATCTCCAGAGACAATTCCAAGAACACGCTG

TATCTGCAAATGAACAGCCTGAGAGCCGAGGACACGGCTGTATATTACTGTGCGAGTCT

AGTGGGAGCTACCAACTACTACGGTATGGACGTCTGGGGCCAAGGGACCACGGTCACCG

TCTCCTCA (SEQ ID NO: 260)

H1 Protein
QVQLVESGGGVVQPGRSLRLSCAASGFTFSNYGMHWVRQAPGKGLEWVAVIWYDGSNKY

YADSVKGRFTISRDNSKNTLYLQMNSLRAEDTAVYYCASLVGATNYYGMDVWGQGTTVTV

SS (SEQ ID NO: 261)

L1 DNA
TCTTCTGAGCTGACTCAGGACCCTGCTGTGTCTGTGGCCTTGGGACAGACAGTCAGGATC

ACATGCCAAGGAGACAGCCTCAGAAGCTATTATGCAAGCTGGTACCAGCAGAAGCCAGG

ACAGGCCCCTGTACTTGTCATCTCTGGTAAAAACTACCGGCCCTCAGGGATCCCAGACCG

ATTCTCTGGCTCCAGCTCAGGAAACACAGCTTCCTTGACCATCACTGGGGCTCAGGCGGA

AGATGAGGCTGACTACTACTGTAACTCCCGGGACAGAAGTGGTAACCATCTGGTGTTTTC

GGCGGAGGGACCAAGCTGACCGTCCTA (SEQ ID NO: 262)

L1 Protein
SSELTQDPAVSVALGQTVRITCQGDSLRSYYASWYQQKPGQAPVLVISGKNYRPSGIPDRFSG

SSSGNTASLTITGAQAEDEADYYCNSRDRSGNHLVFGGGTKLTVL (SEQ ID NO: 263)

H2 DNA
GAAGTGCAGCTGGTGGAGTCTGGGGGAGTCGTGGTACAGCCTGGGGGGTCCCTGAGACT

CTCCTGTGCAGCCTCTGGATTCACCTTTGATGATTTTACCATGCACTGGGTCCGTCAAGCT

CCGGGGAAGGGTCTGGAGTGGGTCTCTCTTATTAGTTGGGATGGTGGTAGCACATACTAT

GCAGACTCTGTGAAGGGCCGATTCACCATCTCCAGAGACAACAGCAAAAACTCCCTGTA

TATGCAAATGAACAGTCTGAGAACTGAGGACAGCGCCTTGTATTACTGTGCAAGAGGTC

CTTACTACTACTTCTACGGTATGGACGTCTGGGGCCAAGGGACCACGGTCACCGTCTCCT

CA (SEQ ID NO: 264)

TABLE 2-continued

H2 Protein
EVQLVESGGVVVQPGGSLRLSCAASGFTFDDFTMHWVRQAPGKGLEWVSLISWDGGSTYY

ADSVKGRFTISRDNSKNSLYMQMNSLRTEDSALYYCARGPYYYFYGMDVWGQGTTVTVSS (SEQ ID NO: 265)

L2 DNA
TCTTCTGAGCTGACTCAGGACCCTGCTGTGTCTGTGGCCTTGGGACAGACAGTCAGGATC

ACATGCCAAGGAGACAGCCTCAGAACCTATTATGCAAGCTGGTACCAGCAGAAGCCAGG

ACAGGCCCCTATACTTGTCATCTCTGATAAAAACAACCGGCCCTCAGGGATCCCAGACCG

ATTCTCTGGCTCCAGCTCAGGAAACACAGCTTCCTTGACCATCACTGGGGCTCAGGCGGA

AGATGAGGCTGACTATTACTGTAACTCCCGGGACAGCAGTGATAACCATCTAGTGGTATT

TCGGCGGAGGGACCAAGCTGACCGTCCTA (SEQ ID NO: 266)

L2 Protein
SSELTQDPAVSVALGQTVRITCQGDSLRTYYASWYQQKPGQAPILVISDKNNRPSGIPDRFSG

SSSGNTASLTITGAQAEDEADYYCNSRDSSDNHLVVFGGGTKLTVL (SEQ ID NO: 267)

H3 DNA
CAGGTGCAGCTGGTGCAGTCTGGGGCTGAGGTGAAGAAGCCTGGGGCCTCAGTGAAGGT

CTCCTGCAAGGCTTCTGGATACACCTTCACCGACTACTATATGTACTGGGTGCGACAGGC

CCCTGGACAAGGGCCTGAGTGGATGGGATGGATCAACCCTAACAGTGGTGGCACAAACT

ATGTACAGAAGTTTCAGGGCAGGGTCACCATGACCAGGGACACGTCCATCAGCACAGCC

TACATGGAGCTGAGCAGGATGAGATCCGACGACACGGCCGTGTATTACTGTGCGAGAGA

TGGGGGTAGCAGTGGCTGGCCCCTCTTTGCCTACTGGGGCCTGGGAACCCTGGTCACCGT

CTCCTA (SEQ ID NO: 268)

H3 Protein
QVQLVQSGAEVKKPGASVKVSCKASGYTFTDYYMYWVRQAPGQGPEWMGWINPNSGGTN

YVQKFQGRVTMTRDTSISTAYMELSRMRSDDTAVYYCARDGGSSGWPLFAYWGLGTLVTV

SS (SEQ ID NO: 269)

L3 DNA
CAGTCTGTGCTGACGCAGCCGCCCTCAGTGTCTGGGGCCCCAGGGCAGAGGGTCACCAT

CTCCTGCACTGGGAGCAGCTCCAACATCGGGGCAGGTTTTGATGTACACTGGTACCAGCA

GCTTCCAGGAACAGCCCCCAAACTCCTCATCTATGATAACAACAATCGGCCCTCAGGGGT

CCCTGACCGATTCTCTGGCTCCAAGTCTGGCACCTCAGCCTCCCTGGCCATCACTGGGCT

CCAGGCTGAGGATGAGGCTGATTATTACTGCAGTCCTATGACAGCAACCTGAGTGGTTC

GATTGTGGTTTTCGGCGGAGGGACCAAGCTGACCGTCCTA (SEQ ID NO: 270)

TABLE 2-continued

L3 Protein
QSVLTQPPSVSGAPGQRVTISCTGSSSNIGAGFDVHWYQQLPGTAPKLLIYDNNNRPSGVPDR

FSGSKSGTSASLAITGLQAEDEADYYCQSYDSNLSGSIVVFGGGTKLTVL (SEQ ID NO: 271)

H4 DNA
CAGGTGCAGCTGGTGCAGTCTGGGGCTGAGGTGAAGAAGCCTGGGGCCTCAGTGAAGGT

CTCCTGCAAGGCTTCTGGATACATCTTCACCGGCGACTATATGCACTGGGTGCGACAGGC

CCCTGGACAAGGGCTGGAGTGGATGGGATGGATCAACCCTAACAGTGGTGGCACAAACC

ATGCACGGAAGTTTCAGGGCAGGGTCACCATGACCAGGGACACGTCCATCAGCACAGCC

TACATGGAGCTGAGCAGGCTGAGATCTGACGACACGGCCGTGTATTACTGTGTGAGAGA

TAGGGGTACCAGTGGCTGGCCACTCTTTGACTATTGGGGCCAGGGAACACTGGTCACCGT

CTCCTCA (SEQ ID NO: 272)

H4 Protein
QVQLVQSGAEVKKPGASVKVSCKASGYIFTGDYMHWVRQAPGQGLEWMGWINPNSGGTN

HARKFQGRVTMTRDTSISTAYMELSRLRSDDTAVYYCVRDRGTSGWPLFDYWGQGTLVTV

SS (SEQ ID NO: 273)

L4 DNA
CAGTCTGTGCTGACGCAGCCGCCCTCAGTGTCTGGGGCCCCAGGGCAGAGGGTCACCAT

CTCCTGCACTGGGAGCAGCTCCAACATCGGGGCAGGTTTTGATGTGCACTGGTACCAGCT

GCTTCCAGGAACAGCCCCCAAACTCCTCATCTTTGATAACAACAATCGCCCCTCAGGGGT

CCCTGACCGATTCTCTGGCTCCAAGTCTGGCACCTCAGCCTCCCTGGCCATCACTGGGCT

CCAGGCTGAGGATGAGGCTGATTATTACTGCCAGTCCTATGACAGCAACCTGAGTGGTTC

GATTGTGGTATTTCGGCGGAGGGACCAAGCTGACCGTCCTA (SEQ ID NO: 274)

L4 Protein
QSVLTQPPSVSGAPGQRVTISCTGSSSNIGAGFDVHWYQLLPGTAPKLLIFDNNNRPSGVPDR

FSGSKSGTSASLAITGLQAEDEADYYCQSYDSNLSGSIVVFGGGTKLTVL (SEQ ID NO: 275)

H5 DNA
CAGATGCAGCTGGTGGAGTCTGGGGGAGGCGTGGTCCAGCCTGGGAGGTCCCTGAGACT

CTCCTGTGCAGCGTCTGGATTCACCTTCAGAACCTATGGCATGCACTGGGTCCGCCAGGC

TCCAGGCAAGGGACTGGAGTGGGTGGCAGTTATATGGTATGATGGAAGTAATAAACACT

ATGCAGACTCCGTGAAGGGCCGATTCACCATCACCAGAGACAATTCCAAGAACACTCTG

AATCTGCAAATGAACAGCCTGAGAGCCGAGGACACGGCTGTGTATTACTGTGCGAGAGC

CCCTCAGTGGGAGCTAGTTCATGAAGCTTTTGATATCTGGGGCCAAGGGACAATGGTCAC

CGTCTCTTCA (SEQ ID NO: 360)

TABLE 2-continued

H5 Protein
QMQLVESGGGVVQPGRSLRLSCAASGFTFRTYGMHWVRQAPGKGLEWVAIWYDGSNKH

YADSVKGRFTITRDNSKNTLNLQMNSLRAEDTAVYYCARAPQWELVHEAFDIWGQGTMVT

VSS (SEQ ID NO: 361)

L5 DNA
TCCTATGTGCTGACTCAGCCACCCTCGGTGTCAGTGGCCCCAGGACAGACGGCCAGGATT

ACCTGTGGGGGAAACAACCTTGGAAGTAAAAGTGTGCACTGGTACCAGCAGAAGCCAGG

CCAGGCCCCTGTGCTGGTCGTCTATGATGATAGCGACCGGCCCTCATGGATCCCTGAGCG

ATTCTCTGGCTCCAACTCTGGGAACACGGCCACCCTGACCATCAGCAGGGGCGAAGCCG

GGGATGAGGCCGACTATTACTGTCAGGTGTGGGATAGTAGTAGTGATCATGTGGTATTTC

GGCGGAGGGACCAAGCTGACCGTCCTA (SEQ ID NO: 362)

L5 Protein
SYVLTQPPSVSVAPGQTARITCGGNNLGSKSVHWYQQKPGQAPVLVVYDDSDRPSWIPERFS

GSNSGNTATLTISRGEAGDEADYYCQVWDSSSDHVVFGGGTKLTVL (SEQ ID NO: 363)

H6 DNA
CAGGTGCAGCTGGTGGAGTCTGGGGGAGGCGTGGTCCAGCCTGGGAGGTCCCTGAGACT

CTCCTGTGCAGCCTCTGGATTCATTTTCAGTAGCTATGGCATTCACTGGGTCCGCCAGGCT

CCAGGCAAGGGGCTGGAGTGGGTGGCAGTTATATCATATGATGGAAGTTATAAATACTA

TGCAGACTCCGTGAAGGGCCGATTCACCATCTCCAGAGACAATTCCAAGAACACGCTGT

ATCTGCAAATGAACAGCCTGAGAGCTGAGGACACGGCTGTGTATTACTGTGCGAGAGGG

GACTCCTGGAACGACAGATTAAACTACTACTTCTACGATATGGACGTCTGGGGCCAAGG

GACCACGGTCACCGTCTCCTCA (SEQ ID NO: 276)

H6 Protein
QVQLVESGGGVVQPGRSLRLSCAASGFIFSSYGIHWVRQAPGKGLEWVAVISYDGSYKYYA

DSVKGRFTISRDNSKNTLYLQMNSLRAEDRAVYYCARGDSWNDRLNYYFYDMDVWGQT

TVTVSS (SEQ ID NO: 277)

L6 DNA
TCCTATGAGCTGACTCAGGCACCCTCAGTGTCCGTGTCCCCAGGACAGACAGCCAGCATC

ACCTGCTCTGGAGATAAATTGGGGGATAAATATGCTTGCTGGTATCAGCAGAAGCCAGG

CCAGTCCCCTGTGCTGGTCATCTATCAAGATAAGAAGCGGCCCTCAGGGATCCCTGAGCG

ATTCTCTGGCTCCAACTCTGGGAACACAGCCACTCTGACCATCAGCGGGACCCAGGCTAT

GGATGAGGCTGACTATTACTGTCAGGCGTGGACAGCAGCACTGTGGTATTTCGGCGGA

GGGACCAAGCTGACCGTCCTA (SEQ ID NO: 278)

TABLE 2-continued

L6 Protein
SYELTQAPSVSVSPGQTASITCSGDKLGDKYACWYQQKPGQSPVLVIYQDKKRPSGIPERFSG

SNSGNTATLTISGTQAMDEADYYCQAWDSSTVVFGGGTKLTVL (SEQ ID NO: 279)

H7 DNA
CAGGTGCAGCTGCAGGAGTCGGGCCCAGGACTGGTGAAGCCTTCACAGACCCTGTCCCT

CACCTGCACTGTCTCTGGTGGCTCCATCAGCAGTGGTGGTTACTACTGGAGCTGGATCCG

CCAGCACCCAGGGAAGGGCCTGGAGTGGATTGGGTTCATCCATTACAGTGGGACCACCT

ACTACAACCCGTCCCTCAAGAGTCGACTTACCCTATCAGTAGACACGTCTAAGAGCCAGT

TCTCCCTGAAGCTGAACTCTGTGACTGCCGCGGACACGGCCGTGTATTACTGTGCGAGAG

AAGTTGGCAGCTCGTCGGGTAACTGGTTCGACCCCTGGGGCCAGGGAACCCTGGTCACC

GTCTCCTCA (SEQ ID NO: 280)

H7 Protein
QVQLQESGPGLVKPSQTLSLTCTVSGGSISSGGYYWSWIRQHPGKGLEWIGFIHYSGTTYYNP

SLKSRLTLSVDTSKSQFSLKLNSVTAADTAVYYCAREVGSSSGNWFDPWGQGTLVTVSS (SEQ ID NO: 281)

L7 DNA
TCCTATGAGCTGACTCAGCCACCCTCAGTGTCCGTGTCCCCAGGACAGACAGCCAGCATC

ACCTGCTCTGGAGATAAATTGGGGGATAAATATGCTTGCTGGTATCAGCAGAAGCCAGG

CCAGTCCCCTGTGGTGGTCATCTATCAAGATAACAAGCGGCCCTCAGGGATCCCTGAGCG

ATTCTCTGGCTCCAACTCTGGGAACACAGCCACTTTGACCATCAGCGGGACCCAGGCTAT

GGATGAGGCTGACTATTACTGTCAGGCGTGGGACAGCACCACTGCGATATTTCGGCGGA

GGGACCAAGCTGACCGTCCTA (SEQ ID NO: 282)

L7 Protein
SYELTQPPSVSVSPGQTASITCSGDKLGDKYACWYQQKPGQSPVVVIYQDNKRPSGIPERFSG

SNSGNTATLTISGTQAMDEADYYCQAWDSTTAIFGGGTKLTVL (SEQ ID NO: 283)

H8 DNA
CAGGTGCAGCTGGTGGAGTCTGGGGGAGGCGTGGTCCAGCCTGGGAGGTCCCTGAGACT

CTCCTGTGCAGCCTCTGGATTCACCTTCAGTAGCTATGGCATTCACTGGGTCCGCCAGGC

TCCAGGCAAGGGGCTGGAGTGGGTGGCAGTTATATCATATGATGGAAGTAATAAATACT

ATGCAGACTCCGTGAAGGGCCGATTCACCATCTCCAGAGACAATTCCAAGAACACGCTG

TATCTGCAAATGAACAGCCTGAGAGCTGAGGACACGGCTGTGTATTACTGTGCGAGAGG

GGACTCCTGGAACGACAGATTAAACTACTACTTCTACGATATGGACGTCTGGGGCCAAG

GGACCACGGTCACCGTCTCCTCA (SEQ ID NO: 284)

TABLE 2-continued

H8 Protein
QVQLVESGGGVVQPGRSLRLSCAASGFTFSSYGIHWVRQAPGKGLEWVAVISYDGSNKYYA

DSVKGRFTISRDNSKNTLYLQMNSLRAEDTAVYYCARGDSWNDRLNYYFYDMDVWGQGT

TVTVSS (SEQ ID NO: 285)

L8 DNA
TCCTATGAGCTGACTCAGCCACCCTCAGTGTCCGTGTCCCCAGGACAGACAGCCAGCATC

ACCTGCTCTGGAGATAAATTGGGGGATAAATATGCTTGCTGGTATCAGCAGAAGCCAGG

CCAGTCCCCTGTACTGGTCATCTATCAAGATAACAAGCGGCCCTCAGGGATCCCTGAGCG

ATTCTCTGGCTCCAACTCTGGGAACACAGCCACTTTGACCATCAGCGGGACCCAGGCTAT

GGATGAGGCTGACTATTACTGTCAGGCGTGGGACAGCAGCACTGTGGTATTTCGGCGGA

GGGACCAAGCTGACCGTCCTA (SEQ ID NO: 286)

L8 Protein
SYELTQPPSVSVSPGQTASITCSGDKLGDKYACWYQQKPGQSPVLVIYQDNKRPSGIPERFSG

SNSGNTATLTISGTQAMDEADYYCQAWDSSTVVFGGGTKLTVL (SEQ ID NO: 287)

H9 DNA
CAGGTGCAGTTGGTGGAGTCTGGGGGAGGCGTGGTCCAGCCTGGGAGGTCCCTGAGACT

CTCCTGTGCAGCGTCTGGATATACCTTCAATAGCTATGGCATGCACTGGGTCCGCCAGGC

TCCAGGCAAGGGGCTGGAGTGGGTGGCAGTTATATGGTATGATGGAAGTAATACATACT

ATGCAGACTCCGTGAAGGGCCGATTCACCATCTCCAGAGACATTTCCAAGAACACTCTGT

ATCTGCAAATGAACAGCCTGAGAGCCGAGGACACGGCTGTGTATTACTGTGCGAGAGAG

GTCCGGGCGTATAGCAGTGGCTGGTACGCCGCCTTTGACTACTGGGGCCAGGGAACCCT

GGTCACCGTCTCCTCA (SEQ ID NO: 288)

H9 Protein
QVQLVESGGGVVQPGRSLRLSCAASGYTFNSYGMHWVRQAPGKGLEWVAVIWYDGSNTY

YADSVKGRFTISRDISKNTLYLQMNSLRAEDTAVYYCAREVRAYSSGWYAAFDYWGQGTL

VTVSS (SEQ ID NO: 289)

L9 DNA
TCTTCTGAGCTGACTCAGGACCCTGCTGTGTCTGTGGCCTTGGGACAGACAGTCAGGATC

ACATGCCAAGGAGACAGCCTCAGAATCTTTTATGCAAACTGGTACCAGCAGAAGCCAGG

ACAGGCCCCTGTAGTTGTCTTCTATGGTAAAAACAACCGGCCCTCAGGGATCCCAGACCG

ATTCTCTGGCTCCAGCTCAGGAAACACAGCTTCCTTGACCATCACTGCGGCTCAGGCGGA

AGATGAGGCTGACTATTATTGTAACTCCCGGGACAGCAGTGGTAACCATGTGGTATTTCG

GCGGAGGGACCACGCTGACCGTCCTA (SEQ ID NO: 290)

TABLE 2-continued

L9 Protein
SSELTQDPAVSVALGQTVRITCQGDSLRIFYANWYQQKPGQAPVVVFYGKNNRPSGIPDRFS

GSSSGNTASLTITAAQAEDEADYYCNSRDSSGNHVVFGGGTTLTVL (SEQ ID NO: 291)

H10 DNA
CAGGTGCAGCTGGTGGAGTCTGGGGGAGGCGTGGTCCAGCCTGGGAGGTCCCTGAGACT

CTCCTGTGCAACGTCTGGATTCACCTTCAGTAGTTATGGCATGCACTGGGTCCGCCAGGC

TCCAGGCAAGGGGCTGGAGTGGGTGGCAGTTATATGGTATGATGGAAGTAGTAAATACT

ATGCAGACTCCGTGAAGGGCCGATTCACCATCTCCAGAGACAATTCCAAGAACACGCTG

TATCTGCAAATGAACAGCCTGAGAGCCGAGGACACGGCGTGTATTACTGTGCAGAGAGT

AAGAAGTGGGAGCTACTACGAACAGTATTACTACGGTATGGACGTCTGGGGCCAAGGGA

CCACGGTCGCCGTCTCCTCA (SEQ ID NO: 292)

H10 Protein
QVQLVESGGGVVQPGRSLRLSCATSGFTFSSYGMHWVRQAPGKGLEWVAVIWYDGSSKYY

ADSVKGRFTISRDNSKNTLYLQMNSLRAEDTAVYYCARVRSGSYYEQYYYGMDVWGQGTT

VAVSS (SEQ ID NO: 293)

L10 DNA
GACATCCAGATGACCCAGTCTCCATCCTCCCTGTCTGCATCTGTAGGAGACAGAGTCACC

ATCACTTGCCGGGCAAATCAGTACATTAGCACCTATTTAAATTGGTATCAGCAGAAACCA

GGGAAAGCCCCTAAGGTCCTGATTTATGCTGCATCCAGTTTGCAAAGTGGGGTCCCATCA

AGGTTCAGTGGCAGTGGATTTGAGACAGATTTCACTCTCACCATCAGCAGTCTGCAACCT

GAAGATTTTGCAACTTACTACTGTCAGCAGAGCTACACTACCCCGATCACCTTTCGGCCA

AGGGACACGACTGGAGATTAAA (SEQ ID NO: 294)

L10 Protein
DIQMTQSPSSLSASVGDRVTITCRANQYISTYLNWYQQKPGKAPKVLIYAASSLQSGVPSRFS

GSGFETDFTLTISSLQPEDFATYYCQQSYTTPITFGQGTRLEIK (SEQ ID NO: 295)

H11 DNA
GAGGTGCAGCTGGTGGAGTCTGGGGGAGGCTTGGTACAGCCTGGGGGGTCCCTGAGACT

CTCCTGTGCAGCCTCTGGATTCACCTTCAGTAGTTATAGCATGAACTGGGTCCGCCAGGC

TCCAGGGAAGGGGCTGGAGTGGGTTTCATACATTAGTGGTCGTACTAGTAGCGTATACTA

CGCAGACTCTGTGAAGGGCCGATTCACCATCTCCAGAGACAATGCCAAGAACTCACTGT

ATCTGCACATGAACAGCCTGAGAGACGAGGACACGGCTGTGTATTACTGTGCGAGAAGT

GGGATCTACTACGACTACTACGGTATGGACGTCTGGGGCCAAGGGACCACGGTCACCGT

CTCCTCA (SEQ ID NO: 296)

TABLE 2-continued

H11 Protein
EVQLVESGGGLVQPGGSLRLSCAASGFTFSSYSMNWVRQAPGKGLEWVSYISGRTSSVYYA

DSVKGRFTISRDNAKNSLYLHMNSLRDEDTAVYYCARSGIYYDYYGMDVWGQGTTVTVSS (SEQ ID NO: 297)

L11 DNA
GACATCGTGATGACCCAGTCTCCAGACTCCCTGGCTGTGTCTCTGGGCGAGAGGGCCCCC

ATCAACTGCAAGTCCAGCCAGAGTGTTTTAAACAGCTCCAACAATAAGAACTACTTAGCT

TGGTACCAGCAGAAACCAGGACAGCCTCCTAAGCTGCTCATTTACTGGACATCCACCCGG

GAAGGCGGGGTCCCTGACCGATTCAGTGGCAGCGGGTCTGGGACAGATTTCACTCTCAC

CATCAGCAGCCTGCAGGCTGAAGATGTGGCAGTTTATTACTGTCAGCAGTATTTTACTAC

TCCGTGGACGTTTCGGCCAAGGGACCAAGGTGGAGATCAAA (SEQ ID NO: 298)

L11 Protein
DIVMTQSPDSLAVSLGERAPINCKSSQSVLNSSNNKNYLAWYQQKPGQPPKLLIYWTSTREG

GVPDRFSGSGSGTDFTLTISSLQAEDVAVYYCQQYFTTPWTFGQGTKVEIK (SEQ ID NO: 299)

H12 DNA
CAGGTGCAGCTGGTGGAGTCTGGGGGAGGCGTGGTCCAGCCTGGGAGGTCCCTGAGACT

CTCCTGTGCAGCGTCTGGATTCACCTTCAGTAGCTATGGCATGCACTGGGTCCGCCAGGC

TCCAGGCAAGGGGCTGGAGTGGGTGGCAGTTATATGGTATGATGGAAGTAATAAATACT

ATGCAGACTCCGTGAAGGGCCGATTCACCATCTCCAGAGACAATTCCAAGAACACGCTG

TATCTGCAAATGAACAGCCTGAGAGCCGAGGACACGGCTGTGTATTACTGTGCGAGAGG

GGCAGCCACTGCTATAGATTACTACTACTCCTACGGTATGGACGTCTGGGGCCTAGGGAC

CACGGTCACCGTCTCCTCA (SEQ ID NO: 300)

H12 Protein
QVQLVESGGGVVQPGRSLRLSCAASGFTFSSYGMHWVRQAPGKGLEWVAVIWYDGSNKYY

ADSVKGRFTISRDNSKNTLYLQMNSLRAEDTAVYYCARGAATAIDYYYSYGMDVWGLGTT

VTVSS (SEQ ID NO: 301)

L12 DNA
GACATCCAGATGACCCAGTCTCCATCTTCCGTGTCTGCATCTGTGGGAGACAGAGTCACC

ATCACTTGTCGGGCGAGTCAGGGTATTAGTAGCTGGTTAGCCTGGTATCAGCGGAAACCA

GGAAAAGCCCCTAAGTTCCTGATCTATACTGCATCCAGTTTGCAAAGTGGGGTCCCATCA

CGGTTCAGCGGCAGTGGATCTGGGACAGATTTCACTCTCACCATCAGCAGCCTGCAGCCT

GAAGATTCTGCAACTTACTATTGTCAACAGGCTGACAGTTTCCCGCTCACTTTTCGGCGG

AGGGACCAAGGTGGAGATCAAA (SEQ ID NO: 302)

TABLE 2-continued

L12 Protein
DIQMTQSPSSVSASVGDRVTITCRASQGISSWLAWYQRKPGKAPKFLIYTASSLQSGVPSRFS

GSGSGTDFTLTISSLQPEDSATYYCQQADSFPLTFGGGTKVEIK (SEQ ID NO: 303)

H13 DNA
CAGGTGCAGCTGGTGGAGTCTGGGGGAGGCGTGGTCCAGCCTGGGAGGTCCCTGAGACT

CTCCTGTGCAGCGTCTGGATTCACCTTCAGTAGCTATGGCATGCACTGGGTCCGCCAGGC

TCCAGGCAAGGGGCTGGAGTGGGTGGCAGTTATATGGTATGATGGAAGTAATAAATACT

ATGCAGACTCCGTGAAGGGCCGATTCACCATCTCCAGAGACAATTCCAAGAACACGCTG

TATCTGCAAATGAACAGCCTGAGAGCCGAGGACACGGCTGTGTATTACTGTGCGAGAGG

GGGGGGTATACCAGTAGCTGACTACTACTACTACGGTATGGACGTCTGGGGCCAAGGGA

CCACGGTCACCGTCTCCTCA (SEQ ID NO: 304)

H13 Protein
QVQLVESGGGVVQPGRSLRLSCAASGFTFSSYGMHWVRQAPGKGLEWVAVIWYDGSNKYY

ADSVKGRFTISRDNSKNTLYLQMNSLRAEDTAVYYCARGGGIPVADYYYYGMDVWGQGTT

VTVSS (SEQ ID NO: 305)

L13.1 DNA
GATGTTGTGATGACTCAGTCTCCACTCTCCCTGCCCGTCACCCTTGGACAGCCGGCCTCC

ATCTCCTGCAGGTCTAGTCAAAGCCTCGTCTACAGTGATGGAGACACCTACTTGAATTGG

TTTCAGCAGAGGCCAGGCCAATCTCCAAGGCGCCTAATTTATAAGGTTTCTAACTGGGAC

TCTGGGGTCCCATACAGATTCAGCGGCAGTGGGTCAGGCACTGATTTCACACTGCAAATC

AGCAGGGTGGAGGCTGAGGATGTTGGGATTTACTACTGCATGCAAGGTACACACTGGCC

TCCGGCCTTTCGGCCAAGGGACACGACTGGAGATTAAA (SEQ ID NO: 306)

L13.1 Protein
DVVMTQSPLSLPVTLGQPASISCRSSQSLVYSDGDTYLNWFQQRPGQSPRRLIYKVSNWDSG

VPYRFSGSGSGTDFTLQISRVEAEDVGIYYCMQGTHWPPAFGQGTRLEIK (SEQ ID NO: 307)

L13.2 DNA
GACATCCAGATGACCCAGTCTCCATCTTCCGTGTCTGCATCTGTAGGAGACAGAGTCACC

ATCACTTGTCGGGCGAGTCAGGGTCTTAGCAGCTGGTTAGCCTGGTATCAGCAGAAACCA

GGGAAAGCCCCCAAGCTCCTGATGTATAACACATCCAGTTTGCAAAGTGGGGTCCCATC

AAGGTTCAGCGGCAGTGGATCTGGGACAGATTTCAGTCTCACCATCAGCAGCCTGCAGC

CTGAAGATTTTGCAAGTTACTATTGTCAACAGGCTAACAGTTTCCCTCTCACTTTTCGGCG

GAGGGACCAAGGTGGAGATCAAA (SEQ ID NO: 308)

TABLE 2-continued

L13.2 Protein
DIQMTQSPSSVSASVGDRVTITCRASQGLSSWLAWYQQKPGKAPKLLMYNTSSLQSGVPSRF

SGSGSGTDFSLTISSLQPEDFASYYCQQANSFPLTFGGGTKVEIK (SEQ ID NO: 309)

H14 DNA
CAGGTGCAGCTGGTGGAGTCTGGGGGAGGCGTGGTCCAGCCTGGGAGGTCCCTGAGACT

CTCCTGTGCAGCGTCTGGATTCACCTTCAGTAGCTATGGCATGCACTGGGTCCGCCAGGC

TCCAGGCAAGGGGCTGGAGTGGGTGGCAGTTATATGGTATGATGGAAGTAATAAATACT

ATGCAGACTCCGTGAAGGGCCGATTCACCATCTCCAGAGACAATTCCAAGAACACGCTG

TATCTGCAAATGAACAGCCTGAGAGCCGAGGACACGGCTGTGTATTACTGTGCGAGAGG

GGGGGGTATACCAGTAGCTGACTACTACTACTACGGTATGGACGTCTGGGGCCAAGGGA

CCACGGTCACCGTCTCCTCA (SEQ ID NO: 304)

H14 Protein
QVQLVESGGGVVQPGRSLRLSCAASGFTFSSYGMHWVRQAPGKGLEWVAVIWYDGSNKYY

ADSVKGRFTISRDNSKNTLYLQMNSLRAEDTAVYYCARGGGIPVADYYYYGMDVWGQGTT

VTVSS (SEQ ID NO: 305)

L14.1 DNA
GATGTTGTGATGACTCAGTCTCCACTCTCCCTGCCCGTCACCCTTGGACAGCCGGCCTCC

ATCTCCTGCAGGTCTAGTCAAAGCCTCGTCTACAGTGATGGAAACACCTACTTGAATTGG

TTTCAGCAGAGGCCAGGCCAATCTCCAAGGCGCCTAATTTATAAGGTTTCTAACTGGGAC

TCTGGGGTCCCAGACAGATTCAGCGGCATTGGGTCAGGCACTGACTTCACACTGAAAATC

AGCAGGGTGGAGGCTGAGGATGTTGGGGTTTACTACTGCATGCAAGGTACACACTGGCC

TCCGGCCTTTCGGCCAAGGGACACGACTGGAGATTAAA (SEQ ID NO: 310)

L14.1 Protein
DVVMTQSPLSLPVTLGQPASISCRSSQSLVYSDGNTLYNWFQQRPGQSPRRLIYKVSNWDGG

VPDRFSGIGSGTDFTLKISRVEAEDVGVYYCMQGTHWPPAFGQGTRLEIK (SEQ ID NO: 311)

L14.2 DNA
GACATCCAGATCACCCAGTCTCCATCTTCCGTGTCTGCATCTGTAGGAGACAGAGTCACC

ATCACTTGTCGGGCGAGTCAGGGTCTTAGCAGCTGGTTAGCCTGGTATCAGCAGAAACCA

GGGAAAGCCCCCAAGCTCCTGATGTATAACACATCCAGTTTGCAAAGTGGGGTCCCATC

AAGGTTCAGCGGCAGTGGATCTGGGACAGATTTCAGTCTCACCATCAGCAGCCTGCAGC

CTGAAGATTTTGCAAGTTACTATTGTCAACAGGCTAACAGTTTCCCTCTCACTTTTCGGCG

GAGGGACCAAGGTGGAGATCAAA (SEQ ID NO: 312)

TABLE 2-continued

L14.2 Protein
DIQMTQSPSSVSASVGDRVTITCRASQGLSSWLAWYQQKPGKAPKLLMYNTSSLQSGVPSRF

SGSGSGTDFSLTISSLQPEDFASYYCQQANSFPLTFGGGTKVEIK (SEQ ID NO: 309)

H15 DNA
CAGGTGCAGCTGGTGGAGTCTGGGGGAGGCGTGGTCCAGCCTGGGAAGTCCCTGAGACT

CTCCTGTGCAGCGTCTGGATTCCCCTTCAGTAACTATGGCATGCACTGGGTCCGCCAGGC

TCCAGGCAAGGGACTGGAATGGGTGGCAGTTATATGGTTTGATGGAAGTAATAAATACT

ATGCGGACTCCGTGAAGGGCCGATTCACCATCTCCAGAGACAATCCCAAGAACACGCTG

TATCTGCAAATGAACAGCCTGAGAGCCGAGGACACGGCTGTGTATTACTGTGCGAGAGG

GGGGGGTATAGCAGTGGCTGACTACTACTTCTACGGTATGGACGTCTGGGGCCAAGGGA

CCACGGTCACCGTCTCCTCA (SEQ ID NO: 313)

H15 Protein
QVQLVESGGGVVQPGKSLRLSCAASGFPFSNYGMHWVRQAPGKGLEWVAVIWFDGSNKYY

ADSVKGRFTISRDNPKNTLYLQMNSLRAEDTAVYYCARGGGIAVADYYFYGMDVWGQGTT

VTVSS (SEQ ID NO: 314)

L15.1 DNA
GATGTTGTGATGACTCAGTCTCCACTCTCCCTGCCCGTCACCCTTGGACAGCCGGCCTCC

ATCTCCTGCAGGTCTAGTCAAAGCCTCATATACAGTGATGGAAACACTTACTTGAATTGG

TTTCAACAGAGGCCAGGCCAATCTCCAAGGCGCCTAATTTATAAGGTTTCTAACTGGGAC

TCTGGGGTCCCAGACAGATTCAGCGGCAGTGGGTCAGGCACTGATTTCACACTGAAAAT

CAGCAGGGTGGAGGCTGAGGATGTTGGGATTTATTACTGCATGCAAGGTACACACTGGC

CTCCGGCCTTTCGGCCAAGGGACACGACTGGAGATTAAA (SEQ ID NO: 315)

L15.1 Protein
DVVMTQSPLSLPVTLGQPASISCRSSQSLIYSDGNTYLNWFQQRPGQSPRRLIYKVSNWDSGV

PDRFSGSGSGTDFTLKISRVEAEDVGIYYCMQGTHWPPAFGQGTRLEIK (SEQ ID NO: 316)

L15.2 DNA
GACATCCAGATGACCCAGTCTCCATCTTCCGTGTCTGCATCTGTAGGAGACAGAGTCACC

ATTACTTGTCGGGCGAGTCAGGGTATTAGCAGCTGGTTAGCCTGGTATCAGCAGAAACCA

GGGAAAGCCCCTAAGGTCCTGACCTATACTACATCCAGTTTGCAAAGTGGGGTCCCATCA

AGGTTCAGCGGCAGTGGATCTGGGACAGATTTCACTCTCACCATCAGCAGCCTGCAGCCT

GAAGATTTTGCTACTTACTTTTGTCAACAGGCTGACAGTTTCCCTCTCACTTTTCGGCGGG

GGGACCAAGGTGGAGATCAAA (SEQ ID NO: 317)

TABLE 2-continued

L15.2 Protein
DIQMTQSPSSVSASVGDRVTITCRASQGISSWLAWYQQKPGKAPKVLTYTTSSLQSGVPSRFS

GSGSGTDFTLTISSLQPEDFATYFCQQADSFPLTFGGGTKVEIK (SEQ ID NO: 318)

H16 DNA
CAGGTGCAACTGGTGGAGTCTGGGGGAGGCGTGGTCCAGCCTGGGAGGTCCCTGAGACT

CTCCTGTGCAGCGTCTGGATTCACCTTCAGTAACTATGGCATGCACTGGGTCCGCCAGGC

TCCAGGCAAGGGGCTGGAGTGGGTGGCAGTTATATGGTATGATGGAAGTAATAAATACT

ATGCAGACTCCGTGAAGGGCCGATTCACCATCTCCAGAGACAATTCCAAGAACACGCTG

TATCTGCAAATGAACAGCCTGAGAGCCGAGGACACGGCTGTGTATTACTGTGCGAGAGG

GGGGGGTATAGCAGTGGCTGACTACTACTACTACGGTATGGACGTCTGGGGCCAAGGGAA

CCACGGTCACCGTCTCCTCA (SEQ ID NO: 319)

H16 Protein
QVQLVESGGGVVQPGRSLRLSCAASGFTFSNYGMHWVRQAPGKGLEWVAVIWYDGSNKY

YADSVKGRFTISRDNSKNTLYLQMNSLRAEDTAVYYCARGGGIAVADYYYYGMDVWGQG

TTVTVSS (SEQ ID NO: 320)

L16.1 DNA
GATGTTGTGATGACTCAGTCTCCACTCTCCCTGCCCGTCACCCTTGGACAGCCGGCCTCC

ATCTCCTGCAGGTCTAGTCAAAGCCTCGTATACAGTGATGGAAACACCTACTTGAATTGG

TTTCAGCAGAGGCCAGGCCAATCTCCAAGGCGCCTAATTTATAAGGTTTCTTACTGGGAC

TCTGGGGTCCCAGACAGATTCAGCGGCAGTGGGTCAAGCACTGATTTCACACTGAAAAT

CAGTAGGGTGGAGGCTGAGGATGTTGGGGTTTATTACTGCATGCAAGGTACACACTGGC

CTCCGGCCTTTCGGCCAAGGGACACGACTGGAGATTAAA (SEQ ID NO: 321)

L16.1 Protein
DVVMTQSPLSLPVTLGQPASISCRSSQSLVYSDGNTYLNWFQQRPGQSPRRLIYKVSYWDSG

VPDRFSGSGSSTDFTLKISRVEAEDVGVYYCMQGTHWPPAFGQGTRLEIK (SEQ ID NO: 322)

L16.2 DNA
GACATCCAGATGACCCAGTCTCCATCTTCCGTGTCTGCATCTGTAGGAGACAGAGTCACC

ATCACTTGTCGGGCGAGTCAGAGTCTTAGCAGCTGGTTAGCCTGGTATCAGCAGAAACCA

GGGAAAGCCCCTAAACTCCTGCTCCATAATGCATCCAGTTTGCAAAGTGGGGTCCCATCA

AGGTTCAGCGGCAGTGGATCTGGGACAGATTTCACTCTCACCATCAGCAGCCTGCAGCCT

GAAGATTTTGTAAATTACTATTGTCAACAGGCTAACAGTTTCCCTCTCACTTTTCGGCGGA

GGGACCAGGGTGGAGATCAAA (SEQ ID NO: 323)

TABLE 2-continued

L16.2 Protein
DIQMTQSPSSVSASVGDRVTITCRASQSLSSWLAWYQQKPGKAPKLLLHNASSLQSGVPSRFS

GSGSGTDFTLTISSLQPEDFVNYYCQQANSFPLTFGGGTRVEIK (SEQ ID NO: 324)

H17 DNA
CAGGTGCAGCTGGTGGAGTCTGGGGGAGGCGTGGTCCAGCCTGGGAGGTCCCTAAGACT

CTCCTGTGCAGCGTCTGGATTCACCTTAAGTAGTTATGGCATGCTCTGGGTCCGCCAGGC

TCCAGGCAAGGGGCTGGAGTGGGTGGCAGTTTTATGGTTTCATGGAAGTTATAAAAACT

ATGCAGACTCCGTGAAGGGCCGATTCACCATCTCCAGAGACAATTCCAAGAACACGCTG

TATCTGCAAATGAACAGCCTGCGAGCCGAGGACACGGCTGTGTATTACTGTGCGAGAGA

TAGTACAACTATGGCCCACTTTGACTACTGGGGCCAGGGAACCCTGGTCACCGTCTCCTC

A (SEQ ID NO: 325)

H17 Protein
QVQLVESGGGVVQPGRSLRLSCAASGFTLSSYGMLWVRQAPGKGLEWVAVLWFDGSYKNY

ADSVKGRFTISRDNSKNTLYLQMNSLRAEDTAVYYCARDSTTMAHFDYWGQGTLVTVSS (SEQ ID NO: 326)

L17 DNA
CAGACTGTGGTGACCCAGGAGCCATCGTTCTCAGTGTCCCCTGGAGGGACAGTCACACTC

ACTTGTGGCTTGAACTCTGGCTCAGTCTCTACTAGTTACTTCCCCAGCTGGTACCAGCAG

ACCCCAGGCCAGGCTCCACGCACGCTCATCTACAGCACAAACAGTCGCTCTTCTGGGGTC

CCTGATCGCTTCTCTGGCTCCATCCTTGGGAACAAAGCTGCCCTCACCATCACGGGGGCC

CAGGCAGATGATGAATCTGATTATTACTGTGTGCTGTATATGGGTAGAGGCATTTGGGTG

TTTCGGCGGAGGGACCAAGCTGACCGTCCTA (SEQ ID NO: 327)

L17 Protein
QTVVTQEPSFSVSPGGTVTLTCGLNSGSVSTSYFPSWYQQTPGQAPRTLIYSTNSRSSGVPDRF

SGSILGNKAALTITGAQADDESDYYCVLYMGRGIWVFGGGTKLTVL (SEQ ID NO: 328)

H18 DNA
CAGGTGCAACTGGTGGAGTCTGGGGGAGGCGTGGTCCAGCCTGGGAGGTCCCTGAGACT

CTCCTGTGCAGCGTCTGGATTCACCTTCAGTAACTATGGCATGCACTGGGTCCGCCAGGC

TCCAGGCAAGGGGCTGGAGTGGGTGGCAGTTATATGGTATGATGGAAGTAATAAATACT

ATGCAGACTCCGTGAAGGGCCGATTCACCATCTCCAGAGACAATTCCAAGAACACGCTG

TATCTGCAAATGAACAGCCTGAGAGCCGAGGACACGGCTGTGTATTACTGTGCGAGAGG

GGGGGGTATAGCAGTGGCTGACTACTACTACTACGGTATGGACGTCTGGGGCCAAGGGA

CCACGGTCACCGTCTCCTCA (SEQ ID NO: 319)

TABLE 2-continued

H18 Protein
QVQLVESGGGVVQPGRSLRLSCAASGFTFSNYGMHWVRQAPGKGLEWVAVIWYDGSNKY

YADSVKGRFTISRDNSKNTLYLQMNSLRAEDTAVYYCARGGGIAVADYYYYGMDVWGQG

TTVTVSS (SEQ ID NO: 320)

L18.1 DNA
GATGTTGTGATGACTCAGTTCCACTCTCCCTGCCCGTCACCCTTGGACAGCCGGCCTCC

ATCTCCTGCAGGTCTAGTCAAAGCCTCGTATACAGTGATGGAAACACCTACTTGAATTGG

TTTCAGCAGAGGCCAGGCCAATCTCCAAGGCGCCTAATTTATAAGGTTTCTTACTGGGAC

TCTGGGGTCCCAGACAGATTCAGCGGCAGTGGGTCAGGCACTGATTTCACACTGAAAAT

CAGTAGGGTGGAGGCTGAGGATGTTGGGGTTTATTACTGCATGCAAGGTACACACTGGC

CTCCGGCCTTTCGGCCAAGGGACACGACTGGAGATCAAA (SEQ ID NO: 329)

L18.1 Protein
DVVMTQSPLSLPVTLGQPASISCRSSQSLVYSDGNTYLNWFQQRPGQSPRRLIYKVSYWDSG

VPDRFSGSGSGTDFTLKISRVEAEDVGVYYCMQGTHWPPAFGQGTRLEIK (SEQ ID NO: 330)

L18.2 DNA
GACATCCAGATGACCCAGTCTCCATCTTCCGTGTCTGCATCTGTAGGAGACAGAGTCACC

ATCACTTGTCGGGCGAGTCAGAGTCTTAGCAGCTGGTTAGCCTGGTATCAGCAGAAACCA

GGGAAAGCCCCTAAACTCCTGCTCTATAATGCATCCAGTTTGCAAAGTGGGGCCCCATCA

AGGTTCAGCGGCAGTGGATCTGGGACAGATTTCACTCTCACCATCAGCAGCCTGCAGCCT

GAAGATTTTGTAACTTACTATTGTCAACAGGCTAACAGTTTCCCTCTCACTTTTCGGCGGA

GGGACCAGGGTGGAGATCAAA (SEQ ID NO: 331)

L18.2 Protein
DIQMTQSPSSVSASVGDRVTITCRASQSLSSWLAWYQQKPGKAPKLLLYNASSLQSGAPSRFS

GSGSGTDFTLTISSLQPEDFVTYYCQQANSFPLTFGGGTRVEIK (SEQ ID NO: 332)

H19 DNA
CAGGTGCAGCTGGTGGAGTCTGGGGGAGGCGTGGTCCAGCCTGGGAGGTCCCTGAGACT

CTCCTGTGCAGCGTCTGGATTCACCTTCAGTAGCTATGGCATGCACTGGGTCCGCCAGGC

TCCAGGCAAGGGGCTGGAGTGGGTGGCAGTTATATGGTATGATGGAAGTAATAAATACT

ATGCAGACTCCGTGAAGGGCCGATTCACCATCTCCAGAGACAATTCCAAGAACACGCTG

TATCTGCAAATGAACAGCCTGAGAGCCGAGGACACGGCTGTGTATTACTGTGCGAGAGG

GGGGGGTATACCAGTAGCTGACTACTACTACTACGGTATGGACGTCTGGGGCCAAGGGA

CCACGGTCACCGTCTCCTCA (SEQ ID NO: 304)

TABLE 2-continued

H19 Protein
QVQLVESGGGVVQPGRSLRLSCAASGFTFSSYGMHWVRQAPGKGLEWVAVIWYDGSNKYY

ADSVKGRFTISRDNSKNTLYLQMNSLRAEDTAVYYCARGGGIPVADYYYYGMDVWGQGTT

VTVSS (SEQ ID NO: 305)

L19.1 DNA
GATGTTGTGATGACTCAGTCTCCACTCTCCCTGCCCGTCACCCTTGGACAGCCGGCCTCC

ATCTCCTGCAGGTCTAGTCAAAGCCTCGTCTACAGTGATGGAGACACCTACTTGAATTGG

TTTCAGCAGAGGCCAGGCCAATCTCCAAGGCGCCTAATTTATAAGGTTTCTAACTGGGAC

TCTGGGGTCCCATACAGATTCAGCGGCAGTGGGTCAGGCACTGATTTCACACTGCAAATC

AGCAGGGTGGAGGCTGAGGATGTTGGGATTTACTACTGCATGCAAGGTACACACTGGCC

TCCGGCCTTTCGGCCAAGGGACACGACTGGAGATTAAA (SEQ ID NO: 306)

L19.1 Protein
DVVMTQSPLSLPVTLGQPASISCRSSQSLVYSDGDTYLNWFQQRPGQSPRRLIYKVSNWDSG

VPYRFSGSGSGTDFTLQISRVEAEDVGIYYCMQGTHWPPAFGQGTRLEIK (SEQ ID NO: 307)

L19.2 DNA
GACATCCAGATGACCCAGTCTCCATCTTCCGTGTCTGATCTGTAGGAGACAGAGTCACC

ATCACTTGTCGGGCGAGTCAGGGTCTTAGCAGCTGGTTAGCCTGGTATCAGCAGAAACCA

GGGAAAGCCCCCAAGCTCCTGATGTATAACACATCCAGTTTGCAAAGTGGGGTCCCATC

AAGGTTCAGCGGCAGTGGATCTGGGACAGATTTCAGTCTCACCATCAGCAGCCTGCAGC

CTGAAGATTTTGCAAGTTACTATTGTCAACAGGCTAACAGTTTCCCTCTCACTTTTCGGCG

GAGGGACCAAGGTGGAGATCAAA (SEQ ID NO: 308)

L19.2 Protein
DIQMTQSPSSVSASVGDRVTITCRASQGLSSWLAWYQQKPGKAPKLLMYNTSSLQSGVPSRF

SGSGSGTDFSLTISSLQPEDFASYYCQQANSFPLTFGGGTKVEIK (SEQ ID NO: 309)

H20 DNA
CAGGTGCAGCTGGTGGAGTCTGGGGGAGGCGTGGTCCAGCCTGGGAGGTCCCTGAGACT

CTCCTGTGCAGCGTCTGGATTCACCTTCAGTAGCTATGGCATGCACTGGGTCCGCCAGGC

TCCAGGCAAGGGGCTGGAGTGGGTGGCAGTTATATGGTATGATGGAAGTAATAAATACT

ATGCAGACTCCGTGAAGGGCCGATTCACCATCTCCAGAGACAATTCCAAGAACACGCTG

TATCTGCAAATGAACAGCCTGAGAGCCGAGGACACGGCTGTGTATTACTGTGCGAGAGG

GGGGGGTATACCAGTAGCTGACTACTACTACTACGGTATGGACGTCTGGGGCCAAGGGA

CCACGGTCACCGTCTCCTCA (SEQ ID NO: 304)

TABLE 2-continued

H20 Protein
QVQLVESGGGVVQPGRSLRLSCAASGFTFSSYGMHWVRQAPGKGLEWVAVIWYDGSNKYY

ADSVKGRFTISRDNSKNTLYLQMNSLRAEDTAVYYCARGGGIPVADYYYYGMDVWGQGTT

VTVSS (SEQ ID NO: 305)

L20.1 DNA
GATGTTGTGATGACTCAGTCTCCACTCTCCCTGCCCGTCACCCTTGGACAGCCGGCCTCC

ATCTCCTGCAGGTCTAGTCAAAGCCTCGTCTACAGTGATGGAGACACCTACTTGAATTGG

TTTCAGCAGAGGCCAGGCCAATCTCCAAGGCGCCTAATTTATAAGGTTTCTAACTGGGAC

TCTGGGGTCCCATACAGATTCAGCGGCAGTGGGTCAGGCACTGATTTCACACTGCAAATC

AGCAGGGTGGAGGCTGAGGATGTTGGGATTTACTACTGCATGCAAGGTACACACTGGCC

TCCGGCCTTTCGGCCAAGGGACACGACTGGAGATTAAA (SEQ ID NO: 306)

L20.1 Protein
DVVMTQSPLSLPVTLGQPASISCRSSQSLVYSDGDTYLNWFQQRPGQSPRRLIYKVSNWDSG

VPYRFSGSGSGTDFTLQISRVEAEDVGIYYCMQGTHWPPAFGQGTRLEIK (SEQ ID NO: 307)

L20.2 DNA
GACATCCAGATGACCCAGTCCCCATCTTCCGTGTCTGCATCTGTAGGAGACAGAGTCACC

ATCACTTGTCGGGCGAGTCAGGGTCTTAGCAGCTGGTTAGCCTGGTATCAGCAGAAACCA

GGGAAAGCCCCCAAGCTCCTGATGTATAACACATCCAGTTTGCAAAGTGGGGTCCCATC

AAGGTTCAGCGGCAGTGGATCTGGGACAGATTTCAGTCTCACCATCAGCAGCCTGCAGC

CTGAAGATTTTGCAAGTTACTATTGTCAACAGGCTAACAGTTTCCCTCTCACTTTTCGGCG

GAGGGACCAAGGTGGAGATCAAA (SEQ ID NO: 333)

L20.2 Protein
DIQMTQSPSSVSASVGDRVTITCRASQGLSSWLAWYQQKPGKAPKLLMYNTSSLQSGVPSRF

SGSGSGTDFSLTISSLQPEDFASYYCQQANSFPLTFGGGTKVEIK (SEQ ID NO: 309)

H21 DNA
GAGGTGCAGCTGTTGGAGTCTGGGGGAGGCTTGGTACAGCCTGGGGGGTCCCTGAGACT

CTCCTGTGCAGCCTCTGGATTCACCTTTAGCAGCTATGCCATGAGCTGGGTCCGCCAGGC

TCCAGGGAAGGGGCTGGAGTGGGTCTCAGCAATTAGTGGTAGTGGTGGAAGTACACACT

ACGCAGACTCCGTGAAGGGCCGGTTCACCATCTCCAGAGACAATTCCAAGAACACGCTG

TATCTGCAAATGAACAGCCTGAGAGCCGAGGACACGGCCGTATATTACTGTGCGAAAGA

TCTCAACTGGGGAGCTTTTGATATCTGGGGCCAAGGGACAATGGTCACCGTCTCTTCA (SEQ ID NO: 334)

H21 Protein
EVQLLESGGGLVQPGGSLRLSCAASGFTFSSYAMSWVRQAPGKGLEWVSAISGSGGSTHYA

DSVKGRFTISRDNSKNTLYLQMNSLRAEDTAVYYCAKDLNWGAFDIWGQGTMVTVSS (SEQ ID NO: 335)

TABLE 2-continued

L21 DNA
CAGTCTGTGCTGACGCAGCCGCCCTCAGTGTCTGGGGCCCCAGGGCAGAGGGTCACCAT
CTCCTGCACTGGGAGCAGCTCCAACATTGGGGCGGGTTATGTTGTACATTGGTACCAGCA
GCTTCCAGGAACAGCCCCCAAACTCCTCATCTATGGTAACAGCAATCGGCCCTCAGGGGT
CCCTGACCAATTCTCTGGCTCCAAGTCTGGCACCTCAGCCTCCCTGGCCATCACTGGACT
CCAGTCTGAGGATGAGGCTGATTATTACTGCAAAGCATGGGATAACAGCCTGAATGCTC
AAGGGGTATTTCGGCGGAGGGACCAAGCTGACCGTCCTA (SEQ ID NO: 336)

L21 Protein
QSVLTQPPSVSGAPGQRVTISCTGSSSNIGAGYVVHWYQQLPGTAPKLLIYGNSNRPSGVPDQ
FSGSKSGTSASLAITGLQSEDEADYYCKAWDNSLNAQGVFGGGTKLTVL (SEQ ID NO: 337)

H22 DNA
GAGGTGCAGCTGTTGGAGTCTGGGGGAGGCTTGGCACAGCCGGGGGGGTCCCTGAGACT
CTCCTGTGCAGGCTCTGGATTCTCCTTTAGAGGCTATGTCATGACTTGGGTCCGCCAGGCT
CCAGGGAAGGGGCTGGAGTGGGTCTCAGGAATTAGTGGTAGTGGTGGTAGCACATACTA
CGCAGACTCCGTGAAGGGCCGGTTCACCATCTCCAGAGACAATTCCAAGAACACGCTGT
GTCTGCAAATGAACAGCCTGAGAGCCGAGGACACGGCCGTATATTACTGTGCGAAAGGA
GACAGCTCGAACTACTACTCCGGTATGGACGTCTGGGGCCAAGGGACCACGGTCATCGT
CTCCTCA (SEQ ID NO: 338)

H22 Protein
EVQLLESGGGLAQPGGSLRLSCAGSGFSFRGYVMTWVRQAPGKGLEWVSGISGSGGSTYYA
DVSKGRFTISRDNSKNTLCLQMNSLRAEDTAVYYCAKGDSSNYYSGMDVWGQGTTVIVSS (SEQ ID NO: 339)

L22 DNA
GACATCGTGATGACCCAGTCTCCAGACTCCCTGGCTGTGTCTCTGGGCGAGAGGGCCACC
ATCAACTGCAAGTCCAGCCAGAGTGTTTTATACAACTCCAACAATAAGAACTACTTAGCT
TGGTACCAGCAGAAACCAGGACAGCCTCCTAAGCTGCTCATTTACTGGGCTTCTACCCGG
GAATCCGGGGTCCCTGACCGATTCAGTGGCAGCGGGTCTGGGACAGATTTCACTCTCACC
ATCAGCAGCCTGCAGGCTGAGGATGTGGCAATTTATTACTGTCAGCAATTTTATGGTCCT
CCTCTCACTTTTCGGCGGAGGGACCAAGGTGGAAATCAAA (SEQ ID NO: 340)

L22 Protein
DIVMTQSPDSLAVSLGERATINCKSSQSVLYNSNNKNYLAWYQQKPGQPPKLLIYWASTRES
GVPDRFSGSGSGTDFTLTISSLQAEDVAIYYCQQFYGPPLTFGGGTKVEIK (SEQ ID NO: 341)

TABLE 2-continued

H23 DNA
CAGGTGCAGCTGGTGCAGTCTGGGGCTGAGGTGAAGAAGCCTGGGGCCTCAGTGAAGGT
CTCCTGCAAGGCTTCTGGATACACCTTCACCGGCTACTATATGCACTGGGTGCGACAGGC
CCCTGGACAAGGGCTTGAGTGGATGGGATGGATCAACCCTAACAATGGTGGCACAAACT
ATGGACAGAAGTTTCAGGGCAGGGTCACCATGACCAGGGACACGTCCATCAGCACAGCC
TACATGGAGCTGAGCAGGCTGAGATCTGACGACACGGCCGTGTATTACTGTGCGAGAGG
GAACTGGAACGACGATGCTTTTGATATCTGGGGCCAAGGGACAATGGTCACCGTCTCTTC
A (SEQ ID NO: 342)

H23 Protein
QVQLVQSGAEVKKPGASVKVSCKASGYTFTGYYMHWVRQAPGQGLEWMGWINPNNGGTN
YGQKFQGRVTMTRDTSISTAYMELSRLRSDDTAVYYCARGNWNDDAFDIWGQGTMVTVSS (SEQ ID NO: 343)

L23 DNA
TCCTATGAGCTGACTCAGTCACCCTCAGTGTCCGTGTCCCCAGGACAGACAGCCAGCATC
ACCTGTTCTGGTGATAAATTGGGGGATAAATTTGCTTTCTGGTATCAGCAGAAGCCAGGC
CAGTCCCCTGTGCTGGTCATCTATCAAGATAGCAAGCGGCCCTCAGGGATCCCTGAGCGA
TTCTCTGGCTCCAACTCTGGGAACACAGCCACTCTGACCATCAGCGGGACCCAGGCTATG
GATGAGGCTGACTATTACTGTCAGGCGTGGGACAGCAGCGCCGGGGGGGTATTTCGGCG
GAGGGACCAAGTTGACCGTCCTA (SEQ ID NO: 344)

L23 Protein
SYELTQSPSVSVSPGQTASITCSGDKLGDKFAFWYQQKPGQSPVLVIYQDSKRPSGIPERFSGS
NSGNTATLTISGTQAMDEADYYCQAWDSSAGGVFGGGTKLTVL (SEQ ID NO: 345)

H24 DNA
CAGGTGCAACTGGAGGAGTCTGGGGGAGGCGTGGTCCAGCCTGGGAGGTCCCTGAGACT
CTCCTGTGCAGCGTCTGGATTCACCTTCAGTAGCTATGGCATGCACTGGGTCCGCCAGGC
TCCAGGCAAGGGGCTGGAGTGGGTGGCAGTTATATGGTATGATGGAAGTAATAAATACT
ATGTAGACTCCGTGAAGGGCCGATTCACCATCTCCAGAGACAATTCCAAGAACACGCTG
TATCTGCAAATGAACAGCCTGAGAGCCGAGGACACGGCTGTGTATTACTGTGCGAGAAT
GGGGTTTACTATGGTTCGGGGAGCCCTCTACTACGGTATGGACGTCTGGGGCCAAGGGA
CCACGGTCACCGTCTCCTCA (SEQ ID NO: 346)

H24 Protein
QVQLEESGGGVVQPGRSLRLSCAASGFTFSSYGMHWVRQAPGKGLEWVAVIWYDGSNKYY
VDSVKGRFTISRDNSKNTLYLQMNSLRAEDTAVYYCARMGFTMVRGALYYGMDVWGQT
TVTVSS (SEQ ID NO: 347)

TABLE 2-continued

L24 DNA
TCTTCTGAGCTGACTCAGGACCCTGCTGTGTCTGTGGCCTTGGGACAGACAGTCAGGATC
ACATGCCAAGGAGACAGCCTCAGAAGCTATCATGCAAGCTGGTACCAGCAGAAGCCAGG
ACAGGCCCCTGTACTTGTCATCTATGGTGAAAACAACCGGCCCTCAGGGATCCCAGACCG
ATTCTCTGACTCCAGTTCAGGAAACACAGCTTCCTTGACCATCACTGGGGCTCAGGCGGA
AGATGAGGCTGACTATTATTGTAATTATCGGGACAACAGTGGTAACCATCTGGTGTTTCG
GCGGAGGGACCAAGCTGACCGTCCTA (SEQ ID NO: 348)

L24 Protein
SSELTQDPAVSVALGQTVRITCQGDSLRSYHASWYQQKPGQAPVLVIYGENNRPSGIPDRFSD
SSSGNTASLTITGAQAEDEADYYCNYRDNSGNHLVFGGGTKLTVL (SEQ ID NO: 349)

H25 DNA
GAGGTGCAGCTGTTGGAATCTGGGGGAGGCTTGGTACAGCCTGGGGGGTCCCTGAGACT
CTCCTGTGCAGCCTCTGGATTCACCTTTAGCAGCTATGCCATGAGCTGGGTCCGCCAGGC
TCCAGGGAAGGGGCTGGAGTGGGTCTCAGCTATTAGTCGTAGTGGTAGTACCACATACT
ACGCAGACTCCGTGAAGGGCCGGTTCACCATCTCCAGAGACAATTCCAAGAACACGCTG
TATCTGCAAATGAACAGCCTGAGAGCCGAGGACACGGCCGTATATTACTGTGTGGAACC
GAGATATTTTGACTGGTTATTAGGCGACTGGGGCCAGGGAACCCTGGTCACCGTCTCCTC
A (SEQ ID NO: 350)

H25 Protein
EVQLLESGGGLVQPGGSLRLSCAASGFTFSSYAMSWVRQAPGKGLEWVSAISRSGSTTYYAD
SVKGRFTISRDNSKNTLYLQMNSLRAEDTAVYYCVEPRYFDWLLGDWGQGTLVTVSS (SEQ ID NO: 351)

L25 DNA
GACATCGTGATGACCCAGTCTCCAGACTCCCTGGCTGTGTCTCTGGGCGAGAGGGCCACC
ATCAACTGCAAGTCCAGCCAGAGTGTTTTATACAACTCCAACAATAAGAACTACTTAGCT
TGGTACCAGCAGAAACCAGGACAGCCTCCTAAGCTGCTCATTTACTGGGCTTCTACCCGGG
GAATCCGGGGTCCCTGACCGATTCAGTGGCAGCGGGTCTGGGACAGATTTCACTCTCACC
ATCAGCAGCCTGCAGGCTGAGGATGTGGCAATTTATTACTGTCAGCAATTTTATGGTCCT
CCTCTCACTTTTCGGCGGAGGGACCAAGGTGGAAATCAAA (SEQ ID NO: 340)

L25 Protein
DIVMTQSPDSLAVSLGERATINCKSSQSVLYNSNNKNYLAWYQQKPGQPPKLLIYWASTRES
GVPDRFSGSGSGTDFTLTISSLQAEDVAIYYCQQFYGPPLTFGGGTKVEIK (SEQ ID NO: 341)

TABLE 2-continued

H26 DNA
CAGGTGCAGCTGGTGGAGTCGGGGGGAGGCGTGGTCCAGCCTGGGAGGTCCCTGAGACT
CTCCTGTGCAGCGTCTGGATTCACCTTCAGTAGCTATGGCATGCACTGGGTCCGCCAGGC
TCCAGGCAAGGGGCTGGAGTGGGTGGCAGTTAAATGGTATGAAGGAAGTAATAAATACT
ATGGAGACTCCGTGAAGGGCCGATTCACCATCTCCAGAGACAATTCCAAGAACACGCTG
TATTTGCAAATGAACAGTCTGAGAGGCGAGGATACGGCTGTGTATTACTGTGCGAGAGG
CGCCCACGACTACGGTGACTTCTACTACGGTATGGACGTCTGGGGCCAAGGGACCACGG
TCACCGTCTCCTCA (SEQ ID NO: 352)

H26 Protein
QVQLVESGGGVVQPGRSLRLSCAASGFTFSSYGMHWVRQAPGKGLEWVAVKWYEGSNKY
YGDSVKGRFTISRDNSKNTLYLQMNSLRGEDTAVYYCARGAHDYGDFYYGMDVWGQGTT
VTVSS (SEQ ID NO: 353)

L26 DNA
TCCTATGAACTGACTCAGCCAGCCTCAGTGTCCGTGTCCCCAGGACAGATAGCCAGCATC
ACCTGCTCTGGAGATAATTTGGGGGATAAATATATTTGCTGGTATCAGCAGAAGCCAGGC
CAGTCCCCTGTGCGGGTCATCTATCAAGATAACAAGCGGCCCTCAGGGATCCCTGAGCGT
TTCTCTGGCTCCAATTCTGGGAACACAGCCACTCTGACCATCAGCGGGACCCAGGCTATG
GATGAGGCTGACTATTACTGTCAGGCGTGGGACAGCAGCACTGTGGTATTTCGGCGGAG
GGACCAAGCTGACCGTCCTA (SEQ ID NO: 354)

L26 Protein
SYELTQPASVSVSPGQIASITCSGDNLGDKYICWYQQKPGQSPVRVIYQDNKRPSGIPERFSGS
NSGNTATLTISGTQAMDEADYYCQAWDSSTVVFGGGTKLTVL (SEQ ID NO: 355)

H27 DNA
GAGGTGCAGCTGTTGGAGTCTGGGGGAGGCTTGGTACAGCCTGGGGGGTCCCTGAGACT
CTCCTGTGCAGCCTCTGGATTCACCTTTAGCAGCTATGCCATGAGCTGGGTCCGCCAGGC
TCCAGGGAAGGGGCTGGAGTGGGTCTCAGCTATTAGTTATAGTGGCGGTAGCACATACT
ACGCAGGCTCCGTGAAGGGCCGGTTCACCATCTCCAGAGACAATTCCAAGAACACGCTG
TATCTGCAAATGAACAGCCTGAGAGCCGAGGACACGGCCGTATATTACTGTGCGAAAGA
TCGGGAGGGAGCGACTTGGTACTACGGTATGGACGTCTGGGGCCAAGGGACCACGGTCA
CCGTCTCCTCA (SEQ ID NO: 356)

H27 Protein
EVQLLESGGGLVQPGGSLRLSCAASGFTFSSYAMSWVRQAPGKGLEWVSAISYSGGSTYYA
GSVKGRFTISRDNSKNTLYLQMNSLRAEDTAVYYCAKDREGATWYYGMDVWGQGTTVTV
SS (SEQ ID NO: 357)

TABLE 2-continued

L27 DNA
TCCTATGAACTGACTCAGCCACCCTCAGTGTCCGTGTCCCCAGGACAGACAGCCAGCATC

ACCTGCTCTGGAGATAAATTGGGGGAAAGCTATGCTTGCTGGTATCAGCAGAAGCCAGG

CCAGTCCCCTGTACTGGTCATCTATCAAGATTACAAGCGGCCCTCAGGGATCCCTGAGCG

CTTCTCTGGCTCCAACTCTGGGAACACAGCCACTCTGACCATCAGCGGGACCCAGGCTAT

GGATGAGGCTGACTATTACTGTCAGGCGTGGGACAGAAGTACTGTACTATTTCGGCGGA

GGGACCAAGCTGACCGTCCTA (SEQ ID NO: 358)

L27 Protein
SYELTQPPSVSVSPGQTASITCSGDKLGESYACWYQQKPGQSPVLVIYQDYKRPSGIPERFSGS

NSGNTATLTISGTQAMDEADYYCQAWDRSTVLFGGGTKLTVL (SEQ ID NO: 359)

Particular embodiments of antigen binding proteins of the present invention comprise one or more amino acid sequences that are identical to the amino acid sequences of one or more of the CDRs and may further comprise one or more FRs illustrated above. In one embodiment, the antigen binding protein comprises a light chain CDR1 sequence illustrated above. In another embodiment, the antigen binding protein comprises a light chain CDR2 sequence illustrated above. In another embodiment, the antigen binding protein comprises a light chain CDR3 sequence illustrated above. In another embodiment, the antigen binding protein comprises a heavy chain CDR1 sequence illustrated in above. In another embodiment, the antigen binding protein comprises a heavy chain CDR2 sequence illustrated above. In another embodiment, the antigen binding protein comprises a heavy chain CDR3 sequence illustrated above. In another embodiment, the antigen binding protein further comprises a light chain FR1 sequence illustrated above. In another embodiment, the antigen binding protein further comprises a light chain FR2 sequence illustrated above. In another embodiment, the antigen binding protein further comprises a light chain FR3 sequence illustrated above. In another embodiment, the antigen binding protein further comprises a light chain FR4 sequence illustrated above. In another embodiment, the antigen binding protein further comprises a heavy chain FR1 sequence illustrated above. In another embodiment, the antigen binding protein further comprises a heavy chain FR2 sequence illustrated above. In another embodiment, the antigen binding protein further comprises a heavy chain FR3 sequence illustrated above. In another embodiment, the antigen binding protein further comprises a heavy chain FR4 sequence illustrated above.

In one embodiment, the present disclosure provides an antigen binding protein comprising a light chain variable domain comprising a sequence of amino acids that differs from the sequence of a light chain variable domain selected from the group consisting of L1 through L27 only at 15, 14, 13, 12, 11, 10, 9, 8, 7, 6, 5, 4, 3, 2, 1 or 0 residues, wherein each such sequence difference is independently either a deletion, insertion, or substitution of one amino acid residue. In another embodiment, the light-chain variable domain comprises a sequence of amino acids that is at least 70%, 75%, 80%, 85%, 90%, 95%, 97%, or 99% identical to the sequence of a light chain variable domain selected from the group consisting of L1-L27. In another embodiment, the light chain variable domain comprises a sequence of amino acids that is encoded by a nucleotide sequence that is at least 70%, 75%, 80%, 85%, 90%, 95%, 97%, or 99% identical to a nucleotide sequence that encodes a light chain variable domain selected from the group consisting of L1-L27. In another embodiment, the light chain variable domain comprises a sequence of amino acids that is encoded by a polynucleotide that hybridizes under moderately stringent conditions to the complement of a polynucleotide that encodes a light chain variable domain selected from the group consisting of L1-L27. In another embodiment, the light chain variable domain comprises a sequence of amino acids that is encoded by a polynucleotide that hybridizes under highly stringent conditions to a complement of a light chain polynucleotide of L1-L27.

In another embodiment, the present invention provides an antigen binding protein comprising a heavy chain variable domain comprising a sequence of amino acids that differs from the sequence of a heavy chain variable domain selected from the group consisting of H1-H27 only at 15, 14, 13, 12, 11, 10, 9, 8, 7, 6, 5, 4, 3, 2, 1 or 0 residue(s), wherein each such sequence difference is independently either a deletion, insertion, or substitution of one amino acid residue. In another embodiment, the heavy chain variable domain comprises a sequence of amino acids that is at least 70%, 75%, 80%, 85%, 90%, 95%, 97%, or 99% identical to the sequence of a heavy chain variable domain selected from the group consisting of H1-H27. In another embodiment, the heavy chain variable domain comprises a sequence of amino acids that is encoded by a nucleotide sequence that is at least 70%, 75%, 80%, 85%, 90%, 95%, 97%, or 99% identical to a nucleotide sequence that encodes a heavy chain variable domain selected from the group consisting of H1-H27. In another embodiment, the heavy chain variable domain comprises a sequence of amino acids that is encoded by a polynucleotide that hybridizes under moderately stringent conditions to the complement of a polynucleotide that encodes a heavy chain variable domain selected from the group consisting of H1-H27. In another embodiment, the heavy chain variable domain comprises a sequence of amino acids that is encoded by a polynucleotide that hybridizes under highly stringent conditions to the complement of a polynucleotide that encodes a heavy chain variable domain selected from the group consisting of H1-H27.

In some of the embodiments provided in Table 2 above, two light chains are associated with a single heavy chain, identified, for example as L-12.1, L-12.2, etc. These alternative light chains are each paired with a single heavy chain. In these embodiments, light chain and heavy chain combination may be assayed as described below and the combination of light chain and heavy chain that provides the greater TSLP neutralizing activity may be selected.

Additional embodiments include antigen binding proteins comprising the combinations L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, and L27H27.

Antigen binding proteins (e.g., antibodies, antibody fragments, and antibody derivatives) of the invention can further comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

In one embodiment, the antigen binding proteins comprise an IgG, such as IgG1, IgG2, IgG3, or IgG4.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lantto et al., 2002, Methods Mol. Biol. 178:303-16.

In one embodiment, an antigen binding protein of the invention comprises the IgG1 heavy chain constant domain or a fragment of the IgG1 heavy chain domain. In one embodiment, an antigen binding protein of the invention further comprises the constant light chain kappa or lambda domains or a fragment of these. Light chain constant regions and polynucleotides encoding them are provided in Table 3 below. In another embodiment, an antigen binding protein of the invention further comprises a heavy chain constant domain, or a fragment thereof, such as the IgG2 heavy chain constant region shown below in Table 3.

The nucleic acid (DNA) encoding constant heavy and constant light chain domains, and the amino acids sequences of heavy and light chain domains are provided below. Lambda variable domains can be fused to lambda constant domains and kappa variable domains can be fused to kappa constant domains.

TABLE 3

IgG2 Heavy Constant domain DNA
(SEQ ID NO: 364)
gctagcaccaagggcccatcggtcttccccctggcgccctgctccag
gagcacctccgagagcacagcggccctgggctgcctggtcaaggact
acttccccgaaccggtgacggtgtcgtggaactcaggcgctctgacc TABLE 3-continued agcggcgtgcacaccttcccagctgtcctacagtcctcaggactcta
ctccctcagcagcgtggtgaccgtgccctccagcaacttcggcaccc
agacctacacctgcaacgtagatcacaagcccagcaacaccaaggtg
gacaagacagttgagcgcaaatgttgtgtcgagtgcccaccgtgccc
agcaccacctgtggcaggaccgtcagtcttcctcttcccccccaaaac
ccaaggacaccctcatgatctcccggacccctgaggtcacgtgcgtg
gtggtggacgtgagccacgaagaccccgaggtccagttcaactggta
cgtggacggcgtggaggtgcataatgccaagacaaagccacgggagg
agcagttcaacagcacgttccgtgtggtcagcgtcctcaccgttgtg
caccaggactggctgaacggcaaggagtacaagtgcaaggtctccaa
caaaggcctcccagccccatcgagaaaaccatctccaaaaccaaag
ggcagccccgagaaccacaggtgtacaccctgcccccatcccgggag
gagatgaccaagaaccaggtcagcctgacctgcctggtcaaaggctt
ctaccccagcgacatcgccgtggagtgggagagcaatgggcagccgg
agaacaactacaagaccacacctcccatgctggactccgacggctcc
ttcttcctctacagcaagctcaccgtggacaagagcaggtggcagca
ggggaacgtcttctcatgctccgtgatgcatgaggctctgcacaacc
actacacgcagaagagcctctccctgtctccgggtaaatga IgG2 Heavy Constant domain Protein
(SEQ ID NO: 365)
ASTKGPSVFPLAPCSRSTSESTAALGCLVKDYFPEPVTVSWNSGALT
SGVHTFPAVLQSSGLYSLSSVVTVPSSNFGTQTYTCNVDHKPSNTKV
DKTVERKCCVECPPCPAPPVAGPSVFLFPPKPKDTLMISRTPEVTCV
VVDVSHEDPEVQFNWYVDGVEVHNAKTKPREEQFNSTFRVVSVLTVV
HQDWLNGKEYKCKVSNKGLPAPIEKTISKTKGQPREPQVYTLPPSRE
EMTKNQVSLTCLVKGFYPSDIAVEWESNGQPENNYKTTPPMLDSDGS
FFLYSKLTVDKSRWQQGNVFSCSVMHEALHNHYTQKSLSLSPGK*

Kappa Light Constant domain DNA
(SEQ ID NO: 366)
cgtacggtggctgcaccatctgtcttcatcttcccgccatctgatga
gcagttgaaatctggaactgcctctgttgtgtgcctgctgaataact
tctatcccagagaggccaaagtacagtggaaggtggataacgcctc
caatcgggtaactcccaggagagtgtcacagagcaggacagcaagga
cagcacctacagcctcagcagcaccctgacgctgagcaaagcagact
acgagaaacacaaagtctacgcctgcgaagtcacccatcagggcctg
agctcgcccgtcacaaagagcttcaacaggggagagtgttag Kappa Light Constant domain Protein
(SEQ ID NO: 367)
RTVAAPSVFIFPPSDEQLKSGTASVVCLLNNFYPREAKVQWKVEDNA
LQSGNSQESVTEQDSKDSTYSLSSTLTLSKADYEKHKVYACEVTHQG
LSSPVTKSFNRGEC*

Lambda Light Constant domain DNA
(SEQ ID NO: 368)
ggccaaccgaaagcggcgccctcggtcactctgttcccgccctcctc
tgaggagcttcaagccaacaaggccacactggtgtgtctcataagtg
acttctacccgggagccgtgacagtggcctggaaggcagatagcagc
cccgtcaaggcgggagtggagaccaccacaccctccaaacaaagcaa
caacaagtacgcggccagcagctatctgagcctgacgcctgagcagt
ggaagtcccacagaagctacagctgccaggtcacgcatgaagggagc
accgtggagaagacagtggcccctacagaatgttcatag Lambda Light Constant domain Protein
(SEQ ID NO: 369)
GQPKAAPSVTLFPPSSEELQANKATLVCLISDFYPGAVTVAWKADSS
PVKAGVETTTPSKQSNNKYAASSYLSLTPEQWKSHRSYSCQVTHEGS
TVEKTVAPTECS*

The antigen binding proteins of the present invention include those comprising, for example, the variable domain combinations L1H1, L2H2, L3H3, L4H4, L5H5, L6H6, L7H7, L8H8, L9H9, L10H10, L11H11, L12H12, L13.1H13, L13.2H13, L14.1H14, L14.2H14, L15.1H15, L15.2H15, L16.1H16, L16.2H16, L17H17, L18.1H18, L18.2H18, L19.1H19, L19.2H19, L20.1H20, L20.2H20, L21H21, L22H22, L23H23, L24H24, L25H25, L26H26, and L27H27, having a desired isotype (for example, IgA, IgG1, IgG2, IgG3, IgG4, IgM, IgE, and IgD) as well as Fab or F(ab')$_2$ fragments thereof. Moreover, if an IgG4 is desired, it may also be desired to introduce a point mutation in the hinge region as described in Bloom et al., 1997, Protein Science 6:407 (incorporated by reference herein) to alleviate a tendency to form intra-H chain disulfide bonds that can lead to heterogeneity in the IgG4 antibodies.

Antibodies and Antibody Fragments

As used herein, the term "antibody" refers to an intact antibody, or an antigen binding fragment thereof, as described in the definition section herein. An antibody may comprise a complete antibody molecule (including polyclonal, monoclonal, chimeric, humanized, or human versions having full length heavy and/or light chains), or comprise an antigen binding fragment thereof. Antibody fragments include F(ab')$_2$, Fab, Fab', Fv, Fc, and Fd fragments, and can be incorporated into single domain antibodies, monovalent antibodies, single-chain antibodies, maxibodies, minibodies, intrabodies, diabodies, triabodies, tetrabodies, v-NAR and bis-scFv (See e.g., Hollinger and Hudson, 2005, Nature Biotechnology, 23, 9, 1126-1136). Antibody polypeptides are also disclosed in U.S. Pat. No. 6,703,199, including fibronectin polypeptide monobodies. Other antibody polypeptides are disclosed in U.S. Patent Publication 2005/0238646, which are single-chain polypeptides. Monovalent antibody fragments are disclosed in U.S. Patent Publication 20050227324.

Antigen binding fragments derived from an antibody can be obtained, for example, by proteolytic hydrolysis of the antibody, for example, pepsin or papain digestion of whole antibodies according to conventional methods. By way of example, antibody fragments can be produced by enzymatic cleavage of antibodies with pepsin to provide a 5 S fragment termed F(ab')$_2$. This fragment can be further cleaved using a thiol reducing agent to produce 3.5 S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoff et al., Arch. Biochem. Biophys. 89:230, 1960; Porter, Biochem. J. 73:119, 1959; Edelman et al., in Methods in Enzymology 1:422 (Academic Press 1967); and by Andrews, S. M. and Titus, J. A. in Current Protocols in Immunology (Coligan J. E., et al., eds), John Wiley & Sons, New York (2003), pages 2.8.1-2.8.10 and 2.10A.1-2.10A.5. Other methods for cleaving antibodies, such as separating heavy chains to form monovalent light-heavy chain fragments (Fd), further cleaving of fragments, or other enzymatic, chemical, or genetic techniques may also be used, so long as the fragments bind to the antigen that is recognized by the intact antibody.

An antibody fragment may also be any synthetic or genetically engineered protein. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker (scFv proteins).

Another form of an antibody fragment is a peptide comprising one or more complementarity determining regions (CDRs) of an antibody. CDRs (also termed "minimal recognition units", or "hypervariable region") can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., Methods: A Companion to Methods in Enzymology 2:106, 1991; Courtenay-Luck, "Genetic Manipulation of Monoclonal Antibodies," in Monoclonal Antibodies: Production, Engineering and Clinical Application, Ritter et al. (eds.), page 166 (Cambridge University Press 1995); and Ward et al., "Genetic Manipulation and Expression of Antibodies," in Monoclonal Antibodies: Principles and Applications, Birch et al., (eds.), page 137 (Wiley-Liss, Inc. 1995)).

Thus, in one embodiment, the binding agent comprises at least one CDR as described herein. The binding agent may comprise at least two, three, four, five or six CDR's as described herein. The binding agent further may comprise at least one variable region domain of an antibody described herein. The variable region domain may be of any size or amino acid composition and will generally comprise at least one CDR sequence responsible for binding to TSLP, for example heavy chain CDR1, CDR2, CDR3 and/or the light chain CDRs specifically described herein and which is adjacent to or in frame with one or more framework sequences. In general terms, the variable (V) region domain may be any suitable arrangement of immunoglobulin heavy ($V_H$) and/or light ($V_L$) chain variable domains. Thus, for example, the V region domain may be monomeric and be a $V_H$ or $V_L$ domain, which is capable of independently binding human TSLP with an affinity at least equal to $1 \times 10^{-7}$M or less as described below. Alternatively, the V region domain may be dimeric and contain $V_H$-$V_H$, $V_H$-$V_L$, or $V_L$-$V_L$, dimers. The V region dimer comprises at least one $V_H$ and at least one $V_L$ chain that may be non-covalently associated (hereinafter referred to as $F_v$). If desired, the chains may be covalently coupled either directly, for example via a disulfide bond between the two variable domains, or through a linker, for example a peptide linker, to form a single chain Fv (scF$_v$).

The variable region domain may be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly a $V_L$ domain may be linked to a $C_K$ domain or a fragment thereof. In this way, for example, the antibody may be a Fab fragment wherein the antigen binding domain contains associated $V_H$ and $V_L$ domains covalently linked at their C-termini to a CH1 and $C_K$ domain, respectively. The CH1 domain may be extended with further amino acids, for example to provide a hinge region or a portion of a hinge region domain as found in a Fab' fragment, or to provide further domains, such as antibody CH2 and CH3 domains.

Derivatives of Antigen Binding Proteins

The nucleotide sequences shown in FIG. 1A-1F, FIG. 2A-2F, and Table 2 above can be altered, for example, by random mutagenesis or by site-directed mutagenesis (e.g., oligonucleotide-directed site-specific mutagenesis) to create an altered polynucleotide comprising one or more particular nucleotide substitutions, deletions, or insertions as compared to the non-mutated polynucleotide. Examples of techniques for making such alterations are described in Walder et al., 1986, Gene 42:133; Bauer et al. 1985, Gene 37:73; Craik, BioTechniques, January 1985, 12-19; Smith et al., 1981, Genetic Engineering: Principles and Methods, Plenum Press; and U.S. Pat. Nos. 4,518,584 and 4,737,462. These and other methods can be used to make, for example, derivatives of TSLP antigen binding proteins that have a desired property, for example, increased affinity, avidity, or specificity for TSLP, increased activity or stability in vivo or in vitro, or reduced in vivo side-effects as compared to the underivatized antigen binding proteins.

Other derivatives of anti-TSLP antigen binding proteins including antibodies within the scope of this invention include covalent or aggregative conjugates of anti-TSLP antibodies, or fragments thereof, with other proteins or polypeptides, such as by expression of recombinant fusion proteins comprising heterologous polypeptides fused to the N-terminus or C-terminus of an anti-TSLP antibody polypeptide. For example, the conjugated peptide may be a heterologous signal (or leader) polypeptide, e.g., the yeast alpha-factor leader, or a peptide such as an epitope tag. Antigen binding protein-containing fusion proteins can comprise peptides added to facilitate purification or identification of antigen binding protein (e.g., poly-His). An antigen binding protein also can be linked to the FLAG peptide as described in Hopp et al., Bio/Technology 6:1204, 1988, and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Oligomers that contain one or more antigen binding proteins may be employed as TSLP antagonists. Oligomers may be in the form of covalently-linked or non-covalently-linked dimers, trimers, or higher oligomers. Oligomers comprising two or more antigen binding proteins are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins capable of binding to TSLP. The antigen binding proteins of the oligomer may be in any form, such as any of the forms described above, e.g., variants or fragments.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins", in Current Protocols in Immunology, Suppl. 4, pages 10.19.1-10.19.11.

One embodiment of the present invention is directed to a dimer comprising two fusion proteins created by fusing a fragment of an anti-TSLP antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of an anti-TSLP antibody may be substituted for the variable portion of an antibody heavy and/or light chain.

Alternatively, the oligomer is a fusion protein comprising multiple antigen binding proteins, with or without peptide linkers (spacer peptides). Among the suitable peptide linkers are those described in U.S. Pat. Nos. 4,751,180 and 4,935,233.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising an anti-TSLP antibody fragment or derivative fused to a leucine zipper peptide are expressed in suitable host cells, and the soluble oligomeric anti-TSLP antibody fragments or derivatives that form are recovered from the culture supernatant.

As described herein, antibodies comprise at least one CDR. For example, one or more CDR may be incorporated into known antibody framework regions (IgG1, IgG2, etc.), or conjugated to a suitable vehicle to enhance the half-life thereof. Suitable vehicles include, but are not limited to Fc, polyethylene glycol (PEG), albumin, transferrin, and the like. These and other suitable vehicles are known in the art. Such conjugated CDR peptides may be in monomeric, dimeric, tetrameric, or other form. In one embodiment, one or more water-soluble polymer is bonded at one or more specific position, for example at the amino terminus, of a binding agent.

In certain preferred embodiments, an antibody comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative binding agent comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

It will be appreciated that an antibody of the present invention may have at least one amino acid substitution, deletion, or addition, providing that the antibody retains binding specificity. Therefore, modifications to the antibody structures are encompassed within the scope of the invention. These may include amino acid substitutions, which may be conservative or non-conservative, that do not destroy the human TSLP binding capability of an antibody. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution may also involve a substitution of a native amino acid residue with a normative residue such that there is little or no effect on the polarity or charge of the amino acid residue at that position.

Non-conservative substitutions may involve the exchange of a member of one class of amino acids or amino acid mimetics for a member from another class with different physical properties (e.g. size, polarity, hydrophobicity, charge). Such substituted residues may be introduced into regions of the human antibody that are homologous with non-human antibodies, or into the non-homologous regions of the molecule.

Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Cuff. Opin. Struct. Biol., 7(3): 377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-4358 (1987)), and "evolutionary linkage" (See Holm, supra (1999), and Brenner, supra (1997)).

It will be understood by one skilled in the art that some proteins, such as antibodies, may undergo a variety of post-translational modifications. The type and extent of these modifications often depends on the host cell line used to express the protein as well as the culture conditions. Such modifications may include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in Harris, R. J. Journal of Chromatography 705:129-134, 1995).

In certain embodiments, variants of antibodies include glycosylation variants wherein the number and/or type of glycosylation site has been altered compared to the amino acid sequences of a parent polypeptide. In certain embodiments, variants comprise a greater or a lesser number of N-linked glycosylation sites than the native protein. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Desired amino acid substitutions (whether conservative or non-conservative) can be determined by those skilled in the art at the time such substitutions are desired. In certain embodiments, amino acid substitutions can be used to identify important residues of antibodies to human TSLP, or to increase or decrease the affinity of the antibodies to human TSLP described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

In certain embodiments, antibodies of the invention may be chemically bonded with polymers, lipids, or other moieties.

In addition, the antigen binding proteins may comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LAC1-D1, Z domain and tendamistat domains may be used (See e.g., Nygren and Uhlen, 1997, Current Opinion in Structural Biology, 7, 463-469).

Additionally, in another embodiment, one skilled in the art will recognize that the antigen binding proteins can include one or more of heavy chain CDR1, CDR2, CDR3, and/or light chain CDR1, CDR2 and CDR3 having one amino acid substitution, provided that the antibody retains the binding specificity of the non-substituted CDR. The non-CDR portion of the antibody may be a non-protein molecule, wherein the binding agent cross-blocks the binding of an antibody disclosed herein to human TSLP and/or inhibits TSLP activity. The non-CDR portion of the antibody may be a non-protein molecule in which the antibody exhibits a similar binding pattern to human TSLP proteins in a competition binding assay as that exhibited by at least one of antibodies A1-A27, and/or neutralizes the activity of TSLP. The non-CDR portion of the antibody may be composed of amino acids, wherein the antibody is a recombinant binding protein or a synthetic peptide, and the recombinant binding protein cross-blocks binding of an antibody disclosed herein to human TSLP and/or neutralizes TSLP in vitro or in vivo. The non-CDR portion of the antibody may be composed of amino acids, wherein the antibody is a recombinant antibody, and the recombinant antibody exhibits a similar binding pattern to human TSLP polypeptides in a competition binding assay as exhibited by at least one of the antibodies A1-A27, and/or neutralizes TSLP activity.

Methods of Making Antigen Binding Proteins, Specifically Antibodies.

An antigen binding protein such as an antibody comprising one or more of heavy chain CDR1, CDR2, CDR3, and/or light chain CDR1, CDR2 and CDR3 as described above, may be obtained by expression from a host cell containing DNA coding for these sequences. A DNA coding for each CDR sequence may be determined on the basis of the amino acid sequence of the CDR and synthesized together with any desired antibody variable region framework and constant region DNA sequences using oligonucleotide synthesis techniques, site-directed mutagenesis and polymerase chain reaction (PCR) techniques as appropriate. DNA coding for variable region frameworks and constant regions is widely available to those skilled in the art from genetic sequences databases such as GenBank®.

Additional embodiments include chimeric antibodies, e.g., humanized versions of non-human (e.g., murine) monoclonal antibodies. Such humanized antibodies may be prepared by known techniques, and offer the advantage of reduced immunogenicity when the antibodies are administered to humans. In one embodiment, a humanized monoclonal antibody comprises the variable domain of a murine antibody (or all or part of the antigen binding site thereof) and a constant domain derived from a human antibody. Alternatively, a humanized antibody fragment may comprise the antigen binding site of a murine monoclonal antibody and a variable domain fragment (lacking the antigen-binding site) derived from a human antibody. Procedures for the production of chimeric and further engineered monoclonal antibodies include those described in Riechmann et al., 1988, Nature 332:323, Liu et al., 1987, Proc. Nat. Acad. Sci. USA 84:3439, Larrick et al., 1989, Bio/Technology 7:934, and Winter et al., 1993, TIPS 14:139. In one embodiment, the chimeric antibody is a CDR grafted antibody. Techniques for humanizing antibodies are discussed in, e.g., U.S. Pat. Nos. 5,869,619, 5,225,539, 5,821,337, 5,859,205, 6,881,557, Padlan et al., 1995, FASEB J. 9:133-39, and Tamura et al., 2000, J. Immunol. 164:1432-41. Addition techniques for producing humanized antibodies such as those are described in Zhang, W., et al., Molecular Immunology. 42(12):1445-1451, 2005; Hwang W. et al., Methods. 36(1):35-42, 2005; Da11'Acqua W F, et al., Methods 36(1):43-60, 2005; and Clark, M., Immunology Today. 21(8):397-402, 2000).

Procedures have been developed for generating human or partially human antibodies in non-human animals. For example, mice in which one or more endogenous immunoglobulin genes have been inactivated by various means have been prepared. Human immunoglobulin genes have been introduced into the mice to replace the inactivated mouse genes. Antibodies produced in the animal incorporate human immunoglobulin polypeptide chains encoded by the human genetic material introduced into the animal. In one embodiment, a non-human animal, such as a transgenic mouse, is immunized with TSLP protein, for example, such that antibodies directed against various TSLP polypeptides are generated in the animal. Examples of suitable immunogens are provided in the Examples below.

Examples of techniques for production and use of transgenic animals for the production of human or partially human antibodies are described in U.S. Pat. Nos. 5,814,318, 5,569,825, and 5,545,806, Davis et al., 2003, Production of human antibodies from transgenic mice in Lo, ed. Antibody Engineering: Methods and Protocols, Humana Press, NJ:191-200, Kellermann et al., 2002, Curr Opin Biotechnol. 13:593-97, Russel et al., 2000, Infect Immun. 68:1820-26, Gallo et al., 2000, Eur J Immun 30:534-40, Davis et al., 1999, Cancer Metastasis Rev. 18:421-25, Green, 1999, J Immunol Methods. 231:11-23, Jakobovits, 1998, Advanced Drug Delivery Reviews 31:33-42, Green et al., 1998, J Exp Med. 188:483-95, Jakobovits A, 1998, Exp. Opin. Invest. Drugs. 7:607-14, Tsuda et al., 1997, Genomics. 42:413-21, Mendez et al., 1997, Nat. Genet. 15:146-56, Jakobovits, 1994, Curr Biol. 4:761-63, Arbones et al., 1994, Immunity. 1:247-60, Green et al., 1994, Nat. Genet. 7:13-21, Jakobovits et al., 1993, Nature. 362:255-58, Jakobovits et al., 1993, Proc Natl Acad Sci USA. 90:2551-55. Chen, J., M. Trounstine, F. W. Alt, F. Young, C. Kurahara, J. Loring, D. Huszar. "Immunoglobulin gene rearrangement in B-cell deficient mice generated by targeted deletion of the JH locus." International Immunology 5 (1993): 647-656, Choi et al., 1993, Nature Genetics 4: 117-23, Fishwild et al., 1996, Nature Biotechnology 14: 845-51, Harding et al., 1995, Annals of the New York Academy of Sciences, Lonberg et al., 1994, Nature 368: 856-59, Lonberg, 1994, Transgenic Approaches to Human Monoclonal Antibodies in Handbook of Experimental Pharmacology 113: 49-101, Lonberg et al., 1995, Internal Review of Immunology 13: 65-93, Neuberger, 1996, Nature Biotechnology 14: 826, Taylor et al., 1992, Nucleic Acids Research 20: 6287-95, Taylor et al., 1994, International Immunology 6: 579-91, Tomizuka et al., 1997, Nature Genetics 16: 133-43, Tomizuka et al., 2000, Proceedings of the National Academy of Sciences USA 97: 722-27, Tuaillon et al., 1993, Proceedings of the National Academy of Sciences USA 90: 3720-24, and Tuaillon et al., 1994, Journal of Immunology 152: 2912-20.

In another aspect, the present invention provides monoclonal antibodies that bind to human TSLP. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In one embodiment, a hybridoma cell line is produced by immunizing an animal (e.g., a transgenic animal having human immunoglobulin sequences) with a TSLP immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds a TSLP polypeptide. Such hybridoma cell lines, and TSLP monoclonal antibodies produced by them, are encompassed by the present invention.

Monoclonal antibodies secreted by a hybridoma cell line can be purified using any technique known in the art. Hybridomas or mAbs may be further screened to identify mAbs with particular properties, such as blocking a TSLP activity such as osteoprotegerin (OPG) production from primary human dendritic cells. Examples of such assays are provided in the examples below.

Molecular evolution of the complementarity determining regions (CDRs) in the center of the antibody binding site also has been used to isolate antibodies with increased affinity, for example, as described by Schier et al., 1996, J. Mol. Biol. 263:551. Accordingly, such techniques are useful in preparing antibodies to human TSLP.

Antigen binding proteins directed against human TSLP can be used, for example, in assays to detect the presence of TSLP either in vitro or in vivo.

Although human, partially human, or humanized antibodies will be suitable for many applications, particularly those involving administration of the antibody to a human subject, other types of antigen binding proteins will be suitable for certain applications. The non-human antibodies of the invention can be, for example, derived from any antibody-producing animal, such as mouse, rat, rabbit, goat, donkey, or non-human primate (such as monkey (e.g., cynomologus or rhesus monkey) or ape (e.g., chimpanzee)). Non-human antibodies of the invention can be used, for example, in in vitro and cell-culture based applications, or any other application where an immune response to the antibody of the invention does not occur, is insignificant, can be prevented, is not a concern, or is desired. In one embodiment, a non-human antibody of the invention is administered to a non-human subject. In another embodiment, the non-human antibody does not elicit an immune response in the non-human subject. In another embodiment, the non-human antibody is from the same species as the non-human subject, e.g., a mouse antibody of the invention is administered to a mouse. An antibody from a particular species can be made by, for example, immunizing an animal of that species with the desired immunogen or using an artificial system for generating antibodies of that species (e.g., a bacterial or phage display-based system for generating antibodies of a particular species), or by converting an antibody from one species into an antibody from another species by replacing, e.g., the constant region of the antibody with a constant region from the other species, or by replacing one or more amino acid residues of the antibody so that it more closely resembles the sequence of an antibody from the other species. In one embodiment, the antibody is a chimeric antibody comprising amino acid sequences derived from antibodies from two or more different species.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example E. coli or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, EMBO J. 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure is described in the Examples below. Polypeptides contemplated for use herein include substantially homogeneous recombinant mammalian anti-TSLP antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an TSLP antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol. Biol. 178:379-87. Single chain antibodies derived from antibodies provided herein include, but are not limited to, scFvs comprising the variable domain combinations L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, and L27H27 are encompassed by the present invention.

Once synthesized, the DNA encoding an antibody of the invention or fragment thereof may be propagated and expressed according to any of a variety of well-known procedures for nucleic acid excision, ligation, transformation, and transfection using any number of known expression vectors. Thus, in certain embodiments expression of an antibody fragment may be preferred in a prokaryotic host, such as Escherichia coli (see, e.g., Pluckthun et al., 1989 Methods Enzymol. 178:497-515). In certain other embodiments, expression of the antibody or a fragment thereof may be preferred in a eukaryotic host cell, including yeast (e.g., Saccharomyces cerevisiae, Schizosaccharomyces pombe, and Pichia pastoris), animal cells (including mammalian cells) or plant cells. Examples of suitable animal cells include, but are not limited to, myeloma (such as a mouse NSO line), COS, CHO, or hybridoma cells. Examples of plant cells include tobacco, corn, soybean, and rice cells. One or more replicable expression vectors containing DNA encoding an antibody variable and/or constant region may be prepared and used to transform an appropriate cell line, for example, a non-producing myeloma cell line, such as a mouse NSO line or a bacteria, such as E. coli, in which production of the antibody will occur. In order to obtain efficient transcription and translation, the DNA sequence in each vector should include appropriate regulatory sequences, particularly a promoter and leader sequence operatively linked to the variable domain sequence. Particular methods for producing antibodies in this way are generally well-known and routinely used. For example, basic molecular biology procedures are described by Maniatis et al. (Molecular Cloning, A Laboratory Manual, 2nd ed., Cold Spring Harbor Laboratory, New York, 1989; see also Maniatis et al, 3rd ed., Cold Spring Harbor Laboratory, New York, (2001)). DNA sequencing can be performed as described in Sanger et al. (PNAS 74:5463, (1977)) and the Amersham International plc sequencing handbook, and site directed mutagenesis can be carried out according to methods known in the art (Kramer et al., Nucleic Acids Res. 12:9441, (1984); Kunkel Proc. Natl. Acad. Sci. USA 82:488-92 (1985); Kunkel et al., Methods in Enzymol. 154:367-82 (1987); the Anglian Biotechnology Ltd. handbook). Additionally, numerous publications describe techniques suitable for the preparation of antibodies by manipulation of DNA, creation of expression vectors, and transformation and culture of appropriate cells (Mountain A and Adair, J R in Biotechnology and Genetic Engineering Reviews (ed. Tombs, M P, 10, Chapter 1, 1992, Intercept, Andover, UK); "Current Protocols in Molecular Biology", 1999, F. M. Ausubel (ed.), Wiley Interscience, New York).

Where it is desired to improve the affinity of antibodies according to the invention containing one or more of the above-mentioned CDRs can be obtained by a number of affinity maturation protocols including maintaining the CDRs (Yang et al., J. Mol. Biol., 254, 392-403, 1995), chain shuffling (Marks et al., Bio/Technology, 10, 779-783, 1992), use of mutation strains of *E. coli*. (Low et al., J. Mol. Biol., 250, 350-368, 1996), DNA shuffling (Patten et al., Curr. Opin. Biotechnol., 8, 724-733, 1997), phage display (Thompson et al., J. Mol. Biol., 256, 7-88, 1996) and PCR (Crameri, et al., Nature, 391, 288-291, 1998). All of these methods of affinity maturation are discussed by Vaughan et al. (Nature Biotechnology, 16, 535-539, 1998).

Other antibodies according to the invention may be obtained by conventional immunization and cell fusion procedures as described herein and known in the art. Monoclonal antibodies of the invention may be generated using a variety of known techniques. In general, monoclonal antibodies that bind to specific antigens may be obtained by methods known to those skilled in the art (see, for example, Kohler et al., Nature 256:495, 1975; Coligan et al. (eds.), Current Protocols in Immunology, 1:2.5.12.6.7 (John Wiley & Sons 1991); U.S. Pat. Nos. RE 32,011, 4,902,614, 4,543,439, and 4,411,993; Monoclonal Antibodies, Hybridomas: A New Dimension in Biological Analyses, Plenum Press, Kennett, McKearn, and Bechtol (eds.) (1980); and Antibodies: A Laboratory Manual, Harlow and Lane (eds.), Cold Spring Harbor Laboratory Press (1988); Picksley et al., "Production of monoclonal antibodies against proteins expressed in *E. coli*," in DNA Cloning 2: Expression Systems, 2nd Edition, Glover et al. (eds.), page 93 (Oxford University Press 1995)). Antibody fragments may be derived therefrom using any suitable standard technique such as proteolytic digestion, or optionally, by proteolytic digestion (for example, using papain or pepsin) followed by mild reduction of disulfide bonds and alkylation. Alternatively, such fragments may also be generated by recombinant genetic engineering techniques as described herein.

Monoclonal antibodies can be obtained by injecting an animal, for example, a rat, hamster, a rabbit, or preferably a mouse, including for example a transgenic or a knock-out, as known in the art, with an immunogen comprising human TSLP of SEQ ID NO: 2, other TSLP polypeptide sequences as described herein, or a fragment thereof, according to methods known in the art and described herein. The presence of specific antibody production may be monitored after the initial injection and/or after a booster injection by obtaining a serum sample and detecting the presence of an antibody that binds to human TSLP or fragment thereof using any one of several immunodetection methods known in the art and described herein. From animals producing the desired antibodies, lymphoid cells, most commonly cells from the spleen or lymph node, are removed to obtain B-lymphocytes. The B lymphocytes are then fused with a drug-sensitized myeloma cell fusion partner, preferably one that is syngeneic with the immunized animal and that optionally has other desirable properties (e.g., inability to express endogenous Ig gene products, e.g., P3×63-Ag 8.653 (ATCC No. CRL 1580); NSO, SP20) to produce hybridomas, which are immortal eukaryotic cell lines.

The lymphoid (e.g., spleen) cells and the myeloma cells may be combined for a few minutes with a membrane fusion-promoting agent, such as polyethylene glycol or a nonionic detergent, and then plated at low density on a selective medium that supports the growth of hybridoma cells but not unfused myeloma cells. A preferred selection media is HAT (hypoxanthine, aminopterin, thymidine). After a sufficient time, usually about one to two weeks, colonies of cells are observed. Single colonies are isolated, and antibodies produced by the cells may be tested for binding activity to human TSLP using any one of a variety of immunoassays known in the art and described herein. The hybridomas are cloned (e.g., by limited dilution cloning or by soft agar plaque isolation) and positive clones that produce an antibody specific to human TSLP are selected and cultured. The monoclonal antibodies from the hybridoma cultures may be isolated from the supernatants of hybridoma cultures.

An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in Methods in Molecular Biology, Vol. 10, pages 79-104 (The Humana Press, Inc. 1992)). Monoclonal antibodies may be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anticonstant region (light chain or heavy chain) antibody, an anti-idiotype antibody, and TSLP, or fragment or variant thereof.

An antibody of the present invention may also be a fully human monoclonal antibody. Fully human monoclonal antibodies may be generated by any number of techniques as those previsously described above. Such methods further include, but are not limited to, Epstein Barr Virus (EBV) transformation of human peripheral blood cells (e.g., containing B lymphocytes), in vitro immunization of human B-cells, fusion of spleen cells from immunized transgenic mice carrying inserted human immunoglobulin genes, isolation from human immunoglobulin V region phage libraries, or other procedures as known in the art and based on the disclosure herein. For example, fully human monoclonal antibodies may be obtained from transgenic mice that have been engineered to produce specific human antibodies in response to antigenic challenge. Methods for obtaining fully human antibodies from transgenic mice are described, for example, by Green et al., Nature Genet. 7:13, 1994; Lonberg et al., Nature 368:856, 1994; Taylor et al., Int. Immun 6:579, 1994; U.S. Pat. No. 5,877,397; Bruggemann et al., 1997 Curr. Opin. Biotechnol. 8:455-58; Jakobovits et al., 1995 Ann. N.Y. Acad. Sci. 764: 525-35. In this technique, elements of the human heavy and light chain locus are introduced into strains of mice derived from embryonic stem cell lines that contain targeted disruptions of the endogenous heavy chain and light chain loci (see also Bruggemann et al., Curr. Opin. Biotechnol. 8:455-58 (1997)). For example, human immunoglobulin transgenes may be mini-gene constructs, or transloci on yeast artificial chromosomes, which undergo B-cell-specific DNA rearrangement and hypermutation in the mouse lymphoid tissue. Fully human monoclonal antibodies may be obtained by immunizing the transgenic mice, which may then produce human antibodies specific for human TSLP. Lymphoid cells of the immunized transgenic mice can be used to produce human antibody-secreting hybridomas according to the methods described herein. Polyclonal sera containing fully human antibodies may also be obtained from the blood of the immunized animals.

One exemplary method for generating human antibodies of the invention includes immortalizing human peripheral blood cells by EBV transformation, as described, for example, in U.S. Pat. No. 4,464,456. Such an immortalized B-cell line (or lymphoblastoid cell line) producing a monoclonal antibody that specifically binds to human TSLP can be identified by immunodetection methods as provided herein, for example, an ELISA, and then isolated by standard cloning techniques. The stability of the lymphoblastoid cell line producing an anti-TSLP antibody may be improved by fusing the transformed cell line with a murine myeloma to produce a mouse-human hybrid cell line according to methods known in the art (see, e.g., Glasky et al., Hybridoma 8:377-89 (1989)). Still another method to generate human monoclonal antibodies is in vitro immunization, which includes priming human splenic B-cells with human TSLP followed by fusion of primed B-cells with a heterohybrid fusion partner. See, e.g., Boerner et al., 1991 J. Immunol. 147:86-95.

In certain embodiments, a B-cell that is producing an anti-human TSLP antibody is selected and the light chain and heavy chain variable regions are cloned from the B-cell according to molecular biology techniques known in the art (WO 92/02551; U.S. Pat. No. 5,627,052; Babcook et al., Proc. Natl. Acad. Sci. USA 93:7843-48 (1996)) and described herein. B-cells from an immunized animal may be isolated from the spleen, lymph node, or peripheral blood sample by selecting a cell that is producing an antibody that specifically binds to TSLP. B-cells may also be isolated from humans, for example, from a peripheral blood sample. Methods for detecting single B-cells that are producing an antibody with the desired specificity are well known in the art, for example, by plaque formation, fluorescence-activated cell sorting, in vitro stimulation followed by detection of specific antibody, and the like. Methods for selection of specific antibody-producing B-cells include, for example, preparing a single cell suspension of B-cells in soft agar that contains human TSLP. Binding of the specific antibody produced by the B-cell to the antigen results in the formation of a complex, which may be visible as an immunoprecipitate. After the B-cells producing the desired antibody are selected, the specific antibody genes may be cloned by isolating and amplifying DNA or mRNA according to methods known in the art and described herein.

An additional method for obtaining antibodies of the invention is by phage display. See, e.g., Winter et al., 1994 Annu. Rev. Immunol. 12:433-55; Burton et al., 1994 Adv. Immunol. 57:191-280. Human or murine immunoglobulin variable region gene combinatorial libraries may be created in phage vectors that can be screened to select Ig fragments (Fab, Fv, sFv, or multimers thereof) that bind specifically to TSLP or variant or fragment thereof. See, e.g., U.S. Pat. No. 5,223,409; Huse et al., 1989 Science 246:1275-81; Sastry et al., Proc. Natl. Acad. Sci. USA 86:5728-32 (1989); Alting-Mees et al., Strategies in Molecular Biology 3:1-9 (1990); Kang et al., 1991 Proc. Natl. Acad. Sci. USA 88:4363-66; Hoogenboom et al., 1992 J. Molec. Biol. 227:381-388; Schlebusch et al., 1997 Hybridoma 16:47-52 and references cited therein. For example, a library containing a plurality of polynucleotide sequences encoding Ig variable region fragments may be inserted into the genome of a filamentous bacteriophage, such as M13 or a variant thereof, in frame with the sequence encoding a phage coat protein. A fusion protein may be a fusion of the coat protein with the light chain variable region domain and/or with the heavy chain variable region domain. According to certain embodiments, immunoglobulin Fab fragments may also be displayed on a phage particle (see, e.g., U.S. Pat. No. 5,698,426).

Heavy and light chain immunoglobulin cDNA expression libraries may also be prepared in lambda phage, for example, using λImmunoZap™ (H) and λImmunoZap™ (L) vectors (Stratagene, La Jolla, Calif.). Briefly, mRNA is isolated from a B-cell population, and used to create heavy and light chain immunoglobulin cDNA expression libraries in the λImmunoZap(H) and λImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid that allows high level expression of monoclonal antibody fragments from E. coli.

In one embodiment, in a hybridoma the variable regions of a gene expressing a monoclonal antibody of interest are amplified using nucleotide primers. These primers may be synthesized by one of ordinary skill in the art, or may be purchased from commercially available sources. (See, e.g., Stratagene (La Jolla, Calif.), which sells primers for mouse and human variable regions including, among others, primers for $V_{Ha}$, $V_{Hb}$, $V_{Hc}$, $V_{Hd}$, $C_{H1}$, $V_L$ and $C_L$ regions.) These primers may be used to amplify heavy or light chain variable regions, which may then be inserted into vectors such as ImmunoZAP™H or ImmunoZAP™L (Stratagene), respectively. These vectors may then be introduced into E. coli, yeast, or mammalian-based systems for expression. Large amounts of a single-chain protein containing a fusion of the $V_H$ and $V_L$ domains may be produced using these methods (see Bird et al., Science 242:423-426, 1988).

Once cells producing antibodies according to the invention have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described previously to generate other antibodies according to the invention.

Antigen binding proteins of the present invention preferably modulate TSLP activity in one of the cell-based assay described herein and/or the in vivo assay described herein and/or cross-block the binding of one of the antibodies described in this application and/or are cross-blocked from binding TSLP by one of the antibodies described in this application. Particularly useful are antigen binding proteins that cross-compete with an exemplary antibody described herein, i.e., cross-block the binding of one of the exemplary antibodies described in this application and are cross-blocked from binding TSLP by one of the exemplary antibodies. Accordingly such binding agents can be identified using the assays described herein.

In certain embodiments, antibodies are generated by first identifying antibodies that bind to TSLP and/or neutralize in the cell-based assays described herein and/or cross-block the antibodies described in this application and/or are cross-blocked from binding TSLP by one of the antibodies described in this application. The CDR regions from these antibodies are then used to insert into appropriate biocompatible frameworks to generate antigen binding proteins. The non-CDR portion of the binding agent may be composed of amino acids, or may be a non-protein molecule. The assays described herein allow the characterization of binding agents. Preferably the binding agents of the present invention are antibodies as defined herein.

Antigen binding proteins of the present invention include those that bind to the same epitope as an exemplary antibody described herein. As discussed in Example 9, epitopes may be structural or functional. Structural epitopes may be thought of as the patch of the target which is covered by the antibody. Functional epitopes are a subset of the structural epitopes and comprise those residues which directly contribute to the affinity of the interaction (e.g. hydrogen bonds, ionic interactions). One method of determining the epitope of an antibody is by using scanning mutations in the target molecule and measuring the effect of the mutation on binding. Given the three-dimensional structure of the antibody binding region, mutations in the epitope can decrease or increase the binding affinity of the antibody for the mutated target.

Antigen binding proteins may be defined by their epitopes. As seen in Table 6, although the antibodies may all bind to TSLP, they are affected differently by the mutation of certain residues in TSLP an indication that their respective epitopes do not completely overlap. Preferred antigen binding proteins include those that share at least a portion of the structural epitope of a reference antibody described herein.

For example, a preferred antigen binding protein is one that shares at least a portion of the same structural epitope as A2. This is evidenced by an increase in binding affinity as compared to for wild-type TSLP when TSLP has mutation K67E, K97E, K98E, R100E, K101E, or K103E. This may also be evidenced by a decrease in binding affinity as compared to for wild-type TSLP when TSLP has mutation K21E, T25R, S28R, S64R, or K73E. Although the antigen binding protein and A2 may be affected similarly by some mutations and not others, the more identity there is between the antigen binding protein and A2 on the effect of mutations in certain residues of TSLP, the more the antigen binding protein and reference antibody share a structural epitope.

Another preferred antigen binding protein is one that shares at least a portion of the same structural epitope as A4. This is evidenced by an increase in binding affinity as compared to for wild-type TSLP when TSLP has mutation K97E, K98E, R100E, K101E, or K103E. This may also be evidenced by a decrease in binding affinity as compared to for wild-type TSLP when TSLP has mutation K10E, A14R, K21E, D22R, K73E, K75E, or A76R.

Another preferred antigen binding protein is one that shares at least a portion of the same structural epitope as A5. This is evidenced by a decrease in binding affinity as compared to for wild-type TSLP when TSLP has mutation K12E, D22R, S40R, R122E, N124E, R125E, or K129E.

Another preferred antigen binding protein is one that shares at least a portion of the same structural epitope as A6. This is evidenced by a decrease in binding affinity as compared to for wild-type TSLP when TSLP has mutation S40R, S42R, H46R, R122E, or K129E.

Another preferred antigen binding protein is one that shares at least a portion of the same structural epitope as A7. This is evidenced by an increase in binding affinity as compared to for wild-type TSLP when TSLP has mutation K101E. This may also be evidenced by a decrease in binding affinity as compared to for wild-type TSLP when TSLP has mutation D2R, T4R, D7R, S42R, H46R, T49R, E50R, Q112R, R122E, R125E, or K129E.

Another preferred antigen binding protein is one that shares at least a portion of the same structural epitope as A10. This is evidenced by an increase in binding affinity as compared to for wild-type TSLP when TSLP has mutation K97E, K98E, R100E, K101E, or K103E. This may also be evidenced by a decrease in binding affinity as compared to for wild-type TSLP when TSLP has mutation N5R, S17R, T18R, K21E, D22R, T25R, T33R, H46R, A63R, S64R, A66R, E68R, K73E, K75E, A76R, A92R, T93R, Q94R, or A95R.

Another preferred antigen binding protein is one that shares at least a portion of the same structural epitope as A21. This is evidenced by an increase in binding affinity as compared to for wild-type TSLP when TSLP has mutation K97E, K98E, R100E, K101E, or K103E. This may also be evidenced by a decrease in binding affinity as compared to for wild-type TSLP when TSLP has mutation K21E, K21R, D22R, T25R, T33R, S64R, K73E, K75E, E111R, or S114R.

Another preferred antigen binding protein is one that shares at least a portion of the same structural epitope as A23. This is evidenced by an increase in binding affinity as compared to for wild-type TSLP when TSLP has mutation K67E, K97E, K98E, R100E, K101E, or K103E. This may also be evidenced by a decrease in binding affinity as compared to for wild-type TSLP when TSLP has mutation E9R, K10E, K12E, A13R, S17R, S20R, K21E, K21R, K73E, K75E, N124E, or R125E.

Another preferred antigen binding protein is one that shares at least a portion of the same structural epitope as A26. This is evidenced by an increase in binding affinity as compared to for wild-type TSLP when TSLP has mutation K97E, K98E, R100E, K101E, or K103E. This may also be evidenced by a decrease in binding affinity as compared to for wild-type TSLP when TSLP has mutation A14R, K21E, D22R, A63R, S64R, K67E, K73E, A76R, A92R, or A95R.

Comparing the mutations that affect binding amongst the antibody, it suggests that certain residues of TSLP tend to be part of the antibodies ability to bind TSLP and block TSLP activity. Such residues include K21, D22, K73, and K129. Thus, preferred antigen binding protein include those that have a higher affinity for wild-type TSLP than for a TSLP comprising mutation K21E, those that have a higher affinity for wild-type TSLP than for a TSLP comprising mutation D21R, those that have a higher affinity for wild-type TSLP than for a TSLP comprising mutation K73E, and those that have a higher affinity for wild-type TSLP than for a TSLP comprising mutation K129E.

Furthermore, many of the exemplary antigen binding proteins described herein share the attribute that the affinity for TSLP increases when the basic patch of amino acids at positions 97-103 are changed to acidic amino acids.

Nucleic Acids

In one aspect, the present invention provides isolated nucleic acid molecules. The nucleic acids comprise, for example, polynucleotides that encode all or part of an antigen binding protein, for example, one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids encoding antibody polypeptides (e.g., heavy or light chain, variable domain only, or full length) may be isolated from B-cells of mice that have been immunized with a TSLP antigen. The nucleic acid may be isolated by conventional procedures such as polymerase chain reaction (PCR).

Nucleic acid sequences encoding the variable regions of the heavy and light chain variable regions are shown above. The skilled artisan will appreciate that, due to the degeneracy of the genetic code, each of the polypeptide sequences disclosed herein is encoded by a large number of other nucleic acid sequences. The present invention provides each degenerate nucleotide sequence encoding each antigen binding protein of the invention.

The invention further provides nucleic acids that hybridize to other nucleic acids (e.g., nucleic acids comprising a nucleotide sequence of any of A1-A27) under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA.

Changes can be introduced by mutation into a nucleic acid, thereby leading to changes in the amino acid sequence of a polypeptide (e.g., an antigen binding protein) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. In one embodiment, a nucleotide sequence provided herein for A1-A27, or a desired fragment, variant, or derivative thereof, is mutated such that it encodes an amino acid sequence comprising one or more deletions or substitutions of amino acid residues that are shown herein for A1-A27 to be residues where two or more sequences differ. In another embodiment, the mutagenesis inserts an amino acid adjacent to one or more amino acid residues shown herein for A1-A27 to be residues where two or more sequences differ. Alternatively, one or more mutations can be introduced into a nucleic acid that selectively change the biological activity. (e.g., binding to TSLP) of a polypeptide that it encodes. For example, the mutation can quantitatively or qualitatively change the biological activity. Examples of quantitative changes include increasing, reducing or eliminating the activity. Examples of qualitative changes include changing the antigen specificity of an antigen binding protein.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., a TSLP binding portion) of a polypeptide of the invention.

Probes based on the sequence of a nucleic acid of the invention can be used to detect the nucleic acid or similar nucleic acids, for example, transcripts encoding a polypeptide of the invention.

The probe can comprise a label group, e.g., a radioisotope, a fluorescent compound, an enzyme, or an enzyme co-factor. Such probes can be used to identify a cell that expresses the polypeptide.

In another aspect, the present invention provides vectors comprising a nucleic acid encoding a polypeptide of the invention or a portion thereof. Examples of vectors include, but are not limited to, plasmids, viral vectors, non-episomal mammalian vectors and expression vectors, for example, recombinant expression vectors.

The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell (for example, E. coli) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Indications

TSLP is involved in promoting various inflammatory disorders, in particular allergic inflammatory disorders. As used herein the term "allergic inflammation" refers to the manifestations of immunoglobulin E (IgE)-related immunological responses. (*Manual of Allergy and Immunology*, Chapter 2, Alvin M. Sanico, Bruce S. Bochner, and Sarbjit S. Saini, Adelman et al, ed., Lippincott, Williams, Wilkins, Philadelphia, Pa., (2002)). Allergic inflammation as used herein is generally characterized by the infiltration into the affected tissue of type 2 helper T cells ($T_H2$ cells) (Kay, supra). Allergic inflammation includes pulmonary inflammatory diseases such as allergic rhinosinusitis, asthma, allergic conjunctivitis, in addition to inflammatory skin conditions such as atopic dermatis (*Manual of Allergy and Immunology*, supra). As used herein the term "TSLP-related allergic inflammation" refers to allergic inflammation conditions in which TSLP is upregulated, or is demonstrated to be otherwise involved.

Allergic asthma is a chronic inflammatory disorder of the airways characterized by airway eosinophilia, high levels of serum IgE and mast cell activation, which contribute to airway hyperresponsiveness, epithelial damage and mucus hypersecretion (Wills-Karp, M, Ann. Rev. Immunol. 17:255-281 (1999), *Manual of Allergy and Immunology*, supra). Studies have demonstrated that varying degrees of chronic inflammation are present in the airways of all asthmatics, even during symptom-free periods. In susceptible individuals, this inflammation causes recurrent episodes of wheezing, breathlessness, chest tightness, and coughing. (*Manual of Allergy and Immunology*, supra).

Atopic dermatitis is a chronic pruritic inflammatory skin disease characterized by skin lesions, featuring an elevated serum total IgE, eosinophilia, and increased release of histamine from basophils and mast cells. Persons suffering from atopic dermatitis exhibit exaggerated $T_H2$ responses and initiation of atopic dermatitis lesions is thought to be mediated by means of early skin infiltration of $T_H2$ lymphocytes releasing high levels of IL-4, IL-5 and IL-13 (Leung, J. Allergy Clin Immunol 105:860-76 (2000)). The relationship between TSLP and other inflammatory cytokines is described in U.S. application Ser. No. 11/205,904, publication 2006/0039910, which is herein incorporated by reference.

Human TSLP expression as detected by in situ hybridization was reported to be increased in asthmatic airways correlating with disease severity (Ying et al., J. Immunology 174: 8183-8190 (2005)). Analysis of TSLP mRNA levels in asthmatic patient lung samples showed increased expression of TSLP compared to controls. In addition, TSLP protein levels are detectable in the concentrated bronchoalveolar lavage (BAL) fluid of asthma patients, lung transplant patients, and cystic fibrosis patients. TSLP has recently been found to be released in response to microbes and trauma as well as inflammation, and to activate mast cells (Allakhverdi et al., J. Exp. Med. 20492: 253-258 (2007).

Human TSLP protein was shown to correlate with disease in bronchial mucosa and BAL fluid of subjects with moderate/severe asthma and COPD. (Ying et al., J Immunol 181(4): 2790-8 (2008).

Over-expression of TSLP in the lungs of transgenic mice leads to asthma-like airway inflammation (Zhou et al., Nat. Immunol 10:1047-1053 (2005). In addition, it has been reported that TSLPR deficient mice failed to develop asthma in OVA-asthma models, demonstrating that TSLP is required for development of asthma in airway inflammation models (Zhou et al, supra, Carpino et al., Mol. Cell. Biol. 24:2584-2592 (2004).

In addition to asthma, increased levels of TSLP protein and mRNA are found in the lesional skin of atopic dermatitis (AD) patients and in inflamed tonsilar epithelial cells (Soumelis et al., Nature Immunol: 3 (7): 673-680 (2002). Over-expression of TSLP in the skin of transgenic mice leads to an AD-like phenotype. (Yoo et al., J Exp Med 202:541-549 (2005)).

Therefore, TSLP antagonists, specifically the TSLP antigen binding proteins and antibodies of the instant application, are useful as therapeutic treatment for allergic inflammation, in particular, asthma and atopic dermatitis.

In addition, TSLP antagonists, particularly the TSLP antigen binding proteins and antibodies of the present disclosure are also useful for treating fibrotic disorders. TSLP has been demonstrated to be involved in promoting fibrotic disorders, as described in application Ser. No. 11/344,379. TSLP has been found to induce fibroblast accumulation and collagen deposition in animals. Injection of murine TSLP, for example, intradermally into mice resulted in fibrosis within the subcutis of the mice, characterized by fibroblast proliferation and collagen deposition. Antagonizing TSLP activity would result in preventing or decreasing fibroblast proliferation and collagen deposition in a tissue.

As used herein the term "fibroproliferative disease" or "fibrotic disease or disorder" refers to conditions involving fibrosis in one or more tissues. As used herein the term "fibrosis" refers to the formation of fibrous tissue as a reparative or reactive process, rather than as a normal constituent of an organ or tissue. Fibrosis is characterized by fibroblast accumulation and collagen deposition in excess of normal deposition in any particular tissue. As used herein the term "fibrosis" is used synonymously with "fibroblast accumulation and collagen deposition". Fibroblasts are connective tissue cells, which are dispersed in connective tissue throughout the body. Fibroblasts secrete a nonrigid extracellular matrix containing type I and/or type III collagen. In response to an injury to a tissue, nearby fibroblasts migrate into the wound, proliferate, and produce large amounts of collagenous extracellular matrix. Collagen is a fibrous protein rich in glycine and proline that is a major component of the extracellular matrix and connective tissue, cartilage, and bone. Collagen molecules are triple-stranded helical structures called α-chains, which are wound around each other in a ropelike helix. Collagen exists in several forms or types; of these, type I, the most common, is found in skin, tendon, and bone; and type III is found in skin, blood vessels, and internal organs.

Fibrotic disorders include, but are not limited to, systemic and local scleroderma, keloids and hypertrophic scars, atherosclerosis, restenosis, pulmonary inflammation and fibrosis, idiopathic pulmonary fibrosis, liver cirrhosis, fibrosis as a result of chronic hepatitis B or C infection, kidney disease, heart disease resulting from scar tissue, and eye diseases such as macular degeneration, and retinal and vitreal retinopathy. Additional fibrotic diseases include fibrosis resulting from chemotherapeutic drugs, radiation-induced fibrosis, and injuries and burns.

Scleroderma is a fibrotic disorder characterized by a thickening and induration of the skin caused by the overproduction of new collagen by fibroblasts in skin and other organs. Scleroderma may occur as a local or systemic disease. Systemic scleroderma may affect a number of organs. Systemic sclerosis is characterized by formation of hyalinized and thickened collagenous fibrous tissue, with thickening of the skin and adhesion to underlying tissues, especially of the hands and face. The disease may also be characterized by dysphagia due to loss of peristalsis and submucosal fibrosis of the esophagus, dyspnea due to pulmonary fibrosis, myocardial fibrosis, and renal vascular changes. (Stedman's Medical Dictionary, 26th Edition, Williams & Wilkins, 1995)). Pulmonary fibrosis affects 30 to 70% of scleroderma patients, often resulting in restrictive lung disease (Atamas et al. Cytokine and Growth Factor Rev 14: 537-550 (2003)). Idiopathic pulmonary fibrosis is a chronic, progressive and usually lethal lung disorder, thought to be a consequence of a chronic inflammatory process (Kelly et al., Curr Pharma Design 9: 39-49 (2003)).

Therefore, TSLP antagonists, specifically the TSLP antigen binding proteins and antibodies of the instant application, are useful as therapeutic treatment for fibrotic diseases, including but not limited to scleroderma, interstitial lung disease, idiopathic pulmonary fibrosis, fibrosis arising from chronic hepatitis B or C, radiation-induced fibrosis, and fibrosis arising from wound healing.

Although the above indications are preferred, other disease, disorder, or condition may be amenable to treatment with or may be prevented by administration of an antigen binding to a subject. Such diseases, disorders, and conditions include, but are not limited to, inflammation, autoimmune disease, cartilage inflammation, fibrotic disease and/or bone degradation, arthritis, rheumatoid arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, SEA Syndrome (Seronegativity, Enthesopathy, Arthropathy Syndrome), dermatomyositis, psoriatic arthritis, scleroderma, systemic lupus erythematosus, vasculitis, myolitis, polymyolitis, dermatomyolitis, osteoarthritis, polyarteritis nodossa, Wegener's granulomatosis, arteritis, ploymyalgia rheumatica, sarcoidosis, scleroderma, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease (IBD), Crohn's disease, ulcerative colitis, celiac disease, multiple schlerosis (MS), asthma, COPD, Guillain-Barre disease, Type I diabetes mellitus, Graves' disease, Addison's disease, Raynaud's phenomenon, autoimmune hepatitis, GVHD, and the like. In specific embodiments, pharmaceutical compositions comprising a therapeutically effective amount of TSLP antigen binding proteins are provided.

The term "treatment" encompasses alleviation or prevention of at least one symptom or other aspect of a disorder, or reduction of disease severity, and the like. An antigen binding protein need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient an antigen binding protein in an amount and for a time sufficient to induce a sustained improvement over baseline of an indicator that reflects the severity of the particular disorder.

Pharmaceutical Compositions

In some embodiments, the invention provides pharmaceutical compositions comprising a therapeutically effective amount of one or a plurality of the antigen binding proteins of the invention together with a pharmaceutically acceptable diluent, carrier, solubilizer, emulsifier, preservative, and/or adjuvant. In addition, the invention provides methods of treating a patient by administering such pharmaceutical composition. The term "patient" includes human and animal subjects.

Pharmaceutical compositions comprising one or more antigen binding proteins may be used to reduce TSLP activity. Pharmaceutical compositions comprising one or more antigen binding proteins may be used in treating the consequences, symptoms, and/or the pathology associated with TSLP activity. Pharmaceutical compositions comprising one or more antigen binding proteins may be used in methods of inhibiting binding and/or signaling of TSLP to TSLPR comprising providing the antigen binding protein of the invention to TSLP.

In certain embodiments, acceptable formulation materials preferably are nontoxic to recipients at the dosages and concentrations employed. In certain embodiments, the pharmaceutical composition may contain formulation materials for modifying, maintaining or preserving, for example, the pH, osmolality, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, sucrose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antigen binding proteins of the invention. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefor. In certain embodiments of the invention, TSLP antigen binding protein compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the TSLP antigen binding protein product may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. The formulation components are present preferably in concentrations that are acceptable to the site of administration. In certain embodiments, buffers are used to maintain the composition at physiological pH or at a slightly lower pH, typically within a pH range of from about 5 to about 8. Including about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, and about 8.0.

When parenteral administration is contemplated, the therapeutic compositions for use in this invention may be provided in the form of a pyrogen-free, parenterally acceptable aqueous solution comprising the desired TSLP antigen binding protein in a pharmaceutically acceptable vehicle. A particularly suitable vehicle for parenteral injection is sterile distilled water in which the TSLP antigen binding protein is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antigen binding protein.

Pharmaceutical compositions of the invention can be formulated for inhalation. In these embodiments, TSLP antigen binding proteins are advantageously formulated as a dry, inhalable powder. In specific embodiments, TSLP antigen binding protein inhalation solutions may also be formulated with a propellant for aerosol delivery. In certain embodiments, solutions may be nebulized. Pulmonary administration and formulation methods therefore are further described in International Patent Application No. PCTUS94/001875, which is incorporated by reference and describes pulmonary delivery of chemically modified proteins.

It is also contemplated that formulations can be administered orally. TSLP antigen binding proteins that are administered in this fashion can be formulated with or without carriers customarily used in the compounding of solid dosage forms such as tablets and capsules. In certain embodiments, a capsule maybe designed to release the active portion of the formulation at the point in the gastrointestinal tract when bioavailability is maximized and pre-systemic degradation is minimized. Additional agents can be included to facilitate absorption of the TSLP antigen binding protein. Diluents, flavorings, low melting point waxes, vegetable oils, lubricants, suspending agents, tablet disintegrating agents, and binders may also be employed.

A pharmaceutical composition of the invention is preferably provided to comprise an effective quantity of one or a plurality of TSLP antigen binding proteins in a mixture with non-toxic excipients that are suitable for the manufacture of tablets. By dissolving the tablets in sterile water, or another appropriate vehicle, solutions may be prepared in unit-dose form.

Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving TSLP antigen binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions.

Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al, 1983, Biopolymers 2:547-556), poly(2-hydroxyethyl-inethacrylate) (Langer et al, 1981, J. Biomed. Mater. Res. 15:167-277 and Langer, 1982, Chem. Tech. 12:98-105), ethylene vinyl acetate (Langer et al, 1981, supra) or poly-D(-)-3-hydroxybutyric acid (European Patent Application Publication No. EP 133,988).

Sustained release compositions may also include liposomes that can be prepared by any of several methods known in the art. See, e.g., Eppstein et al, 1985, Proc. Natl. Acad. Sci. U.S.A. 82.3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Aspects of the invention includes self-buffering TSLP antigen binding protein formulations, which can be used as pharmaceutical compositions, as described in international patent application WO 0613818 1A2 (PCT/US2006/022599), which is incorporated by referencein its entirety herein. One embodiment provides self-buffering TSLP antigen binding protein formulations comprising an TSLP antigen binding protein in which the total salt concentration is less than 150 mM.

The therapeutically effective amount of TSLP antigen binding protein-containing pharmaceutical composition to be employed will depend, for example, upon the therapeutic context and objectives. One skilled in the art will appreciate that the appropriate dosage levels for treatment will vary depending, in part, upon the molecule delivered, the indication for which the TSLP antigen binding protein is being used, the route of administration, and the size (body weight, body surface or organ size) and/or condition (the age and general health) of the patient.

In certain embodiments, the clinician may titer the dosage and modify the route of administration to obtain the optimal therapeutic effect. A typical dosage may range from about 0.1 µg/kg to up to about 30 mg/kg or more, depending on the factors mentioned above. In specific embodiments, the dosage may range from 0.1 µg/kg up to about 30 mg/kg, optionally from 1 µg/kg up to about 30 mg/kg or from 10 µg/kg up to about 5 mg/kg.

Dosing frequency will depend upon the pharmacokinetic parameters of the particular TSLP antigen binding protein in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them.

Appropriate dosages may be ascertained through use of appropriate dose-response data. In certain embodiments, the antigen binding proteins of the invention can be administered to patients throughout an extended time period. Chronic administration of an antigen binding protein of the invention minimizes the adverse immune or allergic response commonly associated with antigen binding proteins that are not fully human, for example an antibody raised against a human antigen in a non-human animal, for example, a non-fully human antibody or non-human antibody produced in a non-human species.

The route of administration of the pharmaceutical composition is in accord with known methods, e.g., orally, through injection by intravenous, intraperitoneal, intracerebral (intraparenchymal), intracerebroventricular, intramuscular, intraocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

Combination Therapies

In further embodiments, antigen binding protein are administered in combination with other agents useful for treating the condition with which the patient is afflicted. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but also include treatment regimens in which an antigen binding protein is administered at least once during a course of treatment that involves administering at least one other therapeutic agent to the patient.

The invention having been described, the following examples are offered by way of illustration, and not limitation.

Example 1

Preparation of Antigen

Several forms of recombinant TSLP were used as immunogens. Human TSLP was expressed both in *E. coli* and in mammalian cells. The *E. coli* produced human TSLP was an untagged full-length protein. TSLP protein was produced in COS PKB cells having a deleted furin cleavage site produced by deleting nucleotides 382-396 (AGAAAAAGGAAAGTC, SEQ ID NO: 370) corresponding to amino acids 128-132 (RKRKV, SEQ ID NO: 371). This protein contained a C terminal polyHIS-Flag tag (Nucleotide sequence=ATGTTCCCTTTTGCCTTACTATATGTTCTGTCAGTTTCTTTCAGGAAAATCTTCATCTTACAACTTGTAGGGCTGGTGTTAACTTACGACTTCACTAACTGTGACTTTGAGAAGATTAAAGCAGCCTATCTCAGTACTATTTCTAAAGACCTGATTACATATATGAGTGGGACCAAAAGTACCGAGTTCAACAACACCGTCTCTTGTAGCAATCGGCCACATTGCCTTACTGAAATCCAGAGCCTAACCTTCAATCCCACCGCCGGCTGCGCGTCGCTCGCCAAAGAAATGTTCGCCATGAAAACTAAGGCTGCCTTAGCTATCTGGTGCCCAGGCTATTCGGAAACTCAGATAAATGCTACTCAGGCAATGAAGAAGAGGACAACCAATAAATGTCTGGAACAAGTGTCACAATTACAAGGATTGTGGCGTCGCTTCAATCGACCTTTACTGAAACAACAGCATCACCATCACCATCACGACTACAAAGACGATGACGACAAA (SEQ ID NO: 372);

Protein sequence=MFPFALLYVLSVSFRKIFILQLVGLVLTYDFTNCDFEKIKAAYLSTISKDLITYMSGTKSTEFNNTVSCSNRPHCLTEIQSLTFNPTAGCASLAKEMFAMKTKAALAIWCPGYSETQINATQAMKKRTTNKCLEQVSQLQGLWRRFNRPLLKQQHHHHHHDYKDDDDK (SEQ ID NO: 373).

In another campaign, a full length TSLP C terminal poly-HIS-Flag tagged protein was produced in COS PKB cells (Nucleotide sequence=ATGTTCCCTTTTGCCTTACTATATGTTCTGTCAGTTTCTTTCAGGAAAATCTTCATCTTACAACTTGTAGGGCTGGTGTTAACTTACGACTTCACTAACTGTGACTTTGAGAAGATTAAAGCAGCCTATCTCAGTACTATTTCTAAAGACCTGATTACATATATGAGTGGGACCAAAAGTACCGTCTCTTGTAGCAATCGGCCACATTGCCTTACTGAAATCCAGAGCCTAACCTTCAATCCCACCGCCGGCTGCGCGTCGCTCGCCAAAGAAATGTTCGCCATGAAAACTAAGGCTGCCTTAGCTATCTGGTGCCCAGGCTATTCGGAAACTCAGATAAATGCTACTCAGGCAATGAAGA- AGAGGAGAAAAAGGAAAGTCACAACCAATAAATG-
TCTGGAACAAGTGTCACAATTACAAGGATTGTGGC-
GTCGCTTCAATCGACCTTTACTGAAACAACAGCAT-
CACCATCACCATCACGACTACAAAGACGATGACGA-
CAAA (SEQ ID NO: 374); Protein sequence=MFPFAL-
LYVLSVSFRKIFILQLVGLVLTYDFTNCDFEKIKAAYL-
STISKDLITYMSGTKSTEFNN TV SC SNRPHCLTEIQS-
LTFNPTAGCASLAKEMFAMKTKAALAIWCPGYSET-
QINATQAMKKRRKRKVTTNKCLEQVSQLQGLWRRF-
NRPLLKQQHHHHHHDYKDDDDK (SEQ ID NO: 375).
Note that the amino acid sequence 1-28 (MFPFALLYVLS-
VSFRKIFILQLVGLVLT, SEQ ID NO: 376) is a signal peptide cleaved from the mature product of both these proteins.

In addition, cynomolgus TSLP was cloned and subcloned/expressed similarly with either the furin cleavage site (nucleotide 358-372 (AGAAAAAGGAAAGTC, SEQ ID NO: 370) corresponding to amino acids 120-124 (RKRKV, SEQ ID NO: 371)) deleted (DNA=ATGGAGACAGACACACTC-
CTGCTATGGGTACTGCTGCTCTGGGTTCCAGGTTC-
CACCGGTTACGACTTCACTAACTGTGACTTTCAGA-
AGATTGAAGCAGACTATCTCCGTACTATTTCTAAAG-
ACCTGATTACATATATGAGTGGGACTAAAAGTACCG-
ACTTCAACAACACCGTCTCCTGTAGCAATCGGCCA-
CACTGCCTTACTGAAATCCAGAGCCTAACCTTCAAT-
CCCACCCCCGCTGCGCGTCGCTCGCCAAGGAAA-
TGTTCGCCAGGAAAACTAAGGCTACCCTCGCTCTC-
TGGTGCCCAGGCTATTCGGAAACTCAGATAAATGC-
TACTCAGGCAATGAAGAAGAGGACAACCAATAAAT-
GTCTGGAACAAGTGTCACAATTACTAGGATTGTGG-
CGTCGCTTCATTCGAACTTTACTGAAACAACAGCA-
CCACCACCACCACCATGACTATAAAGACGATGACG-
ACAAAT (SEQ ID NO: 377); Protein=METDTLLLWVL-
LLWVPGSTGYDFTNCDFQKIEADYLRTISKDLITYMS-
GTKSTDFNNTVSCSNRPHCLTEIQSLTFNPTPRCASL-
AKEMFARKTKATLALWCPGYSETQINATQAMKKRT-
TNKCLEQVSQLLGLWRRFIRTLLKQQHHHHHHDYK-
DDDDK (SEQ ID NO: 378) or as a full-length/native product
(nucleotide sequence=ATGGAGACAGACACACTCCTG-
CTATGGGTACTGCTGCTCTGGGTTCCAGGTTCCAC-
CGGTTACGACTTCACTAACTGTGACTTTCAGAAGAT-
TGAAGCAGACTATCTCCGTACTATTTCTAAAGACCT-
GATTACATATATGAGTGGGACTAAAAGTACCGACTT-
CAACAACACCGTCTCCTGTAGCAATCGGCCACACT-
GCCTTACTGAAATCCAGAGCCTAACCTTCAATCCC-
AACCCCCGCTGCGCGTCGCTCGCCAAGGAAATGT-
TCGCCAGGAAAACTAAGGCTACCCTCGCTCTCTGG-
TGCCCAGGCTATTCGGAAACTCAGATAAATGCTACT-
CAGGCAATGAAGAAGAGGAGAAAAAGGAAAGTC-
ACAACCAATAAATGTCTGGAACAAGTGTCACAATT-
ACTAGGATTGTGGCGTCGCTTCATTCGAACTTTACT-
GAAACAACAGCACCACCACCACCACCATGACTATA-
AAGACGATGACGACAAA (SEQ ID NO: 379); Protein=
METDTLLLWVLLLWVPGSTGYDFTNCDFQKIEADY-
LRTISKDLITYMSGTKSTDFNNTVSCSNRPHCLTEIQS-
LTFNPTPRCASLAKEMFARKTKATLALWCPGYSETQ-
INATQAMKKRRKRKVTTNKCLEQVSQLLGLWRRFI-
RTLLKQQHHHHHHDYKDDDDK (SEQ ID NO: 380)
fused to the same C terminal polyHIS-Flag in COS PKB cells.
Note that the amino acid sequence 1-20 (METDTLLLWV-
LLLWVPGSTG, SEQ ID NO: 381) is a signal peptide cleaved from the mature product of both these cynomolgus proteins.

Example 2

Mouse Anti-Human TSLP Antibodies hTSLP-Fc was used for immunization of Balb/c mice (Jackson Laboratories, Bar Harbor, Me.). After several rounds of immunization, lymphocytes were released from the spleen and were fused with mouse myeloma cells, NS1 (ATCC) by chemical fusion with 50% PEG/DMSO (Sigma). The fused cells were seeded in 96-well plates at the density of $2\times10^4$ cells/well in 200 ul of DMEM HAT (0.1 mM hypoxanthine, 0.16 mM thymidine, 4 mM aminopterin, Sigma) media supplemented with 10% FBS, 5% Origen Cloning Factor (BioVeris™), 1× Penicillin-Streptomycin-Glutamine, Sodium Pyruvate (Invitrogen). Medium was replaced 7 days post-fusion with DMEM HT (0.1 mM hypoxanthine, 0.16 mM thymidine) media supplemented with 10% FBS, 5% Origen Cloning Factor (BioVeris™), 1× Penicillin-Streptomycin-Glutamine, Sodium Pyruvate (Invitrogen). Conditioned media was collected two days after medium change and preceded for primary screening.

Example 3

Fully Human Antibody Generation

Fully human monoclonal antibodies specific for TSLP were generated using the XenoMouse® technology according to protocols described, for example, in U.S. 2005/0118643, U.S. Pat. Nos. 6,114,598, 6,162,963, 7,049,426, 7,064,244, Green et al., Nature Genetics 7:13-21 (1994), Medez et al. Nature Genetics 15:146-156 (1997), Green and Jakobovitis J. Ex. Med. 188:483-495 (1998) (all of which are incorporated by reference herein), and as described below.

Two campaigns were conducted. In campaign 1, IgG2 and IgG4 cohorts of XenoMouse® were utilized. 50% of the mice received *E. coli* produced human TSLP and 50% received mammalian produced human TSLP (described above). Serum titers were monitored by ELISA (described below) and mice with the best titers were fused to generate hybridomas using the following protocols.

Selected mice were sacrificed and the draining lymph nodes harvested and pooled from each cohort. The lymphoid cells were enriched for B cells and the B cells fused with myeloma cells to create hybridomas. The fused hybridoma lines were then plated in hybridoma media and cultured for 10-14 days at 37° C. The hybridoma supernatants were screened for IgG antibodies binding to TSLP by ELISA as described below.

A second campaign was initiated in which two cohorts of IgG2 XenoMouse® were immunized with mammalian produced human TSLP, and one cohort was boosted with cynomolgus TSLP. After several rounds of immunization, lymphocytes from lymph nodes were fused and cultured as described above. After culturing, hybridoma supernatants were screened for binding to TSLP by ELISA, as described below.

The polyclonal supernatants from both campaigns were selected for further subcloning on the basis of the assays set out below. The hybridomas containing antibodies that are potent inhibitors of TSLP activity were identified, and cross-reactivity with cyno TSLP was further determined The results are shown in Example 5 below. Promising hybridoma supernatants were selected on the basis of their performance in the primary DC assay described below. Those hybridomas were single cell cloned and expanded for further testing. The antibodies were then purified as described below.

Antibodies were purified from conditioned media of the hybridomas using Mab Select (GE Healthcare) resin. 100 ul of a 1:2 slurry of Mab Select resin equilibrated in PBS was added to between 7 and 10 ml of conditioned media (CM). The tubes were placed on rotators at 4-8° C. overnight. The tubes were centrifuged at 1,000×g for 5 minutes and the non-bound fraction was decanted. The resin was washed with 5 ml of PBS, and centrifuged and decanted as above. The resin was then transferred to a SPIN-X, 0.45 um, 2 ml tube. The resin was washed an additional two times with 0.5 ml of PBS and centrifuged. The Mabs were eluted with 0.2 ml of 0.1M acetic acid by incubating at room temperature with occasional mixing for 10 minutes. The tubes were centrifuged, and 30 ul of 1M Tris buffer Ph 8.0 is added to the eluate. Purified Mab's were stored 4-8° C.

Example 4

Antibody Assays

A. ELISA to Detect Presence of Anti-TSLP Antibody

ELISAs were performed by coating Costar 3368 medium binding 96 well plates with recombinantly produced wtHuTSLP or pHisFlag at 2 ug/ml 50 ul/well in 1×PBS/0.05% azide, and incubated overnight at 4° C. The plates were washed and blocked with 250 ul of 1×PBS/1% milk (the assay diluent), and incubated at least 30 minutes at room temperature.

Approximately 50 ul/well hybridoma supernatants, positive control mouse antibody M385, or negative control were added, and incubated at room temperature for 2 hours. The plates were washed, and a secondary antibody, goat anti-human IgG Fc HPR (Pierce), or alternatively a goat anti-mouse IgG HPR (Jackson Labs), was applied at 400 ng/ml in assay diluent. The plates were incubated 1 hr at RT, washed, and the OD at 450 nm read.

B Screening of Anti-TSLP Hybridoma Supernatants was Performed Using One of the Following Functional Assays 1. 96 well plates were coated with soluble huIL-7Ra-huTSLPR-Fc protein, with an 8 aa acid linker (SGGAPMLS, SEQ ID NO: 382) between the receptor and a human Fc, and incubated overnight at 4° C.

2. The plates were washed and blocked for 1 hour at RT with PBS+1% BSA+5% sucrose.

3. The plates were incubated with biotinylated huTSLPHFdel (HF stands for polyHis Flag, where the TSLP has the furin cleavage site deleted) (del). The plates were then incubated (+/−) hybridoma supernatants or mouse anti-human TSLP (M385) as a positive control for 2 h at RT.

4. SA-HRP detection (streptavidin-horseradish peroxidase). SA binds strongly to the biotin portion of biotinylated huTSLPHFdel and HRP catalyzes the oxidation of the chromogen, TMB (which turns blue), by hydrogen peroxide.

B. Cell Based Assays

1) The inhibition of TSLP-induced proliferation of stable BAF cell line expressing the human TSLPR-IL7R complex by hybridoma supernatants or purified antibodies was determined according to the following protocol.

1. BAF: Hu TSLPR stable cell lines in growth media, RPMI 1640+10% FBS+1% L-Glutamine+0.1% Pen/Strep+0.1% 2-ME were washed to remove TSLP used in maintenance media, that is the same as the growth media but with the addition of 10 ng/mL of huTSLPHFwt.

2. HuTSLPwtpHF (+/−) or cynomolgus TSLPwtpHF (+/−) were incubated with hybridoma supernatants/purified antibody/or mouse anti-human TSLP (M385) for 30 minutes at room temperature in wells.

3. $5\times10^4$ BAF cells/well were added and incubated for 3 days.

4. The cells were pulsed with tritiated thymidine (1 uCi/well) overnight. Cell proliferation of the BAF cells, or the inhibition thereof, was assessed by the amount of tritiated thymidine incorporation (CPM) by the cells.

2) Primary cell assay. Inhibition of TSLP induced osteoprotegerin (OPG) (described in U.S. Pat. No. 6,284,728) production from primary human dendritic cells (DC) by hybridomas or purified antibodies was determined according to the following protocol.

1. Peripheral blood CD11c+ myeloid DCs were enriched from normal inhouse donor leukapheresis packs using CD1c (BDCA-1) DC isolation kit (Miltenyi Biotec).

2. huTSLPwtpHF (+/−) or cynomolgus TSLPwtpHF were incubated with supernatants or purified antibody or mouse anti-human TSLP for 30 minutes at room temperature.

3. $1\times10^5$ cells/well were added and incubated for 48 hours. Supernatants were harvested and assayed for human OPG production by ELISA, and the inhibition of OPG production by the hybridoma supernatants or purified antibodies was determined The OPG ELISA was performed using an R&D systems DuoSet® development kit. Anti-TSLP antibodies inhibited OPG production from cells in a dose-dependent manner.

3) Cynomolgus Peripheral Blood Mononuclear Cell Assay Inhibition of CynoTSLP induced CCL22/MDC production by hybridoma supernatants or purified antibodies was determined according to the following protocol.

1. Peripheral blood mononuclear cells (PBMC) from peripheral blood obtained from cynomolgus monkeys (SNBL) were obtained by overlaying 1:1 blood:PBS mixture over isolymph.

2. Cynomolgus TSLPwtpHF(+/−) supernatants/purified antibody or soluble huIL-7Ra-huTSLPR-Fc were incubated for 30 minutes at room temperature.

3. $4\times10^5$ cells/well were added and incubated for 5 days. The supernatants were harvested and assayed for cynomolgus CCL22/MDC production by ELISA.

Example 5

$K_D$ Determinations

The surface plasmon resonance experiments described in this patent application were conducted at 25° C. using a BIACORE 3000 instrument (Biacore International AB, Uppsala, Sweden) equipped with a CM4 sensor chip. Anti-Fcγ specific capture antibodies were covalently immobilized to two flow cells on the CM4 chip using standard amine-coupling chemistry with HBS-EP as the running buffer. Briefly, each flow cell was activated with a 1:1 (v/v) mixture of 0.1 M NHS and 0.4 M EDC. AffiniPure Goat Anti-Human IgG, Fcγ Fragment Specific antibody (Jackson ImmunoResearch Inc. West Grove, Pa.) at 30 ug/ml in 10 mM sodium acetate, pH 5.0 was immobilized with a target level of 3,000 RUs on two flow cells. Residual reactive surfaces were deactivated with an injection of 1 M ethanolamine The running buffer was then switched to HBS-EP+0.1 mg/ml BSA for all remaining steps.

The following antibodies were tested. A5 IgG2 was a purified clonal antibody, A2 IgG1 and IgG2 were recombinant purified antibodies, and A3 IgG4 and A4 IgG4 were clonal supernatants. The antibodies were diluted appropriately in running buffer so that a 2 minute injection at 10 μl/min over the test flow cell resulted in approximately 110-175 response units of antibody captured on the test flow cell surface. No antibody was captured on the control flow cell surface. Human, cyno, or murine TSLP at various concentrations, along with buffer blanks were then flown over the two flow cells. The concentration ranges for human and cyno TSLP were from 0.44-100 nM while the concentration range for murine TSLP was from 8.2-6000 nM. A flow rate of 50 ul/min was used and a 2 minute association phase followed by a 10-30 minute dissociation phase. After each cycle the surfaces were regenerated with a 30 second injection of 10 mM glycine pH 1.5. Fresh antibody was then captured on the test flow cell to prepare for the next cycle.

Data was double referenced by subtracting the control surface responses to remove bulk refractive index changes, and then subtracting the averaged buffer blank response to remove systematic artifacts from the experimental flow cells. The TSLP data were processed and globally fit to a 1:1 interaction model with a local Rmax in BIA evaluation Software v 4.1. (Biacore International AB, Uppsala, Sweden). Association ($k_a$) and dissociation ($k_d$) rate constants were determined and used to calculate the dissociation equilibrium constant ($K_D$). The dissociation rate constants and dissociation equilibrium constants are summarized in the table found in Example 6.

Example 6

In Vitro Activity of Antibodies

The following antibodies were characterized using the BIACORE assay described above for kd and KD. The primary dendritic cell assay was used for determining IC50 (pM). The data for A5 was generated with purified clonal antibody, for A2 was generated with recombinant purified antibody, and data for A3 and A4 was generated using clonal supernatant. All versions of TSLP were generated from mammalian cells.

| Antibody | TSLP | kd (1/x) off-rate | KD (pM) | IC50 (pM) |
|---|---|---|---|---|
| A5 IgG2 | Hu TSLP | $7.36 \times 10^{-5}$ | 29.2 | 100-220 |
| | Cyno TSLP | $8.64 \times 10^{-5}$ | 51.2 | 680-970 |
| | Mu TSLP | $8.81 \times 10^{-4}$ | 377,000 | Nd |
| A2 IgG1 | Hu TSLP | $3.49 \times 10^{-4}$ | 203 | 600-1700 |
| | Cyno TSLP | $1.04 \times 10^{-4}$ | 46.8 | 250-860 |
| | Mu TSLP | — | — | — |
| A2 IgG2 | Hu TSLP | $2.85 \times 10^{-4}$ | 157 | 6-24 |
| | Cyno TSLP | $9.42 \times 10^{-5}$ | 37.6 | Nd |
| | Mu TSLP | no binding | no binding | n/a |
| A3 IgG4 | Hu TSLP | $2.7 \times 10^{-4}$ | 170 | 6-24 |
| | Cyno TSLP | Nd | nd | Nd |
| | Mu TSLP | Nd | nd | Nd |
| A4 IgG4 | Hu TSLP | $3.30 \times 10^{-4}$ | 340 | 30-59 |
| | Cyno TSLP | Nd | nd | Nd |
| | Mu TSLP | Nd | nd | Nd |

Example 7

Recombinant Expression and Purification of Antibodies

Development of Stable Cell Line Expressing Antibodies

Overlapping oligonucleotides were synthesized corresponding to the primary sequence of the light chain or heavy chain variable domain for both the sense and anti-sense strand. This oligonucleotide pool was employed in a standard PCR. Product from this first reaction was used as template in a second PCR amplification. Amplified variable heavy chain and variable light chain fragments were sub-cloned into an intermediate vector and sequenced to identify error-free products. The variable heavy chain fragment was cloned into a transient expression vector containing a signal peptide and human IgG2 constant region. The variable light chain fragment was cloned into a transient expression vector containing a signal peptide and human lambda constant region. The complete heavy chain gene was transferred into the vector pDC324. The complete light chain gene was transferred into the expression vector, pDC323.

The CS-9 host cells used for transfection of the anti-TSLP expression plasmids are a CHO cell line derived from DXB-11 cells through adaptation to serum-free media (Rasmussen et al, Cytotechnology 28:31-42, 1998). The anti-TSLP cell lines were created by transfecting CS-9 host cells with the expression plasmids pDC323-anti-TSLP-lambda and pDC324-anti-TSLP-IgG2 using a standard electroporation or lipofection procedure. After transfection of the host cell line with the expression plasmids, the cells were grown in selection medium for 2-3 weeks to allow for selection of the plasmids and recovery of the cells. In some cases, the medium was supplemented with 3% dialyzed fetal bovine serum (ds or dFBS). If serum was used, it was removed from the medium after the selection period. The cells were grown in selective medium until they achieved>85% viability. This pool of transfected cells was then cultured in culture medium.

Cell Line Cloning

A cell bank was made of selected clones according to the following procedure. The cloning step ensures that clonal populations and cell banks were generated enabling a reproducible performance in commercial manufacturing. An amplified pool of antibody-expressing cells was seeded under limiting dilution in 96-well plates, and candidate clones were evaluated for growth and productivity performance in small-scale studies Example 8

Antibody Cross-Competition

A common way to define epitopes is through competition experiments. Antibodies that compete with each other can be thought of as binding the same site on the target. This example describes a method of determining competition for binding to TSLP and the results of the method when applied to a number of antibodies described herein.

Binning experiments can be conducted in a number of ways, and the method employed may have an effect on the assay results. Common to these methods is that TSLP is typically bound by one reference antibody and probed by another. If the reference antibody prevents the binding of the probe antibody then the antibodies are said to be in the same bin. The order in which the antibodies are employed is important. If antibody A is employed as the reference antibody and blocks the binding of antibody B the converse is not always true: antibody B used as the reference antibody will not necessarily block antibody A. There are a number of factors in play here: the binding of an antibody can cause conformational changes in the target which prevent the binding of the second antibody, or epitopes which overlap but do not completely occlude each other may allow for the second antibody to still have enough high-affinity interactions with the target to allow binding. Antibodies with a much higher affinity may have a greater ability to bump a blocking antibody out of the way. In general, if competition is observed in either order the antibodies are said to bin together, and if both antibodies can block each other then it is likely that the epitopes overlap more completely.

For this Example, a modification of the Multiplexed Binning method described by Jia, et al (J. Immunological Methods, 288 (2004) 91-98) was used. Because the presence of a furin cleavage site within TSLP can lead to heterogeneity of TSLP protein preps, a TSLP having the arginine within the furin cleavage site mutated to alanine was used. See U.S. Pat.

No. 7,288,633. Each Bead Code of streptavidin-coated Luminex beads (Luminex, #L100-L1XX-01, XX specifies the bead code) was incubated in 100 ul of 6 pg/bead biotinylated monovalent mouse-anti-human IgG capture antibody (BD Pharmingen, #555785) for 1 hour at room temperature in the dark, then washed 3× with PBSA, phosphate buffered saline (PBS) plus 1% bovine serum albumin (BSA). Each bead code was separately incubated with 100 ul of a 1:10 dilution anti-TSLP antibody (Coating Antibody) for 1 hour then washed. The beads were pooled then dispensed to a 96-well filter plate (Millipore, #MSBVN1250). 100 ul of 2 ug/ml parental TSLP was added to half the wells and buffer to the other half and incubated for 1 hour then washed. 100 ul of a 1:10 dilution anti-TSLP antibody (Detection Ab) was added to one well with TSLP and one well without TSLP, incubated for 1 hour then washed. An irrelevant human-IgG (Jackson, #009-000-003) as well as a no antibody condition (blank) were run as negative controls. 20 ul PE-conjugated monovalent mouse-anti-human IgG (BD Pharmingen, #555787) was added to each well and incubated for 1 hour then washed. Beads were resuspended in 75 ul PBSA and at least 100 events/bead code were collected on the BioPlex instrument (BioRad).

Median Fluorescent Intensity (MFI) of the antibody pair without TSLP was subtracted from signal of the corresponding reaction containing TSLP. For the antibody pair to be considered bound simultaneously, and therefore in different bins, the value of the reaction had to meet two criteria: 1) the values had to be 2 times greater than the coating antibody paired with itself, the irrelevant or the blank, whichever was highest, and 2) the values had to be greater than the signal of the detection antibody present with the irrelevant or the blank coated bead.

Analysis of competition between the antibodies was complicated by the fact that there was an incongruity between the performance of antibodies as probes versus their performance as blockers. However, if one considers only those bins of antibodies that are unambiguous (i.e. each antibody will block the others when used as a reference) a minimum of eight bins were found as shown in Table 4 below.

TABLE 4

| Bin 1 | 2 | 3 | 4 | 5 | 6 | 7 | 8 |
|---|---|---|---|---|---|---|---|
| A5 | A6 | A27 | A24 | A10 | A4 | A2 | A23 |
| A17 | A7 | A11 | A12 | A26 | A23 | A21 | A6 |
| A6 | A11 | A24 | A10 | A4 | | A23 | |
| | | | A26 | | | | |

It is notable that some antibodies, such as A23 and A6, are found in multiple bins. It is possible to determine other binning relationships, and the inclusion or exclusion of antibodies from these bins was biased towards exclusion.

The results of the assay determined which of the other antibodies cross-compete for binding with the reference antibody. By "cross-competes for binding" it is meant that the reference antibody when used as the blocking antibody is able to block binding of the other antibody when used as a probe and vice versa. In other words, if the reference antibody was able to block the other antibody but the other antibody was not able to block the reference antibody, the antibodies were not said to cross-compete. A list of cross-competing antibodies is provided in Table 5.

TABLE 5

| Reference Antibody | Exemplary Cross-Competing Antibodies |
|---|---|
| A2 | A21, A23 |
| A4 | A10, A23, A26 |
| A5 | A6, A8, A11, A17 |
| A6 | A5, A7, A8, A11, A17, A23 |
| A7 | A6, A8, A11, A17 |
| A8 | A5, A6, A7, A17, A23 |
| A10 | A4, A12, A24, A26 |
| A11 | A5, A6, A7, A17, A24, A27 |
| A12 | A10, A24, A26 |
| A17 | A5, A6, A7, A8, A11 |
| A21 | A2, A23, A27 |
| A23 | A2, A4, A6, A8, A21 |
| A24 | A10, A11, A12, A26, A27 |
| A26 | A4, A10, A12, A24 |
| A27 | A11, A21, A24 |

Example 9

Epitope Mapping

While epitopes are often thought of as linear sequences, it is more often the case that an antibody recognizes a face of the target which is composed of discontinuous amino acids. These amino acids may be far apart on the linear sequence but brought close together through the folding of the target, and antibodies which recognize such an epitope are known as conformation-sensitive or just conformational antibodies. This kind of binding may be defined through the use of denatured Western blots, wherein prior to running on a gel the target is heated in the presence of detergent and reducing agent to unfold it. The blot from this gel may then be probed by antibodies, and an antibody which is able to recognize the target after this treatment probably recognizes a linear epitope. Although the epitopes of antibodies which bind linear sequences may be defined through binding to peptides (e.g. PepSpot), conformational antibodies would not be expected to bind standard peptides with high affinity.

Reduced, heat-denatured, purified parental TSLP protein was loaded on 10% Bis-Tris Nupage gel in MES SDS Running Buffer. Protein was transferred to PVDF Membrane, blocked with 5% Non-fat Dry Milk (NFDM) in PBS+0.05% Tween (PBST), and incubated with TSLP antibodies for 1 hour at RT. The blots were washed 3× in PBST then incubated with a goat anti-huIgG secondary antibody for 1 hour at RT. The blots were washed again and incubated with an anti-goat IgG:Alexa 680. After washing 3× in PBST, the blots were scanned on the LiCor to visualize bands.

Antibodies A2, A4, A5, A6, A7, A10, A21, A23, and A26 were characterized using this method. Antibodies A2, A4, and A5 bound to the linear epitope as evidenced by a strong band on the Western Blot. All other antibodies were conformational as due to no or extremely weak bands on the Western Blot.

Epitopes may be further defined as structural or functional. Functional epitopes are generally a subset of the structural epitopes and consist of those residues which directly contribute to the affinity of the interaction (e.g. hydrogen bonds, ionic interactions). Structural epitopes may be thought of as the patch of the target which is covered by the antibody.

Scanning mutagenesis was employed to further define the epitopes bound by the antibodies. Alanine scanning mutagenesis is used frequently to define functional epitopes; the substitution of alanine (methyl sidechain) is essentially an amputation of the wild-type amino acid sidechain and is fairly subtle. Interactions with the protein backbone, such as hydrogen bonding to the amide linkages, would likely not be revealed with alanine scanning. Instead, arginine and glutamic acid scanning mutagenesis was used. These two sidechains were chosen due to their large steric bulk and their charge, which allows mutations which occur in the structural epitope to have a greater effect on antibody binding. Arginine was generally employed except when the WT reside was arginine or lysine, and in these cases the residue was mutated to glutamic acid to switch the charge. In a few cases, the WT residue was mutated to both arginine and glutamic acid.

Ninety-five amino acids, distributed throughout TSLP, were selected for mutation to arginine or glutamic acid. As hydrophobic residues are generally found inside the folded core of a protein, the selection was biased towards charged or polar amino acids to reduce the likelihood of the mutation resulting in misfolded protein. As there was no crystal structure, these residues were chosen essentially at random and distributed throughout TSLP. As described in Example 8, a TSLP containing a mutated furin cleavage site was used.

BIOPLEX™ binding assay was used to measure binding anti-TSLP antibodies to mutant TSLP. A biotinylated Penta-His Ab (Qiagen, Lot#: 130163339) was bound onto 100 bead codes of streptavidin-coated beads (Luminex, #L100-L1XX-01, XX specifies the bead code). These were used to capture the his-tagged protein. The 100 bead codes allowed the multiplexing of all 85 mutants, 3 parental controls, an irrelevant protein and 12 blanks. Antibody binding to mutant protein was compared to antibody binding to the parental.

100 ul of a 1:5 dilution of the TSLP mutants and parental in supernatant and 1 ug/mL purified TSLP WT, 1 ug/mL irrelevant protein or no protein were bound to the coated beads for 1 hour at RT with vigorous shaking. The beads were washed and aliquoted into a 96-well filter plate (Millipore). 100 ul anti-TSLP antibodies in 4-fold dilutions were added to triplicate wells, incubated for 0.5 hours at RT and washed. 100 ul of 1:250 dilution of PE-conjugated anti-human IgG Fc (Jackson, #109-1,6-170) was added to each well, incubated for 0.5 hours and washed. Beads were resuspended in 75 uL, shaken for at least 3 mins, and read on the BIOPLEX™

A residue was considered part of the structural epitope (a "hit") when mutating it to arginine or glutamic acid disrupted antibody binding. This was seen as a shift in the EC50 or a reduction of maximum signal compared to antibody binding to parental TSLP.

Statistical analyses of antibody binding curves to parental and mutants were used to identify statistically significant EC50 shifts. The analysis took into consideration variation in the assay and curve fitting.

The EC50s of the mutant binding curves and parental binding curves were compared. Statistically significant differences were identified as hits for further consideration. The curves with "nofit" or "badfit" flags were excluded from this analysis.

Two sources of variations were considered in the comparison of EC50 estimates, variation from the curve fit and the bead-bead variation. Parental and mutants were linked to different beads, hence their difference were confounded with the bead-bead difference. The curve fit variation was estimated by the standard error of the log EC50 estimates. Bead-bead variation was experimentally determined using an experiment where parental controls were linked to each one of the beads. The bead variation in EC50 estimates of parental binding curve were used to estimate the bead-bead variation.

The comparisons of two EC50s (in log scale) were conducted using Student's t-test. A t-statistics is calculated as the ratio between delta (the absolute differences between EC50 estimates) and the standard deviation of delta. The variance of delta is estimated by the sum of the three components, variance estimate of EC50 for mutant and parental curves in the nonlinear regression and two times the bead-bead variance estimated from a separate experiment. The multiple of two for the bead-bead variance is due to the assumption that both mutant and parental beads have the same variance.

The degree of freedom of the standard deviation of delta was calculated using the Satterthwaite's (1946) approximation. Individual p-values and confidence intervals (95% and 99%) were derived based on Student's t distribution for each comparison. In the case of multiple parental controls, a conservative approach was implemented by picking the parental control that was most similar to the mutant, i.e., picking the ones with the largest p-values.

Multiplicity adjustments were important to control the false positives while conducting a large number of tests simultaneously. Two forms of multiplicity adjustment were implemented for this analysis: family wise error (FWE) control and false discovery rate (FDR) control. The FWE approach controls the probability that one or more hits are not real; FDR approach controls the expected proportion of false positive among the selected hits. The former approach is more conservative and less powerful than the latter one. There are many methods available for both approaches, for this analysis, Hochberg's (1988) method was chosen for FWE analysis and Benjamini-Hochberg's (1995) FDR method for FDR analysis. Adjusted p-values for both approaches were calculated either for each antibody or the whole assay.

Mutations whose EC50 was significantly different from parental, i.e. having an FWE adjusted p-value for each antibody of less than 0.01, or a maximal signal below 50% of parental were considered part of the structural epitope (Table 6). Mutations that were significant by either EC50 shirt or max signal reduction for all antibodies were considered misfolded. These mutations were; Y15R, T55R, T74R and A77R.

TABLE 6

Summary of mutations that affect antibody binding in the BIOPLEX and are part of the structural epitope.

| Antibody | Linear | Increased Binding Affinity | Decreased Binding Afinity |
|---|---|---|---|
| A2 | Yes | K67E, K97E, K98E, R100E, K101E, K103E | K21E, T25R, S28R, S64R, K73E |
| A4 | Yes | K97E, K98E, R100E, K101E, K103E | K10E, A14R, K21E, D22R, K73E, K75E, A76R |
| A5 | Yes | | K12E, D22R, S40R, R122E, N124E, R125E, K129E |
| A6 | No | | S40R, S42R, H46R, R122E, K129E |
| A7 | No | K101E | D2R, T4R, D7R, S42R, H46R, T49R, E50R, Q112R, R122E, R125E, K129E |

TABLE 6-continued

Summary of mutations that affect antibody binding in the BIOPLEX and are part of the structural epitope.

| Antibody | Linear | Increased Binding Affinity | Decreased Binding Afinity |
|---|---|---|---|
| A10 | No | K97E, K98E, R100E, K101E, K103E | N5R, S17R, T18R, K21E, D22R, T25R, T33R, H46R, A63R, S64R, A66R, E68R, K73E, K75E, A76R, A92R, T93R, Q94R, A95R |
| A21 | No | K97E, K98E, R100E, K101E, K103E | K21E, K21R, D22R, T25R, T33R, S64R, K73E, K75E, E111R, S114R |
| A23 | No | K67E, K97E, K98E, R100E, K101E, K103E | E9R, K10E, K12E, A13R, S17R, S20R, K21E, K21R, K73E, K75E, N124E, R125E |
| A26 | No | K97E, K98E, R100E, K101E, K103E | A14R, K21E, D22R, A63R, S64R, K67E, K73E, A76R, A92R, A95R |

There were several mutations that disrupted the binding of multiple antibodies, notably K73E, K21E, and D22R. The mutagenesis serves to verify the data generated by binning and to further narrow in on the epitope space. The mutations in TSLP appear to affect clusters of antibodies that bin together.

Example 10

Toxicology

Antibodies that bind human TSLP yet also cross-react with TSLP of other species allow for toxicology testing in those species. In this example, an antibody that cross-reacts with cynomolgus monkey TSLP was administered to cynomolgus monkeys. The monkeys were then observed for toxic effects.

A single-dose safety pharmacology study in cynomolgus monkeys indicated that a single 300 mg/kg intravenous dose of the antibody had no cardiovascular, respiratory, body temperature, or neurobehavioral effects.

Cynomolgus monkeys (5/sex/group) were given 30, 100, or 300 mg/kg doses once weekly for 4 weeks, subcutaneously. No adverse toxicology was observed at any dose. The antibody did not affect clinical observations, body weight, ophthalmology, ECGs, clinical pathology or anatomic pathology.

In a separate study, four male telemeterized cynomolgus monkeys were given a single intravenous dose of vehicle (day 1) and 300 mg/kg antibody (day 3). Over a four day observation period no effects on cardiovascular, respiratory, or neurological function was observed.

The antibody was further tested to determine cross-reactivity with normal human and cynomolgus monkey tissue as recommended in the FDA guideline "Points to Consider in the Manufacture and Testing of Monoclonal Anitbody Prducts for Human Use" (FDA Center for Biologics Evaluation and Research, 28 Feb. 1997). No staining of normal tissue at 1 or 50 ug/mL was observed.

The above results suggest that the antibody is not expected to produce toxic effects in humans.

What is claimed is:

1. A method of treating a TSLP-related inflammatory condition in a subject in need of such treatment comprising administering a therapeutically effective amount of a composition comprising an isolated TSLP antagonist antigen binding protein that specifically binds to a TSLP polypeptide as set forth in amino acids 29-159 of SEQ ID NO:2, wherein said TSLP antagonist antigen binding protein comprises:
   a. a light chain variable domain comprising:
      i. a light chain CDR1 sequence comprising the amino acid sequence set forth in SEQ ID NO:13;
      ii. a light chain CDR2 sequence comprising the amino acid sequence set forth in SEQ ID NO:60; and
      iii. a light chain CDR3 sequence comprising the amino acid sequence set forth in SEQ ID NO:105; and
   b. a heavy chain variable domain comprising:
      i. a heavy chain CDR1 sequence comprising the amino acid sequence set forth in SEQ ID NO:145;
      ii. a heavy chain CDR2 sequence comprising the amino acid sequence set forth in SEQ ID NO:173, and
      iii. a heavy chain CDR3 sequence comprising the amino acid sequence set forth in SEQ ID NO:212.

2. The method of claim 1, wherein said TSLP antagonist antigen binding protein comprises either:
   a. a light chain variable domain sequence selected from the group consisting of:
      i. a sequence of amino acids at least 80% identical to SEQ ID NO:363;
      ii. a sequence of amino acids encoded by a polynucleotide sequence that is at least 80% identical to SEQ ID NO:362; and
      iii. a sequence of amino acids encoded by a polynucleotide that hybridizes under moderately stringent conditions to the complement of a polynucleotide consisting of SEQ ID NO:362;
   b. a heavy chain variable domain selected from the group consisting of:
      i. a sequence of amino acids that is at least 80% identical to SEQ ID NO:361;
      ii. a sequence of amino acids encoded by a polynucleotide sequence that is at least 80% identical to SEQ ID NO:360; and
      iii. a sequence of amino acids encoded by a polynucleotide that hybridizes under moderately stringent conditions to the complement of a polynucleotide consisting of SEQ ID NO:360; or
   c. a light chain variable domain of (a) and a heavy chain variable domain of (b).

3. The method of claim 2, wherein said TSLP antagonist antigen binding protein comprises either:
   a. a light chain variable domain comprising the amino acid sequence as set forth in SEQ ID NO:363;
   b. a heavy chain variable domain comprising the amino acid sequence as set forth in SEQ ID NO:361; or
   c. the light chain variable domain of (a) and the heavy chain variable domain of (b).

4. The method of claim 3, wherein said TSLP antagonist antigen binding protein comprises the light chain variable domain of (a) and the heavy chain variable domain of (b).

5. The method of claim 1, wherein said TSLP antagonist antigen binding protein binds to TSLP with substantially the same Kd as an antibody comprising a) a light chain comprising a light chain variable domain comprising the amino acid sequence as set forth in SEQ ID NO:363 and a lambda light chain constant domain comprising the amino acid sequence as set forth in SEQ ID NO:369; and b) a heavy chain comprising a heavy chain variable domain comprising the amino acid sequence as set forth in SEQ ID NO:361 and an IgG2 heavy constant domain comprising the amino acid sequence as set forth in SEQ ID NO:365.

6. The method of claim 1, wherein said TSLP antagonist antigen binding protein inhibits TSLP activity to block osteoprotegerin (OPG) production from primary human dendritic cells with the same IC50 as an antibody comprising a) a light chain comprising a light chain variable domain comprising the amino acid sequence as set forth in SEQ ID NO:363 and a lambda light chain constant comprising the amino acid sequence as set forth in SEQ ID NO:369; and b) a heavy chain comprising a heavy chain variable domain comprising the amino acid sequence as set forth in SEQ ID NO:361 and an IgG2 heavy constant domain comprising the amino acid sequence as set forth in SEQ ID NO:365.

7. The method of claim 1, wherein said TSLP antagonist antigen binding protein is selected from the group consisting of a human antibody, a humanized antibody, a chimeric antibody, a monoclonal antibody, a recombinant antibody, an antigen-binding antibody fragment, a single chain antibody, a monomeric antibody, a diabody, a triabody, a tetrabody, a Fab fragment, an IgD antibody, an IgE antibody, an IgM antibody, an IgG1 antibody, an IgG2 antibody, an IgG3 antibody, and an IgG4 antibody.

8. The method of claim 1, wherein said TSLP antagonist antigen binding protein is a human antibody.

9. The method of claim 1, wherein said TSLP antagonist antigen binding protein is a monoclonal antibody comprising one or more light chains and one or more heavy chains.

10. The method of claim 9, wherein said TSLP antagonist antigen binding protein comprises a) a light chain comprising a light chain variable domain comprising the amino acid sequence as set forth in SEQ ID NO:363 and a lambda light chain constant domain comprising the amino acid sequence as set forth in SEQ ID NO:369; and b) a heavy chain comprising a heavy chain variable domain comprising the amino acid sequence as set forth in SEQ ID NO:361 and an IgG2 heavy constant domain comprising the amino acid sequence as set forth in SEQ ID NO:365.

11. The method of any of claims 1-10, wherein the TSLP-related inflammatory condition is an allergic inflammatory disorder.

12. The method of claim 11, wherein the allergic inflammatory disorder is a pulmonary inflammatory disease.

13. The method of claim 12, wherein the pulmonary inflammatory disease is allergic asthma.

14. The method of any of claims 1-10, wherein the TSLP-related inflammatory condition is asthma.

* * * * *

SEQUENCE LISTING

```
<160> NUMBER OF SEQ ID NOS: 382

<210> SEQ ID NO 1
<211> LENGTH: 743
<212> TYPE: DNA
<213> ORGANISM: Homo sapiens
<220> FEATURE:
<221> NAME/KEY: CDS
<222> LOCATION: (200)..(676)

<400> SEQUENCE: 1
gcagccagaa agctctggag catcagggag actccaactt aaggcaacag catgggtgaa      60
taagggcttc ctgtggactg gcaatgagag gcaaaacctg gtgcttgagc actggcccct     120
aaggcaggcc ttacagatct cttacactcg tggtgggaag agtttagtgt gaaactgggg     180
tggaattggg tgtccacgt atg ttc cct ttt gcc tta cta tat gtt ctg tca      232
                     Met Phe Pro Phe Ala Leu Leu Tyr Val Leu Ser
                     1               5                   10 gtt tct ttc agg aaa atc ttc atc tta caa ctt gta ggg ctg gtg tta      280
Val Ser Phe Arg Lys Ile Phe Ile Leu Gln Leu Val Gly Leu Val Leu
            15                  20                  25 act tac gac ttc act aac tgt gac ttt gag aag att aaa gca gcc tat      328
Thr Tyr Asp Phe Thr Asn Cys Asp Phe Glu Lys Ile Lys Ala Ala Tyr
        30                  35                  40
```

| | | | | | | | | | | | | | | | | |
|---|---|---|---|---|---|---|---|---|---|---|---|---|---|---|---|---|
| ctc | agt | act | att | tct | aaa | gac | ctg | att | aca | tat | atg | agt | ggg | acc | aaa | 376 |
| Leu | Ser | Thr | Ile | Ser | Lys | Asp | Leu | Ile | Thr | Tyr | Met | Ser | Gly | Thr | Lys | |
| | 45 | | | | 50 | | | | | 55 | | | | | | |
| agt | acc | gag | ttc | aac | aac | acc | gtc | tct | tgt | agc | aat | cgg | cca | cat | tgc | 424 |
| Ser | Thr | Glu | Phe | Asn | Asn | Thr | Val | Ser | Cys | Ser | Asn | Arg | Pro | His | Cys | |
| 60 | | | | | 65 | | | | | 70 | | | | | 75 | |
| ctt | act | gaa | atc | cag | agc | cta | acc | ttc | aat | ccc | acc | gcc | ggc | tgc | gcg | 472 |
| Leu | Thr | Glu | Ile | Gln | Ser | Leu | Thr | Phe | Asn | Pro | Thr | Ala | Gly | Cys | Ala | |
| | | | | 80 | | | | | 85 | | | | | 90 | | |
| tcg | ctc | gcc | aaa | gaa | atg | ttc | gcc | atg | aaa | act | aag | gct | gcc | tta | gct | 520 |
| Ser | Leu | Ala | Lys | Glu | Met | Phe | Ala | Met | Lys | Thr | Lys | Ala | Ala | Leu | Ala | |
| | | 95 | | | | | 100 | | | | | 105 | | | | |
| atc | tgg | tgc | cca | ggc | tat | tcg | gaa | act | cag | ata | aat | gct | act | cag | gca | 568 |
| Ile | Trp | Cys | Pro | Gly | Tyr | Ser | Glu | Thr | Gln | Ile | Asn | Ala | Thr | Gln | Ala | |
| | | 110 | | | | | 115 | | | | | 120 | | | | |
| atg | aag | aag | agg | aga | aaa | agg | aaa | gtc | aca | acc | aat | aaa | tgt | ctg | gaa | 616 |
| Met | Lys | Lys | Arg | Arg | Lys | Arg | Lys | Val | Thr | Thr | Asn | Lys | Cys | Leu | Glu | |
| 125 | | | | | 130 | | | | | 135 | | | | | | |
| caa | gtg | tca | caa | tta | caa | gga | ttg | tgg | cgt | cgc | ttc | aat | cga | cct | tta | 664 |
| Gln | Val | Ser | Gln | Leu | Gln | Gly | Leu | Trp | Arg | Arg | Phe | Asn | Arg | Pro | Leu | |
| 140 | | | | 145 | | | | | 150 | | | | | 155 | | |
| ctg | aaa | caa | cag | taaaccatct | ttattatggt | catatttcac | agcccaaaat | | | | | | | | | 716 |
| Leu | Lys | Gln | Gln | | | | | | | | | | | | | |

| | | |
|---|---|---|
| aaatcatctt tattaagtaa aaaaaaa | | 743 |

<210> SEQ ID NO 2
<211> LENGTH: 159
<212> TYPE: PRT
<213> ORGANISM: Homo sapiens

<400> SEQUENCE: 2

Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
    50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Arg Arg
        115                 120                 125

Lys Arg Lys Val Thr Thr Asn Lys Cys Leu Glu Gln Val Ser Gln Leu
    130                 135                 140

Gln Gly Leu Trp Arg Arg Phe Asn Arg Pro Leu Leu Lys Gln Gln
145                 150                 155

<210> SEQ ID NO 3
<211> LENGTH: 1116
<212> TYPE: DNA
<213> ORGANISM: Homo sapiens
<220> FEATURE:
<221> NAME/KEY: CDS
<222> LOCATION: (1)..(1116)

-continued

```
<400> SEQUENCE: 3 atg ggg cgg ctg gtt ctg ctg tgg gga gct gcc gtc ttt ctg ctg gga        48
Met Gly Arg Leu Val Leu Leu Trp Gly Ala Ala Val Phe Leu Leu Gly
1               5                   10                  15 ggc tgg atg gct ttg ggg caa gga gga gca gca gaa gga gta cag att        96
Gly Trp Met Ala Leu Gly Gln Gly Gly Ala Ala Glu Gly Val Gln Ile
            20                  25                  30 cag atc atc tac ttc aat tta gaa acc gtg cag gtg aca tgg aat gcc       144
Gln Ile Ile Tyr Phe Asn Leu Glu Thr Val Gln Val Thr Trp Asn Ala
        35                  40                  45 agc aaa tac tcc agg acc aac ctg act ttc cac tac aga ttc aac ggt       192
Ser Lys Tyr Ser Arg Thr Asn Leu Thr Phe His Tyr Arg Phe Asn Gly
    50                  55                  60 gat gag gcc tat gac cag tgc acc aac tac ctt ctc cag gaa ggt cac       240
Asp Glu Ala Tyr Asp Gln Cys Thr Asn Tyr Leu Leu Gln Glu Gly His
65                  70                  75                  80 act tca ggg tgc ctc cta gac gca gag cag cga gac gac att ctc tat       288
Thr Ser Gly Cys Leu Leu Asp Ala Glu Gln Arg Asp Asp Ile Leu Tyr
                85                  90                  95 ttc tcc atc agg aat ggg acg cac ccc gtt ttc acc gca agt cgc tgg       336
Phe Ser Ile Arg Asn Gly Thr His Pro Val Phe Thr Ala Ser Arg Trp
            100                 105                 110 atg gtt tat tac ctg aaa ccc agt tcc ccg aag cac gtg aga ttt tcg       384
Met Val Tyr Tyr Leu Lys Pro Ser Ser Pro Lys His Val Arg Phe Ser
        115                 120                 125 tgg cat cag gat gca gtg acg gtg acg tgt tct gac ctg tcc tac ggg       432
Trp His Gln Asp Ala Val Thr Val Thr Cys Ser Asp Leu Ser Tyr Gly
    130                 135                 140 gat ctc ctc tat gag gtt cag tac cgg agc ccc ttc gac acc gag tgg       480
Asp Leu Leu Tyr Glu Val Gln Tyr Arg Ser Pro Phe Asp Thr Glu Trp
145                 150                 155                 160 cag tcc aaa cag gaa aat acc tgc aac gtc acc ata gaa ggc ttg gat       528
Gln Ser Lys Gln Glu Asn Thr Cys Asn Val Thr Ile Glu Gly Leu Asp
                165                 170                 175 gcc gag aag tgt tac tct ttc tgg gtc agg gtg aag gct atg gag gat       576
Ala Glu Lys Cys Tyr Ser Phe Trp Val Arg Val Lys Ala Met Glu Asp
            180                 185                 190 gta tat ggg cca gac aca tac cca agc gac tgg tca gag gtg aca tgc       624
Val Tyr Gly Pro Asp Thr Tyr Pro Ser Asp Trp Ser Glu Val Thr Cys
        195                 200                 205 tgg cag aga ggc gag att cgg gat gcc tgt gca gag aca cca acg cct       672
Trp Gln Arg Gly Glu Ile Arg Asp Ala Cys Ala Glu Thr Pro Thr Pro
    210                 215                 220 ccc aaa cca aag ctg tcc aaa ttt att tta att tcc agc ctg gcc atc       720
Pro Lys Pro Lys Leu Ser Lys Phe Ile Leu Ile Ser Ser Leu Ala Ile
225                 230                 235                 240 ctt ctg atg gtg tct ctc ctc ttg tct tta tgg aaa tta tgg aga            768
Leu Leu Met Val Ser Leu Leu Leu Ser Leu Trp Lys Leu Trp Arg
                245                 250                 255 gtg aag aag ttt ctc att ccc agc gtg cca gac ccg aaa tcc atc ttc       816
Val Lys Lys Phe Leu Ile Pro Ser Val Pro Asp Pro Lys Ser Ile Phe
            260                 265                 270 ccc ggg ctc ttt gag ata cac caa ggg aac ttc cag gag tgg atc aca       864
Pro Gly Leu Phe Glu Ile His Gln Gly Asn Phe Gln Glu Trp Ile Thr
        275                 280                 285 gac acc cag aac gtg gcc cac ctc cac aag atg gca ggt gca gag caa       912
Asp Thr Gln Asn Val Ala His Leu His Lys Met Ala Gly Ala Glu Gln
    290                 295                 300 gaa agt ggc ccc gag gag ccc ctg gta gtc cag ttg gcc aag act gaa       960
Glu Ser Gly Pro Glu Glu Pro Leu Val Val Gln Leu Ala Lys Thr Glu
```

```
                305                 310                 315                 320
gcc gag tct ccc agg atg ctg gac cca cag acc gag gag aaa gag gcc           1008
Ala Glu Ser Pro Arg Met Leu Asp Pro Gln Thr Glu Glu Lys Glu Ala
            325                 330                 335 tct ggg gga tcc ctc cag ctt ccc cac cag ccc ctc caa ggc ggt gat           1056
Ser Gly Gly Ser Leu Gln Leu Pro His Gln Pro Leu Gln Gly Gly Asp
        340                 345                 350 gtg gtc aca atc ggg ggc ttc acc ttt gtg atg aat gac cgc tcc tac           1104
Val Val Thr Ile Gly Gly Phe Thr Phe Val Met Asn Asp Arg Ser Tyr
    355                 360                 365 gtg gcg ttg tga                                                           1116
Val Ala Leu
    370

<210> SEQ ID NO 4
<211> LENGTH: 371
<212> TYPE: PRT
<213> ORGANISM: Homo sapiens

<400> SEQUENCE: 4

Met Gly Arg Leu Val Leu Leu Trp Gly Ala Val Phe Leu Leu Gly
1               5                   10                  15

Gly Trp Met Ala Leu Gly Gln Gly Gly Ala Ala Glu Gly Val Gln Ile
            20                  25                  30

Gln Ile Ile Tyr Phe Asn Leu Glu Thr Val Gln Val Thr Trp Asn Ala
        35                  40                  45

Ser Lys Tyr Ser Arg Thr Asn Leu Thr Phe His Tyr Arg Phe Asn Gly
    50                  55                  60

Asp Glu Ala Tyr Asp Gln Cys Thr Asn Tyr Leu Leu Gln Glu Gly His
65                  70                  75                  80

Thr Ser Gly Cys Leu Leu Asp Ala Glu Gln Arg Asp Asp Ile Leu Tyr
                85                  90                  95

Phe Ser Ile Arg Asn Gly Thr His Pro Val Phe Thr Ala Ser Arg Trp
            100                 105                 110

Met Val Tyr Tyr Leu Lys Pro Ser Ser Pro Lys His Val Arg Phe Ser
        115                 120                 125

Trp His Gln Asp Ala Val Thr Val Thr Cys Ser Asp Leu Ser Tyr Gly
    130                 135                 140

Asp Leu Leu Tyr Glu Val Gln Tyr Arg Ser Pro Phe Asp Thr Glu Trp
145                 150                 155                 160

Gln Ser Lys Gln Glu Asn Thr Cys Asn Val Thr Ile Glu Gly Leu Asp
                165                 170                 175

Ala Glu Lys Cys Tyr Ser Phe Trp Val Arg Val Lys Ala Met Glu Asp
            180                 185                 190

Val Tyr Gly Pro Asp Thr Tyr Pro Ser Asp Trp Ser Glu Val Thr Cys
        195                 200                 205

Trp Gln Arg Gly Glu Ile Arg Asp Ala Cys Ala Glu Thr Pro Thr Pro
    210                 215                 220

Pro Lys Pro Lys Leu Ser Lys Phe Ile Leu Ile Ser Ser Leu Ala Ile
225                 230                 235                 240

Leu Leu Met Val Ser Leu Leu Leu Ser Leu Trp Lys Leu Trp Arg
                245                 250                 255

Val Lys Lys Phe Leu Ile Pro Ser Val Pro Asp Pro Lys Ser Ile Phe
            260                 265                 270

Pro Gly Leu Phe Glu Ile His Gln Gly Asn Phe Gln Glu Trp Ile Thr
        275                 280                 285
```

```
Asp Thr Gln Asn Val Ala His Leu His Lys Met Ala Gly Ala Glu Gln
        290                 295                 300

Glu Ser Gly Pro Glu Pro Leu Val Val Gln Leu Ala Lys Thr Glu
305                 310                 315                 320

Ala Glu Ser Pro Arg Met Leu Asp Pro Gln Thr Glu Glu Lys Glu Ala
                325                 330                 335

Ser Gly Gly Ser Leu Gln Leu Pro His Gln Pro Leu Gln Gly Gly Asp
            340                 345                 350

Val Val Thr Ile Gly Gly Phe Thr Phe Val Met Asn Asp Arg Ser Tyr
        355                 360                 365

Val Ala Leu
    370

<210> SEQ ID NO 5
<211> LENGTH: 33
<212> TYPE: DNA
<213> ORGANISM: Homo sapiens

<400> SEQUENCE: 5
caaggagaca gcctcagaag ctattatgca agc                                33

<210> SEQ ID NO 6
<211> LENGTH: 11
<212> TYPE: PRT
<213> ORGANISM: Homo sapiens

<400> SEQUENCE: 6

Gln Gly Asp Ser Leu Arg Ser Tyr Tyr Ala Ser
1               5                   10

<210> SEQ ID NO 7
<211> LENGTH: 33
<212> TYPE: DNA
<213> ORGANISM: Homo sapiens

<400> SEQUENCE: 7
caaggagaca gcctcagaac ctattatgca agc                                33

<210> SEQ ID NO 8
<211> LENGTH: 11
<212> TYPE: PRT
<213> ORGANISM: Homo sapiens

<400> SEQUENCE: 8

Gln Gly Asp Ser Leu Arg Thr Tyr Tyr Ala Ser
1               5                   10

<210> SEQ ID NO 9
<211> LENGTH: 42
<212> TYPE: DNA
<213> ORGANISM: Homo sapiens

<400> SEQUENCE: 9
actgggagca gctccaacat cggggcaggt tttgatgtac ac                      42

<210> SEQ ID NO 10
<211> LENGTH: 14
<212> TYPE: PRT
<213> ORGANISM: Homo sapiens

<400> SEQUENCE: 10

Thr Gly Ser Ser Ser Asn Ile Gly Ala Gly Phe Asp Val His
1               5                   10
```

<210> SEQ ID NO 11
<211> LENGTH: 42
<212> TYPE: DNA
<213> ORGANISM: Homo sapiens

<400> SEQUENCE: 11
actgggagca gctccaacat cggggcaggt tttgatgtgc ac                42

<210> SEQ ID NO 12
<211> LENGTH: 33
<212> TYPE: DNA
<213> ORGANISM: Homo sapiens

<400> SEQUENCE: 12
gggggaaaca accttggaag taaaagtgtg cac                          33

<210> SEQ ID NO 13
<211> LENGTH: 11
<212> TYPE: PRT
<213> ORGANISM: Homo sapiens

<400> SEQUENCE: 13

Gly Gly Asn Asn Leu Gly Ser Lys Ser Val His
1               5                   10

<210> SEQ ID NO 14
<211> LENGTH: 33
<212> TYPE: DNA
<213> ORGANISM: Homo sapiens

<400> SEQUENCE: 14
tctggagata aattggggga taaatatgct tgc                          33

<210> SEQ ID NO 15
<211> LENGTH: 11
<212> TYPE: PRT
<213> ORGANISM: Homo sapiens

<400> SEQUENCE: 15

Ser Gly Asp Lys Leu Gly Asp Lys Tyr Ala Cys
1               5                   10

<210> SEQ ID NO 16
<211> LENGTH: 33
<212> TYPE: DNA
<213> ORGANISM: Homo sapiens

<400> SEQUENCE: 16
caaggagaca gcctcagaat cttttatgca aac                          33

<210> SEQ ID NO 17
<211> LENGTH: 11
<212> TYPE: PRT
<213> ORGANISM: Homo sapiens

<400> SEQUENCE: 17

Gln Gly Asp Ser Leu Arg Ile Phe Tyr Ala Asn
1               5                   10

<210> SEQ ID NO 18
<211> LENGTH: 33
<212> TYPE: DNA
<213> ORGANISM: Homo sapiens -continued

```
<400> SEQUENCE: 18
cgggcaaatc agtacattag cacctattta aat                                    33

<210> SEQ ID NO 19
<211> LENGTH: 11
<212> TYPE: PRT
<213> ORGANISM: Homo sapiens

<400> SEQUENCE: 19

Arg Ala Asn Gln Tyr Ile Ser Thr Tyr Leu Asn
1               5                   10

<210> SEQ ID NO 20
<211> LENGTH: 51
<212> TYPE: DNA
<213> ORGANISM: Homo sapiens

<400> SEQUENCE: 20
aagtccagcc agagtgtttt aaacagctcc aacaataaga actacttagc t               51

<210> SEQ ID NO 21
<211> LENGTH: 17
<212> TYPE: PRT
<213> ORGANISM: Homo sapiens

<400> SEQUENCE: 21

Lys Ser Ser Gln Ser Val Leu Asn Ser Asn Asn Lys Asn Tyr Leu
1               5                   10                  15

Ala

<210> SEQ ID NO 22
<211> LENGTH: 33
<212> TYPE: DNA
<213> ORGANISM: Homo sapiens

<400> SEQUENCE: 22
cgggcgagtc agggtattag tagctggtta gcc                                    33

<210> SEQ ID NO 23
<211> LENGTH: 11
<212> TYPE: PRT
<213> ORGANISM: Homo sapiens

<400> SEQUENCE: 23

Arg Ala Ser Gln Gly Ile Ser Ser Trp Leu Ala
1               5                   10

<210> SEQ ID NO 24
<211> LENGTH: 48
<212> TYPE: DNA
<213> ORGANISM: Homo sapiens

<400> SEQUENCE: 24
aggtctagtc aaagcctcgt ctacagtgat ggagacacct acttgaat                    48

<210> SEQ ID NO 25
<211> LENGTH: 16
<212> TYPE: PRT
<213> ORGANISM: Homo sapiens

<400> SEQUENCE: 25

Arg Ser Ser Gln Ser Leu Val Tyr Ser Asp Gly Asp Thr Tyr Leu Asn
1               5                   10                  15
```

-continued

<210> SEQ ID NO 26
<211> LENGTH: 33
<212> TYPE: DNA
<213> ORGANISM: Homo sapiens

<400> SEQUENCE: 26
cgggcgagtc agggtcttag cagctggtta gcc                         33

<210> SEQ ID NO 27
<211> LENGTH: 11
<212> TYPE: PRT
<213> ORGANISM: Homo sapiens

<400> SEQUENCE: 27

Arg Ala Ser Gln Gly Leu Ser Ser Trp Leu Ala
1               5                   10

<210> SEQ ID NO 28
<211> LENGTH: 48
<212> TYPE: DNA
<213> ORGANISM: Homo sapiens

<400> SEQUENCE: 28
aggtctagtc aaagcctcgt ctacagtgat ggaaacacct acttgaat          48

<210> SEQ ID NO 29
<211> LENGTH: 16
<212> TYPE: PRT
<213> ORGANISM: Homo sapiens

<400> SEQUENCE: 29

Arg Ser Ser Gln Ser Leu Val Tyr Ser Asp Gly Asn Thr Tyr Leu Asn
1               5                   10                  15

<210> SEQ ID NO 30
<211> LENGTH: 48
<212> TYPE: DNA
<213> ORGANISM: Homo sapiens

<400> SEQUENCE: 30
aggtctagtc aaagcctcat atacagtgat ggaaacactt acttgaat          48

<210> SEQ ID NO 31
<211> LENGTH: 16
<212> TYPE: PRT
<213> ORGANISM: Homo sapiens

<400> SEQUENCE: 31

Arg Ser Ser Gln Ser Leu Ile Tyr Ser Asp Gly Asn Thr Tyr Leu Asn
1               5                   10                  15

<210> SEQ ID NO 32
<211> LENGTH: 48
<212> TYPE: DNA
<213> ORGANISM: Homo sapiens

<400> SEQUENCE: 32
aggtctagtc aaagcctcgt atacagtgat ggaaacacct acttgaat          48

<210> SEQ ID NO 33
<211> LENGTH: 16
<212> TYPE: PRT
<213> ORGANISM: Homo sapiens

<400> SEQUENCE: 33

```
Arg Ser Ser Gln Ser Leu Val Tyr Ser Asp Gly Asn Thr Tyr Leu Asn
1               5                   10                  15
```

<210> SEQ ID NO 34
<211> LENGTH: 33
<212> TYPE: DNA
<213> ORGANISM: Homo sapiens

<400> SEQUENCE: 34
cgggcgagtc agagtcttag cagctggtta gcc                                33

<210> SEQ ID NO 35
<211> LENGTH: 11
<212> TYPE: PRT
<213> ORGANISM: Homo sapiens

<400> SEQUENCE: 35

```
Arg Ala Ser Gln Ser Leu Ser Ser Trp Leu Ala
1               5                   10
```

<210> SEQ ID NO 36
<211> LENGTH: 42
<212> TYPE: DNA
<213> ORGANISM: Homo sapiens

<400> SEQUENCE: 36
ggcttgaact ctggctcagt ctctactagt tacttcccca gc                      42

<210> SEQ ID NO 37
<211> LENGTH: 14
<212> TYPE: PRT
<213> ORGANISM: Homo sapiens

<400> SEQUENCE: 37

```
Gly Leu Asn Ser Gly Ser Val Ser Thr Ser Tyr Phe Pro Ser
1               5                   10
```

<210> SEQ ID NO 38
<211> LENGTH: 48
<212> TYPE: DNA
<213> ORGANISM: Homo sapiens

<400> SEQUENCE: 38
aggtctagtc aaagcctcgt ctacagtgat ggagacacct acttgaat                48

<210> SEQ ID NO 39
<211> LENGTH: 16
<212> TYPE: PRT
<213> ORGANISM: Homo sapiens

<400> SEQUENCE: 39

```
Arg Ser Ser Gln Ser Leu Val Tyr Ser Asp Gly Asp Thr Tyr Leu Asn
1               5                   10                  15
```

<210> SEQ ID NO 40
<211> LENGTH: 42
<212> TYPE: DNA
<213> ORGANISM: Homo sapiens

<400> SEQUENCE: 40
actgggagca gctccaacat tggggcgggt tatgttgtac at                      42

<210> SEQ ID NO 41
<211> LENGTH: 14

```
-continued

<212> TYPE: PRT
<213> ORGANISM: Homo sapiens

<400> SEQUENCE: 41

Thr Gly Ser Ser Ser Asn Ile Gly Ala Gly Tyr Val Val His
1               5                   10

<210> SEQ ID NO 42
<211> LENGTH: 51
<212> TYPE: DNA
<213> ORGANISM: Homo sapiens

<400> SEQUENCE: 42
aagtccagcc agagtgtttt atacaactcc aacaataaga actacttagc t        51

<210> SEQ ID NO 43
<211> LENGTH: 17
<212> TYPE: PRT
<213> ORGANISM: Homo sapiens

<400> SEQUENCE: 43

Lys Ser Ser Gln Ser Val Leu Tyr Asn Ser Asn Asn Lys Asn Tyr Leu
1               5                   10                  15

Ala

<210> SEQ ID NO 44
<211> LENGTH: 33
<212> TYPE: DNA
<213> ORGANISM: Homo sapiens

<400> SEQUENCE: 44
tctggtgata aattggggga taaatttgct ttc                              33

<210> SEQ ID NO 45
<211> LENGTH: 11
<212> TYPE: PRT
<213> ORGANISM: Homo sapiens

<400> SEQUENCE: 45

Ser Gly Asp Lys Leu Gly Asp Lys Phe Ala Phe
1               5                   10

<210> SEQ ID NO 46
<211> LENGTH: 33
<212> TYPE: DNA
<213> ORGANISM: Homo sapiens

<400> SEQUENCE: 46
caaggagaca gcctcagaag ctatcatgca agc                              33

<210> SEQ ID NO 47
<211> LENGTH: 11
<212> TYPE: PRT
<213> ORGANISM: Homo sapiens

<400> SEQUENCE: 47

Gln Gly Asp Ser Leu Arg Ser Tyr His Ala Ser
1               5                   10

<210> SEQ ID NO 48
<211> LENGTH: 33
<212> TYPE: DNA
<213> ORGANISM: Homo sapiens

<400> SEQUENCE: 48
```

-continued

```
tctggagata atttggggga taaatatatt tgc                              33

<210> SEQ ID NO 49
<211> LENGTH: 11
<212> TYPE: PRT
<213> ORGANISM: Homo sapiens

<400> SEQUENCE: 49

Ser Gly Asp Asn Leu Gly Asp Lys Tyr Ile Cys
1               5                   10

<210> SEQ ID NO 50
<211> LENGTH: 33
<212> TYPE: DNA
<213> ORGANISM: Homo sapiens

<400> SEQUENCE: 50
tctggagata aattggggga aagctatgct tgc                              33

<210> SEQ ID NO 51
<211> LENGTH: 11
<212> TYPE: PRT
<213> ORGANISM: Homo sapiens

<400> SEQUENCE: 51

Ser Gly Asp Lys Leu Gly Glu Ser Tyr Ala Cys
1               5                   10

<210> SEQ ID NO 52
<211> LENGTH: 21
<212> TYPE: DNA
<213> ORGANISM: Homo sapiens

<400> SEQUENCE: 52
ggtaaaaact accggccctc a                                           21

<210> SEQ ID NO 53
<211> LENGTH: 7
<212> TYPE: PRT
<213> ORGANISM: Homo sapiens

<400> SEQUENCE: 53

Gly Lys Asn Tyr Arg Pro Ser
1               5

<210> SEQ ID NO 54
<211> LENGTH: 21
<212> TYPE: DNA
<213> ORGANISM: Homo sapiens

<400> SEQUENCE: 54
gataaaaaca accggccctc a                                           21

<210> SEQ ID NO 55
<211> LENGTH: 7
<212> TYPE: PRT
<213> ORGANISM: Homo sapiens

<400> SEQUENCE: 55

Asp Lys Asn Asn Arg Pro Ser
1               5

<210> SEQ ID NO 56
<211> LENGTH: 21
```

```
<212> TYPE: DNA
<213> ORGANISM: Homo sapiens

<400> SEQUENCE: 56
gataacaaca atcggccctc a                                              21

<210> SEQ ID NO 57
<211> LENGTH: 7
<212> TYPE: PRT
<213> ORGANISM: Homo sapiens

<400> SEQUENCE: 57

Asp Asn Asn Asn Arg Pro Ser
1               5

<210> SEQ ID NO 58
<211> LENGTH: 21
<212> TYPE: DNA
<213> ORGANISM: Homo sapiens

<400> SEQUENCE: 58
gataacaaca atcgcccctc a                                              21

<210> SEQ ID NO 59
<211> LENGTH: 21
<212> TYPE: DNA
<213> ORGANISM: Homo sapiens

<400> SEQUENCE: 59
gatgatagcg accggccctc a                                              21

<210> SEQ ID NO 60
<211> LENGTH: 7
<212> TYPE: PRT
<213> ORGANISM: Homo sapiens

<400> SEQUENCE: 60

Asp Asp Ser Asp Arg Pro Ser
1               5

<210> SEQ ID NO 61
<211> LENGTH: 21
<212> TYPE: DNA
<213> ORGANISM: Homo sapiens

<400> SEQUENCE: 61
caagataaga agcggccctc a                                              21

<210> SEQ ID NO 62
<211> LENGTH: 7
<212> TYPE: PRT
<213> ORGANISM: Homo sapiens

<400> SEQUENCE: 62

Gln Asp Lys Lys Arg Pro Ser
1               5

<210> SEQ ID NO 63
<211> LENGTH: 21
<212> TYPE: DNA
<213> ORGANISM: Homo sapiens

<400> SEQUENCE: 63
caagataaca agcggccctc a                                              21
```

```
<210> SEQ ID NO 64
<211> LENGTH: 8
<212> TYPE: PRT
<213> ORGANISM: Homo sapiens

<400> SEQUENCE: 64

Gln Lys Asn Lys Pro Arg Pro Ser
1               5

<210> SEQ ID NO 65
<211> LENGTH: 7
<212> TYPE: PRT
<213> ORGANISM: Homo sapiens

<400> SEQUENCE: 65

Gln Asp Asn Lys Arg Pro Ser
1               5

<210> SEQ ID NO 66
<211> LENGTH: 21
<212> TYPE: DNA
<213> ORGANISM: Homo sapiens

<400> SEQUENCE: 66
ggtaaaaaca accggccctc a                                    21

<210> SEQ ID NO 67
<211> LENGTH: 7
<212> TYPE: PRT
<213> ORGANISM: Homo sapiens

<400> SEQUENCE: 67

Gly Lys Asn Asn Arg Pro Ser
1               5

<210> SEQ ID NO 68
<211> LENGTH: 21
<212> TYPE: DNA
<213> ORGANISM: Homo sapiens

<400> SEQUENCE: 68
gctgcatcca gtttgcaaag t                                    21

<210> SEQ ID NO 69
<211> LENGTH: 7
<212> TYPE: PRT
<213> ORGANISM: Homo sapiens

<400> SEQUENCE: 69

Ala Ala Ser Ser Leu Gln Ser
1               5

<210> SEQ ID NO 70
<211> LENGTH: 21
<212> TYPE: DNA
<213> ORGANISM: Homo sapiens

<400> SEQUENCE: 70
tggacatcca cccgggaagg c                                    21

<210> SEQ ID NO 71
<211> LENGTH: 7
<212> TYPE: PRT
<213> ORGANISM: Homo sapiens
```

```
<400> SEQUENCE: 71

Trp Thr Ser Thr Arg Glu Gly
1               5

<210> SEQ ID NO 72
<211> LENGTH: 21
<212> TYPE: DNA
<213> ORGANISM: Homo sapiens

<400> SEQUENCE: 72
actgcatcca gtttgcaaag t                                              21

<210> SEQ ID NO 73
<211> LENGTH: 7
<212> TYPE: PRT
<213> ORGANISM: Homo sapiens

<400> SEQUENCE: 73

Thr Ala Ser Ser Leu Gln Ser
1               5

<210> SEQ ID NO 74
<211> LENGTH: 21
<212> TYPE: DNA
<213> ORGANISM: Homo sapiens

<400> SEQUENCE: 74
aaggtttcta actgggactc t                                              21

<210> SEQ ID NO 75
<211> LENGTH: 7
<212> TYPE: PRT
<213> ORGANISM: Homo sapiens

<400> SEQUENCE: 75

Lys Val Ser Asn Trp Asp Ser
1               5

<210> SEQ ID NO 76
<211> LENGTH: 21
<212> TYPE: DNA
<213> ORGANISM: Homo sapiens

<400> SEQUENCE: 76
aacacatcca gtttgcaaag t                                              21

<210> SEQ ID NO 77
<211> LENGTH: 7
<212> TYPE: PRT
<213> ORGANISM: Homo sapiens

<400> SEQUENCE: 77

Asn Thr Ser Ser Leu Gln Ser
1               5

<210> SEQ ID NO 78
<211> LENGTH: 21
<212> TYPE: DNA
<213> ORGANISM: Homo sapiens

<400> SEQUENCE: 78
actacatcca gtttgcaaag t                                              21

<210> SEQ ID NO 79
```

```
<211> LENGTH: 7
<212> TYPE: PRT
<213> ORGANISM: Homo sapiens

<400> SEQUENCE: 79

Thr Thr Ser Ser Leu Gln Ser
1               5

<210> SEQ ID NO 80
<211> LENGTH: 21
<212> TYPE: DNA
<213> ORGANISM: Homo sapiens

<400> SEQUENCE: 80
aaggtttctt actgggactc t                                      21

<210> SEQ ID NO 81
<211> LENGTH: 7
<212> TYPE: PRT
<213> ORGANISM: Homo sapiens

<400> SEQUENCE: 81

Lys Val Ser Tyr Trp Asp Ser
1               5

<210> SEQ ID NO 82
<211> LENGTH: 21
<212> TYPE: DNA
<213> ORGANISM: Homo sapiens

<400> SEQUENCE: 82
aatgcatcca gtttgcaaag t                                      21

<210> SEQ ID NO 83
<211> LENGTH: 7
<212> TYPE: PRT
<213> ORGANISM: Homo sapiens

<400> SEQUENCE: 83

Asn Ala Ser Ser Leu Gln Ser
1               5

<210> SEQ ID NO 84
<211> LENGTH: 21
<212> TYPE: DNA
<213> ORGANISM: Homo sapiens

<400> SEQUENCE: 84
agcacaaaca gtcgctcttc t                                      21

<210> SEQ ID NO 85
<211> LENGTH: 7
<212> TYPE: PRT
<213> ORGANISM: Homo sapiens

<400> SEQUENCE: 85

Ser Thr Asn Ser Pro Ser Ser
1               5

<210> SEQ ID NO 86
<211> LENGTH: 7
<212> TYPE: PRT
<213> ORGANISM: Homo sapiens

<400> SEQUENCE: 86
```

Asn Thr Ser Ser Lys Gln Ser
1               5

<210> SEQ ID NO 87
<211> LENGTH: 21
<212> TYPE: DNA
<213> ORGANISM: Homo sapiens

<400> SEQUENCE: 87
ggtaacagca atcggccctc a                                        21

<210> SEQ ID NO 88
<211> LENGTH: 7
<212> TYPE: PRT
<213> ORGANISM: Homo sapiens

<400> SEQUENCE: 88

Gly Asn Ser Asn Arg Pro Ser
1               5

<210> SEQ ID NO 89
<211> LENGTH: 21
<212> TYPE: DNA
<213> ORGANISM: Homo sapiens

<400> SEQUENCE: 89
tgggcttcta cccgggaatc c                                        21

<210> SEQ ID NO 90
<211> LENGTH: 7
<212> TYPE: PRT
<213> ORGANISM: Homo sapiens

<400> SEQUENCE: 90

Trp Ala Ser Thr Arg Glu Ser
1               5

<210> SEQ ID NO 91
<211> LENGTH: 21
<212> TYPE: DNA
<213> ORGANISM: Homo sapiens

<400> SEQUENCE: 91
caagatagca agcggccctc a                                        21

<210> SEQ ID NO 92
<211> LENGTH: 7
<212> TYPE: PRT
<213> ORGANISM: Homo sapiens

<400> SEQUENCE: 92

Gln Asp Ser Lys Arg Pro Ser
1               5

<210> SEQ ID NO 93
<211> LENGTH: 21
<212> TYPE: DNA
<213> ORGANISM: Homo sapiens

<400> SEQUENCE: 93
ggtgaaaaca accggccctc a                                        21

<210> SEQ ID NO 94
<211> LENGTH: 7
<212> TYPE: PRT

<213> ORGANISM: Homo sapiens

<400> SEQUENCE: 94

Gly Glu Asn Asn Arg Pro Ser
1               5

<210> SEQ ID NO 95
<211> LENGTH: 21
<212> TYPE: DNA
<213> ORGANISM: Homo sapiens

<400> SEQUENCE: 95
caagattaca agcggccctc a                                              21

<210> SEQ ID NO 96
<211> LENGTH: 7
<212> TYPE: PRT
<213> ORGANISM: Homo sapiens

<400> SEQUENCE: 96

Gln Asp Tyr Lys Arg Pro Ser
1               5

<210> SEQ ID NO 97
<211> LENGTH: 35
<212> TYPE: DNA
<213> ORGANISM: Homo sapiens

<400> SEQUENCE: 97
aactcccggg acagaagtgg taaccatctg gtgtt                               35

<210> SEQ ID NO 98
<211> LENGTH: 11
<212> TYPE: PRT
<213> ORGANISM: Homo sapiens

<400> SEQUENCE: 98

Asn Ser Arg Asp Arg Ser Gly Asn His Leu Val
1               5                   10

<210> SEQ ID NO 99
<211> LENGTH: 37
<212> TYPE: DNA
<213> ORGANISM: Homo sapiens

<400> SEQUENCE: 99
aactcccggg acagcagtga taaccatcta gtggtat                             37

<210> SEQ ID NO 100
<211> LENGTH: 12
<212> TYPE: PRT
<213> ORGANISM: Homo sapiens

<400> SEQUENCE: 100

Asn Ser Arg Asp Ser Ser Asp Asn His Leu Val Val
1               5                   10

<210> SEQ ID NO 101
<211> LENGTH: 40
<212> TYPE: DNA
<213> ORGANISM: Homo sapiens

<400> SEQUENCE: 101
cagtcctatg acagcaacct gagtggttcg attgtggttt                          40

```
<210> SEQ ID NO 102
<211> LENGTH: 13
<212> TYPE: PRT
<213> ORGANISM: Homo sapiens

<400> SEQUENCE: 102

Gln Ser Tyr Asp Ser Asn Leu Ser Gly Ser Ile Val Val
1               5                   10

<210> SEQ ID NO 103
<211> LENGTH: 40
<212> TYPE: DNA
<213> ORGANISM: Homo sapiens

<400> SEQUENCE: 103
cagtcctatg acagcaacct gagtggttcg attgtggtat                                40

<210> SEQ ID NO 104
<211> LENGTH: 34
<212> TYPE: DNA
<213> ORGANISM: Homo sapiens

<400> SEQUENCE: 104
caggtgtggg atagtagtag tgatcatgtg gtat                                      34

<210> SEQ ID NO 105
<211> LENGTH: 11
<212> TYPE: PRT
<213> ORGANISM: Homo sapiens

<400> SEQUENCE: 105

Gln Val Trp Asp Ser Ser Ser Asp His Val Val
1               5                   10

<210> SEQ ID NO 106
<211> LENGTH: 28
<212> TYPE: DNA
<213> ORGANISM: Homo sapiens

<400> SEQUENCE: 106
caggcgtggg acagcagcac tgtggtat                                             28

<210> SEQ ID NO 107
<211> LENGTH: 9
<212> TYPE: PRT
<213> ORGANISM: Homo sapiens

<400> SEQUENCE: 107

Gln Ala Trp Asp Ser Ser Thr Val Val
1               5

<210> SEQ ID NO 108
<211> LENGTH: 28
<212> TYPE: DNA
<213> ORGANISM: Homo sapiens

<400> SEQUENCE: 108
caggcgtggg acagcaccac tgcgatat                                             28

<210> SEQ ID NO 109
<211> LENGTH: 9
<212> TYPE: PRT
<213> ORGANISM: Homo sapiens

<400> SEQUENCE: 109
```

```
Gln Ala Trp Asp Ser Thr Thr Ala Ile
1               5
```

<210> SEQ ID NO 110
<211> LENGTH: 34
<212> TYPE: DNA
<213> ORGANISM: Homo sapiens

<400> SEQUENCE: 110
aactcccggg acagcagtgg taaccatgtg gtat                     34

<210> SEQ ID NO 111
<211> LENGTH: 11
<212> TYPE: PRT
<213> ORGANISM: Homo sapiens

<400> SEQUENCE: 111

```
Asn Ser Arg Asp Ser Ser Gly Asn His Val Val
1               5                   10
```

<210> SEQ ID NO 112
<211> LENGTH: 28
<212> TYPE: DNA
<213> ORGANISM: Homo sapiens

<400> SEQUENCE: 112
cagcagagct acactacccc gatcacct                            28

<210> SEQ ID NO 113
<211> LENGTH: 9
<212> TYPE: PRT
<213> ORGANISM: Homo sapiens

<400> SEQUENCE: 113

```
Gln Gln Ser Tyr Thr Thr Pro Ile Thr
1               5
```

<210> SEQ ID NO 114
<211> LENGTH: 28
<212> TYPE: DNA
<213> ORGANISM: Homo sapiens

<400> SEQUENCE: 114
cagcagtatt ttactactcc gtggacgt                            28

<210> SEQ ID NO 115
<211> LENGTH: 9
<212> TYPE: PRT
<213> ORGANISM: Homo sapiens

<400> SEQUENCE: 115

```
Gln Gln Tyr Phe Thr Thr Pro Trp Thr
1               5
```

<210> SEQ ID NO 116
<211> LENGTH: 28
<212> TYPE: DNA
<213> ORGANISM: Homo sapiens

<400> SEQUENCE: 116
caacaggctg acagtttccc gctcactt                            28

<210> SEQ ID NO 117
<211> LENGTH: 9

```
<212> TYPE: PRT
<213> ORGANISM: Homo sapiens

<400> SEQUENCE: 117

Gln Gln Ala Asp Ser Phe Pro Leu Thr
1               5

<210> SEQ ID NO 118
<211> LENGTH: 28
<212> TYPE: DNA
<213> ORGANISM: Homo sapiens

<400> SEQUENCE: 118
atgcaaggta cacactggcc tccggcct                                            28

<210> SEQ ID NO 119
<211> LENGTH: 9
<212> TYPE: PRT
<213> ORGANISM: Homo sapiens

<400> SEQUENCE: 119

Met Gln Gly Thr His Trp Pro Pro Ala
1               5

<210> SEQ ID NO 120
<211> LENGTH: 28
<212> TYPE: DNA
<213> ORGANISM: Homo sapiens

<400> SEQUENCE: 120
caacaggcta acagtttccc tctcactt                                            28

<210> SEQ ID NO 121
<211> LENGTH: 9
<212> TYPE: PRT
<213> ORGANISM: Homo sapiens

<400> SEQUENCE: 121

Gln Gln Ala Asn Ser Phe Pro Leu Thr
1               5

<210> SEQ ID NO 122
<211> LENGTH: 27
<212> TYPE: DNA
<213> ORGANISM: Homo sapiens

<400> SEQUENCE: 122
atgcaaggta cacactggcc tccggcc                                             27

<210> SEQ ID NO 123
<211> LENGTH: 28
<212> TYPE: DNA
<213> ORGANISM: Homo sapiens

<400> SEQUENCE: 123
caacaggctg acagtttccc tctcactt                                            28

<210> SEQ ID NO 124
<211> LENGTH: 31
<212> TYPE: DNA
<213> ORGANISM: Homo sapiens

<400> SEQUENCE: 124
gtgctgtata tgggtagagg catttgggtg t                                        31
```

<210> SEQ ID NO 125
<211> LENGTH: 10
<212> TYPE: PRT
<213> ORGANISM: Homo sapiens

<400> SEQUENCE: 125

Val Leu Tyr Met Gly Arg Gly Ile Trp Val
1               5                   10

<210> SEQ ID NO 126
<211> LENGTH: 37
<212> TYPE: DNA
<213> ORGANISM: Homo sapiens

<400> SEQUENCE: 126
aaagcatggg ataacagcct gaatgctcaa ggggtat                              37

<210> SEQ ID NO 127
<211> LENGTH: 12
<212> TYPE: PRT
<213> ORGANISM: Homo sapiens

<400> SEQUENCE: 127

Lys Ala Trp Asp Asn Ser Leu Asn Ala Gln Gly Val
1               5                   10

<210> SEQ ID NO 128
<211> LENGTH: 28
<212> TYPE: DNA
<213> ORGANISM: Homo sapiens

<400> SEQUENCE: 128
cagcaatttt atggtcctcc tctcactt                                       28

<210> SEQ ID NO 129
<211> LENGTH: 9
<212> TYPE: PRT
<213> ORGANISM: Homo sapiens

<400> SEQUENCE: 129

Gln Gln Phe Tyr Gly Pro Pro Leu Thr
1               5

<210> SEQ ID NO 130
<211> LENGTH: 30
<212> TYPE: DNA
<213> ORGANISM: Homo sapiens

<400> SEQUENCE: 130
caggcgtggg acagcagcgc cggggggta                                      30

<210> SEQ ID NO 131
<211> LENGTH: 10
<212> TYPE: PRT
<213> ORGANISM: Homo sapiens

<400> SEQUENCE: 131

Gln Ala Trp Asp Ser Ser Ala Gly Gly Val
1               5                   10

<210> SEQ ID NO 132
<211> LENGTH: 34
<212> TYPE: DNA
<213> ORGANISM: Homo sapiens

<400> SEQUENCE: 132
aattatcggg acaacagtgg taaccatctg gtgt     34

<210> SEQ ID NO 133
<211> LENGTH: 11
<212> TYPE: PRT
<213> ORGANISM: Homo sapiens

<400> SEQUENCE: 133

Asn Tyr Arg Asp Asn Ser Gly Asn His Leu Val
1               5                   10

<210> SEQ ID NO 134
<211> LENGTH: 28
<212> TYPE: DNA
<213> ORGANISM: Homo sapiens

<400> SEQUENCE: 134
caggcgtggg acagaagtac tgtactat     28

<210> SEQ ID NO 135
<211> LENGTH: 9
<212> TYPE: PRT
<213> ORGANISM: Homo sapiens

<400> SEQUENCE: 135

Gln Ala Trp Asp Arg Ser Thr Val Leu
1               5

<210> SEQ ID NO 136
<211> LENGTH: 15
<212> TYPE: DNA
<213> ORGANISM: Homo sapiens

<400> SEQUENCE: 136
aactatggca tgcac     15

<210> SEQ ID NO 137
<211> LENGTH: 5
<212> TYPE: PRT
<213> ORGANISM: Homo sapiens

<400> SEQUENCE: 137

Asn Tyr Gly Met His
1               5

<210> SEQ ID NO 138
<211> LENGTH: 15
<212> TYPE: DNA
<213> ORGANISM: Homo sapiens

<400> SEQUENCE: 138
gattttacca tgcac     15

<210> SEQ ID NO 139
<211> LENGTH: 5
<212> TYPE: PRT
<213> ORGANISM: Homo sapiens

<400> SEQUENCE: 139

Asp Phe Thr Met His
1               5

<210> SEQ ID NO 140

```
<211> LENGTH: 15
<212> TYPE: DNA
<213> ORGANISM: Homo sapiens

<400> SEQUENCE: 140
gactactata tgtac                                                    15

<210> SEQ ID NO 141
<211> LENGTH: 5
<212> TYPE: PRT
<213> ORGANISM: Homo sapiens

<400> SEQUENCE: 141

Asp Tyr Tyr Met Tyr
1               5

<210> SEQ ID NO 142
<211> LENGTH: 15
<212> TYPE: DNA
<213> ORGANISM: Homo sapiens

<400> SEQUENCE: 142
ggcgactata tgcac                                                    15

<210> SEQ ID NO 143
<211> LENGTH: 5
<212> TYPE: PRT
<213> ORGANISM: Homo sapiens

<400> SEQUENCE: 143

Gly Asp Tyr Met His
1               5

<210> SEQ ID NO 144
<211> LENGTH: 15
<212> TYPE: DNA
<213> ORGANISM: Homo sapiens

<400> SEQUENCE: 144
acctatggca tgcac                                                    15

<210> SEQ ID NO 145
<211> LENGTH: 5
<212> TYPE: PRT
<213> ORGANISM: Homo sapiens

<400> SEQUENCE: 145

Thr Tyr Gly Met His
1               5

<210> SEQ ID NO 146
<211> LENGTH: 15
<212> TYPE: DNA
<213> ORGANISM: Homo sapiens

<400> SEQUENCE: 146
agctatggca ttcac                                                    15

<210> SEQ ID NO 147
<211> LENGTH: 5
<212> TYPE: PRT
<213> ORGANISM: Homo sapiens

<400> SEQUENCE: 147

Ser Tyr Gly Ile His
```

<210> SEQ ID NO 148
<211> LENGTH: 21
<212> TYPE: DNA
<213> ORGANISM: Homo sapiens

<400> SEQUENCE: 148
agtggtggtt actactggag c                                          21

<210> SEQ ID NO 149
<211> LENGTH: 7
<212> TYPE: PRT
<213> ORGANISM: Homo sapiens

<400> SEQUENCE: 149

Ser Gly Gly Tyr Tyr Trp Ser
1               5

<210> SEQ ID NO 150
<211> LENGTH: 15
<212> TYPE: DNA
<213> ORGANISM: Homo sapiens

<400> SEQUENCE: 150
agctatggca tgcac                                                 15

<210> SEQ ID NO 151
<211> LENGTH: 5
<212> TYPE: PRT
<213> ORGANISM: Homo sapiens

<400> SEQUENCE: 151

Ser Tyr Gly Met His
1               5

<210> SEQ ID NO 152
<211> LENGTH: 15
<212> TYPE: DNA
<213> ORGANISM: Homo sapiens

<400> SEQUENCE: 152
agttatggca tgcac                                                 15

<210> SEQ ID NO 153
<211> LENGTH: 15
<212> TYPE: DNA
<213> ORGANISM: Homo sapiens

<400> SEQUENCE: 153
agttatagca tgaac                                                 15

<210> SEQ ID NO 154
<211> LENGTH: 5
<212> TYPE: PRT
<213> ORGANISM: Homo sapiens

<400> SEQUENCE: 154

Ser Tyr Ser Met Asn
1               5

<210> SEQ ID NO 155
<211> LENGTH: 15
<212> TYPE: DNA
<213> ORGANISM: Homo sapiens

<400> SEQUENCE: 155
agttatggca tgctc                                                    15

<210> SEQ ID NO 156
<211> LENGTH: 5
<212> TYPE: PRT
<213> ORGANISM: Homo sapiens

<400> SEQUENCE: 156

Ser Tyr Gly Met Leu
1               5

<210> SEQ ID NO 157
<211> LENGTH: 15
<212> TYPE: DNA
<213> ORGANISM: Homo sapiens

<400> SEQUENCE: 157
agctatgcca tgagc                                                    15

<210> SEQ ID NO 158
<211> LENGTH: 5
<212> TYPE: PRT
<213> ORGANISM: Homo sapiens

<400> SEQUENCE: 158

Ser Tyr Ala Met Ser
1               5

<210> SEQ ID NO 159
<211> LENGTH: 15
<212> TYPE: DNA
<213> ORGANISM: Homo sapiens

<400> SEQUENCE: 159
ggctatgtca tgact                                                    15

<210> SEQ ID NO 160
<211> LENGTH: 5
<212> TYPE: PRT
<213> ORGANISM: Homo sapiens

<400> SEQUENCE: 160

Gly Tyr Val Met Thr
1               5

<210> SEQ ID NO 161
<211> LENGTH: 15
<212> TYPE: DNA
<213> ORGANISM: Homo sapiens

<400> SEQUENCE: 161
ggctactata tgcac                                                    15

<210> SEQ ID NO 162
<211> LENGTH: 5
<212> TYPE: PRT
<213> ORGANISM: Homo sapiens

<400> SEQUENCE: 162

Gly Tyr Tyr Met His
1               5

```
<210> SEQ ID NO 163
<211> LENGTH: 5
<212> TYPE: PRT
<213> ORGANISM: Homo sapiens

<400> SEQUENCE: 163

Asp Phe Thr Met His
1               5

<210> SEQ ID NO 164
<211> LENGTH: 51
<212> TYPE: DNA
<213> ORGANISM: Homo sapiens

<400> SEQUENCE: 164
gttatatggt atgatggaag taataaatac tatgcagact ccgtgaaggg c          51

<210> SEQ ID NO 165
<211> LENGTH: 17
<212> TYPE: PRT
<213> ORGANISM: Homo sapiens

<400> SEQUENCE: 165

Val Ile Trp Tyr Asp Gly Ser Asn Lys Tyr Tyr Ala Asp Ser Val Lys
1               5                   10                  15

Gly

<210> SEQ ID NO 166
<211> LENGTH: 51
<212> TYPE: DNA
<213> ORGANISM: Homo sapiens

<400> SEQUENCE: 166
cttattagtt gggatggtgg tagcacatac tatgcagact ctgtgaaggg c          51

<210> SEQ ID NO 167
<211> LENGTH: 17
<212> TYPE: PRT
<213> ORGANISM: Homo sapiens

<400> SEQUENCE: 167

Leu Ile Ser Trp Asp Gly Gly Ser Thr Tyr Tyr Ala Asp Ser Val Lys
1               5                   10                  15

Gly

<210> SEQ ID NO 168
<211> LENGTH: 51
<212> TYPE: DNA
<213> ORGANISM: Homo sapiens

<400> SEQUENCE: 168
tggatcaacc ctaacagtgg tggcacaaac tatgtacaga gtttcaggg c           51

<210> SEQ ID NO 169
<211> LENGTH: 17
<212> TYPE: PRT
<213> ORGANISM: Homo sapiens

<400> SEQUENCE: 169

Trp Ile Asn Pro Asn Ser Gly Gly Thr Asn Tyr Val Gln Lys Phe Gln
1               5                   10                  15

Gly
```

```
<210> SEQ ID NO 170
<211> LENGTH: 51
<212> TYPE: DNA
<213> ORGANISM: Homo sapiens

<400> SEQUENCE: 170
tggatcaacc ctaacagtgg tggcacaaac catgcacgga agtttcaggg c           51

<210> SEQ ID NO 171
<211> LENGTH: 17
<212> TYPE: PRT
<213> ORGANISM: Homo sapiens

<400> SEQUENCE: 171

Trp Ile Asn Pro Asn Ser Gly Gly Thr Asn His Ala Arg Lys Phe Gln
1               5                   10                  15

Gly

<210> SEQ ID NO 172
<211> LENGTH: 51
<212> TYPE: DNA
<213> ORGANISM: Homo sapiens

<400> SEQUENCE: 172
gttatatggt atgatggaag taataaacac tatgcagact ccgtgaaggg c           51

<210> SEQ ID NO 173
<211> LENGTH: 17
<212> TYPE: PRT
<213> ORGANISM: Homo sapiens

<400> SEQUENCE: 173

Val Ile Trp Tyr Asp Gly Ser Asn Lys His Tyr Ala Asp Ser Val Lys
1               5                   10                  15

Gly

<210> SEQ ID NO 174
<211> LENGTH: 51
<212> TYPE: DNA
<213> ORGANISM: Homo sapiens

<400> SEQUENCE: 174
gttatatcat atgatggaag ttataaatac tatgcagact ccgtgaaggg c           51

<210> SEQ ID NO 175
<211> LENGTH: 17
<212> TYPE: PRT
<213> ORGANISM: Homo sapiens

<400> SEQUENCE: 175

Val Ile Ser Tyr Asp Gly Ser Tyr Lys Tyr Tyr Ala Asp Ser Val Lys
1               5                   10                  15

Gly

<210> SEQ ID NO 176
<211> LENGTH: 48
<212> TYPE: DNA
<213> ORGANISM: Homo sapiens

<400> SEQUENCE: 176
ttcatccatt acagtgggac cacctactac aacccgtccc tcaagagt              48

<210> SEQ ID NO 177
```

-continued

```
<211> LENGTH: 16
<212> TYPE: PRT
<213> ORGANISM: Homo sapiens

<400> SEQUENCE: 177

Phe Ile His Tyr Ser Gly Thr Thr Tyr Tyr Asn Pro Ser Leu Lys Ser
1               5                   10                  15

<210> SEQ ID NO 178
<211> LENGTH: 51
<212> TYPE: DNA
<213> ORGANISM: Homo sapiens

<400> SEQUENCE: 178
gttatatcat atgatggaag taataaatac tatgcagact ccgtgaaggg c          51

<210> SEQ ID NO 179
<211> LENGTH: 17
<212> TYPE: PRT
<213> ORGANISM: Homo sapiens

<400> SEQUENCE: 179

Val Ile Ser Tyr Asp Gly Ser Asn Lys Tyr Tyr Ala Asp Ser Val Lys
1               5                   10                  15

Gly

<210> SEQ ID NO 180
<211> LENGTH: 51
<212> TYPE: DNA
<213> ORGANISM: Homo sapiens

<400> SEQUENCE: 180
gttatatggt atgatggaag taatacatac tatgcagact ccgtgaaggg c          51

<210> SEQ ID NO 181
<211> LENGTH: 17
<212> TYPE: PRT
<213> ORGANISM: Homo sapiens

<400> SEQUENCE: 181

Val Ile Trp Tyr Asp Gly Ser Asn Thr Tyr Tyr Ala Asp Ser Val Lys
1               5                   10                  15

Gly

<210> SEQ ID NO 182
<211> LENGTH: 51
<212> TYPE: DNA
<213> ORGANISM: Homo sapiens

<400> SEQUENCE: 182
gttatatggt atgatggaag tagtaaatac tatgcagact ccgtgaaggg c          51

<210> SEQ ID NO 183
<211> LENGTH: 17
<212> TYPE: PRT
<213> ORGANISM: Homo sapiens

<400> SEQUENCE: 183

Val Ile Trp Tyr Asp Gly Ser Ser Lys Tyr Tyr Ala Asp Ser Val Lys
1               5                   10                  15

Gly

<210> SEQ ID NO 184
```

```
<211> LENGTH: 51
<212> TYPE: DNA
<213> ORGANISM: Homo sapiens

<400> SEQUENCE: 184
tacattagtg gtcgtactag tagcgtatac tacgcagact ctgtgaaggg c          51

<210> SEQ ID NO 185
<211> LENGTH: 17
<212> TYPE: PRT
<213> ORGANISM: Homo sapiens

<400> SEQUENCE: 185

Tyr Ile Ser Gly Arg Thr Ser Ser Val Tyr Tyr Ala Asp Ser Val Lys
 1               5                  10                  15

Gly

<210> SEQ ID NO 186
<211> LENGTH: 51
<212> TYPE: DNA
<213> ORGANISM: Homo sapiens

<400> SEQUENCE: 186
gttatatggt ttgatggaag taataaatac tatgcggact ccgtgaaggg c          51

<210> SEQ ID NO 187
<211> LENGTH: 17
<212> TYPE: PRT
<213> ORGANISM: Homo sapiens

<400> SEQUENCE: 187

Val Ile Trp Phe Asp Gly Ser Asn Lys Tyr Tyr Ala Asp Ser Val Lys
 1               5                  10                  15

Gly

<210> SEQ ID NO 188
<211> LENGTH: 51
<212> TYPE: DNA
<213> ORGANISM: Homo sapiens

<400> SEQUENCE: 188
gttttatggt ttgatggaag ttataaaaac tatgcagact ccgtgaaggg c          51

<210> SEQ ID NO 189
<211> LENGTH: 17
<212> TYPE: PRT
<213> ORGANISM: Homo sapiens

<400> SEQUENCE: 189

Val Leu Trp Phe Asp Gly Ser Tyr Lys Asn Tyr Ala Asp Ser Val Lys
 1               5                  10                  15

Gly

<210> SEQ ID NO 190
<211> LENGTH: 51
<212> TYPE: DNA
<213> ORGANISM: Homo sapiens

<400> SEQUENCE: 190
gcaattagtg gtagtggtgg aagtacacac tacgcagact ccgtgaaggg c          51

<210> SEQ ID NO 191
<211> LENGTH: 17
```

```
<212> TYPE: PRT
<213> ORGANISM: Homo sapiens

<400> SEQUENCE: 191

Ala Ile Ser Gly Ser Gly Gly Ser Thr His Tyr Ala Asp Ser Val Lys
1               5                   10                  15
Gly

<210> SEQ ID NO 192
<211> LENGTH: 51
<212> TYPE: DNA
<213> ORGANISM: Homo sapiens

<400> SEQUENCE: 192
ggaattagtg gtagtggtgg tagcacatac tacgcagact ccgtgaaggg c          51

<210> SEQ ID NO 193
<211> LENGTH: 17
<212> TYPE: PRT
<213> ORGANISM: Homo sapiens

<400> SEQUENCE: 193

Gly Ile Ser Gly Ser Gly Gly Ser Thr Tyr Tyr Ala Asp Ser Val Lys
1               5                   10                  15
Gly

<210> SEQ ID NO 194
<211> LENGTH: 51
<212> TYPE: DNA
<213> ORGANISM: Homo sapiens

<400> SEQUENCE: 194
tggatcaacc ctaacaatgg tggcacaaac tatggacaga gtttcaggg c           51

<210> SEQ ID NO 195
<211> LENGTH: 17
<212> TYPE: PRT
<213> ORGANISM: Homo sapiens

<400> SEQUENCE: 195

Trp Ile Asn Pro Asn Asn Gly Gly Thr Asn Tyr Gly Gln Lys Phe Gln
1               5                   10                  15
Gly

<210> SEQ ID NO 196
<211> LENGTH: 51
<212> TYPE: DNA
<213> ORGANISM: Homo sapiens

<400> SEQUENCE: 196
gttatatggt atgatggaag taataaatac tatgtagact ccgtgaaggg c          51

<210> SEQ ID NO 197
<211> LENGTH: 17
<212> TYPE: PRT
<213> ORGANISM: Homo sapiens

<400> SEQUENCE: 197

Val Ile Trp Tyr Asp Gly Ser Asn Lys Tyr Tyr Val Asp Ser Val Lys
1               5                   10                  15
Gly
```

```
<210> SEQ ID NO 198
<211> LENGTH: 51
<212> TYPE: DNA
<213> ORGANISM: Homo sapiens

<400> SEQUENCE: 198
gctattagtc gtagtggtag taccacatac tacgcagact ccgtgaaggg c          51

<210> SEQ ID NO 199
<211> LENGTH: 17
<212> TYPE: PRT
<213> ORGANISM: Homo sapiens

<400> SEQUENCE: 199

Ala Ile Ser Arg Ser Gly Ser Thr Thr Tyr Tyr Ala Asp Ser Val Lys
1               5                   10                  15

Gly

<210> SEQ ID NO 200
<211> LENGTH: 51
<212> TYPE: DNA
<213> ORGANISM: Homo sapiens

<400> SEQUENCE: 200
gttaaatggt atgaaggaag taataaatac tatggagact ccgtgaaggg c          51

<210> SEQ ID NO 201
<211> LENGTH: 51
<212> TYPE: DNA
<213> ORGANISM: Homo sapiens

<400> SEQUENCE: 201
gctattagtt atagtggcgg tagcacatac tacgcaggct ccgtgaaggg c          51

<210> SEQ ID NO 202
<211> LENGTH: 17
<212> TYPE: PRT
<213> ORGANISM: Homo sapiens

<400> SEQUENCE: 202

Ala Ile Ser Tyr Ser Gly Gly Ser Thr Tyr Tyr Ala Gly Ser Val Lys
1               5                   10                  15

Gly

<210> SEQ ID NO 203
<211> LENGTH: 36
<212> TYPE: DNA
<213> ORGANISM: Homo sapiens

<400> SEQUENCE: 203
ctagtgggag ctaccaacta ctacggtatg gacgtc                            36

<210> SEQ ID NO 204
<211> LENGTH: 12
<212> TYPE: PRT
<213> ORGANISM: Homo sapiens

<400> SEQUENCE: 204

Leu Val Gly Ala Thr Asn Tyr Tyr Gly Met Asp Val
1               5                   10

<210> SEQ ID NO 205
<211> LENGTH: 30
<212> TYPE: DNA
```

<213> ORGANISM: Homo sapiens

<400> SEQUENCE: 205
ccttactact acttctacgg tatggacgtc                    30

<210> SEQ ID NO 206
<211> LENGTH: 10
<212> TYPE: PRT
<213> ORGANISM: Homo sapiens

<400> SEQUENCE: 206

Pro Tyr Tyr Tyr Phe Tyr Gly Met Asp Val
1               5                   10

<210> SEQ ID NO 207
<211> LENGTH: 36
<212> TYPE: DNA
<213> ORGANISM: Homo sapiens

<400> SEQUENCE: 207
gatgggggta gcagtggctg gcccctcttt gcctac             36

<210> SEQ ID NO 208
<211> LENGTH: 12
<212> TYPE: PRT
<213> ORGANISM: Homo sapiens

<400> SEQUENCE: 208

Asp Gly Gly Ser Ser Gly Trp Pro Leu Phe Ala Tyr
1               5                   10

<210> SEQ ID NO 209
<211> LENGTH: 36
<212> TYPE: DNA
<213> ORGANISM: Homo sapiens

<400> SEQUENCE: 209
gataggggta ccagtggctg gccactcttt gactat             36

<210> SEQ ID NO 210
<211> LENGTH: 12
<212> TYPE: PRT
<213> ORGANISM: Homo sapiens

<400> SEQUENCE: 210

Asp Arg Gly Thr Ser Gly Trp Pro Leu Phe Asp Tyr
1               5                   10

<210> SEQ ID NO 211
<211> LENGTH: 39
<212> TYPE: DNA
<213> ORGANISM: Homo sapiens

<400> SEQUENCE: 211
gcccctcagt gggagctagt tcatgaagct tttgatatc          39

<210> SEQ ID NO 212
<211> LENGTH: 13
<212> TYPE: PRT
<213> ORGANISM: Homo sapiens

<400> SEQUENCE: 212

Ala Pro Gln Trp Glu Leu Val His Glu Ala Phe Asp Ile
1               5                   10

```
<210> SEQ ID NO 213
<211> LENGTH: 51
<212> TYPE: DNA
<213> ORGANISM: Homo sapiens

<400> SEQUENCE: 213
ggggactcct ggaacgacag attaaactac tacttctacg atatggacgt c          51

<210> SEQ ID NO 214
<211> LENGTH: 17
<212> TYPE: PRT
<213> ORGANISM: Homo sapiens

<400> SEQUENCE: 214

Gly Asp Ser Trp Asn Asp Arg Leu Asn Tyr Tyr Phe Tyr Asp Met Asp
1               5                   10                  15

Val

<210> SEQ ID NO 215
<211> LENGTH: 36
<212> TYPE: DNA
<213> ORGANISM: Homo sapiens

<400> SEQUENCE: 215
gaagttggca gctcgtcggg taactggttc gacccc                            36

<210> SEQ ID NO 216
<211> LENGTH: 12
<212> TYPE: PRT
<213> ORGANISM: Homo sapiens

<400> SEQUENCE: 216

Glu Val Gly Ser Ser Ser Gly Asn Trp Phe Asp Pro
1               5                   10

<210> SEQ ID NO 217
<211> LENGTH: 45
<212> TYPE: DNA
<213> ORGANISM: Homo sapiens

<400> SEQUENCE: 217
gaggtccggg cgtatagcag tggctggtac gccgcctttg actac                  45

<210> SEQ ID NO 218
<211> LENGTH: 15
<212> TYPE: PRT
<213> ORGANISM: Homo sapiens

<400> SEQUENCE: 218

Glu Val Arg Ala Tyr Ser Ser Gly Trp Tyr Ala Ala Phe Asp Tyr
1               5                   10                  15

<210> SEQ ID NO 219
<211> LENGTH: 48
<212> TYPE: DNA
<213> ORGANISM: Homo sapiens

<400> SEQUENCE: 219
gtaagaagtg ggagctacta cgaacagtat tactacggta tggacgtc               48

<210> SEQ ID NO 220
<211> LENGTH: 16
<212> TYPE: PRT
<213> ORGANISM: Homo sapiens
```

```
<400> SEQUENCE: 220

Val Arg Ser Gly Ser Tyr Tyr Glu Gln Tyr Tyr Tyr Gly Met Asp Val
1               5                   10                  15

<210> SEQ ID NO 221
<211> LENGTH: 36
<212> TYPE: DNA
<213> ORGANISM: Homo sapiens

<400> SEQUENCE: 221
agtgggatct actacgacta ctacggtatg gacgtc                               36

<210> SEQ ID NO 222
<211> LENGTH: 12
<212> TYPE: PRT
<213> ORGANISM: Homo sapiens

<400> SEQUENCE: 222

Ser Gly Ile Tyr Tyr Asp Tyr Tyr Gly Met Asp Val
1               5                   10

<210> SEQ ID NO 223
<211> LENGTH: 48
<212> TYPE: DNA
<213> ORGANISM: Homo sapiens

<400> SEQUENCE: 223
ggggcagcca ctgctataga ttactactac tcctacggta tggacgtc                  48

<210> SEQ ID NO 224
<211> LENGTH: 16
<212> TYPE: PRT
<213> ORGANISM: Homo sapiens

<400> SEQUENCE: 224

Gly Ala Ala Thr Ala Ile Asp Tyr Tyr Tyr Ser Tyr Gly Met Asp Val
1               5                   10                  15

<210> SEQ ID NO 225
<211> LENGTH: 48
<212> TYPE: DNA
<213> ORGANISM: Homo sapiens

<400> SEQUENCE: 225
ggggggggta ccagtagc tgactactac tactacggta tggacgtc                    48

<210> SEQ ID NO 226
<211> LENGTH: 16
<212> TYPE: PRT
<213> ORGANISM: Homo sapiens

<400> SEQUENCE: 226

Gly Gly Gly Ile Pro Val Ala Asp Tyr Tyr Tyr Gly Met Asp Val
1               5                   10                  15

<210> SEQ ID NO 227
<211> LENGTH: 48
<212> TYPE: DNA
<213> ORGANISM: Homo sapiens

<400> SEQUENCE: 227
ggggggggta tagcagtggc tgactactac ttctacggta tggacgtc                  48
```

<210> SEQ ID NO 228
<211> LENGTH: 16
<212> TYPE: PRT
<213> ORGANISM: Homo sapiens

<400> SEQUENCE: 228

Gly Gly Gly Ile Ala Val Ala Asp Tyr Tyr Phe Tyr Gly Met Asp Val
1               5                   10                  15

<210> SEQ ID NO 229
<211> LENGTH: 48
<212> TYPE: DNA
<213> ORGANISM: Homo sapiens

<400> SEQUENCE: 229 gggggggta tagcagtggc tgactactac tactacggta tggacgtc          48

<210> SEQ ID NO 230
<211> LENGTH: 16
<212> TYPE: PRT
<213> ORGANISM: Homo sapiens

<400> SEQUENCE: 230

Gly Gly Gly Ile Ala Val Ala Asp Tyr Tyr Tyr Gly Met Asp Val
1               5                   10                  15

<210> SEQ ID NO 231
<211> LENGTH: 30
<212> TYPE: DNA
<213> ORGANISM: Homo sapiens

<400> SEQUENCE: 231
gatagtacaa ctatggccca ctttgactac                              30

<210> SEQ ID NO 232
<211> LENGTH: 10
<212> TYPE: PRT
<213> ORGANISM: Homo sapiens

<400> SEQUENCE: 232

Asp Ser Thr Thr Met Ala His Phe Asp Tyr
1               5                   10

<210> SEQ ID NO 233
<211> LENGTH: 27
<212> TYPE: DNA
<213> ORGANISM: Homo sapiens

<400> SEQUENCE: 233
gatctcaact ggggagcttt tgatatc                                 27

<210> SEQ ID NO 234
<211> LENGTH: 9
<212> TYPE: PRT
<213> ORGANISM: Homo sapiens

<400> SEQUENCE: 234

Asp Leu Asn Trp Gly Ala Phe Asp Ile
1               5

<210> SEQ ID NO 235
<211> LENGTH: 36
<212> TYPE: DNA
<213> ORGANISM: Homo sapiens

<400> SEQUENCE: 235
ggagacagct cgaactacta ctccggtatg gacgtc                     36

<210> SEQ ID NO 236
<211> LENGTH: 12
<212> TYPE: PRT
<213> ORGANISM: Homo sapiens

<400> SEQUENCE: 236

Gly Asp Ser Ser Asn Tyr Tyr Ser Gly Met Asp Val
1               5                   10

<210> SEQ ID NO 237
<211> LENGTH: 30
<212> TYPE: DNA
<213> ORGANISM: Homo sapiens

<400> SEQUENCE: 237
gggaactgga acgacgatgc ttttgatatc                            30

<210> SEQ ID NO 238
<211> LENGTH: 10
<212> TYPE: PRT
<213> ORGANISM: Homo sapiens

<400> SEQUENCE: 238

Gly Asn Trp Asn Asp Asp Ala Phe Asp Ile
1               5                   10

<210> SEQ ID NO 239
<211> LENGTH: 48
<212> TYPE: DNA
<213> ORGANISM: Homo sapiens

<400> SEQUENCE: 239
atggggttta ctatggttcg gggagccctc tactacggta tggacgtc         48

<210> SEQ ID NO 240
<211> LENGTH: 16
<212> TYPE: PRT
<213> ORGANISM: Homo sapiens

<400> SEQUENCE: 240

Met Gly Phe Thr Met Val Arg Gly Ala Leu Tyr Tyr Gly Met Asp Val
1               5                   10                  15

<210> SEQ ID NO 241
<211> LENGTH: 30
<212> TYPE: DNA
<213> ORGANISM: Homo sapiens

<400> SEQUENCE: 241
ccgagatatt ttgactggtt attaggcgac                            30

<210> SEQ ID NO 242
<211> LENGTH: 10
<212> TYPE: PRT
<213> ORGANISM: Homo sapiens

<400> SEQUENCE: 242

Arg Pro Tyr Phe Asp Trp Leu Leu Gly Asp
1               5                   10

<210> SEQ ID NO 243
<211> LENGTH: 42

```
<212> TYPE: DNA
<213> ORGANISM: Homo sapiens

<400> SEQUENCE: 243
ggcgcccacg actacggtga cttctactac ggtatggacg tc                    42

<210> SEQ ID NO 244
<211> LENGTH: 39
<212> TYPE: DNA
<213> ORGANISM: Homo sapiens

<400> SEQUENCE: 244
gatcgggagg gagcgacttg gtactacggt atggacgtc                        39

<210> SEQ ID NO 245
<211> LENGTH: 13
<212> TYPE: PRT
<213> ORGANISM: Homo sapiens

<400> SEQUENCE: 245

Asp Arg Glu Gly Ala Thr Trp Tyr Tyr Gly Met Asp Val
1               5                   10

<210> SEQ ID NO 246
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (7)..(7)
<223> OTHER INFORMATION: Val or Ile
<220> FEATURE:
<221> NAME/KEY: MOD_RES
<222> LOCATION: (12)..(12)
<223> OTHER INFORMATION: Asn or Asp

<400> SEQUENCE: 246

Arg Ser Ser Gln Ser Leu Xaa Tyr Ser Asp Gly Xaa Thr Tyr Leu Asn
1               5                   10                  15

<210> SEQ ID NO 247
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (4)..(4)
<223> OTHER INFORMATION: Tyr or Asn

<400> SEQUENCE: 247

Lys Val Ser Xaa Trp Asp Ser
1               5

<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 248

Met Gln Gly Thr His Gln Pro Pro Ala
```

```
<210> SEQ ID NO 249
<211> LENGTH: 11
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (5)..(5)
<223> OTHER INFORMATION: Gly or Ser
<220> FEATURE:
<221> NAME/KEY: MOD_RES
<222> LOCATION: (6)..(6)
<223> OTHER INFORMATION: Leu or Ile

<400> SEQUENCE: 249

Arg Ala Ser Gln Xaa Xaa Ser Ser Trp Leu Ala
1               5                   10

<210> SEQ ID NO 250
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Asn or Thr
<220> FEATURE:
<221> NAME/KEY: MOD_RES
<222> LOCATION: (2)..(2)
<223> OTHER INFORMATION: Thr or Ala

<400> SEQUENCE: 250

Xaa Xaa Ser Ser Leu Gln Ser
1               5

<210> SEQ ID NO 251
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (4)..(4)
<223> OTHER INFORMATION: Asn or Asp

<400> SEQUENCE: 251

Gln Gln Ala Xaa Ser Phe Pro Leu Thr
1               5

<210> SEQ ID NO 252
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (3)..(3)
<223> OTHER INFORMATION: Lys or Asn

<400> SEQUENCE: 252

Gln Asp Xaa Lys Arg Pro Ser
```

```
1               5

<210> SEQ ID NO 253
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Ser or Asn

<400> SEQUENCE: 253

Xaa Tyr Gly Met His
1               5

<210> SEQ ID NO 254
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (4)..(4)
<223> OTHER INFORMATION: Tyr or Phe

<400> SEQUENCE: 254

Val Ile Trp Xaa Asp Gly Ser Asn Lys Tyr Tyr Ala Asp Ser Val Lys
1               5                   10                  15

Gly

<210> SEQ ID NO 255
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (5)..(5)
<223> OTHER INFORMATION: Pro or Ala
<220> FEATURE:
<221> NAME/KEY: MOD_RES
<222> LOCATION: (11)..(11)
<223> OTHER INFORMATION: Tyr or Phe

<400> SEQUENCE: 255

Gly Gly Gly Ile Xaa Val Ala Asp Tyr Tyr Xaa Tyr Gly Met Asp Val
1               5                   10                  15

<210> SEQ ID NO 256
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (8)..(8)
<223> OTHER INFORMATION: Tyr or Asn

<400> SEQUENCE: 256

Val Ile Ser Tyr Asp Gly Ser Xaa Lys Tyr Tyr Ala Asp Ser Val Lys
1               5                   10                  15
```

Gly

```
<210> SEQ ID NO 257
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Asp or Gly
<220> FEATURE:
<221> NAME/KEY: MOD_RES
<222> LOCATION: (2)..(2)
<223> OTHER INFORMATION: Tyr or Asp
<220> FEATURE:
<221> NAME/KEY: MOD_RES
<222> LOCATION: (5)..(5)
<223> OTHER INFORMATION: Tyr or His

<400> SEQUENCE: 257

Xaa Xaa Tyr Met Xaa
1               5

<210> SEQ ID NO 258
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (11)..(11)
<223> OTHER INFORMATION: Tyr or His
<220> FEATURE:
<221> NAME/KEY: MOD_RES
<222> LOCATION: (12)..(12)
<223> OTHER INFORMATION: Val or Ala
<220> FEATURE:
<221> NAME/KEY: MOD_RES
<222> LOCATION: (13)..(13)
<223> OTHER INFORMATION: Gln or Arg

<400> SEQUENCE: 258

Trp Ile Asn Pro Asn Ser Gly Gly Thr Asn Xaa Xaa Xaa Lys Phe Gln
1               5                   10                  15

Gly

<210> SEQ ID NO 259
<211> LENGTH: 12
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Gly or Arg
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (11)..(11)
<223> OTHER INFORMATION: Ala or Asp

<400> SEQUENCE: 259

Asp Xaa Gly Xaa Ser Gly Trp Pro Leu Phe Xaa Tyr
```

```
1               5                   10
```

<210> SEQ ID NO 260
<211> LENGTH: 363
<212> TYPE: DNA
<213> ORGANISM: Homo sapiens

<400> SEQUENCE: 260
caggtgcagc tggtggagtc tgggggaggc gtggtccagc ctggggaggtc cctgagactc    60 tcctgtgcag cgtctggatt caccttcagt aactatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga acagcctgag agccgaggac acggctgtat attactgtgc gagtctagtg   300
ggagctacca actactacgg tatggacgtc tggggccaag gaccacggt caccgtctcc   360 tca                                                                 363

<210> SEQ ID NO 261
<211> LENGTH: 121
<212> TYPE: PRT
<213> ORGANISM: Homo sapiens

<400> SEQUENCE: 261

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Val Gly Ala Thr Asn Tyr Tyr Gly Met Asp Val Trp Gly
            100                 105                 110

Gln Gly Thr Thr Val Thr Val Ser Ser
        115                 120

<210> SEQ ID NO 262
<211> LENGTH: 326
<212> TYPE: DNA
<213> ORGANISM: Homo sapiens

<400> SEQUENCE: 262
tcttctgagc tgactcagga ccctgctgtg tctgtggcct tgggacagac agtcaggatc    60
acatgccaag gagacagcct cagaagctat tatgcaagct ggtaccagca gaagccagga   120
caggcccctg tacttgtcat ctctggtaaa aactaccggc cctcaggat cccagaccga   180 ttctctggct ccagctcagg aaacacagct tccttgacca tcactggggc tcaggcggaa   240
gatgaggctg actactactg taactcccgg gacagaagtg gtaaccatct ggtgttttcg   300
gcggagggac caagctgacc gtccta                                       326

<210> SEQ ID NO 263
<211> LENGTH: 108
<212> TYPE: PRT

<213> ORGANISM: Homo sapiens

<400> SEQUENCE: 263

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Ser
        35                  40                  45

Gly Lys Asn Tyr Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Arg Ser Gly Asn His
                85                  90                  95

Leu Val Phe Gly Gly Gly Thr Lys Leu Thr Val Leu
            100                 105

<210> SEQ ID NO 264
<211> LENGTH: 360
<212> TYPE: DNA
<213> ORGANISM: Homo sapiens

<400> SEQUENCE: 264
gaagtgcagc tggtggagtc tgggggagtc gtggtacagc ctggggggtc cctgagactc      60
tcctgtgcag cctctggatt cacctttgat gattttacca tgcactgggt ccgtcaagct     120
ccggggaagg gtctggagtg gtctctctt attagttggg atggtggtag cacatactat     180
gcagactctg tgaagggccg attcaccatc tccagagaca cagcaaaaa ctccctgtat     240
atgcaaatga acagtctgag aactgaggac agcgccttgt attactgtgc aagaggtcct     300
tactactact tctacggtat ggacgtctgg ggccaaggga ccacggtcac cgtctcctca     360

<210> SEQ ID NO 265
<211> LENGTH: 120
<212> TYPE: PRT
<213> ORGANISM: Homo sapiens

<400> SEQUENCE: 265

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Phe
            20                  25                  30

Thr Met His Trp Val Arg Gln Ala Pro Gly Lys Gly Leu Glu Trp Val
        35                  40                  45

Ser Leu Ile Ser Trp Asp Gly Gly Ser Thr Tyr Tyr Ala Asp Ser Val
50                  55                  60

Lys Gly Arg Phe Thr Ile Ser Arg Asp Asn Ser Lys Asn Ser Leu Tyr
65                  70                  75                  80

Met Gln Met Asn Ser Leu Arg Thr Glu Asp Ser Ala Leu Tyr Tyr Cys
                85                  90                  95

Ala Arg Gly Pro Tyr Tyr Tyr Phe Tyr Gly Met Asp Val Trp Gly Gln
            100                 105                 110

Gly Thr Thr Val Thr Val Ser Ser
        115                 120

<210> SEQ ID NO 266
<211> LENGTH: 328

<212> TYPE: DNA
<213> ORGANISM: Homo sapiens

<400> SEQUENCE: 266

```
tcttctgagc tgactcagga ccctgctgtg tctgtggcct tgggacagac agtcaggatc      60
acatgccaag agacagcct cagaacctat tatgcaagct ggtaccagca gaagccagga     120
caggccccta tacttgtcat ctctgataaa acaaccggc cctcagggat cccagaccga     180
ttctctggct ccagctcagg aaacacagct tccttgacca tcactgggc tcaggcggaa     240
gatgaggctg actattactg taactcccgg gacagcagtg ataaccatct agtggtattt     300
cggcggaggg accaagctga ccgtccta                                        328
```

<210> SEQ ID NO 267
<211> LENGTH: 109
<212> TYPE: PRT
<213> ORGANISM: Homo sapiens

<400> SEQUENCE: 267

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Ile Leu Val Ile Ser
        35                  40                  45

Asp Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Asp Asn His
                85                  90                  95

Leu Val Val Phe Gly Gly Gly Thr Lys Leu Thr Val Leu
            100                 105

<210> SEQ ID NO 268
<211> LENGTH: 363
<212> TYPE: DNA
<213> ORGANISM: Homo sapiens

<400> SEQUENCE: 268

```
caggtgcagc tggtgcagtc tggggctgag gtgaagaagc ctggggcctc agtgaaggtc      60
tcctgcaagg cttctggata caccttcacc gactactata tgtactgggt gcgacaggcc     120
cctggacaag ggcctgagtg gatgggatgg atcaacccta cagtggtgg cacaaactat     180
gtacagaagt ttcagggcag ggtcaccatg accaggaca cgtccatcag cacagcctac     240
atggagctga gcaggatgag atccgacgac acggccgtgt attactgtgc gagagatggg     300
ggtagcagtg gctggcccct ctttgcctac tggggcctgg aaccctggt caccgtctcc     360
tca                                                                   363
```

<210> SEQ ID NO 269
<211> LENGTH: 121
<212> TYPE: PRT
<213> ORGANISM: Homo sapiens

<400> SEQUENCE: 269

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr

```
                        20                  25                  30
Tyr Met Tyr Trp Val Arg Gln Ala Pro Gly Gln Gly Pro Glu Trp Met
            35                  40                  45
Gly Trp Ile Asn Pro Asn Ser Gly Gly Thr Asn Tyr Val Gln Lys Phe
        50                  55                  60
Gln Gly Arg Val Thr Met Thr Arg Asp Thr Ser Ile Ser Thr Ala Tyr
65                  70                  75                  80
Met Glu Leu Ser Arg Met Arg Ser Asp Asp Thr Ala Val Tyr Tyr Cys
                85                  90                  95
Ala Arg Asp Gly Gly Ser Ser Gly Trp Pro Leu Phe Ala Tyr Trp Gly
            100                 105                 110
Leu Gly Thr Leu Val Thr Val Ser Ser
        115                 120

<210> SEQ ID NO 270
<211> LENGTH: 340
<212> TYPE: DNA
<213> ORGANISM: Homo sapiens

<400> SEQUENCE: 270
cagtctgtgc tgacgcagcc gccctcagtg tctggggccc cagggcagag ggtcaccatc    60
tcctgcactg ggagcagctc caacatcggg gcaggttttg atgtacactg gtaccagcag   120
cttccaggaa cagcccccaa actcctcatc tatgataaca acaatcggcc ctcagggstc   180
cctgaccgat tctctggctc caagtctggc acctcagcct ccctggccat cactgggctc   240
caggctgagg atgaggctga ttattactgc cagtcctatg acagcaacct gagtggttcg   300
attgtggttt tcggcggag ggaccaagct gaccgtccta                          340

<210> SEQ ID NO 271
<211> LENGTH: 113
<212> TYPE: PRT
<213> ORGANISM: Homo sapiens

<400> SEQUENCE: 271

Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Gly
            20                  25                  30
Phe Asp Val His Trp Tyr Gln Gln Leu Pro Gly Thr Ala Pro Lys Leu
        35                  40                  45
Leu Ile Tyr Asp Asn Asn Asn Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Gln Ser Tyr Asp Ser Asn
                85                  90                  95
Leu Ser Gly Ser Ile Val Val Phe Gly Gly Gly Thr Lys Leu Thr Val
            100                 105                 110
Leu

<210> SEQ ID NO 272
<211> LENGTH: 363
<212> TYPE: DNA
<213> ORGANISM: Homo sapiens

<400> SEQUENCE: 272
caggtgcagc tggtgcagtc tggggctgag gtgaagaagc ctggggcctc agtgaaggtc    60
```

-continued

```
tcctgcaagg cttctggata catcttcacc ggcgactata tgcactgggt gcgacaggcc      120
cctggacaag ggctggagtg gatgggatgg atcaaccota acagtggtgg cacaaaccat      180
gcacggaagt tcagggcag ggtcaccatg accagggaca cgtccatcag cacagcctac      240
atggagctga gcaggctgag atctgacgac acggccgtgt attactgtgt gagagatagg      300
ggtaccagtg ctggccact ctttgactat tggggccagg gaacactggt caccgtctcc      360
tca                                                                    363
```

<210> SEQ ID NO 273
<211> LENGTH: 121
<212> TYPE: PRT
<213> ORGANISM: Homo sapiens

<400> SEQUENCE: 273

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Asp
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn His Ala Arg Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Arg Asp Arg Gly Thr Ser Gly Trp Pro Leu Phe Asp Tyr Trp Gly
            100                 105                 110

Gln Gly Thr Leu Val Thr Val Ser Ser
        115                 120
```

<210> SEQ ID NO 274
<211> LENGTH: 340
<212> TYPE: DNA
<213> ORGANISM: Homo sapiens

<400> SEQUENCE: 274

```
cagtctgtgc tgacgcagcc gccctcagtg tctggggccc cagggcagag ggtcaccatc      60
tcctgcactg ggagcagctc caacatcggg gcaggttttg atgtgcactg gtaccagctg      120
cttccaggaa cagcccccaa actcctcatc tttgataaca caatcgcccc tcagggggtc      180
cctgaccgat tctctggctc caagtctggc acctcagcct ccctggccat cactgggctc      240
caggctgagg atgaggctga ttattactgc cagtcctatg acagcaacct gagtggttcg      300
attgtggtat tcggcggag ggaccaagct gaccgtccta                              340
```

<210> SEQ ID NO 275
<211> LENGTH: 113
<212> TYPE: PRT
<213> ORGANISM: Homo sapiens

<400> SEQUENCE: 275

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Phe Asp Val His Trp Tyr Gln Leu Leu Pro Gly Thr Ala Pro Lys Leu
```

```
                35                  40                  45
Leu Ile Phe Asp Asn Asn Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Asn
                 85                  90                  95

Leu Ser Gly Ser Ile Val Val Phe Gly Gly Gly Thr Lys Leu Thr Val
            100                 105                 110

Leu

<210> SEQ ID NO 276
<211> LENGTH: 378
<212> TYPE: DNA
<213> ORGANISM: Homo sapiens

<400> SEQUENCE: 276
caggtgcagc tggtggagtc tgggggaggc gtggtccagc ctggagggtc cctgagactc      60
tcctgtgcag cctctggatt cattttcagt agctatggca ttcactgggt ccgccaggct     120
ccaggcaagg ggctggagtg ggtggcagtt atatcatatg atggaagtta taaatactat     180
gcagactccg tgaagggccg attcaccatc tccagagaca attccaagaa cacgctgtat     240
ctgcaaatga acagcctgag agctgaggac acggctgtgt attactgtgc gagaggggac     300
tcctggaacg acagattaaa ctactacttc tacgatatgg acgtctgggg ccaagggacc     360
acggtcaccg tctcctca                                                   378

<210> SEQ ID NO 277
<211> LENGTH: 126
<212> TYPE: PRT
<213> ORGANISM: Homo sapiens

<400> SEQUENCE: 277

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ile Phe Ser Ser Tyr
             20                  25                  30

Gly Ile His Trp Val Arg Gln Ala Pro Gly Lys Gly Leu Glu Trp Val
         35                  40                  45

Ala Val Ile Ser Tyr Asp Gly Ser Tyr Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Asp Ser Trp Asn Asp Arg Leu Asn Tyr Tyr Phe Tyr Asp
            100                 105                 110

Met Asp Val Trp Gly Gln Gly Thr Thr Val Thr Val Ser Ser
        115                 120                 125

<210> SEQ ID NO 278
<211> LENGTH: 319
<212> TYPE: DNA
<213> ORGANISM: Homo sapiens

<400> SEQUENCE: 278
tcctatgagc tgactcaggc accctcagtg tccgtgtccc caggacagac agccagcatc      60
```

```
acctgctctg agataaaatt gggggataaa tatgcttgct ggtatcagca gaagccaggc      120
cagtcccctg tgctggtcat ctatcaagat aagaagcggc cctcaggat cctgagcga      180 ttctctggct ccaactctgg gaacacagcc actctgacca tcagcgggac ccaggctatg      240
gatgaggctg actattactg tcaggcgtgg gacagcagca ctgtggtatt cggcggagg      300 gaccaagctg accgtccta                                                  319
```

```
<210> SEQ ID NO 279
<211> LENGTH: 106
<212> TYPE: PRT
<213> ORGANISM: Homo sapiens

<400> SEQUENCE: 279
```

Ser Tyr Glu Leu Thr Gln Ala Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Lys Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105

```
<210> SEQ ID NO 280
<211> LENGTH: 366
<212> TYPE: DNA
<213> ORGANISM: Homo sapiens

<400> SEQUENCE: 280
caggtgcagc tgcaggagtc gggcccagga ctggtgaagc cttcacagac cctgtccctc       60
acctgcactg tctctggtgg ctccatcagc agtggtggtt actactggag ctggatccgc      120
cagcacccag ggaagggcct ggagtggatt gggttcatcc attacagtgg gaccacctac      180
tacaacccgt ccctcaagag tcgacttacc ctatcagtag acacgtctaa gagccagttc      240
tccctgaagc tgaactctgt gactgccgcg gacacggccg tgtattactg tgcgagagaa      300
gttggcagct cgtcgggtaa ctggttcgac ccctgggcc agggaaccct ggtcaccgtc      360
tcctca                                                                366
```

```
<210> SEQ ID NO 281
<211> LENGTH: 122
<212> TYPE: PRT
<213> ORGANISM: Homo sapiens

<400> SEQUENCE: 281
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Phe Ile His Tyr Ser Gly Thr Thr Tyr Tyr Asn Pro Ser
    50                  55                  60

```
Leu Lys Ser Arg Leu Thr Leu Ser Val Asp Thr Ser Lys Ser Gln Phe
 65                  70                  75                  80

Ser Leu Lys Leu Asn Ser Val Thr Ala Ala Asp Thr Ala Val Tyr Tyr
                 85                  90                  95

Cys Ala Arg Glu Val Gly Ser Ser Gly Asn Trp Phe Asp Pro Trp
            100                 105                 110

Gly Gln Gly Thr Leu Val Thr Val Ser Ser
        115                 120
```

```
<210> SEQ ID NO 282
<211> LENGTH: 319
<212> TYPE: DNA
<213> ORGANISM: Homo sapiens

<400> SEQUENCE: 282
tcctatgagc tgactcagcc accctcagtg tccgtgtccc caggacagac agccagcatc      60
acctgctctg gagataaaat tggggataaa tatgcttgct ggtatcagca gaagccaggc    120
cagtcccctg tggtggtcat ctatcaagat aacaagcggc cctcagggat ccctgagcga    180
ttctctggct ccaactctgg gaacacagcc actttgacca tcagcgggac ccaggctatg    240
gatgaggctg actattactg tcaggcgtgg acagcacca ctgcgatatt cggcggaggg    300
gaccaagctg accgtccta                                                 319
```

```
<210> SEQ ID NO 283
<211> LENGTH: 106
<212> TYPE: PRT
<213> ORGANISM: Homo sapiens

<400> SEQUENCE: 283

Ser Tyr Glu Leu Thr Gln Pro Pro Ser Val Ser Val Ser Pro Gly Gln
 1               5                  10                  15

Thr Ala Ser Ile Thr Cys Ser Gly Asp Lys Leu Gly Asp Lys Tyr Ala
                 20                  25                  30

Cys Trp Tyr Gln Gln Lys Pro Gly Gln Ser Pro Val Val Val Ile Tyr
             35                  40                  45

Gln Asp Asn Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Thr Thr Ala Ile
             85                  90                  95

Phe Gly Gly Gly Thr Lys Leu Thr Val Leu
            100                 105
```

```
<210> SEQ ID NO 284
<211> LENGTH: 378
<212> TYPE: DNA
<213> ORGANISM: Homo sapiens

<400> SEQUENCE: 284
caggtgcagc tggtggagtc tgggggaggc gtggtccagc ctggggaggtc cctgagactc      60 tcctgtgcag cctctggatt caccttcagt agctatggca ttcactgggt ccgccaggct    120
ccaggcaagg ggctggagtg ggtggcagtt atatcatatg atggaagtaa taatactat     180 gcagactccg tgaagggccg attcaccatc tccagagaca attccaagaa cacgctgtat    240
ctgcaaatga acagcctgag agctgaggac acggctgtgt attactgtgc gagaggggac    300
```

-continued

```
tcctggaacg acagattaaa ctactacttc tacgatatgg acgtctgggg ccaagggacc    360
acggtcaccg tctcctca                                                  378
```

<210> SEQ ID NO 285
<211> LENGTH: 126
<212> TYPE: PRT
<213> ORGANISM: Homo sapiens

<400> SEQUENCE: 285

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Ser Trp Asn Asp Arg Leu Asn Tyr Tyr Phe Tyr Asp
            100                 105                 110

Met Asp Val Trp Gly Gln Gly Thr Thr Val Thr Val Ser Ser
        115                 120                 125
```

<210> SEQ ID NO 286
<211> LENGTH: 319
<212> TYPE: DNA
<213> ORGANISM: Homo sapiens

<400> SEQUENCE: 286

```
tcctatgagc tgactcagcc accctcagtg tccgtgtccc caggacagac agccagcatc     60
acctgctctg gagataaaatt gggggataaa tatgcttgct ggtatcagca gaagccaggc   120
cagtcccctg tactggtcat ctatcaagat aacaagcggc cctcagggat ccctgagcga   180
ttctctggct ccaactctgg gaacacagcc actttgacca tcagcgggac ccaggctatg   240
gatgaggctg actattactg tcaggcgtgg gacagcagca ctgtggtatt cggcggaggg   300
gaccaagctg accgtcta                                                  319
```

<210> SEQ ID NO 287
<211> LENGTH: 106
<212> TYPE: PRT
<213> ORGANISM: Homo sapiens

<400> SEQUENCE: 287

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
```

```
                85                  90                  95

Phe Gly Gly Gly Thr Lys Leu Thr Val Leu
            100                 105

<210> SEQ ID NO 288
<211> LENGTH: 372
<212> TYPE: DNA
<213> ORGANISM: Homo sapiens

<400> SEQUENCE: 288
caggtgcagt tggtggagtc tgggggaggc gtggtccagc ctgggaggtc cctgagactc      60
tcctgtgcag cgtctggata taccttcaat agctatggca tgcactgggt ccgccaggct     120
ccaggcaagg ggctggagtg ggtggcagtt atatggtatg atggaagtaa tacatactat     180
gcagactccg tgaagggccg attcaccatc tccagagaca tttccaagaa cactctgtat     240
ctgcaaatga acagcctgag agccgaggac acggctgtgt attactgtgc gagagaggtc     300
cgggcgtata gcagtggctg gtacgccgcc tttgactact ggggccaggg aaccctggtc     360
accgtctcct ca                                                         372

<210> SEQ ID NO 289
<211> LENGTH: 124
<212> TYPE: PRT
<213> ORGANISM: Homo sapiens

<400> SEQUENCE: 289

Gln Val Gln Leu Val Glu Ser Gly Gly Val Val Gln Pro Gly Arg
1               5                   10                  15

Ser Leu Arg Leu Ser Cys Ala Ala Ser Gly Tyr Thr Phe Asn Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Thr Tyr Tyr Ala Asp Ser Val
    50                  55                  60

Lys Gly Arg Phe Thr Ile Ser Arg Asp Ile Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Val Arg Ala Tyr Ser Ser Gly Trp Tyr Ala Ala Phe Asp
            100                 105                 110

Tyr Trp Gly Gln Gly Thr Leu Val Thr Val Ser Ser
        115                 120

<210> SEQ ID NO 290
<211> LENGTH: 325
<212> TYPE: DNA
<213> ORGANISM: Homo sapiens

<400> SEQUENCE: 290
tcttctgagc tgactcagga ccctgctgtg tctgtggcct tgggacagac agtcaggatc      60
acatgccaag agacagcctc agaatctttt tatgcaaact ggtaccagca gaagccagga     120
caggcccctg tagttgtctt ctatggtaaa aacaaccggc cctcagggat cccagaccga     180
ttctctggct ccagctcagg aaacacagct tccttgacca tcactgcggc tcaggcggaa     240
gatgaggctg actattattg taactcccgg gacagcagtg gtaaccatgt ggtatttcgg     300
cggagggacc acgctgaccg tccta                                           325
```

<210> SEQ ID NO 291
<211> LENGTH: 108
<212> TYPE: PRT
<213> ORGANISM: Homo sapiens

<400> SEQUENCE: 291

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ile Phe Tyr Ala
                20                  25                  30

Asn Trp Tyr Gln Gln Lys Pro Gly Gln Ala Pro Val Val Val Phe Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Thr Leu Thr Val Leu
            100                 105

<210> SEQ ID NO 292
<211> LENGTH: 375
<212> TYPE: DNA
<213> ORGANISM: Homo sapiens

<400> SEQUENCE: 292
caggtgcagc tggtggagtc tgggggaggc gtggtccagc ctggagggtc cctgagactc      60
tcctgtgcaa cgtctggatt caccttcagt agttatggca tgcactgggt ccgccaggct     120
ccaggcaagg ggctggagtg ggtggcagtt atatggtatg atggaagtag taaatactat     180
gcagactccg tgaagggccg attcaccatc tccagagaca attccaagaa cacgctgtat     240
ctgcaaatga acagcctgag agccgaggac acggccgtgt attactgtgc gagagtaaga     300
agtgggagct actacgaaca gtattactac ggtatggacg tctggggcca agggaccacg     360
gtcgccgtct cctca                                                      375

<210> SEQ ID NO 293
<211> LENGTH: 125
<212> TYPE: PRT
<213> ORGANISM: Homo sapiens

<400> SEQUENCE: 293

Gln Val Gln Leu Val Glu Ser Gly Gly Gly Val Val Gln Pro Gly Arg
1               5                   10                  15

Ser Leu Arg Leu Ser Cys Ala Thr Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Ser Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Ser Gly Ser Tyr Tyr Glu Gln Tyr Tyr Gly Met
            100                 105                 110

Asp Val Trp Gly Gln Gly Thr Thr Val Ala Val Ser Ser

<210> SEQ ID NO 294
<211> LENGTH: 322
<212> TYPE: DNA
<213> ORGANISM: Homo sapiens

<400> SEQUENCE: 294
gacatccaga tgacccagtc tccatcctcc ctgtctgcat ctgtaggaga cagagtcacc 60
atcacttgcc gggcaaatca gtacattagc acctatttaa attggtatca gcagaaacca 120
gggaaagccc ctaaggtcct gatttatgct gcatccagtt tgcaaagtgg ggtcccatca 180
aggttcagtg gcagtggatt tgagacagat ttcactctca ccatcagcag tctgcaacct 240
gaagattttg caacttacta ctgtcagcag agctacacta ccccgatcac ctttcggcca 300
agggacacga ctggagatta aa 322

<210> SEQ ID NO 295
<211> LENGTH: 107
<212> TYPE: PRT
<213> ORGANISM: Homo sapiens

<400> SEQUENCE: 295

Asp Ile Gln Met Thr Gln Ser Pro Ser Ser Leu Ser Ala Ser Val Gly
1               5                   10                  15

Asp Arg Val Thr Ile Thr Cys Arg Ala Asn Gln Tyr Ile Ser Thr Tyr
            20                  25                  30

Leu Asn Trp Tyr Gln Gln Lys Pro Gly Lys Ala Pro Lys Val Leu Ile
        35                  40                  45

Tyr Ala Ala Ser Ser Leu Gln Ser Gly Val Pro Ser Arg Phe Ser Gly
    50                  55                  60

Ser Gly Phe Glu Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Ile
                85                  90                  95

Thr Phe Gly Gln Gly Thr Arg Leu Glu Ile Lys
            100                 105

<210> SEQ ID NO 296
<211> LENGTH: 363
<212> TYPE: DNA
<213> ORGANISM: Homo sapiens

<400> SEQUENCE: 296
gaggtgcagc tggtggagtc tgggggaggc ttggtacagc ctggggggtc cctgagactc 60
tcctgtgcag cctctggatt caccttcagt agttatagca tgaactgggt ccgccaggct 120
ccagggaagg ggctggagtg ggtttcatac attagtggtc gtactagtag cgtatactac 180
gcagactctg tgaagggccg attcaccatc tccagagaca tgccaagaa ctcactgtat 240 ctgcacatga acagcctgag agacgaggac acggctgtgt attactgtgc gagaagtggg 300
atctactacg actactacgg tatggacgtc tggggccaag ggaccacggt caccgtctcc 360
tca 363

<210> SEQ ID NO 297
<211> LENGTH: 121
<212> TYPE: PRT
<213> ORGANISM: Homo sapiens

<400> SEQUENCE: 297

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Gly Arg Thr Ser Ser Val Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu His Met Asn Ser Leu Arg Asp Glu Asp Thr Ala Val Tyr Tyr Cys
                85                  90                  95

Ala Arg Ser Gly Ile Tyr Tyr Asp Tyr Tyr Gly Met Asp Val Trp Gly
            100                 105                 110

Gln Gly Thr Thr Val Thr Val Ser Ser
        115                 120

<210> SEQ ID NO 298
<211> LENGTH: 340
<212> TYPE: DNA
<213> ORGANISM: Homo sapiens

<400> SEQUENCE: 298
gacatcgtga tgacccagtc tccagactcc ctggctgtgt ctctgggcga gagggccccc      60
atcaactgca gtccagcca gagtgtttta acagctcca acaataagaa ctacttagct      120
tggtaccagc agaaaccagg acagcctcct aagctgctca tttactggac atccacccgg    180
gaaggcgggg tccctgaccg attcagtggc agcgggtctg ggacagattt cactctcacc    240
atcagcagcc tgcaggctga agatgtggca gtttattact gtcagcagta ttttactact    300
ccgtggacgt tcggccaag ggaccaaggt ggagatcaaa                           340

<210> SEQ ID NO 299
<211> LENGTH: 113
<212> TYPE: PRT
<213> ORGANISM: Homo sapiens

<400> SEQUENCE: 299

Asp Ile Val Met Thr Gln Ser Pro Asp Ser Leu Ala Val Ser Leu Gly
1               5                   10                  15

Glu Arg Ala Pro Ile Asn Cys Lys Ser Ser Gln Ser Val Leu Asn Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Thr Ser Thr Arg Glu Gly Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Thr Thr Pro Trp Thr Phe Gly Gln Gly Thr Lys Val Glu Ile
            100                 105                 110

Lys

<210> SEQ ID NO 300
<211> LENGTH: 375
<212> TYPE: DNA

<213> ORGANISM: Homo sapiens

<400> SEQUENCE: 300

```
caggtgcagc tggtggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagaggggca   300
gccactgcta tagattacta ctactcctac ggtatggacg tctggggcct agggaccacg   360
gtcaccgtct cctca                                                    375
```

<210> SEQ ID NO 301
<211> LENGTH: 125
<212> TYPE: PRT
<213> ORGANISM: Homo sapiens

<400> SEQUENCE: 301

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Ala Thr Ala Ile Asp Tyr Tyr Tyr Ser Tyr Gly Met
            100                 105                 110

Asp Val Trp Gly Leu Gly Thr Thr Val Thr Val Ser Ser
        115                 120                 125
```

<210> SEQ ID NO 302
<211> LENGTH: 322
<212> TYPE: DNA
<213> ORGANISM: Homo sapiens

<400> SEQUENCE: 302

```
gacatccaga tgacccagtc tccatcttcc gtgtctgcat ctgtgggaga cagagtcacc    60
atcacttgtc gggcgagtca gggtattagt agctggttag cctggtatca gcggaaacca   120
ggaaaagccc ctaagttcct gatctatact gcatccagtt tgcaaagtgg ggtcccatca   180
cggttcagcg gcagtggatc tgggacagat ttcactctca ccatcagcag cctgcagcct   240
gaagattctg caacttacta ttgtcaacag gctgacagtt tcccgctcac ttttcggcgg   300
agggaccaag gtggagatca aa                                            322
```

<210> SEQ ID NO 303
<211> LENGTH: 107
<212> TYPE: PRT
<213> ORGANISM: Homo sapiens

<400> SEQUENCE: 303

```
Asp Ile Gln Met Thr Gln Ser Pro Ser Ser Val Ser Ala Ser Val Gly
1               5                   10                  15
```

Asp Arg Val Thr Ile Thr Cys Arg Ala Ser Gln Gly Ile Ser Ser Trp
            20                  25                  30

Leu Ala Trp Tyr Gln Arg Lys Pro Gly Lys Ala Pro Lys Phe Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ala Asp Ser Phe Pro Leu
                85                  90                  95

Thr Phe Gly Gly Gly Thr Lys Val Glu Ile Lys
            100                 105

<210> SEQ ID NO 304
<211> LENGTH: 375
<212> TYPE: DNA
<213> ORGANISM: Homo sapiens

<400> SEQUENCE: 304
caggtgcagc tggtggagtc tgggggaggc gtggtccagc ctggggaggtc cctgagactc     60 tcctgtgcag cgtctggatt caccttcagt agctatggca tgcactgggt ccgccaggct    120
ccaggcaagg ggctggagtg ggtggcagtt atatggtatg atggaagtaa taaatactat    180
gcagactccg tgaagggccg attcaccatc tccagagaca attccaagaa cacgctgtat    240
ctgcaaatga acagcctgag agccgaggac acggctgtgt attactgtgc gagggggggg    300
ggtataccag tagctgacta ctactactac ggtatggacg tctggggcca agggaccacg    360
gtcaccgtct cctca                                                     375

<210> SEQ ID NO 305
<211> LENGTH: 125
<212> TYPE: PRT
<213> ORGANISM: Homo sapiens

<400> SEQUENCE: 305

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Ile Pro Val Ala Asp Tyr Tyr Tyr Tyr Gly Met
            100                 105                 110

Asp Val Trp Gly Gln Gly Thr Thr Val Thr Val Ser Ser
        115                 120                 125

<210> SEQ ID NO 306
<211> LENGTH: 337
<212> TYPE: DNA
<213> ORGANISM: Homo sapiens

<400> SEQUENCE: 306

```
gatgttgtga tgactcagtc tccactctcc ctgcccgtca cccttggaca gccggcctcc    60
atctcctgca ggtctagtca aagcctcgtc tacagtgatg agacaccta cttgaattgg    120 tttcagcaga ggccaggcca atctccaagg cgcctaattt ataaggtttc taactgggac   180
tctggggtcc catacagatt cagcggcagt gggtcaggca ctgatttcac actgcaaatc   240
agcagggtgg aggctgagga tgttgggatt tactactgca tgcaaggtac acactggcct   300
ccggcctttc ggccaaggga cacgactgga gattaaa                            337
```

<210> SEQ ID NO 307
<211> LENGTH: 112
<212> TYPE: PRT
<213> ORGANISM: Homo sapiens

<400> SEQUENCE: 307

| Asp | Val | Val | Met | Thr | Gln | Ser | Pro | Leu | Ser | Leu | Pro | Val | Thr | Leu | Gly |
|---|---|---|---|---|---|---|---|---|---|---|---|---|---|---|---|
| 1 | | | | 5 | | | | | 10 | | | | | 15 | |

| Gln | Pro | Ala | Ser | Ile | Ser | Cys | Arg | Ser | Ser | Gln | Ser | Leu | Val | Tyr | Ser |
|---|---|---|---|---|---|---|---|---|---|---|---|---|---|---|---|
| | | | 20 | | | | | 25 | | | | | 30 | | |

| Asp | Gly | Asp | Thr | Tyr | Leu | Asn | Trp | Phe | Gln | Gln | Arg | Pro | Gly | Gln | Ser |
|---|---|---|---|---|---|---|---|---|---|---|---|---|---|---|---|
| | | | 35 | | | | | 40 | | | | | 45 | | |

| Pro | Arg | Arg | Leu | Ile | Tyr | Lys | Val | Ser | Asn | Trp | Asp | Ser | Gly | Val | Pro |
|---|---|---|---|---|---|---|---|---|---|---|---|---|---|---|---|
| | 50 | | | | | 55 | | | | | 60 | | | | |

| Tyr | Arg | Phe | Ser | Gly | Ser | Gly | Ser | Gly | Thr | Asp | Phe | Thr | Leu | Gln | Ile |
|---|---|---|---|---|---|---|---|---|---|---|---|---|---|---|---|
| 65 | | | | | 70 | | | | | 75 | | | | | 80 |

| Ser | Arg | Val | Glu | Ala | Glu | Asp | Val | Gly | Ile | Tyr | Tyr | Cys | Met | Gln | Gly |
|---|---|---|---|---|---|---|---|---|---|---|---|---|---|---|---|
| | | | | 85 | | | | | 90 | | | | | 95 | |

| Thr | His | Trp | Pro | Pro | Ala | Phe | Gly | Gln | Gly | Thr | Arg | Leu | Glu | Ile | Lys |
|---|---|---|---|---|---|---|---|---|---|---|---|---|---|---|---|
| | | | 100 | | | | | 105 | | | | | 110 | | |

<210> SEQ ID NO 308
<211> LENGTH: 322
<212> TYPE: DNA
<213> ORGANISM: Homo sapiens

<400> SEQUENCE: 308

```
gacatccaga tgacccagtc tccatcttcc gtgtctgcat ctgtaggaga cagagtcacc    60
atcacttgtc gggcgagtca gggtcttagc agctggttag cctggtatca gcagaaacca   120
gggaaagccc ccaagctcct gatgtataac acatccagtt tgcaaagtgg ggtcccatca   180
aggttcagcg gcagtggatc tgggacagat ttcagtctca ccatcagcag cctgcagcct   240
gaagattttg caagttacta ttgtcaacag gctaacagtt tccctctcac ttttcggcgg   300
agggaccaag gtggagatca aa                                            322
```

<210> SEQ ID NO 309
<211> LENGTH: 107
<212> TYPE: PRT
<213> ORGANISM: Homo sapiens

<400> SEQUENCE: 309

| Asp | Ile | Gln | Met | Thr | Gln | Ser | Pro | Ser | Ser | Val | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Gln | Gly | Leu | Ser | Ser | Trp |
|---|---|---|---|---|---|---|---|---|---|---|---|---|---|---|---|
| | | | 20 | | | | | 25 | | | | | 30 | | |

| Leu | Ala | Trp | Tyr | Gln | Gln | Lys | Pro | Gly | Lys | Ala | Pro | Lys | Leu | Leu | Met |
|---|---|---|---|---|---|---|---|---|---|---|---|---|---|---|---|
| | | | 35 | | | | | 40 | | | | | 45 | | |

| Tyr | Asn | Thr | Ser | Ser | Leu | Gln | Ser | Gly | Val | Pro | Ser | Arg | Phe | Ser | Gly |

```
                  50                  55                  60
Ser Gly Ser Gly Thr Asp Phe Ser Leu Thr Ile Ser Ser Leu Gln Pro
 65                  70                  75                  80

Glu Asp Phe Ala Ser Tyr Tyr Cys Gln Gln Ala Asn Ser Phe Pro Leu
                 85                  90                  95

Thr Phe Gly Gly Gly Thr Lys Val Glu Ile Lys
            100                 105
```

<210> SEQ ID NO 310
<211> LENGTH: 337
<212> TYPE: DNA
<213> ORGANISM: Homo sapiens

<400> SEQUENCE: 310

```
gatgttgtga tgactcagtc tccactctcc ctgcccgtca cccttggaca gccggcctcc    60
atctcctgca ggtctagtca aagcctcgtc tacagtgatg aaacaccta cttgaattgg   120 tttcagcaga ggccaggcca atctccaagg cgcctaattt ataaggtttc taactgggac   180
tctggggtcc cagacagatt cagcggcatt gggtcaggca ctgacttcac actgaaaatc   240
agcagggtgg aggctgagga tgttggggtt tactactgca tgcaaggtac acactggcct   300
ccggcctttc ggccaaggga cacgactgga gattaaa                             337
```

<210> SEQ ID NO 311
<211> LENGTH: 112
<212> TYPE: PRT
<213> ORGANISM: Homo sapiens

<400> SEQUENCE: 311

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
             20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Val Ser Asn Trp Asp Ser Gly Val Pro
 50                  55                  60

Asp Arg Phe Ser Gly Ile Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Pro Ala Phe Gly Gln Gly Thr Arg Leu Glu Ile Lys
            100                 105                 110
```

<210> SEQ ID NO 312
<211> LENGTH: 322
<212> TYPE: DNA
<213> ORGANISM: Homo sapiens

<400> SEQUENCE: 312

```
gacatccaga tgacccagtc tccatcttcc gtgtctgcat ctgtaggaga cagagtcacc    60
atcacttgtc gggcgagtca gggtcttagc agctggttag cctggtatca gcagaaacca   120
gggaaagccc ccaagctcct gatgtataac acatccagtt tgcaaagtgg ggtcccatca   180
aggttcagcg gcagtggatc tgggacagat ttcagtctca ccatcagcag cctgcagcct   240
gaagattttg caagttacta ttgtcaacag gctaacagtt ccctctcac ttttcggcgg    300 agggaccaag gtggagatca aa                                             322
```

<210> SEQ ID NO 313
<211> LENGTH: 375
<212> TYPE: DNA
<213> ORGANISM: Homo sapiens

<400> SEQUENCE: 313

```
caggtgcagc tggtggagtc tgggggaggc gtggtccagc ctgggaagtc cctgagactc      60
tcctgtgcag cgtctggatt cccttcagt aactatggca tgcactgggt ccgccaggct     120
ccaggcaagg gactggaatg ggtggcagtt atatgtttg atggaagtaa taaatactat     180
gcggactccg tgaagggccg attcaccatc tccagagaca tcccaagaa cacgctgtat     240
ctgcaaatga acagcctgag agccgaggac acggctgtgt attactgtgc gagagggggg     300
ggtatagcag tggctgacta ctacttctac ggtatggacg tctggggcca agggaccacg     360
gtcaccgtct cctca                                                      375
```

<210> SEQ ID NO 314
<211> LENGTH: 125
<212> TYPE: PRT
<213> ORGANISM: Homo sapiens

<400> SEQUENCE: 314

Gln Val Gln Leu Val Glu Ser Gly Gly Gly Val Val Gln Pro Gly Lys
1               5                   10                  15

Ser Leu Arg Leu Ser Cys Ala Ala Ser Gly Phe Pro Phe Ser Asn Tyr
            20                  25                  30

Gly Met His Trp Val Arg Gln Ala Pro Gly Lys Gly Leu Glu Trp Val
        35                  40                  45

Ala Val Ile Trp Phe Asp Gly Ser Asn Lys Tyr Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Ile Ala Val Ala Asp Tyr Tyr Phe Tyr Gly Met
            100                 105                 110

Asp Val Trp Gly Gln Gly Thr Thr Val Thr Val Ser Ser
        115                 120                 125

<210> SEQ ID NO 315
<211> LENGTH: 337
<212> TYPE: DNA
<213> ORGANISM: Homo sapiens

<400> SEQUENCE: 315

```
gatgttgtga tgactcagtc tccactctcc ctgcccgtca cccttggaca gccggcctcc      60
atctcctgca ggtctagtca aagcctcata tacagtgatg gaaacactta cttgaattgg     120
tttcaacaga ggccaggcca atctccaagg cgcctaattt ataaggtttc taactgggac     180
tctggggtcc cagacagatt cagcggcagt gggtcaggca ctgatttcac actgaaaatc     240
agcagggtgg aggctgagga tgttggaatt tattactgca tgcaaggtac acactggcct     300
ccggcctttc ggccaaggga cacgactgga gattaaa                              337
```

<210> SEQ ID NO 316
<211> LENGTH: 112
<212> TYPE: PRT
<213> ORGANISM: Homo sapiens

<400> SEQUENCE: 316

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Ile Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Thr His Trp Pro Pro Ala Phe Gly Gln Gly Thr Arg Leu Glu Ile Lys
            100                 105                 110

<210> SEQ ID NO 317
<211> LENGTH: 322
<212> TYPE: DNA
<213> ORGANISM: Homo sapiens

<400> SEQUENCE: 317
gacatccaga tgacccagtc tccatcttcc gtgtctgcat ctgtaggaga cagagtcacc      60
attacttgtc gggcgagtca gggtattagc agctggttag cctggtatca gcagaaacca     120
gggaaagccc ctaaggtcct gacctatact acatccagtt tgcaaagtgg ggtcccatca     180
aggttcagcg gcagtggatc tgggacagat ttcactctca ccatcagcag cctgcagcct     240
gaagattttg ctacttactt ttgtcaacag gctgacagtt tccctctcac ttttcggcgg     300
ggggaccaag gtggagatca aa                                              322

<210> SEQ ID NO 318
<211> LENGTH: 107
<212> TYPE: PRT
<213> ORGANISM: Homo sapiens

<400> SEQUENCE: 318

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Thr
        35                  40                  45

Tyr Thr Thr Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asp Ser Phe Pro Leu
                85                  90                  95

Thr Phe Gly Gly Gly Thr Lys Val Glu Ile Lys
            100                 105

<210> SEQ ID NO 319
<211> LENGTH: 375
<212> TYPE: DNA
<213> ORGANISM: Homo sapiens

<400> SEQUENCE: 319

```
caggtgcaac tggtggagtc tgggggaggc gtggtccagc ctgggaggtc cctgagactc    60
tcctgtgcag cgtctggatt caccttcagt aactatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagagggggg   300
ggtatagcag tggctgacta ctactactac ggtatggacg tctggggcca agggaccacg   360
gtcaccgtct cctca                                                    375
```

<210> SEQ ID NO 320
<211> LENGTH: 125
<212> TYPE: PRT
<213> ORGANISM: Homo sapiens

<400> SEQUENCE: 320

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Ile Ala Val Ala Asp Tyr Tyr Tyr Tyr Gly Met
            100                 105                 110

Asp Val Trp Gly Gln Gly Thr Thr Val Thr Val Ser Ser
        115                 120                 125
```

<210> SEQ ID NO 321
<211> LENGTH: 337
<212> TYPE: DNA
<213> ORGANISM: Homo sapiens

<400> SEQUENCE: 321

```
gatgttgtga tgactcagtc tccactctcc ctgcccgtca cccttggaca gccggcctcc    60
atctcctgca ggtctagtca agcctcgta tacagtgatg gaaacaccta cttgaattgg   120
tttcagcaga ggccaggcca atctccaagg cgcctaattt ataaggtttc ttactgggac   180
tctggggtcc cagacagatt cagcggcagt gggtcaagca ctgatttcac actgaaaatc   240
agtagggtgg aggctgagga tgttggggtt tattactgca tgcaaggtac acactggcct   300
ccggcctttc ggccaaggga cacgactgga gattaaa                            337
```

<210> SEQ ID NO 322
<211> LENGTH: 112
<212> TYPE: PRT
<213> ORGANISM: Homo sapiens

<400> SEQUENCE: 322

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30
```

```
Asp Gly Asn Thr Tyr Leu Asn Trp Phe Gln Gln Arg Pro Gly Gln Ser
         35                  40                  45

Pro Arg Leu Ile Tyr Lys Val Ser Tyr Trp Asp Ser Gly Val Pro
 50                  55                  60

Asp Arg Phe Ser Gly Ser Gly Ser Ser Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Pro Ala Phe Gly Gln Gly Thr Arg Leu Glu Ile Lys
            100                 105                 110

<210> SEQ ID NO 323
<211> LENGTH: 322
<212> TYPE: DNA
<213> ORGANISM: Homo sapiens

<400> SEQUENCE: 323
gacatccaga tgacccagtc tccatcttcc gtgtctgcat ctgtaggaga cagagtcacc      60
atcacttgtc gggcgagtca gagtcttagc agctggttag cctggtatca gcagaaacca     120
gggaaagccc ctaaactcct gctccataat gcatccagtt tgcaaagtgg ggtcccatca     180
aggttcagcg gcagtggatc tgggacagat ttcactctca ccatcagcag cctgcagcct     240
gaagattttg taaattacta ttgtcaacag gctaacagtt ccctctcac ttttcggcgg      300 agggaccagg gtggagatca aa                                              322

<210> SEQ ID NO 324
<211> LENGTH: 107
<212> TYPE: PRT
<213> ORGANISM: Homo sapiens

<400> SEQUENCE: 324

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Ser Leu Ser Ser Trp
                 20                  25                  30

Leu Ala Trp Tyr Gln Gln Lys Pro Gly Lys Ala Pro Lys Leu Leu Leu
             35                  40                  45

His Asn Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Val Asn Tyr Tyr Cys Gln Gln Ala Asn Ser Phe Pro Leu
                 85                  90                  95

Thr Phe Gly Gly Gly Thr Arg Val Glu Ile Lys
            100                 105

<210> SEQ ID NO 325
<211> LENGTH: 357
<212> TYPE: DNA
<213> ORGANISM: Homo sapiens

<400> SEQUENCE: 325
caggtgcagc tggtggagtc tgggggaggc gtggtccagc ctgggaggtc cctaagactc      60
tcctgtgcag cgtctggatt caccttaagt agttatggca tgctctgggt ccgccaggct     120
ccaggcaagg ggctggagtg ggtggcagtt ttatggtttg atggaagtta taaaaactat     180
gcagactccg tgaagggccg attcaccatc tccagagaca attccaagaa cacgctgtat     240
```

```
ctgcaaatga acagcctgcg agccgaggac acggctgtgt attactgtgc gagagatagt    300
acaactatgg cccactttga ctactggggc cagggaaccc tggtcaccgt ctcctca      357
```

<210> SEQ ID NO 326
<211> LENGTH: 119
<212> TYPE: PRT
<213> ORGANISM: Homo sapiens

<400> SEQUENCE: 326

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Ser Tyr
            20                  25                  30

Gly Met Leu Trp Val Arg Gln Ala Pro Gly Lys Gly Leu Glu Trp Val
        35                  40                  45

Ala Val Leu Trp Phe Asp Gly Ser Tyr Lys Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Thr Thr Met Ala His Phe Asp Tyr Trp Gly Gln Gly
            100                 105                 110

Thr Leu Val Thr Val Ser Ser
        115

<210> SEQ ID NO 327
<211> LENGTH: 331
<212> TYPE: DNA
<213> ORGANISM: Homo sapiens

<400> SEQUENCE: 327

```
cagactgtgg tgacccagga gccatcgttc tcagtgtccc ctggagggac agtcacactc    60
acttgtggct tgaactctgg ctcagtctct actagttact cccccagctg gtaccagcag    120
accccaggcc aggctccacg cacgctcatc tacagcacaa acagtcgctc ttctggggtc    180
cctgatcgct tctctggctc catccttggg aacaaagctg ccctcaccat cacgggggcc    240
caggcagatg atgaatctga ttattactgt gtgctgtata tgggtagagg catttgggtg    300
tttcggcgga gggaccaagc tgaccgtcct a                                   331
```

<210> SEQ ID NO 328
<211> LENGTH: 110
<212> TYPE: PRT
<213> ORGANISM: Homo sapiens

<400> SEQUENCE: 328

Gln Thr Val Val Thr Gln Glu Pro Ser Phe Ser Val Ser Pro Gly Gly
1               5                   10                  15

Thr Val Thr Leu Thr Cys Gly Leu Asn Ser Gly Ser Val Ser Thr Ser
            20                  25                  30

Tyr Phe Pro Ser Trp Tyr Gln Gln Thr Pro Gly Gln Ala Pro Arg Thr
        35                  40                  45

Leu Ile Tyr Ser Thr Asn Ser Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Arg 85                  90                  95
Gly Ile Trp Val Phe Gly Gly Gly Thr Lys Leu Thr Val Leu
                100                 105                 110

<210> SEQ ID NO 329
<211> LENGTH: 337
<212> TYPE: DNA
<213> ORGANISM: Homo sapiens

<400> SEQUENCE: 329
gatgttgtga tgactcagtc tccactctcc ctgcccgtca cccttggaca gccggcctcc      60
atctcctgca ggtctagtca agcctcgta tacagtgatg aaacaccta cttgaattgg     120 tttcagcaga ggccaggcca atctccaagg cgcctaattt ataaggtttc ttactgggac    180
tctggggtcc cagacagatt cagcggcagt gggtcaggca ctgatttcac actgaaaatc    240
agtagggtgg aggctgagga tgttggggtt tattactgca tgcaaggtac acactggcct    300
ccggcctttc ggccaaggga cacgactgga gatcaaa                             337

<210> SEQ ID NO 330
<211> LENGTH: 112
<212> TYPE: PRT
<213> ORGANISM: Homo sapiens

<400> SEQUENCE: 330

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Tyr Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Ala Phe Gly Gln Gly Thr Arg Leu Glu Ile Lys
                100                 105                 110

<210> SEQ ID NO 331
<211> LENGTH: 322
<212> TYPE: DNA
<213> ORGANISM: Homo sapiens

<400> SEQUENCE: 331
gacatccaga tgacccagtc tccatcttcc gtgtctgcat ctgtaggaga cagagtcacc      60
atcacttgtc gggcgagtca gagtcttagc agctggttag cctggtatca gcagaaacca    120
gggaaagccc ctaaactcct gctctataat gcatccagtt tgcaaagtgg ggccccatca    180
aggttcagcg gcagtggatc tgggacagat tcactctca ccatcagcag cctgcagcct    240
gaagattttg taacttacta ttgtcaacag gctaacagtt tccctctcac ttttcggcgg    300
agggaccagg gtggagatca aa                                             322

<210> SEQ ID NO 332
<211> LENGTH: 107
<212> TYPE: PRT
<213> ORGANISM: Homo sapiens

<400> SEQUENCE: 332

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Leu Ser Ser Trp
            20                  25                  30

Leu Ala Trp Tyr Gln Gln Lys Pro Gly Lys Ala Pro Lys Leu Leu Leu
        35                  40                  45

Tyr Asn Ala Ser Ser Leu Gln Ser Gly Ala Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Val Thr Tyr Tyr Cys Gln Gln Ala Asn Ser Phe Pro Leu
                85                  90                  95

Thr Phe Gly Gly Gly Thr Arg Val Glu Ile Lys
            100                 105

<210> SEQ ID NO 333
<211> LENGTH: 322
<212> TYPE: DNA
<213> ORGANISM: Homo sapiens

<400> SEQUENCE: 333
gacatccaga tgacccagtc cccatcttcc gtgtctgcat ctgtaggaga cagagtcacc    60
atcacttgtc gggcgagtca gggtcttagc agctggttag cctggtatca gcagaaacca   120
gggaaagccc ccaagctcct gatgtataac acatccagtt tgcaaagtgg ggtcccatca   180
aggttcagcg gcagtggatc tgggacagat ttcagtctca ccatcagcag cctgcagcct   240
gaagattttg caagttacta ttgtcaacag gctaacagtt ccctctcac ttttcggcgg    300
agggaccaag gtggagatca aa                                            322

<210> SEQ ID NO 334
<211> LENGTH: 354
<212> TYPE: DNA
<213> ORGANISM: Homo sapiens

<400> SEQUENCE: 334
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagca attagtggta gtggtggaag tacacactac   180
gcagactccg tgaagggccg gttcaccatc tccagagaca attccaagaa cacgctgtat   240
ctgcaaatga acagcctgag agccgaggac acggccgtat attactgtgc gaaagatctc   300
aactggggag cttttgatat ctggggccaa gggacaatgg tcaccgtctc ttca         354

<210> SEQ ID NO 335
<211> LENGTH: 118
<212> TYPE: PRT
<213> ORGANISM: Homo sapiens

<400> SEQUENCE: 335

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

```
Ser Ala Ile Ser Gly Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu Asn Trp Gly Ala Phe Asp Ile Trp Gly Gln Gly Thr
            100                 105                 110

Met Val Thr Val Ser Ser
            115

<210> SEQ ID NO 336
<211> LENGTH: 337
<212> TYPE: DNA
<213> ORGANISM: Homo sapiens

<400> SEQUENCE: 336
cagtctgtgc tgacgcagcc gccctcagtg tctggggccc cagggcagag ggtcaccatc      60
tcctgcactg ggagcagctc aacattggg gcgggttatg ttgtacattg gtaccagcag      120
cttccaggaa cagcccccaa actcctcatc tatggtaaca gcaatcggcc ctcagggtc      180 cctgaccaat tctctggctc caagtctggc acctcagcct ccctggccat cactggactc      240
cagtctgagg atgaggctga ttattactgc aaagcatggg ataacagcct gaatgctcaa      300
ggggtatttc ggcggaggga ccaagctgac cgtccta                              337

<210> SEQ ID NO 337
<211> LENGTH: 112
<212> TYPE: PRT
<213> ORGANISM: Homo sapiens

<400> SEQUENCE: 337

Gln Ser Val Leu Thr Gln Pro Pro Ser Val Ser Gly Ala Pro Gly Gln
  1               5                  10                  15

Arg Val Thr Ile Ser Cys Thr Gly Ser Ser Ser Asn Ile Gly Ala Gly
                 20                  25                  30

Tyr Val Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Gln Phe
        50                  55                  60

Ser Gly Ser Lys Ser Gly Thr Ser Ala Ser Leu Ala Ile Thr Gly Leu
 65                  70                  75                  80

Gln Ser Glu Asp Glu Ala Asp Tyr Tyr Cys Lys Ala Trp Asp Asn Ser
                 85                  90                  95

Leu Asn Ala Gln Gly Val Phe Gly Gly Gly Thr Lys Leu Thr Val Leu
            100                 105                 110

<210> SEQ ID NO 338
<211> LENGTH: 363
<212> TYPE: DNA
<213> ORGANISM: Homo sapiens

<400> SEQUENCE: 338
gaggtgcagc tgttggagtc tgggggaggc ttggcacagc cggggggtc cctgagactc       60 tcctgtgcag gctctggatt ctcctttaga ggctatgtca tgacttgggt ccgccaggct     120
ccagggaagg ggctggagtg ggtctcagga attagtggta gtggtggtag cacatactac     180
gcagactccg tgaagggccg gttcaccatc tccagagaca attccaagaa cacgctgtgt     240
```

```
ctgcaaatga acagcctgag agccgaggac acggccgtat attactgtgc gaaggagac    300 agctcgaact actactccgg tatggacgtc tggggccaag ggaccacggt catcgtctcc    360
tca                                                                  363
```

<210> SEQ ID NO 339
<211> LENGTH: 121
<212> TYPE: PRT
<213> ORGANISM: Homo sapiens

<400> SEQUENCE: 339

```
Glu Val Gln Leu Leu Glu Ser Gly Gly Gly Leu Ala Gln Pro Gly Gly
1               5                   10                  15

Ser Leu Arg Leu Ser Cys Ala Gly Ser Gly Phe Ser Phe Arg Gly Tyr
            20                  25                  30

Val Met Thr Trp Val Arg Gln Ala Pro Gly Lys Gly Leu Glu Trp Val
        35                  40                  45

Ser Gly Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Cys
65                  70                  75                  80

Leu Gln Met Asn Ser Leu Arg Ala Glu Asp Thr Ala Val Tyr Tyr Cys
                85                  90                  95

Ala Lys Gly Asp Ser Ser Asn Tyr Tyr Ser Gly Met Asp Val Trp Gly
            100                 105                 110

Gln Gly Thr Thr Val Ile Val Ser Ser
        115                 120
```

<210> SEQ ID NO 340
<211> LENGTH: 340
<212> TYPE: DNA
<213> ORGANISM: Homo sapiens

<400> SEQUENCE: 340

```
gacatcgtga tgacccagtc tccagactcc ctggctgtgt ctctgggcga gagggccacc     60
atcaactgca gtccagcca gagtgtttta tacaactcca acaataagaa ctacttagct    120
tggtaccagc agaaaccagg acagcctcct aagctgctca tttactgggc ttctacccgg    180
gaatccgggg tccctgaccg attcagtggc agcgggtctg ggacagattt cactctcacc    240
atcagcagcc tgcaggctga ggatgtggca atttattact gtcagcaatt ttatggtcct    300
cctctcactt tcggcggag ggaccaaggt ggaaatcaaa                          340
```

<210> SEQ ID NO 341
<211> LENGTH: 113
<212> TYPE: PRT
<213> ORGANISM: Homo sapiens

<400> SEQUENCE: 341

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Asn
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80
```

```
Ile Ser Ser Leu Gln Ala Glu Asp Val Ala Ile Tyr Tyr Cys Gln Gln
                85                  90                  95

Phe Tyr Gly Pro Pro Leu Thr Phe Gly Gly Gly Thr Lys Val Glu Ile
            100                 105                 110

Lys

<210> SEQ ID NO 342
<211> LENGTH: 357
<212> TYPE: DNA
<213> ORGANISM: Homo sapiens

<400> SEQUENCE: 342
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccca acaatggtgg cacaaactat      180
ggacagaagt tcagggcag ggtcaccatg accaggaca cgtccatcag cacagcctac      240
atggagctga gcaggctgag atctgacgac acggccgtgt attactgtgc gagagggaac     300
tggaacgacg atgcttttga tatctggggc caagggacaa tggtcaccgt ctcttca       357

<210> SEQ ID NO 343
<211> LENGTH: 119
<212> TYPE: PRT
<213> ORGANISM: Homo sapiens

<400> SEQUENCE: 343

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Asn Gly Gly Thr Asn Tyr Gly Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asn Trp Asn Asp Asp Ala Phe Asp Ile Trp Gly Gln Gly
            100                 105                 110

Thr Met Val Thr Val Ser Ser
        115

<210> SEQ ID NO 344
<211> LENGTH: 322
<212> TYPE: DNA
<213> ORGANISM: Homo sapiens

<400> SEQUENCE: 344
tcctatgagc tgactcagtc accctcagtg tccgtgtccc caggacagac agccagcatc      60
acctgttctg gtgataaatt gggggataaa tttgcttttct ggtatcagca gaagccaggc    120
cagtcccctg tgctggtcat ctatcaagat agcaagcggc cctcagggat ccctgagcga     180
ttctctggct ccaactctgg gaacacagcc actctgacca tcagcgggac ccaggctatg     240
gatgaggctg actattactg tcaggcgtgg gacagcagcg ccggggggt atttcggcgg      300 agggaccaag ttgaccgtcc ta                                               322
```

<210> SEQ ID NO 345
<211> LENGTH: 107
<212> TYPE: PRT
<213> ORGANISM: Homo sapiens

<400> SEQUENCE: 345

Ser Tyr Glu Leu Thr Gln Ser Pro Ser Val Ser Val Ser Pro Gly Gln
1               5                   10                  15

Thr Ala Ser Ile Thr Cys Ser Gly Asp Lys Leu Gly Asp Lys Phe Ala
            20                  25                  30

Phe Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ala Gly Gly
                85                  90                  95

Val Phe Gly Gly Gly Thr Lys Leu Thr Val Leu
            100                 105

<210> SEQ ID NO 346
<211> LENGTH: 375
<212> TYPE: DNA
<213> ORGANISM: Homo sapiens

<400> SEQUENCE: 346
caggtgcaac tggaggagtc tgggggaggc gtggtccagc ctggagggtc cctgagactc     60
tcctgtgcag cgtctggatt caccttcagt agctatggca tgcactgggt ccgccaggct    120
ccaggcaagg ggctggagtg ggtggcagtt atatggtatg atggaagtaa taaatactat    180
gtagactccg tgaagggccg attcaccatc tccagagaca attccaagaa cacgctgtat    240
ctgcaaatga acagcctgag agccgaggac acggctgtgt attactgtgc gagaatgggg    300
tttactatgg ttcggggagc cctctactac ggtatggacg tctggggcca agggaccacg    360
gtcaccgtct cctca                                                    375

<210> SEQ ID NO 347
<211> LENGTH: 125
<212> TYPE: PRT
<213> ORGANISM: Homo sapiens

<400> SEQUENCE: 347

Gln Val Gln Leu Glu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Gly Phe Thr Met Val Arg Gly Ala Leu Tyr Tyr Gly Met
            100                 105                 110

Asp Val Trp Gly Gln Gly Thr Thr Val Thr Val Ser Ser
        115                 120                 125

<210> SEQ ID NO 348
<211> LENGTH: 325
<212> TYPE: DNA
<213> ORGANISM: Homo sapiens

<400> SEQUENCE: 348
tcttctgagc tgactcagga ccctgctgtg tctgtggcct tgggacagac agtcaggatc      60
acatgccaag agacagcct cagaagctat catgcaagct ggtaccagca gaagccagga     120
caggcccctg tacttgtcat ctatggtgaa acaaccggc cctcagggat cccagaccga     180
ttctctgact ccagttcagg aaacacagct tccttgacca tcactgggc tcaggcggaa     240 gatgaggctg actattattg taattatcgg acaacagtg gtaaccatct ggtgtttcgg     300
cggagggacc aagctgaccg tccta                                          325

<210> SEQ ID NO 349
<211> LENGTH: 108
<212> TYPE: PRT
<213> ORGANISM: Homo sapiens

<400> SEQUENCE: 349

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr His Ala
            20                  25                  30

Ser Trp Tyr Gln Gln Lys Pro Gly Gln Ala Pro Val Leu Val Ile Tyr
        35                  40                  45

Gly Glu Asn Asn Arg Pro Ser Gly Ile Pro Asp Arg Phe Ser Asp Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Tyr Arg Asp Asn Ser Gly Asn His
                85                  90                  95

Leu Val Phe Gly Gly Gly Thr Lys Leu Thr Val Leu
            100                 105

<210> SEQ ID NO 350
<211> LENGTH: 357
<212> TYPE: DNA
<213> ORGANISM: Homo sapiens

<400> SEQUENCE: 350
gaggtgcagc tgttggaatc tgggggaggc ttggtacagc ctgggggtc cctgagactc      60 tcctgtgcag cctctggatt cacctttagc agctatgcca tgagctgggt ccgccaggct    120
ccagggaagg ggctggagtg gtctcagct attagtcgta gtggtagtac cacatactac    180
gcagactccg tgaagggccg gttcaccatc tccagagaca attccaagaa cacgctgtat    240
ctgcaaatga acagcctgag agccgaggac acggccgtat attactgtgt ggaaccgaga    300
tattttgact ggttattagg cgactggggc cagggaaccc tggtcaccgt ctcctca       357

<210> SEQ ID NO 351
<211> LENGTH: 119
<212> TYPE: PRT
<213> ORGANISM: Homo sapiens

<400> SEQUENCE: 351

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Arg Ser Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Glu Pro Arg Tyr Phe Asp Trp Leu Leu Gly Asp Trp Gly Gln Gly
                100                 105                 110

Thr Leu Val Thr Val Ser Ser
            115
```

<210> SEQ ID NO 352
<211> LENGTH: 369
<212> TYPE: DNA
<213> ORGANISM: Homo sapiens

<400> SEQUENCE: 352

```
caggtgcagc tggtggagtc gggggggaggc gtggtccagc ctggagggtc cctgagactc      60
tcctgtgcag cgtctggatt caccttcagt agctatggca tgcactgggt ccgccaggct     120
ccaggcaagg ggctggagtg gtggcagtt aaatggtatg aaggaagtaa taaatactat     180
ggagactccg tgaagggccg attcaccatc tccagagaca attccaagaa cacgctgtat     240
ttgcaaatga acagtctgag aggcgaggat acggctgtgt attactgtgc gagaggcgcc     300
cacgactacg tgacttcta ctacggtatg gacgtctggg gccaagggac cacggtcacc     360
gtctcctca                                                              369
```

<210> SEQ ID NO 353
<211> LENGTH: 123
<212> TYPE: PRT
<213> ORGANISM: Homo sapiens

<400> SEQUENCE: 353

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Lys Trp Tyr Glu Gly Ser Asn Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Gly Ala His Asp Tyr Gly Asp Phe Tyr Tyr Gly Met Asp Val
                100                 105                 110

Trp Gly Gln Gly Thr Thr Val Thr Val Ser Ser
            115                 120
```

```
<210> SEQ ID NO 354
<211> LENGTH: 319
<212> TYPE: DNA
<213> ORGANISM: Homo sapiens

<400> SEQUENCE: 354
tcctatgaac tgactcagcc agcctcagtg tccgtgtccc caggacagat agccagcatc    60
acctgctctg gagataattt gggggataaa tatatttgct ggtatcagca gaagccaggc   120
cagtcccctg tgcgggtcat ctatcaagat aacaagcggc cctcagggat ccctgagcgt   180
ttctctggct ccaattctgg gaacacagcc actctgacca tcagcgggac ccaggctatg   240
gatgaggctg actattactg tcaggcgtgg gacagcagca ctgtggtatt tcggcggagg   300
gaccaagctg accgtccta                                                319

<210> SEQ ID NO 355
<211> LENGTH: 106
<212> TYPE: PRT
<213> ORGANISM: Homo sapiens

<400> SEQUENCE: 355

Ser Tyr Glu Leu Thr Gln Pro Ala Ser Val Ser Val Ser Pro Gly Gln
1               5                   10                  15

Ile Ala Ser Ile Thr Cys Ser Gly Asp Asn Leu Gly Asp Lys Tyr Ile
            20                  25                  30

Cys Trp Tyr Gln Gln Lys Pro Gly Gln Ser Pro Val Arg Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105

<210> SEQ ID NO 356
<211> LENGTH: 366
<212> TYPE: DNA
<213> ORGANISM: Homo sapiens

<400> SEQUENCE: 356
gaggtgcagc tgttggagtc tgggggaggc ttggtacagc ctggggggtc cctgagactc    60
tcctgtgcag cctctggatt caccttagc agctatgcca tgagctgggt ccgccaggct   120
ccagggaagg ggctggagtg gtctcagct attagttata gtggcggtag cacatactac   180
gcaggctccg tgaagggccg gttcaccatc tccagagaca attccaagaa cacgctgtat   240
ctgcaaatga acagcctgag agccgaggac acggccgtat attactgtgc gaaagatcgg   300
gagggagcga cttggtacta cggtatggac gtctggggcc aagggaccac ggtcaccgtc   360
tcctca                                                              366

<210> SEQ ID NO 357
<211> LENGTH: 122
<212> TYPE: PRT
<213> ORGANISM: Homo sapiens

<400> SEQUENCE: 357

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Tyr Ser Gly Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Glu Gly Ala Thr Trp Tyr Tyr Gly Met Asp Val Trp
                100                 105                 110

Gly Gln Gly Thr Thr Val Thr Val Ser Ser
            115                 120

<210> SEQ ID NO 358
<211> LENGTH: 319
<212> TYPE: DNA
<213> ORGANISM: Homo sapiens

<400> SEQUENCE: 358
tcctatgaac tgactcagcc accctcagtg tccgtgtccc caggacagac agccagcatc      60
acctgctctg gagataaaat tggggaaagc tatgcttgct ggtatcagca gaagccaggc     120
cagtcccctg tactggtcat ctatcaagat tacaagcggc cctcagggat ccctgagcgc     180
ttctctggct ccaactctgg gaacacagcc actctgacca tcagcgggac ccaggctatg     240
gatgaggctg actattactg tcaggcgtgg gacagaagta ctgtactatt tcggcggagg     300
gaccaagctg accgtccta                                                 319

<210> SEQ ID NO 359
<211> LENGTH: 106
<212> TYPE: PRT
<213> ORGANISM: Homo sapiens

<400> SEQUENCE: 359

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Glu Ser Tyr Ala
            20                  25                  30

Cys Trp Tyr Gln Gln Lys Pro Gly Gln Ser Pro Val Leu Val Ile Tyr
        35                  40                  45

Gln Asp Tyr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Arg Ser Thr Val Leu
                85                  90                  95

Phe Gly Gly Gly Thr Lys Leu Thr Val Leu
            100                 105

<210> SEQ ID NO 360
<211> LENGTH: 366
<212> TYPE: DNA
<213> ORGANISM: Homo sapiens

<400> SEQUENCE: 360
cagatgcagc tggtggagtc tggggggaggc gtggtccagc ctggggaggtc cctgagactc      60
```

```
tcctgtgcag cgtctggatt caccttcaga acctatggca tgcactgggt ccgccaggct    120
ccaggcaagg gactggagtg ggtggcagtt atatggtatg atggaagtaa taaacactat    180
gcagactccg tgaagggccg attcaccatc accagagaca attccaagaa cactctgaat    240
ctgcaaatga acagcctgag agccgaggac acggctgtgt attactgtgc gagagcccct    300
cagtgggagc tagttcatga agcttttgat atctggggcc aagggacaat ggtcaccgtc    360
tcttca    366
```

<210> SEQ ID NO 361
<211> LENGTH: 122
<212> TYPE: PRT
<213> ORGANISM: Homo sapiens

<400> SEQUENCE: 361

```
Gln Met Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys His Tyr Ala Asp Ser Val
    50                  55                  60

Lys Gly Arg Phe Thr Ile Thr Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Arg Ala Pro Gln Trp Glu Leu Val His Glu Ala Phe Asp Ile Trp
            100                 105                 110

Gly Gln Gly Thr Met Val Thr Val Ser Ser
        115                 120
```

<210> SEQ ID NO 362
<211> LENGTH: 325
<212> TYPE: DNA
<213> ORGANISM: Homo sapiens

<400> SEQUENCE: 362

```
tcctatgtgc tgactcagcc accctcggtg tcagtggccc caggacagac ggccaggatt    60
acctgtgggg gaaacaacct tggaagtaaa agtgtgcact ggtaccagca gaagccaggc    120
caggcccctg tgctggtcgt ctatgatgat agcgaccggc cctcatggat ccctgagcga    180
ttctctggct ccaactctgg gaacacggcc accctgacca tcagcagggg cgaagccggg    240
gatgaggccg actattactg tcaggtgtgg gatagtagta gtgatcatgt ggtatttcgg    300
cggagggacc aagctgaccg tccta    325
```

<210> SEQ ID NO 363
<211> LENGTH: 108
<212> TYPE: PRT
<213> ORGANISM: Homo sapiens

<400> SEQUENCE: 363

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Leu Gly Ser Lys Ser Val
            20                  25                  30

His Trp Tyr Gln Gln Lys Pro Gly Gln Ala Pro Val Leu Val Val Tyr
```

```
                    35                  40                  45
Asp Asp Ser Asp Arg Pro Ser Trp Ile Pro Glu Arg Phe Ser Gly Ser
 50                  55                  60

Asn Ser Gly Asn Thr Ala Thr Leu Thr Ile Ser Arg Gly Glu Ala Gly
 65                  70                  75                  80

Asp Glu Ala Asp Tyr Tyr Cys Gln Val Trp Asp Ser Ser Asp His
                 85                  90                  95

Val Val Phe Gly Gly Gly Thr Lys Leu Thr Val Leu
                100                 105

<210> SEQ ID NO 364
<211> LENGTH: 981
<212> TYPE: DNA
<213> ORGANISM: Homo sapiens

<400> SEQUENCE: 364
gctagcacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggaccctga ggtcacgtgc      420 gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt tgtgcaccag gactggctga acggcaagga gtacaagtgc     600
aaggtctcca acaaaggcct cccagccccc atcgagaaaa ccatctccaa aaccaaaggg     660
cagccccgag aaccacaggt gtacaccctg cccccatccc gggaggagat gaccaagaac     720
caggtcagcc tgacctgcct ggtcaaaggc ttctacccca gcgacatcgc cgtggagtgg     780
gagagcaatg ggcagccgga gaacaactac aagaccacac tcccatgct ggactccgac      840 ggctcctcct cctctacag caagctcacc gtggacaaga gcaggtggca gcaggggaac     900
gtcttctcat gctccgtgat gcatgaggct ctgcacaacc actacacgca gaagagcctc     960
tccctgtctc cgggtaaatg a                                                981

<210> SEQ ID NO 365
<211> LENGTH: 326
<212> TYPE: PRT
<213> ORGANISM: Homo sapiens

<400> SEQUENCE: 365

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
```

```
                    85                  90                  95
Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 366
<211> LENGTH: 324
<212> TYPE: DNA
<213> ORGANISM: Homo sapiens

<400> SEQUENCE: 366
cgtacggtgg ctgcaccatc tgtcttcatc ttcccgccat ctgatgagca gttgaaatct     60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg ttag                                          324

<210> SEQ ID NO 367
<211> LENGTH: 107
<212> TYPE: PRT
<213> ORGANISM: Homo sapiens

<400> SEQUENCE: 367

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30
```

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 368
<211> LENGTH: 321
<212> TYPE: DNA
<213> ORGANISM: Homo sapiens

<400> SEQUENCE: 368
ggccaaccga aagcggcgcc ctcggtcact ctgttcccgc cctcctctga ggagcttcaa      60
gccaacaagg ccacactggt gtgtctcata agtgacttct acccgggagc cgtgacagtg    120
gcctggaagg cagatagcag ccccgtcaag gcggagtgg agaccaccac accctccaaa     180
caaagcaaca acaagtacgc ggccagcagc tatctgagcc tgacgcctga gcagtggaag    240
tcccacagaa gctacagctg ccaggtcacg catgaaggga gcaccgtgga aagacagtg     300 gccccctacag aatgttcata g                                              321

<210> SEQ ID NO 369
<211> LENGTH: 106
<212> TYPE: PRT
<213> ORGANISM: Homo sapiens

<400> SEQUENCE: 369

Gly Gln Pro Lys Ala Ala Pro Ser Val Thr Leu Phe Pro Pro Ser Ser
  1               5                  10                  15

Glu Glu Leu Gln Ala Asn Lys Ala Thr Leu Val Cys Leu Ile Ser Asp
             20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 370
<211> LENGTH: 15
<212> TYPE: DNA
<213> ORGANISM: Homo sapiens

<400> SEQUENCE: 370
agaaaaagga aagtc                                                       15

<210> SEQ ID NO 371
<211> LENGTH: 5
<212> TYPE: PRT
<213> ORGANISM: Homo sapiens

<400> SEQUENCE: 371

Arg Lys Arg Lys Val
1               5

<210> SEQ ID NO 372
<211> LENGTH: 504
<212> TYPE: DNA
<213> ORGANISM: Homo sapiens

<400> SEQUENCE: 372
atgttccctt tgccttact atatgttctg tcagtttctt tcaggaaaat cttcatctta      60
caacttgtag ggctggtgtt aacttacgac ttcactaact gtgactttga agagattaaa    120
gcagcctatc tcagtactat ttctaaagac ctgattacat atatgagtgg gaccaaaagt    180
accgagttca caacaccgt ctcttgtagc aatcggccac attgccttac tgaaatccag     240
agcctaacct tcaatcccac cgccggctgc gcgtcgctcg ccaaagaaat gttcgccatg    300
aaaactaagg ctgccttagc tatctggtgc ccaggctatt cggaaactca gataaatgct    360
actcaggcaa tgaagaagag gacaaccaat aaatgtctgg aacaagtgtc acaattacaa    420
ggattgtggc gtcgcttcaa tcgacctta ctgaaacaac agcatcacca tcaccatcac     480
gactacaaag acgatgacga caaa                                           504

<210> SEQ ID NO 373
<211> LENGTH: 168
<212> TYPE: PRT
<213> ORGANISM: Homo sapiens

<400> SEQUENCE: 373

Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
    50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Arg Thr
        115                 120                 125

Thr Asn Lys Cys Leu Glu Gln Val Ser Gln Leu Gln Gly Leu Trp Arg
    130                 135                 140

Arg Phe Asn Arg Pro Leu Leu Lys Gln Gln His His His His His
145                 150                 155                 160

Asp Tyr Lys Asp Asp Asp Lys
                165

<210> SEQ ID NO 374
<211> LENGTH: 519
<212> TYPE: DNA
<213> ORGANISM: Homo sapiens

<400> SEQUENCE: 374

```
atgttccctt tgccttact atatgttctg tcagtttctt tcaggaaaat cttcatctta      60
caacttgtag ggctggtgtt aacttacgac ttcactaact gtgactttga aagattaaa     120 gcagcctatc tcagtactat ttctaaagac ctgattacat atatgagtgg gaccaaaagt    180
accgagttca acaacaccgt tcttgtagc aatcggccac attgccttac tgaaatccag     240
agcctaacct tcaatcccac cgccggctgc gcgtcgctcg ccaagaaaat gttcgccatg    300
aaaactaagg ctgccttagc tatctggtgc ccaggctatt cggaaactca gataaatgct    360
actcaggcaa tgaagaagag gagaaaaagg aaagtcacaa ccaataaatg tctggaacaa    420
gtgtcacaat tacaaggatt gtggcgtcgc ttcaatcgac ctttactgaa acaacagcat    480
caccatcacc atcacgacta caaagacgat gacgacaaa                           519
```

<210> SEQ ID NO 375
<211> LENGTH: 173
<212> TYPE: PRT
<213> ORGANISM: Homo sapiens

<400> SEQUENCE: 375

```
Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
    50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Arg Arg
        115                 120                 125

Lys Arg Lys Val Thr Thr Asn Lys Cys Leu Glu Gln Val Ser Gln Leu
    130                 135                 140

Gln Gly Leu Trp Arg Arg Phe Asn Arg Pro Leu Leu Lys Gln Gln His
145                 150                 155                 160

His His His His Asp Tyr Lys Asp Asp Asp Lys
                165                 170
```

<210> SEQ ID NO 376
<211> LENGTH: 28
<212> TYPE: PRT
<213> ORGANISM: Homo sapiens

<400> SEQUENCE: 376

```
Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr
            20                  25
```

<210> SEQ ID NO 377
<211> LENGTH: 481
<212> TYPE: DNA
<213> ORGANISM: Homo sapiens

<400> SEQUENCE: 377

| | | |
|---|---|---|
| atggagacag acacactcct gctatgggta ctgctgctct gggttccagg ttccaccggt | 60 |
| tacgacttca ctaactgtga ctttcagaag attgaagcag actatctccg tactatttct | 120 |
| aaagacctga ttacatatat gagtgggact aaaagtaccg acttcaacaa caccgtctcc | 180 |
| tgtagcaatc ggccacactg ccttactgaa atccagagcc taaccttcaa tcccaccccc | 240 |
| cgctgcgcgt cgctcgccaa ggaaatgttc gccaggaaaa ctaaggctac cctcgctctc | 300 |
| tggtgcccag gctattcgga aactcagata aatgctactc aggcaatgaa gaagaggaca | 360 |
| accaataaat gtctggaaca agtgtcacaa ttactaggat tgtggcgtcg cttcattcga | 420 |
| actttactga acaacagca ccaccaccac caccatgact ataaagacga tgacgacaaa | 480 |
| t | 481 |

<210> SEQ ID NO 378
<211> LENGTH: 160
<212> TYPE: PRT
<213> ORGANISM: Homo sapiens

<400> SEQUENCE: 378

```
Met Glu Thr Asp Thr Leu Leu Leu Trp Val Leu Leu Leu Trp Val Pro
1               5                   10                  15

Gly Ser Thr Gly Tyr Asp Phe Thr Asn Cys Asp Phe Gln Lys Ile Glu
            20                  25                  30

Ala Asp Tyr Leu Arg Thr Ile Ser Lys Asp Leu Ile Thr Tyr Met Ser
        35                  40                  45

Gly Thr Lys Ser Thr Asp Phe Asn Asn Thr Val Ser Cys Ser Asn Arg
    50                  55                  60

Pro His Cys Leu Thr Glu Ile Gln Ser Leu Thr Phe Asn Pro Thr Pro
65                  70                  75                  80

Arg Cys Ala Ser Leu Ala Lys Glu Met Phe Ala Arg Lys Thr Lys Ala
                85                  90                  95

Thr Leu Ala Leu Trp Cys Pro Gly Tyr Ser Glu Thr Gln Ile Asn Ala
            100                 105                 110

Thr Gln Ala Met Lys Lys Arg Thr Thr Asn Lys Cys Leu Glu Gln Val
        115                 120                 125

Ser Gln Leu Leu Gly Leu Trp Arg Arg Phe Ile Arg Thr Leu Leu Lys
    130                 135                 140

Gln Gln His His His His His His Asp Tyr Lys Asp Asp Asp Asp Lys
145                 150                 155                 160
```

<210> SEQ ID NO 379
<211> LENGTH: 495
<212> TYPE: DNA
<213> ORGANISM: Homo sapiens

<400> SEQUENCE: 379

| | | |
|---|---|---|
| atggagacag acacactcct gctatgggta ctgctgctct gggttccagg ttccaccggt | 60 |
| tacgacttca ctaactgtga ctttcagaag attgaagcag actatctccg tactatttct | 120 |
| aaagacctga ttacatatat gagtgggact aaaagtaccg acttcaacaa caccgtctcc | 180 |
| tgtagcaatc ggccacactg ccttactgaa atccagagcc taaccttcaa tcccaccccc | 240 |
| cgctgcgcgt cgctcgccaa ggaaatgttc gccaggaaaa ctaaggctac cctcgctctc | 300 |
| tggtgcccag gctattcgga aactcagata aatgctactc aggcaatgaa gaagaggaga | 360 |

```
aaaaggaaag tcacaaccaa taaatgtctg gaacaagtgt cacaattact aggattgtgg    420
cgtcgcttca ttcgaacttt actgaaacaa cagcaccacc accaccacca tgactataaa    480
gacgatgacg acaaa                                                     495
```

```
<210> SEQ ID NO 380
<211> LENGTH: 165
<212> TYPE: PRT
<213> ORGANISM: Homo sapiens

<400> SEQUENCE: 380
```

Met Glu Thr Asp Thr Leu Leu Leu Trp Val Leu Leu Leu Trp Val Pro
1               5                   10                  15

Gly Ser Thr Gly Tyr Asp Phe Thr Asn Cys Asp Phe Gln Lys Ile Glu
            20                  25                  30

Ala Asp Tyr Leu Arg Thr Ile Ser Lys Asp Leu Ile Thr Tyr Met Ser
        35                  40                  45

Gly Thr Lys Ser Thr Asp Phe Asn Asn Thr Val Ser Cys Ser Asn Arg
    50                  55                  60

Pro His Cys Leu Thr Glu Ile Gln Ser Leu Thr Phe Asn Pro Thr Pro
65                  70                  75                  80

Arg Cys Ala Ser Leu Ala Lys Glu Met Phe Ala Arg Lys Thr Lys Ala
                85                  90                  95

Thr Leu Ala Leu Trp Cys Pro Gly Tyr Ser Glu Thr Gln Ile Asn Ala
            100                 105                 110

Thr Gln Ala Met Lys Lys Arg Arg Lys Arg Lys Val Thr Thr Asn Lys
        115                 120                 125

Cys Leu Glu Gln Val Ser Gln Leu Leu Gly Leu Trp Arg Arg Phe Ile
    130                 135                 140

Arg Thr Leu Leu Lys Gln Gln His His His His His Asp Tyr Lys
145                 150                 155                 160

Asp Asp Asp Asp Lys
                165

```
<210> SEQ ID NO 381
<211> LENGTH: 20
<212> TYPE: PRT
<213> ORGANISM: Homo sapiens

<400> SEQUENCE: 381
```

Met Glu Thr Asp Thr Leu Leu Leu Trp Val Leu Leu Leu Trp Val Pro
1               5                   10                  15

Gly Ser Thr Gly
            20

```
<210> SEQ ID NO 382
<211> LENGTH: 8
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 382
```

Ser Gly Gly Ala Pro Met Leu Ser
1               5